United States Patent
McCabe et al.

(10) Patent No.: US 12,319,670 B2
(45) Date of Patent: *Jun. 3, 2025

(54) COMPOUNDS AND METHODS FOR INHIBITING JAK

(71) Applicant: Dizal (Jiangsu) Pharmaceutical Co., Ltd., Wuxi (CN)

(72) Inventors: James McCabe, Macclesfield (GB); Dedong Wu, Waltham, MA (US); Tudor Grecu, Macclesfield (GB); Wenzhan Yang, Waltham, MA (US)

(73) Assignee: Dizal (Jiangsu) Pharmaceutical Co., Ltd., Wuxi (CN)

( * ) Notice: Subject to any disclaimer, the term of this patent is extended or adjusted under 35 U.S.C. 154(b) by 607 days.

This patent is subject to a terminal disclaimer.

(21) Appl. No.: 17/563,913

(22) Filed: Dec. 28, 2021

(65) Prior Publication Data

US 2022/0119372 A1    Apr. 21, 2022

Related U.S. Application Data

(63) Continuation of application No. 16/860,169, filed on Apr. 28, 2020, now Pat. No. 11,247,983, which is a continuation of application No. 16/196,038, filed on Nov. 20, 2018, now Pat. No. 10,654,835, which is a continuation of application No. 15/601,324, filed on May 22, 2017, now Pat. No. 10,167,276, which is a continuation of application No. 15/272,554, filed on Sep. 22, 2016, now Pat. No. 9,714,236.

(60) Provisional application No. 62/232,629, filed on Sep. 25, 2015.

(51) Int. Cl.
C07D 403/14     (2006.01)

(52) U.S. Cl.
CPC .................. *C07D 403/14* (2013.01)

(58) Field of Classification Search
CPC ................................ C07D 403/14
USPC ..................................... 514/252.19
See application file for complete search history.

(56) References Cited

U.S. PATENT DOCUMENTS

| | | | | |
|---|---|---|---|---|
| 9,714,236 B2* | 7/2017 | Grimster | ................ | A61P 37/02 |
| 10,167,276 B2* | 1/2019 | Astrand | .................... | A61P 7/00 |
| 10,654,835 B2* | 5/2020 | Astrand | ................ | A61P 43/00 |
| 11,247,983 B2* | 2/2022 | Astrand | ................ | A61P 35/00 |

* cited by examiner

Primary Examiner — Kristin A Vajda

(57) ABSTRACT

Disclosed are compounds of formula (I), pharmaceutical compositions comprising such compounds and methods/uses of using the same, for example, for treating a JAK-related disorder, such as cancer, cancer cachexia or an immune disorder:

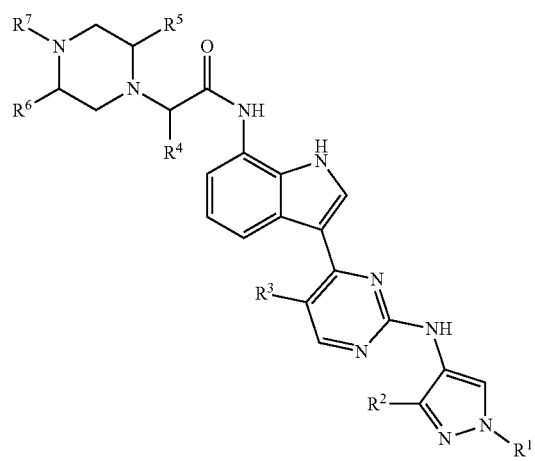

(I)

wherein
$R^1$ is methyl or ethyl;
$R^2$ is selected from methyl, ethyl, methoxy and ethoxy;
$R^3$ is selected from hydrogen, chlorine, fluorine, bromine and methyl;
$R^4$ is selected from methyl, ethyl and —$CH_2OCH_3$;
$R^5$ and $R^6$ are each individually methyl or hydrogen; and
$R^7$ is selected from methyl, ethyl, —$(CH_2)_2OH$ and —$(CH_2)_2OCH_3$, or a pharmaceutically acceptable salt thereof.

24 Claims, 36 Drawing Sheets

COMPOUNDS AND METHODS FOR INHIBITING JAK

CROSS-REFERENCE TO RELATED APPLICATIONS

This application is a Continuation of application Ser. No. 16/860,169, filed Apr. 28, 2020, which in turn is a Continuation of application Ser. No. 16/196,038, filed Nov. 20, 2018, now U.S. Pat. No. 10,654,835, issued May 19, 2020, which in turn is a Continuation Application of U.S. patent application Ser. No. 15/601,324, filed May 22, 2017, now U.S. Pat. No. 10,167,276, issued Jan. 1, 2019, which is a Continuation of application Ser. No. 15/272,554, filed Sep. 22, 2016, now U.S. Pat. No. 9,714,236, issued Jul. 25, 2017, which claims the benefit of U.S. Provisional Patent Application No. 62/232,629, filed Sep. 25, 2015. Each of these applications is hereby incorporated by reference herein in its entirety.

BACKGROUND

The JAK (Janus-associated kinase) family consists of four non-receptor tyrosine kinases, JAK1, JAK2, JAK3 and Tyk2, which play a critical role in cytokine and growth factor mediated signal transduction (Schindler C, and Darnell J E Jr., *Annu. Rev. Biochem.* 1995; 64; 621-651). Cytokine and/or growth factor binding to cell-surface receptors facilitates activation of receptor-associated JAK kinases by autophosphorylation. Activated JAKs directly phosphorylate members of the STAT (signal transducers and activators of transcription) family of transcription factors (STAT1, 2, 3, 4, 5a, 5b and 6) promoting their translocation to the nucleus and the transcriptional activation of target genes.

Constitutive activation (i.e., tyrosine phosphorylation) of members of the STAT family, in particular STAT3, has been documented in a wide range of cancers and hyperproliferative disorders, and associated with poor prognosis in several cancers (Yu H, Jove R., *Nat. Rev. Cancer* 2004; 4:97-105). Persistently activated STAT3 has been shown to be oncogenic (Bromberg J F, et al. *Cell* 1999; 98:295-303) and to drive the expression of cellular proteins contributing to central processes in cancer progression (survival, proliferation, invasion, angiogenesis) (Yu and Jove, 2004, supra). One common mechanism of STAT3 activation in cancer cells is via autocrine or paracrine stimulation of JAK/STAT3 signaling by cytokines, typically members of the interleukin-6 (IL-6) cytokine family (Grivennikov, S. and Karin, M. *Cancer Cell* 2008; 13; 7-9; Bromberg J. and Wang T C. *Cancer Cell* 2009; 15; 79-80). This is primarily mediated by JAK1, the key JAK kinase responsible for STAT3 activation (Guschin et al., *Embo J* 1995; 14; 1421-1429, Kim S M, et al., *Mol. Cancer Ther.* 2012; 11; 2254-2264; Song et. al., *Mol. Cancer Ther.* 2011; 10; 481-494). Inactivation of negative regulatory proteins, such as the SOLS (suppressors of cytokine signalling) or PIAS (protein inhibitor of activated STATs) proteins have also been shown to influence the activation status of the JAK/STAT signalling pathway in cancer (Mottok et al., *Blood* 2007; 110; 3387-90; Ogata et al., *Gastroenterology* 2006; 131; 179-193, Lee et al., *Mol. Cancer Ther.* 2006; 5; 8-19, Brantley et al., *Clin. Cancer Res.* 2008; 14; 4694-4704).

In addition to basal activation of JAK1/STAT3 signaling in multiple human tumors, the pathway has also been shown to be activated as a feedback resistance mechanism in response to inhibition of driver oncogenic pathways in cancer cells, such as the mutated epidermal growth factor receptor (EGFR) in non-small cell lung cancer (NSCLC), or the MAPK pathway in KRAS mutant tumors (Lee et al., *Cancer Cell* 2014; 26; 207-221; VanSchaeybroeck et al., *Cell reports* 2014; 7; 1940-1955). Thus inhibition of JAK1 may provide a means of potentiating the therapeutic benefit of a variety of targeted cancer therapies.

Also, cancer cachexia is a significant contributor to increased mortality and poor response to chemotherapy in patients with advanced cancer. Elevated levels of inflammatory cytokines, such as IL-6, which signal through the JAK/STAT pathway have been shown to play a causal role, indicating the potential benefit of JAK1 inhibition in ameliorating cancer cachexia.

Based on the critical role JAK1 plays in signal transduction mediated by class II cytokine receptors, the $\gamma_c$ receptor subunit, the gp130 subunit and G-CSF, as well as its dominance in driving the activity of the immune-relevant $\gamma_c$ cytokines, JAK1 inhibition may be useful in treating a number of immune disorders, such as bone marrow disorders, rheumatoid arthritis, psoriasis, Crohn's disease, lupus and multiple sclerosis.

SUMMARY

Collectively, the observations of JAKs critical role in proliferative and immune disorders highlight broad potential for JAK inhibition as a therapeutic modality in a number of diseases and disorders. Accordingly, disclosed are compounds that are JAK inhibitors.

In one embodiment, disclosed are compounds of formula (I):

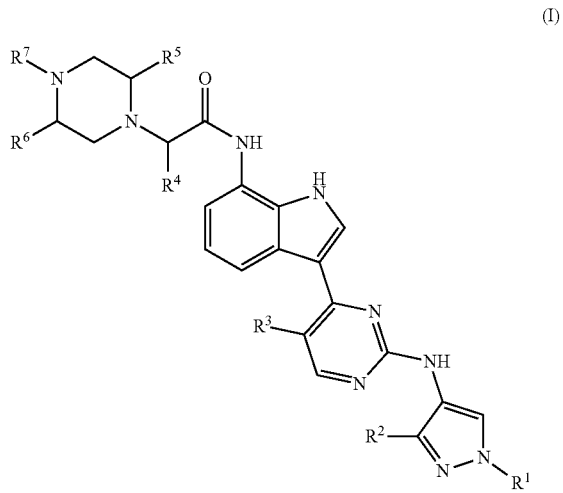

wherein
$R^1$ is methyl or ethyl;
$R^2$ is selected from methyl, ethyl, methoxy and ethoxy;
$R^3$ is selected from hydrogen, chlorine, fluorine, bromine and methyl;
$R^4$ is selected from methyl, ethyl and —$CH_2OCH_3$;
$R^5$ and $R^6$ are each individually methyl or hydrogen; and
$R^7$ is selected from methyl, ethyl, —$(CH_2)_2OH$ and —$(CH_2)_2OCH_3$, or a pharmaceutically acceptable salt thereof.

In one embodiment, disclosed are pharmaceutical compositions comprising a compound of Formula (I), or a pharmaceutically acceptable salt or solid form thereof, and a pharmaceutically acceptable diluent, excipient or carrier.

In another embodiment, disclosed are methods of treating a JAK-related disorder in a subject in need thereof comprising administering to the subject an effective amount of a compound of Formula (I), or a pharmaceutically acceptable salt or solid form thereof.

In another embodiment, disclosed is a compound of Formula (I), or a pharmaceutically acceptable salt or solid form thereof, for use in treating a JAK-related disorder.

In another embodiment, disclosed are pharmaceutical compositions comprising a compound of Formula (I), or a pharmaceutically acceptable salt or solid form thereof, for use in treating a JAK-related disorder.

In another embodiment, disclosed is the use of a compound of Formula (I), or a pharmaceutically acceptable salt or solid form thereof, in the manufacture of a medicament for treating a JAK-related disorder.

In another embodiment, disclosed are methods of treating cancer in a subject in need thereof comprising administering to the subject an effective amount of a compound as of Formula (I), or a pharmaceutically acceptable salt or solid form thereof, in combination with an anti-cancer therapeutic agent, or a pharmaceutically acceptable salt thereof.

In another embodiment, disclosed is a compound of Formula (I), or a pharmaceutically acceptable salt or solid form thereof, in combination with an anti-cancer therapeutic agent, or a pharmaceutically acceptable salt thereof, for use in treating cancer.

In another embodiment, disclosed are pharmaceutical compositions comprising a compound of Formula (I), or a pharmaceutically acceptable salt or solid form thereof, in combination with an anti-cancer therapeutic agent, or a pharmaceutically acceptable salt thereof, for use in treating cancer.

In another embodiment, disclosed is the use of a compound of Formula (I), or a pharmaceutically acceptable salt or solid form thereof, in combination with an anti-cancer therapeutic agent, or a pharmaceutically acceptable salt thereof, in the manufacture of a medicament for treating cancer.

In another embodiment, disclosed are methods of treating cancer cachexia in a subject in need thereof comprising administering to the subject an effective amount of a compound of Formula (I), or a pharmaceutically acceptable salt or solid form thereof.

In another embodiment, disclosed is a compound of Formula (I), or a pharmaceutically acceptable salt or solid form thereof, for use in treating cancer cachexia.

In another embodiment, disclosed are pharmaceutical compositions comprising a compound of Formula (I), or a pharmaceutically acceptable salt or solid form thereof, for use in treating cancer cachexia.

In another embodiment, disclosed is the use of a compound of Formula (I), or a pharmaceutically acceptable salt or solid form thereof, in the manufacture of a medicament for treating cancer cachexia.

In another embodiment, disclosed are methods of treating an immune disorder in a subject in need thereof comprising administering to the subject an effective amount of a compound of Formula (I), or a pharmaceutically acceptable salt or solid form thereof.

In another embodiment, disclosed is a compound of Formula (I), or a pharmaceutically acceptable salt or solid form thereof, for use in treating an immune disorder.

In another embodiment, disclosed are pharmaceutical compositions comprising a compound of Formula (I), or a pharmaceutically acceptable salt or solid form thereof, for use in treating an immune disorder.

In another embodiment, disclosed is the use of a compound of Formula (I), or a pharmaceutically acceptable salt or solid form thereof, in the manufacture of a medicament for treating an immune disorder.

In another embodiment, disclosed are methods of inhibiting JAK in a subject in need thereof comprising administering to the subject an effective amount of a compound of Formula (I), or a pharmaceutically acceptable salt or solid form thereof.

In another embodiment, disclosed is a compound of Formula (I), or a pharmaceutically acceptable salt or solid form thereof, for use in inhibiting JAK.

In another embodiment, disclosed are pharmaceutical compositions comprising a compound of Formula (I), or a pharmaceutically acceptable salt or solid form thereof, for use in inhibiting JAK.

In another embodiment, disclosed is the use of a compound of Formula (I), or a pharmaceutically acceptable salt or solid form thereof, in the manufacture of a medicament for inhibiting JAK.

BRIEF DESCRIPTION OF THE DRAWINGS

FIG. 31A illustrates tumor volume over time after continuous dosing with vehicle for 19 days (◆); 50 mg/kg BID Example 32 administered as a single agent for 19 days (▲); 2.5 mg/kg QD osimertinib administered as a single agent for 26 days (▬); 2.5 mg/kg QD osimertinib administered in combination with 12.5 mg/kg BID Example 32 dosed for 26 days (☆) and 2.5 mg/kg QD osimertinib administered in combination with 50 mg/kg BID Example 32 dosed for 26 days (▽). FIG. 31B illustrates tumor volume over time after dosing with vehicle (◆) for 19 days; 50 mg/kg BID Example 32 administered as a single agent for 19 days (▲); 2.5 mg/kg QD osimertinib administered as a single agent for 26 days (▬); 2.5 mg/kg QD osimertinib administered for 26 days in combination with 25 mg/kg BID Example 32 dosed for 7 days (△); and 2.5 mg/kg QD osimertinib administered for 26 days in combination with 50 mg/kg BID Example 32 dosed for 7 days (▽). FIG. 31C illustrates tumor volume over time after dosing with vehicle for 19 days (◆); 50 mg/kg BID Example 32 as a single agent for 19 days (▲); 2.5 mg/kg QD osimertinib administered as a single agent for 26 days (▬) 2.5 mg/kg QD osimertinib administered for 29 days in combination with 25 mg/kg BID Example 32 dosed 7 days on/7 days off/2 wk (△); and 2.5 mg/kg QD osimertinib administered for 29 days in combination with 50 mg/kg BID Example 32 dosed 7 days on/7 days off/2 wk (▽). FIG. 31D illustrates tumor volume over time after dosing with vehicle for 19 days (◆); 50 mg/kg BID Example 32 administered as a single agent for 19 days (▲); 2.5 mg/kg QD osimertinib administered as a single agent for 26 days (▬); 2.5 mg/kg QD osimertinib administered for 29 days in combination with 25 mg/kg BID Example 32 dosed 4 days on/3 days off/wk (△); and 2.5 mg/kg QD osimertinib administered for 29 days in combination with 50 mg/kg BID Example 32 dosed for 4 days on/3 days off/wk (▽). FIG. 31E illustrates tumor volume over time after dosing with vehicle for 19 days (◆); 50 mg/kg BID Example 32 for 19 days (▲); 2.5 mg/kg QD osimertinib dosed for 26 days (▬); 2.5 mg/kg QD osimertinib dosed for 29 days in combination with 25 mg/kg BID Example 32 dosed for 2 days on/5 days off/wk (△); and 2.5 mg/kg QD osimertinib dosed for 29 days in combination with 50 mg/kg BID Example 32 dosed 2 days on/5 days off/wk (▽).

DETAILED DESCRIPTION

Compounds

Figure 1:
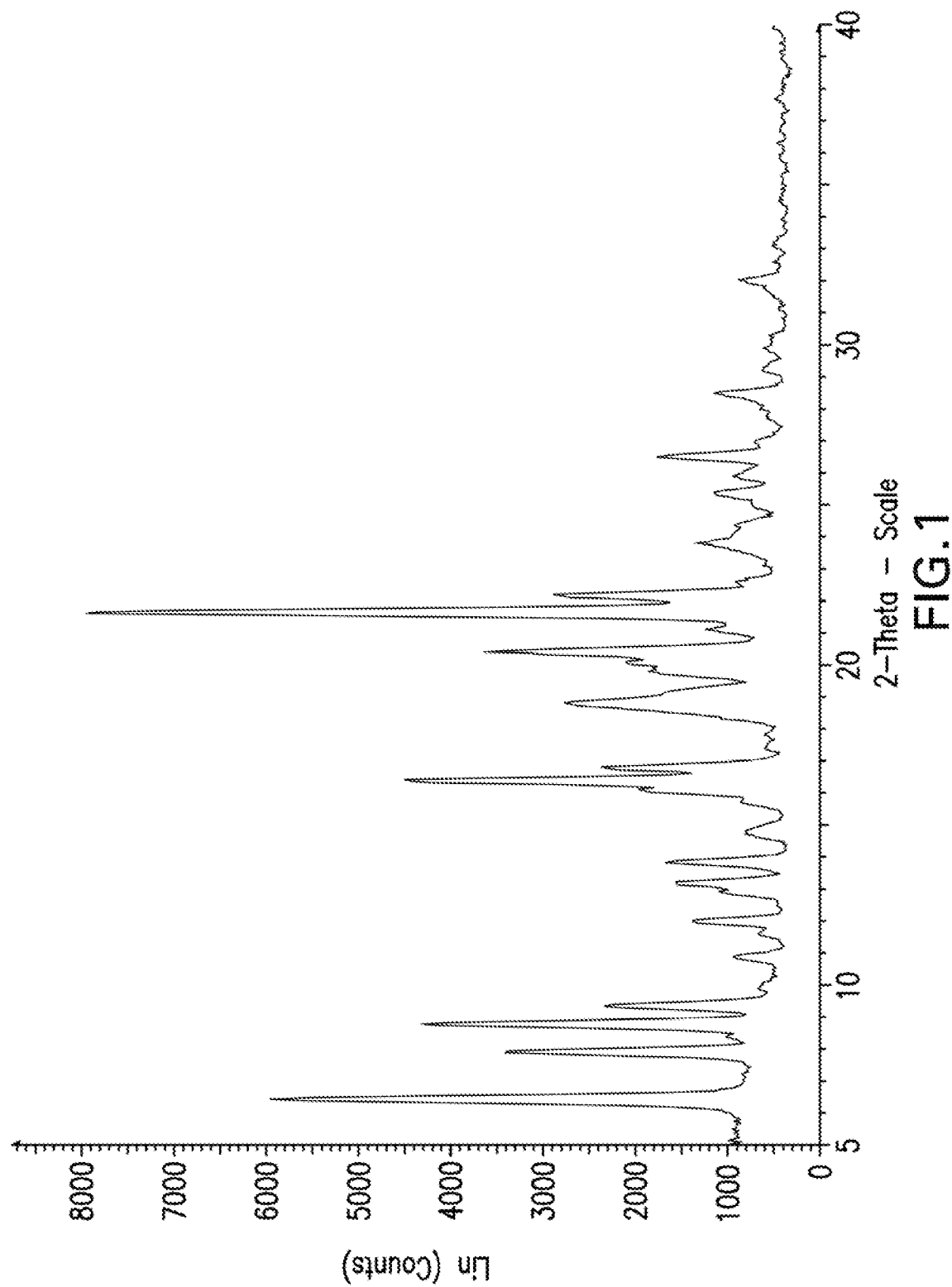
FIG. 1 illustrates the powder X-ray diffraction diagram of Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In one embodiment, disclosed are compounds of formula (I):

(I)

[Chemical structure of Formula (I) showing a piperazine ring with R⁵, R⁶, R⁷ substituents connected via CH(R⁴) to a carbonyl amide linked to an indole, which is connected to a pyrimidine bearing R³ and NH-pyrazole with R², R¹.]

wherein
$R^1$ is methyl or ethyl;
$R^2$ is selected from methyl, ethyl, methoxy and ethoxy;
$R^3$ is selected from hydrogen, chlorine, fluorine, bromine and methyl;
$R^4$ is selected from methyl, ethyl and —CH$_2$OCH$_3$;
$R^5$ and $R^6$ are each individually methyl or hydrogen; and
$R^7$ is selected from methyl, ethyl, —(CH$_2$)$_2$OH and —(CH$_2$)$_2$OCH$_3$, or a pharmaceutically acceptable salt thereof.

In some embodiments, $R^1$ is methyl; $R^2$ is methoxy, ethoxy, methyl or ethyl; $R^3$ is hydrogen, fluorine methyl, chlorine or bromine; $R^4$ is methyl, ethyl or —CH$_2$OCH$_3$; $R^5$ is hydrogen or methyl; $R^6$ is hydrogen or methyl; and $R^7$ is methyl, —(CH$_2$)$_2$OCH$_3$, ethyl or —(CH$_2$)$_2$OH.

In some embodiments, $R^1$ is ethyl; $R^2$ is methoxy or ethoxy; $R^3$ is methyl; $R^4$ is methyl; $R^5$ is hydrogen; $R^6$ is hydrogen and $R^7$ is methyl.

In some embodiments, $R^2$ is methoxy; $R^1$ is methyl or ethyl; $R^3$ is hydrogen, fluorine, methyl, chlorine or bromine; $R^4$ is methyl, ethyl or —CH$_2$OCH$_3$; $R^5$ is hydrogen or methyl; $R^6$ is hydrogen or methyl; and $R^7$ is methyl, ethyl, —(CH$_2$)$_2$OCH$_3$ or —(CH$_2$)$_2$OH.

In some embodiments, $R^2$ is ethoxy; $R^1$ is methyl or ethyl; $R^3$ is fluorine, methyl or chlorine; $R^4$ is methyl, ethyl or —CH$_2$OCH$_3$; $R^5$ is methyl or hydrogen; $R^6$ is methyl or hydrogen; and $R^7$ is ethyl, methyl or —(CH$_2$)$_2$OCH$_3$.

In some embodiments, $R^2$ is methyl; $R^1$ is methyl; $R^3$ is hydrogen, methyl or fluorine; $R^4$ is methyl, ethyl or —CH$_2$OCH$_3$; $R^5$ is hydrogen; $R^6$ is hydrogen and $R^7$ is methyl.

In some embodiments, $R^2$ is ethyl; $R^1$ is methyl; $R^3$ is methyl; $R^4$ is methyl; $R^5$ is hydrogen; $R^6$ is hydrogen and $R^7$ is methyl.

In some embodiments, $R^3$ is hydrogen; $R^1$ is methyl; $R^2$ is methoxy or methyl; $R^4$ is methyl, ethyl or —CH$_2$OCH$_3$; $R^5$ is methyl or hydrogen; $R^6$ is hydrogen or methyl and $R^7$ is methyl, —(CH$_2$)$_2$OCH$_3$ or ethyl.

In some embodiments, $R^3$ is fluorine; $R^1$ is methyl; $R^2$ is methoxy or ethoxy; $R^4$ is methyl, ethyl or —CH$_2$OCH$_3$; $R^5$ is hydrogen or methyl; $R^6$ is hydrogen or methyl and $R^7$ is methyl, ethyl or —(CH$_2$)$_2$OCH$_3$.

In some embodiments, $R^3$ is methyl; $R^1$ is methyl or ethyl; $R^2$ is methoxy, ethoxy, methyl or ethyl; $R^4$ is methyl, ethyl or —CH$_2$OCH$_3$; $R^5$ is hydrogen or methyl; $R^6$ is hydrogen or methyl and $R^7$ is methyl, ethyl, —(CH$_2$)$_2$OCH$_3$ or —(CH$_2$)$_2$OH.

In some embodiments, $R^3$ is chlorine; $R^1$ is methyl; $R^2$ is methoxy or ethoxy; $R^4$ is methyl; $R^5$ is hydrogen; $R^6$ is hydrogen and $R^7$ is methyl.

In some embodiments, $R^3$ is bromine; $R^1$ is methyl; $R^2$ is methoxy; $R^4$ is methyl; $R^5$ is hydrogen; $R^6$ is hydrogen and $R^7$ is methyl.

In some embodiments, $R^4$ is methyl; $R^1$ is methyl or ethyl; $R^2$ is methoxy, ethoxy, methyl or ethyl; $R^3$ is hydrogen, fluorine, methyl, chlorine or bromine; $R^5$ is hydrogen or methyl; $R^6$ is hydrogen or methyl and $R^7$ is methyl, ethyl, —(CH$_2$)$_2$OCH$_3$ or —(CH$_2$)$_2$OH.

In some embodiments, $R^4$ is ethyl; $R^1$ is methyl; $R^2$ is methoxy, methyl or ethoxy; $R^3$ is methyl, hydrogen or fluorine; $R^5$ is hydrogen; $R^6$ is hydrogen and $R^7$ is methyl.

In some embodiments, $R^4$ is —CH$_2$OCH$_3$; $R^1$ is methyl; $R^2$ is methoxy, methyl or ethoxy; $R^3$ is methyl, fluorine or hydrogen; $R^5$ is hydrogen; $R^6$ is hydrogen and $R^7$ is methyl.

In some embodiments, $R^5$ is hydrogen; $R^1$ is methyl or ethyl; $R^2$ is methoxy, ethoxy, methyl or ethyl; $R^3$ is hydrogen, fluorine, methyl, chlorine or bromine; $R^4$ is methyl, ethyl or —CH$_2$OCH$_3$; $R^6$ is hydrogen or methyl and $R^7$ is methyl, ethyl, —(CH$_2$)$_2$OCH$_3$ or —(CH$_2$)$_2$OH.

In some embodiments, $R^5$ is methyl; $R^1$ is methyl; $R^2$ is methoxy or ethoxy; $R^3$ is hydrogen, fluorine or methyl; $R^4$ is methyl; $R^6$ is hydrogen and $R^7$ is methyl.

In some embodiments, $R^6$ is hydrogen; $R^1$ is methyl or ethyl; $R^2$ is methoxy, ethoxy, methyl or ethyl; $R^3$ is hydrogen, fluorine, methyl, chlorine or bromine; $R^4$ is methyl, ethyl or —CH$_2$OCH$_3$; $R^5$ is hydrogen or methyl and $R^7$ is methyl, ethyl, —(CH$_2$)$_2$OCH$_3$ or —(CH$_2$)$_2$OH.

In some embodiments, $R^6$ is methyl; $R^1$ is methyl; $R^2$ is methoxy or ethoxy; $R^3$ is fluorine, methyl or hydrogen; $R^4$ is methyl; $R^5$ is hydrogen and $R^7$ is methyl.

In some embodiments, $R^7$ is methyl; $R^1$ is methyl or ethyl; $R^2$ is methyl, ethyl, methoxy or ethoxy; $R^3$ is hydrogen, chlorine, fluorine, bromine or methyl; $R^4$ is methyl, ethyl or —CH$_2$OCH$_3$; $R^5$ is hydrogen or methyl; and $R^{6-}$ is hydrogen or methyl.

In some embodiments, $R^7$ is ethyl; $R^1$ is methyl; $R^2$ is methoxy or ethoxy; $R^3$ is fluorine, methyl or hydrogen; $R^4$ is methyl; $R^5$ is hydrogen and $R^6$ is hydrogen.

In some embodiments, $R^7$ is —(CH$_2$)$_2$OCH$_3$; $R^1$ is methyl; $R^2$ is methoxy or ethoxy; $R^3$ is fluorine, methyl or hydrogen; $R^4$ is methyl; $R^5$ is hydrogen and $R^6$ is hydrogen.

In some embodiments, $R^7$ is —(CH$_2$)$_2$OH; $R^1$ is methyl, $R^2$ is methoxy; $R^3$ is methyl; $R^4$ is methyl; $R^5$ is hydrogen and $R^6$ is hydrogen.

In some embodiments, $R^1$ is methyl; $R^2$ is methoxy; $R^3$ is hydrogen; $R^4$ is methyl; $R^5$ is methyl; $R^6$ is hydrogen and $R^7$ is methyl.

In some embodiments, $R^1$ is methyl; $R^2$ is methoxy; $R^3$ is fluorine; $R^4$ is methyl; $R^5$ is hydrogen; $R^6$ is methyl and $R^7$ is methyl.

In some embodiments, $R^1$ is methyl; $R^2$ is methoxy; $R^3$ is fluorine; $R^4$ is methyl; $R^5$ is hydrogen; $R^6$ is hydrogen and $R^7$ is —(CH$_2$)$_2$OCH$_3$.

In some embodiments, $R^1$ is methyl; $R^2$ is methoxy; $R^3$ is fluorine; $R^4$ is methyl; $R^5$ is hydrogen; $R^6$ is hydrogen and $R^7$ is ethyl.

In some embodiments, $R^1$ is methyl; $R^2$ is methoxy; $R^3$ is fluorine; $R^4$ is methyl; $R^5$ is methyl; $R^6$ is hydrogen and $R^7$ is methyl.

In some embodiments, $R^1$ is methyl; $R^2$ is ethoxy; $R^3$ is fluorine; $R^4$ is methyl; $R^5$ is hydrogen; $R^6$ is hydrogen and $R^7$ is ethyl.

In some embodiments, $R^1$ is methyl; $R^2$ is ethoxy; $R^3$ is fluorine; $R^4$ is methyl; $R^5$ is hydrogen; $R^6$ is hydrogen and $R^7$ is —(CH$_2$)$_2$OCH$_3$.

In some embodiments, $R^1$ is methyl; $R^2$ is ethoxy; $R^3$ is fluorine; $R^4$ is methyl; $R^5$ is methyl; $R^6$ is hydrogen and $R^7$ is methyl.

In some embodiments, $R^1$ is methyl; $R^2$ is ethoxy; $R^3$ is fluorine; $R^4$ is methyl; $R^5$ is hydrogen; $R^6$ is methyl and $R^7$ is methyl.

In some embodiments, $R^1$ is methyl; $R^2$ is ethoxy; $R^3$ is fluorine; $R^4$ is methyl; $R^5$ is methyl; $R^6$ is hydrogen and $R^7$ is methyl.

In some embodiments, $R^1$ is methyl; $R^2$ is methoxy; $R^3$ is methyl; $R^4$ is methyl; $R^5$ is hydrogen; $R^6$ is methyl and $R^7$ is methyl.

In some embodiments, $R^1$ is methyl; $R^2$ is methoxy; $R^3$ is methyl; $R^4$ is methyl; $R^5$ is hydrogen; $R^6$ is hydrogen and $R^7$ is —(CH$_2$)$_2$OH.

In some embodiments, $R^1$ is methyl; $R^2$ is methoxy; $R^3$ is methyl; $R^4$ is methyl; $R^5$ is hydrogen; $R^6$ is hydrogen and $R^7$ is ethyl.

In some embodiments, $R^1$ is methyl; $R^2$ is methoxy; $R^3$ is methyl; $R^4$ is methyl; $R^5$ is hydrogen; $R^6$ is hydrogen and $R^7$ is —(CH$_2$)$_2$OCH$_3$.

In some embodiments, $R^1$ is methyl; $R^2$ is methoxy; $R^3$ is methyl; $R^4$ is methyl; $R^5$ is methyl; $R^6$ is hydrogen and $R^7$ is methyl.

In some embodiments, $R^1$ is methyl; $R^2$ is ethoxy; $R^3$ is methyl; $R^4$ is methyl; $R^5$ is hydrogen; $R^6$ is hydrogen and $R^7$ is ethyl.

In some embodiments, $R^1$ is methyl; $R^2$ is ethoxy; $R^3$ is methyl; $R^4$ is methyl; $R^5$ is hydrogen; $R^6$ is hydrogen and $R^7$ is —(CH$_2$)$_2$OCH$_3$.

In some embodiments, $R^1$ is methyl; $R^2$ is ethoxy; $R^3$ is methyl; $R^4$ is methyl; $R^5$ is methyl; $R^6$ is hydrogen and $R^7$ is methyl.

In some embodiments, $R^1$ is methyl; $R^2$ is ethoxy; $R^3$ is methyl; $R^4$ is methyl; $R^5$ is hydrogen; $R^6$ is methyl and $R^7$ is methyl.

In some embodiments, $R^1$ is methyl; $R^2$ is methoxy; $R^3$ is fluorine; $R^4$ is methyl; $R^5$ is hydrogen; $R^6$ is hydrogen and $R^7$ is methyl.

In some embodiments, $R^1$ is methyl; $R^2$ is methoxy; $R^3$ is hydrogen; $R^4$ is methyl; $R^5$ is hydrogen; $R^6$ is methyl and $R^7$ is methyl.

In some embodiments, $R^1$ is methyl; $R^2$ is methoxy; $R^3$ is hydrogen; $R^4$ is methyl; $R^5$ is hydrogen; $R^6$ is hydrogen and $R^7$ is —(CH$_2$)$_2$OCH$_3$.

In some embodiments, $R^1$ is methyl; $R^2$ is methoxy; $R^3$ is hydrogen; $R^4$ is methyl; $R^5$ is hydrogen; $R^6$ is hydrogen and $R^7$ is ethyl.

In some embodiments, $R^1$ is methyl; $R^2$ is methoxy; $R^3$ is hydrogen; $R^4$ is methyl; $R^5$ is methyl; $R^6$ is hydrogen and $R^7$ is methyl.

In some embodiments, $R^1$ is methyl; $R^2$ is methoxy; $R^3$ is hydrogen; $R^4$ is methyl; $R^5$ is hydrogen; $R^6$ is methyl and $R^7$ is methyl.

In some embodiments, $R^1$ is methyl; $R^2$ is ethoxy; $R^3$ is methyl; $R^4$ is methyl; $R^5$ is hydrogen; $R^6$ is methyl and $R^7$ is methyl.

In some embodiments, $R^1$ is methyl; $R^2$ is methoxy; $R^3$ is hydrogen; $R^4$ is methyl; $R^5$ is hydrogen; $R^6$ is hydrogen and $R^7$ is methyl.

In some embodiments, $R^1$ is methyl; $R^2$ is methoxy; $R^3$ is methyl; $R^4$ is methyl; $R^5$ is hydrogen; $R^6$ is hydrogen and $R^7$ is methyl.

In some embodiments, $R^1$ is methyl; $R^2$ is ethoxy; $R^3$ is methyl; $R^4$ is methyl; $R^5$ is hydrogen; $R^6$ is hydrogen and $R^7$ is methyl.

In some embodiments, $R^1$ is methyl; $R^2$ is methoxy; $R^3$ is chlorine; $R^4$ is methyl; $R^5$ is hydrogen; $R^6$ is hydrogen and $R^7$ is methyl.

In some embodiments, $R^1$ is methyl; $R^2$ is methoxy; $R^3$ is bromine; $R^4$ is methyl; $R^5$ is hydrogen; $R^6$ is hydrogen and $R^7$ is methyl.

In some embodiments, $R^1$ is methyl; $R^2$ is ethoxy; $R^3$ is fluorine; $R^4$ is methyl; $R^5$ is hydrogen; $R^6$ is hydrogen and $R^7$ is methyl.

In some embodiments, $R^1$ is methyl; $R^2$ is ethoxy; $R^3$ is chlorine; $R^4$ is methyl; $R^5$ is hydrogen; $R^6$ is hydrogen and $R^7$ is methyl.

In some embodiments, $R^1$ is methyl; $R^2$ is methyl; $R^3$ is hydrogen; $R^4$ is methyl; $R^5$ is hydrogen; $R^6$ is hydrogen and $R^7$ is methyl.

In some embodiments, $R^1$ is methyl; $R^2$ is methoxy; $R^3$ is methyl; $R^4$ is ethyl; $R^5$ is hydrogen; $R^6$ is hydrogen and $R^7$ is methyl.

In some embodiments, $R^1$ is methyl; $R^2$ is methoxy; $R^3$ is methyl; $R^4$ is —CH$_2$OCH$_3$; $R^5$ is hydrogen; $R^6$ is hydrogen and $R^7$ is methyl.

In some embodiments, $R^1$ is methyl; $R^2$ is methoxy; $R^3$ is hydrogen; $R^4$ is ethyl; $R^5$ is hydrogen; $R^6$ is hydrogen and $R^7$ is methyl.

In some embodiments, $R^1$ is methyl; $R^2$ is methyl; $R^3$ is fluorine; $R^4$ is ethyl; $R^5$ is hydrogen; $R^6$ is hydrogen and $R^7$ is methyl.

In some embodiments, $R^1$ is methyl; $R^2$ is methoxy; $R^3$ is fluorine; $R^4$ is ethyl; $R^5$ is hydrogen; $R^6$ is hydrogen and $R^7$ is methyl.

In some embodiments, $R^1$ is methyl; $R^2$ is methyl; $R^3$ is fluorine; $R^4$ is —CH$_2$OCH$_3$; $R^5$ is hydrogen; $R^6$ is hydrogen and $R^7$ is methyl.

In some embodiments, $R^1$ is methyl; $R^2$ is ethyl; $R^3$ is methyl; $R^4$ is methyl; $R^5$ is hydrogen; $R^6$ is hydrogen and $R^7$ is methyl.

In some embodiments, $R^1$ is methyl; $R^2$ is methyl; $R^3$ is fluorine; $R^4$ is methyl; $R^5$ is hydrogen; $R^6$ is hydrogen and $R^7$ is methyl.

In some embodiments, $R^1$ is methyl; $R^2$ is methyl; $R^3$ is hydrogen; $R^4$ is methyl; $R^5$ is hydrogen; $R^6$ is hydrogen and $R^7$ is methyl.

In some embodiments, $R^1$ is ethyl; $R^2$ is methoxy; $R^3$ is methyl; $R^4$ is methyl; $R^5$ is hydrogen; $R^6$ is hydrogen and $R^7$ is methyl.

In some embodiments, $R^1$ is ethyl; $R^2$ is ethoxy; $R^3$ is methyl; $R^4$ is methyl; $R^5$ is hydrogen; $R^6$ is hydrogen and $R^7$ is methyl.

In some embodiments, $R^1$ is methyl; $R^2$ is methoxy; $R^3$ is hydrogen; $R^4$ is —CH$_2$OCH$_3$; $R^5$ is hydrogen; $R^6$ is hydrogen and $R^7$ is methyl.

In some embodiments, $R^1$ is methyl; $R^2$ is ethoxy; $R^3$ is methyl; $R^4$ is ethyl; $R^5$ is hydrogen; $R^6$ is hydrogen and $R^7$ is methyl.

In some embodiments, $R^1$ is methyl; $R^2$ is ethoxy; $R^3$ is methyl; $R^4$ is —CH$_2$OCH$_3$; $R^5$ is hydrogen; $R^6$ is hydrogen and $R^7$ is methyl.

In one embodiment, the compounds of formula (I) are compounds of formula (Ia):

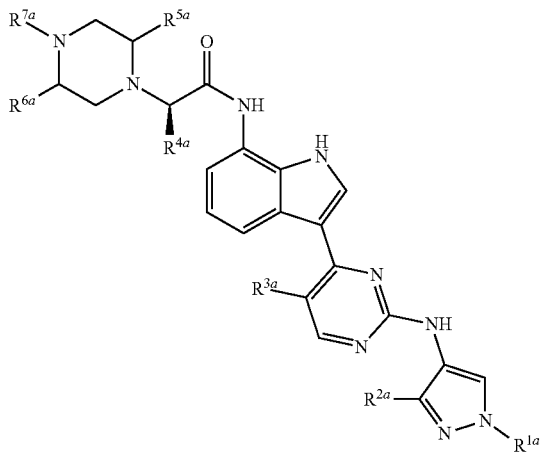

(Ia)

wherein
$R^{1a}$ is methyl or ethyl;
$R^{2a}$ is selected from methyl, ethyl, methoxy and ethoxy;
$R^{3a}$ is selected from hydrogen, chlorine, fluorine, bromine and methyl;
$R^{4a}$ is selected from methyl, ethyl and —CH$_2$OCH$_3$;
$R^{5a}$ and $R^{6a}$ are each individually methyl or hydrogen; and
$R^{7a}$ is selected from methyl, ethyl, —(CH$_2$)$_2$OH and —(CH$_2$)$_2$OCH$_3$, or a pharmaceutically acceptable salt thereof.

In some embodiments, $R^{1a}$ is methyl; $R^{2a}$ is methoxy, ethoxy, methyl or ethyl; $R^{3a}$ is hydrogen, fluorine methyl, chlorine or bromine; $R^{4a}$ is methyl, ethyl or —CH$_2$OCH$_3$; $R^{5a}$ is hydrogen or methyl; $R^{6a}$ is hydrogen or methyl; and $R^{7a}$ is methyl, —(CH$_2$)$_2$OCH$_3$, ethyl or —(CH$_2$)$_2$OH.

In some embodiments, $R^{1a}$ is ethyl; $R^{2a}$ is methoxy or ethoxy; $R^{3a}$ is methyl; $R^{4a}$ is methyl; $R^{5a}$ is hydrogen; $R^{6a}$ is hydrogen and $R^{7a}$ is methyl.

In some embodiments, $R^{2a}$ is methoxy; $R^{1a}$ is methyl or ethyl; $R^{3a}$ is hydrogen, fluorine, methyl, chlorine or bromine; $R^{4a}$ is methyl, ethyl or —CH$_2$OCH$_3$; $R^{5a}$ is hydrogen or methyl; $R^{6a}$ is hydrogen or methyl; and $R^{7a}$ is methyl, ethyl, —(CH$_2$)$_2$OCH$_3$ or —(CH$_2$)$_2$OH.

In some embodiments, $R^{2a}$ is ethoxy; $R^{1a}$ is methyl or ethyl; $R^{3a}$ is fluorine, methyl or chlorine; $R^{4a}$ is methyl, ethyl or —CH$_2$OCH$_3$; $R^{5a}$ is methyl or hydrogen; $R^{6a}$ is methyl or hydrogen; and $R^{7a}$ is ethyl, methyl or —(CH$_2$)$_2$OCH$_3$.

In some embodiments, $R^{2a}$ is methyl; $R^{1a}$ is methyl; $R^{3a}$ is hydrogen, methyl or fluorine; $R^{4a}$ is methyl, ethyl or —CH$_2$OCH$_3$; $R^{5a}$ is hydrogen; $R^{6a}$ is hydrogen and $R^{7a}$ is methyl.

In some embodiments, $R^{2a}$ is ethyl; $R^{1a}$ is methyl; $R^{3a}$ is methyl; $R^{4a}$ is methyl; $R^{5a}$ is hydrogen; $R^{6a}$ is hydrogen and $R^{7a}$ is methyl.

In some embodiments, $R^{6a}$ is hydrogen; $R^{1a}$ is methyl; $R^{2a}$ is methoxy or methyl; $R^{4a}$ is methyl, ethyl or —CH$_2$OCH$_3$; $R^{5a}$ is methyl or hydrogen; $R^{6a}$ is hydrogen or methyl and $R^{7a}$ is methyl, —(CH$_2$)$_2$OCH$_3$ or ethyl.

In some embodiments, $R^{3a}$ is fluorine; $R^{1a}$ is methyl; $R^{2a}$ is methoxy or ethoxy; $R^{4a}$ is methyl, ethyl or —CH$_2$OCH$_3$; $R^{6a}$ is hydrogen or methyl; $R^{6a}$ is hydrogen or methyl and $R^{7a}$ is methyl, ethyl or —(CH$_2$)$_2$OCH$_3$.

In some embodiments, $R^{3a}$ is methyl; $R^{1a}$ is methyl or ethyl; $R^{2a}$ is methoxy, ethoxy, methyl or ethyl; $R^{4a}$ is methyl, ethyl or —CH$_2$OCH$_3$; $R^{5a}$ is hydrogen or methyl; $R^{6a}$ is hydrogen or methyl and $R^{7a}$ is methyl, ethyl, —(CH$_2$)$_2$OCH$_3$ or —(CH$_2$)$_2$OH.

In some embodiments, $R^{3a}$ is chlorine; $R^{1a}$ is methyl; $R^{2a}$ is methoxy or ethoxy; $R^{4a}$ is methyl; $R^{5a}$ is hydrogen; $R^{6a}$ is hydrogen and $R^{7a}$ is methyl.

In some embodiments, $R^{3a}$ is bromine; $R^{1a}$ is methyl; $R^{2a}$ is methoxy; $R^{4a}$ is methyl; $R^{5a}$ is hydrogen; $R^{6a}$ is hydrogen and $R^{7a}$ is methyl.

In some embodiments, $R^{4a}$ is methyl; $R^{1a}$ is methyl or ethyl; $R^{2a}$ is methoxy, ethoxy, methyl or ethyl; $R^{3a}$ is hydrogen, fluorine, methyl, chlorine or bromine; $R^{5a}$ is hydrogen or methyl; $R^{6a}$ is hydrogen or methyl and $R^{7a}$ is methyl, ethyl, —(CH$_2$)$_2$OCH$_3$ or —(CH$_2$)$_2$OH.

In some embodiments, $R^{4a}$ is ethyl; $R^{1a}$ is methyl; $R^{2a}$ is methoxy, methyl or ethoxy; $R^{3a}$ is methyl, hydrogen or fluorine; $R^{5a}$ is hydrogen; $R^{6a}$ is hydrogen and $R^{7a}$ is methyl.

In some embodiments, $R^{4a}$ is —CH$_2$OCH$_3$; $R^{1a}$ is methyl; $R^{2a}$ is methoxy, methyl or ethoxy; $R^{3a}$ is methyl, fluorine or hydrogen; $R^{5a}$ is hydrogen; $R^{6a}$ is hydrogen and $R^{7a}$ is methyl.

In some embodiments, $R^{5a}$ is hydrogen; $R^{1a}$ is methyl or ethyl; $R^{2a}$ is methoxy, ethoxy, methyl or ethyl; $R^{3a}$ is hydrogen, fluorine, methyl, chlorine or bromine; $R^{4a}$ is methyl, ethyl or —CH$_2$OCH$_3$; $R^{6a}$ is hydrogen or methyl and $R^{7a}$ is methyl, ethyl, —(CH$_2$)$_2$OCH$_3$ or —(CH$_2$)$_2$OH.

In some embodiments, $R^{5a}$ is methyl; $R^{1a}$ is methyl; $R^{2a}$ is methoxy or ethoxy; $R^{3a}$ is hydrogen, fluorine or methyl; $R^{4a}$ is methyl; $R^{6a}$ is hydrogen and $R^{7a}$ is methyl.

In some embodiments, $R^{6a}$ is hydrogen; $R^{1a}$ is methyl or ethyl; $R^{2a}$ is methoxy, ethoxy, methyl or ethyl; $R^{3a}$ is hydrogen, fluorine, methyl, chlorine or bromine; $R^{4a}$ is methyl, ethyl or —CH$_2$OCH$_3$; $R^{5s}$ is hydrogen or methyl and $R^{7a}$ is methyl, ethyl, —(CH$_2$)$_2$OCH$_3$ or —(CH$_2$)$_2$OH.

In some embodiments, $R^{6a}$ is methyl; $R^{1a}$ is methyl; $R^{2a}$ is methoxy or ethoxy; $R^{3a}$ is fluorine, methyl or hydrogen; $R^{4a}$ is methyl; $R^{5a}$ is hydrogen and $R^{7a}$ is methyl.

In some embodiments, $R^{7a}$ is methyl; $R^{1a}$ is methyl or ethyl; $R^{2a}$ is methyl, ethyl, methoxy or ethoxy; $R^{3a}$ is hydrogen, chlorine, fluorine, bromine or methyl; $R^{4a}$ is methyl, ethyl or —CH$_2$OCH$_3$; $R^{5a}$ is hydrogen or methyl; and $R^{6a}$ is hydrogen or methyl.

In some embodiments, $R^{7a}$ is ethyl; $R^{1a}$ is methyl; $R^{2a}$ is methoxy or ethoxy; $R^{3a}$ is fluorine, methyl or hydrogen; $R^{4a}$ is methyl; $R^{5a}$ is hydrogen and $R^{6a}$ is hydrogen.

In some embodiments, $R^{7a}$ is —(CH$_2$)$_2$OCH$_3$; $R^{1a}$ is methyl; $R^{2a}$ is methoxy or ethoxy; $R^{3a}$ is fluorine, methyl or hydrogen; $R^{4a}$ is methyl; $R^{5a}$ is hydrogen and $R^{6a}$ is hydrogen.

In some embodiments, $R^{7a}$ is —(CH$_2$)$_2$OH; $R^{1a}$ is methyl, $R^{2a}$ is methoxy; $R^{3a}$ is methyl; $R^{4a}$ is methyl; $R^{5a}$ is hydrogen and $R^{6a}$ is hydrogen.

In some embodiments, $R^{1a}$ is methyl; $R^{2a}$ is methoxy; $R^{3a}$ is hydrogen; $R^{4a}$ is methyl; $R^{5a}$ is methyl; $R^{6a}$ is hydrogen and $R^{7a}$ is methyl.

In some embodiments, $R^{1a}$ is methyl; $R^{2a}$ is methoxy; $R^{3a}$ is fluorine; $R^{4a}$ is methyl; $R^{5a}$ is hydrogen; $R^{6a}$ is methyl and $R^{7a}$ is methyl.

In some embodiments, $R^{1a}$ is methyl; $R^{2a}$ is methoxy; $R^{3a}$ is fluorine; $R^{4a}$ is methyl; $R^{5a}$ is hydrogen; $R^{6a}$ is hydrogen and $R^{7a}$ is —(CH$_2$)$_2$OCH$_3$.

In some embodiments, $R^{1a}$ is methyl; $R^{2a}$ is methoxy; $R^{3a}$ is fluorine; $R^{4a}$ is methyl; $R^{5a}$ is hydrogen; $R^{6a}$ is hydrogen and $R^{7a}$ is ethyl.

In some embodiments, $R^{1a}$ is methyl; $R^{2a}$ is methoxy; $R^{3a}$ is fluorine; $R^{4a}$ is methyl; $R^{5a}$ is methyl; $R^{6a}$ is hydrogen and $R^{7a}$ is methyl.

In some embodiments, $R^{1a}$ is methyl; $R^{2a}$ is ethoxy; $R^{3a}$ is fluorine; $R^{4a}$ is methyl; $R^{5a}$ is hydrogen; $R^{6a}$ is hydrogen and $R^{7a}$ is ethyl.

In some embodiments, $R^{1a}$ is methyl; $R^{2a}$ is ethoxy; $R^{3a}$ is fluorine; $R^{4a}$ is methyl; $R^{5a}$ is hydrogen; $R^{6a}$ is hydrogen and $R^{7a}$ is —$CH_2)_2OCH_3$.

In some embodiments, $R^{1a}$ is methyl; $R^{2a}$ is ethoxy; $R^{3a}$ is fluorine; $R^{4a}$ is methyl; $R^{5a}$ is methyl; $R^{6a}$ is hydrogen and $R^{7a}$ is methyl.

In some embodiments, $R^{1a}$ is methyl; $R^{2a}$ is ethoxy; $R^{3a}$ is fluorine; $R^{4a}$ is methyl; $R^{5a}$ is hydrogen; $R^{6a}$ is methyl and $R^{7a}$ is methyl.

In some embodiments, $R^{1a}$ is methyl; $R^{2a}$ is ethoxy; $R^{3a}$ is fluorine; $R^{4a}$ is methyl; $R^{5a}$ is methyl; $R^{6a}$ is hydrogen and $R^{7a}$ is methyl.

In some embodiments, $R^{1a}$ is methyl; $R^{2a}$ is methoxy; $R^{3a}$ is methyl; $R^{4a}$ is methyl; $R^{5a}$ is hydrogen; $R^{6a}$ is methyl and $R^{7a}$ is methyl.

In some embodiments, $R^{1a}$ is methyl; $R^{2a}$ is methoxy; $R^{3a}$ is methyl; $R^{4a}$ is methyl; $R^{5a}$ is hydrogen; $R^{6a}$ is hydrogen and $R^{7a}$ is —$(CH_2)_2OH$.

In some embodiments, $R^{1a}$ is methyl; $R^{2a}$ is methoxy; $R^{3a}$ is methyl; $R^{4a}$ is methyl; $R^{5a}$ is hydrogen; $R^{6a}$ is hydrogen and $R^{7a}$ is ethyl.

In some embodiments, $R^{1a}$ is methyl; $R^{2a}$ is methoxy; $R^{3a}$ is methyl; $R^{4a}$ is methyl; $R^{5a}$ is hydrogen; $R^{6a}$ is hydrogen and $R^{7a}$ is —$(CH_2)_2OCH_3$.

In some embodiments, $R^{1a}$ is methyl; $R^{2a}$ is methoxy; $R^{3a}$ is methyl; $R^{4a}$ is methyl; $R^{5a}$ is methyl; $R^{6a}$ is hydrogen and $R^{7a}$ is methyl.

In some embodiments, $R^{1a}$ is methyl; $R^{2a}$ is ethoxy; $R^{3a}$ is methyl; $R^{4a}$ is methyl; $R^{5a}$ is hydrogen; $R^{6a}$ is hydrogen and $R^{7a}$ is ethyl.

In some embodiments, $R^{1a}$ is methyl; $R^{2a}$ is ethoxy; $R^{3a}$ is methyl; $R^{4a}$ is methyl; $R^{5a}$ is hydrogen; $R^{6a}$ is hydrogen and $R^{7a}$ is —$(CH_2)_2OCH_3$.

In some embodiments, $R^{1a}$ is methyl; $R^{2a}$ is ethoxy; $R^{3a}$ is methyl; $R^{4a}$ is methyl; $R^{5a}$ is methyl; $R^{6a}$ is hydrogen and $R^{7a}$ is methyl.

In some embodiments, $R^{1a}$ is methyl; $R^{2a}$ is ethoxy; $R^{3a}$ is methyl; $R^{4a}$ is methyl; $R^{5a}$ is hydrogen; $R^{6a}$ is methyl and $R^{7a}$ is methyl.

In some embodiments, $R^{1a}$ is methyl; $R^{2a}$ is methoxy; $R^{3a}$ is fluorine; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is hydrogen; $R^{4a}$ is methyl; $R^{5a}$ is hydrogen; $R^{6a}$ is methyl and $R^{7a}$ is methyl.

In some embodiments, $R^{1a}$ is methyl; $R^{2a}$ is methoxy; $R^{3a}$ is hydrogen; $R^{4a}$ is methyl; $R^{5a}$ is hydrogen; $R^{6a}$ is hydrogen and $R^{7a}$ is —$(CH_2)_2OCH_3$.

In some embodiments, $R^{1a}$ is methyl; $R^{2a}$ is methoxy; $R^{3a}$ is hydrogen; $R^{4a}$ is methyl; $R^{5a}$ is hydrogen; $R^{6a}$ is hydrogen and $R^{7a}$ is ethyl.

In some embodiments, $R^{1a}$ is methyl; $R^{2a}$ is methoxy; $R^{3a}$ is hydrogen; $R^{4a}$ is methyl; $R^{5a}$ is methyl; $R^{6a}$ is hydrogen and $R^{7a}$ is methyl.

In some embodiments, $R^{1a}$ is methyl; $R^{2a}$ is methoxy; $R^{3a}$ is hydrogen; $R^{4a}$ is methyl; $R^{5a}$ is hydrogen; $R^{6a}$ is methyl and $R^{7a}$ is methyl.

In some embodiments, $R^{1a}$ is methyl; $R^{2a}$ is ethoxy; $R^{3a}$ is methyl; $R^{4a}$ is methyl; $R^{5a}$ is hydrogen; $R^{6a}$ is methyl and $R^{7a}$ is methyl.

In some embodiments, $R^{1a}$ is methyl; $R^{2a}$ is methoxy; $R^{3a}$ is hydrogen; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is methyl; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is ethoxy; $R^{3a}$ is methyl; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is chlorine; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is bromine; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is ethoxy; $R^{3a}$ is fluorine; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is ethoxy; $R^{3a}$ is chlorine; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methyl; $R^{3a}$ is hydrogen; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is methyl; $R^{4a}$ is ethyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is methyl; $R^{4a}$ is —$CH_2OCH_3$; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is hydrogen; $R^{4a}$ is ethyl; $R^{5a}$ is hydrogen; $R^{6a}$ is hydrogen and $R^{7a}$ is methyl.

In some embodiments, $R^{1a}$ is methyl; $R^{2a}$ is methyl; $R^{3a}$ is fluorine; $R^{4a}$ is ethyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is fluorine; $R^{4a}$ is ethyl; $R^{5a}$ is hydrogen; $R^{6a}$ is hydrogen and $R^{7a}$ is methyl.

In some embodiments, $R^{1a}$ is methyl; $R^{2a}$ is methyl; $R^{3a}$ is fluorine; $R^{4a}$ is —$CH_2OCH_3$; $R^{5a}$ is hydrogen; $R^{6a}$ is hydrogen and $R^{7a}$ is methyl.

In some embodiments, $R^{1a}$ is methyl; $R^{2a}$ is ethyl; $R^{3a}$ is methyl; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methyl; $R^{3a}$ is fluorine; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methyl; $R^{3a}$ is hydrogen; $R^{4a}$ is methyl; $R^{5a}$ is hydrogen; $R^{6a}$ is hydrogen and $R^{7a}$ is methyl.

In some embodiments, $R^{1a}$ is ethyl; $R^{2a}$ is methoxy; $R^{3a}$ is methyl; $R^{4a}$ is methyl; $R^{5a}$ is hydrogen; $R^{6a}$ is hydrogen and $R^{7a}$ is methyl.

In some embodiments, $R^{1a}$ is ethyl; $R^{2a}$ is ethoxy; $R^{3a}$ is methyl; $R^{4a}$ is methyl; $R^{5a}$ is hydrogen; $R^{6a}$ is hydrogen and $R^{7a}$ is methyl.

In some embodiments, $R^{1a}$ is methyl; $R^{2a}$ is methoxy; $R^{3a}$ is hydrogen; $R^{4a}$ is —$CH_2OCH_3$; $R^{5a}$ is hydrogen; $R^{6a}$ is hydrogen and $R^{7a}$ is methyl.

In some embodiments, $R^{1a}$ is methyl; $R^{2a}$ is ethoxy; $R^{3a}$ is methyl; $R^{4a}$ is ethyl; $R^{5a}$ is hydrogen; $R^{6a}$ is hydrogen and $R^{7a}$ is methyl.

In some embodiments, $R^{1a}$ is methyl; $R^{2a}$ is ethoxy; $R^{3a}$ is methyl; $R^{4a}$ is —$CH_2OCH_3$; $R^{5a}$ is hydrogen; $R^{6a}$ is hydrogen and $R^{7a}$ is methyl.

In one embodiment, the compounds of formula (I) are compounds of formula (Ib):

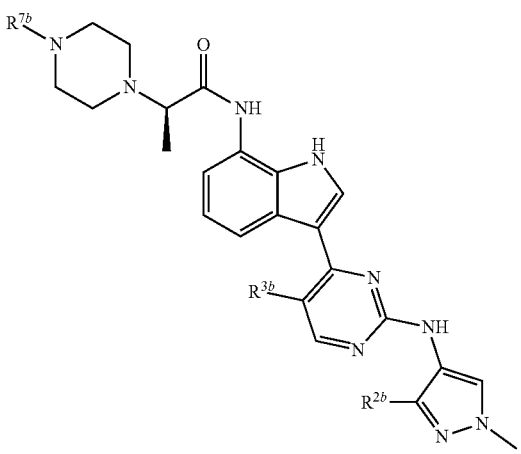

(Ib)

wherein

R$^{2b}$ is selected from methyl, ethyl, methoxy and ethoxy;

R$^{3b}$ is selected from hydrogen, chlorine, fluorine, bromine and methyl; and

R$^{7b}$ is selected from methyl, ethyl, —(CH$_2$)$_2$OH and —(CH$_2$)$_2$OCH$_3$, or a pharmaceutically acceptable salt thereof.

In some embodiments, R$^{2b}$ is methoxy; R$^{3b}$ is hydrogen, fluorine, methyl, chlorine or bromine; and R$^{7b}$ is methyl, ethyl, —(CH$_2$)$_2$OCH$_3$ or —(CH$_2$)$_2$OH.

In some embodiments, R$^{2b}$ is ethoxy; R$^{3b}$ is fluorine, methyl or chlorine; and R$^{7b}$ is ethyl, methyl or —(CH$_2$)$_2$OCH$_3$.

In some embodiments, R$^{2b}$ is methyl; R$^{3b}$ is hydrogen, methyl or fluorine; and R$^{7b}$ is methyl.

In some embodiments, R$^{2b}$ is ethyl; R$^{3b}$ is methyl; and R$^{7b}$ is methyl.

In some embodiments, R$^{3b}$ is hydrogen; R$^{2b}$ is methoxy or methyl; and R$^{7b}$ is methyl, —(CH$_2$)$_2$OCH$_3$ or ethyl.

In some embodiments, R$^{3b}$ is fluorine; R$^{2b}$ is methoxy or ethoxy; R$^{7b}$ is methyl, ethyl or —(CH$_2$)$_2$OCF$_3$.

In some embodiments, R$^{3b}$ is methyl; R$^{2b}$ is methoxy, ethoxy, methyl or ethyl; and R$^{7b}$ is methyl, ethyl, —(CH$_2$)$_2$OCH$_3$ or —(CH$_2$)$_2$OH.

In some embodiments, R$^{3b}$ is chlorine; R$^{2b}$ is methoxy or ethoxy; and R$^{7b}$ is methyl.

In some embodiments, R$^{3b}$ is bromine; R$^{2b}$ is methoxy; and R$^{7b}$ is methyl.

In some embodiments, R$^{7b}$ is methyl; R$^{2b}$ is methyl, ethyl, methoxy or ethoxy; and R$^{3b}$ is hydrogen, chlorine, fluorine, bromine or methyl.

In some embodiments, R$^{7b}$ is ethyl; R$^{2b}$ is methoxy or ethoxy; and R$^{3b}$ is fluorine, methyl or hydrogen.

In some embodiments, R$^{7b}$ is —(CH$_2$)$_2$OCH$_3$; R$^{2b}$ is methoxy or ethoxy; and R$^{3b}$ is fluorine, methyl or hydrogen.

In some embodiments, R$^{7b}$ is —(CH$_2$)$_2$OH; R$^{2b}$ is methoxy; and R$^{3a}$ is methyl.

In some embodiments, R$^{2b}$ is methoxy; R$^{3b}$ is fluorine; and R$^{7b}$ is —(CH$_2$)$_2$OCH$_3$.

In some embodiments, R$^{2b}$ is methoxy; R$^{3b}$ is fluorine; and R$^{7a}$ is ethyl.

In some embodiments, R$^{2b}$ is ethoxy; R$^{3b}$ is fluorine; and R$^{7a}$ is ethyl.

In some embodiments, R$^{2b}$ is ethoxy; R$^{3b}$ is fluorine; and R$^{7b}$ is —(CH$_2$)$_2$OCH$_3$.

In some embodiments, R$^{2b}$ is methoxy; R$^{3b}$ is methyl; and R$^{7b}$ is —(CH$_2$)$_2$OH.

In some embodiments, R$^{2b}$ is methoxy; R$^{3b}$ is methyl; and R$^{7b}$ is ethyl.

In some embodiments, R$^{2b}$ is methoxy; R$^{3b}$ is methyl; and R$^{7b}$ is —(CH$_2$)$_2$OCH$_3$.

In some embodiments, R$^{2b}$ is ethoxy; R$^{3b}$ is methyl; and R$^{7b}$ is ethyl. In some embodiments, R$^{2b}$ is ethoxy; R$^{3b}$ is methyl; and R$^{7b}$ is —(CH$_2$)$_2$OCH$_3$.

In some embodiments, R$^{2b}$ is methoxy; R$^{3b}$ is fluorine; and R$^{7b}$ is methyl.

In some embodiments, R$^{2b}$ is methoxy; R$^{3b}$ is hydrogen; and R$^{7b}$ is —(CH$_2$)$_2$OCH$_3$.

In some embodiments, R$^{2b}$ is methoxy; R$^{3b}$ is hydrogen; and R$^{7b}$ is ethyl.

In some embodiments, R$^{2b}$ is methoxy; R$^{3b}$ is hydrogen; and R$^{7b}$ is methyl.

In some embodiments, R$^{2b}$ is methoxy; R$^{3b}$ is methyl; and R$^{7b}$ is methyl.

In some embodiments, R$^{2b}$ is ethoxy; R$^{3b}$ is methyl; and R$^{7b}$ is methyl.

In some embodiments, R$^{2b}$ is methoxy; R$^{3b}$ is chlorine; and R$^{7b}$ is methyl.

In some embodiments, R$^{2b}$ is methoxy; R$^{3b}$ is bromine; and R$^{7b}$ is methyl.

In some embodiments, R$^{2b}$ is ethoxy; R$^{3b}$ is fluorine; and R$^{7b}$ is methyl.

In some embodiments, R$^{2b}$ is ethoxy; R$^{3b}$ is chlorine; and R$^{7b}$ is methyl.

In some embodiments, R$^{2b}$ is methyl; R$^{3b}$ is hydrogen; and R$^{7b}$ is methyl.

In some embodiments, R$^{2b}$ is ethyl; R$^{3b}$ is methyl; and R$^{7b}$ is methyl.

In some embodiments, R$^{2b}$ is methyl; R$^{3b}$ is fluorine; and R$^{7b}$ is methyl.

In some embodiments, R$^{2b}$ is methyl; R$^{3b}$ is hydrogen; and R$^{7b}$ is methyl.

In some embodiments, disclosed are the compounds of Table 1, or a pharmaceutically acceptable salt thereof:

TABLE 1

| Example No. | Chemical Structure | Name |
| --- | --- | --- |
| Example 1 | 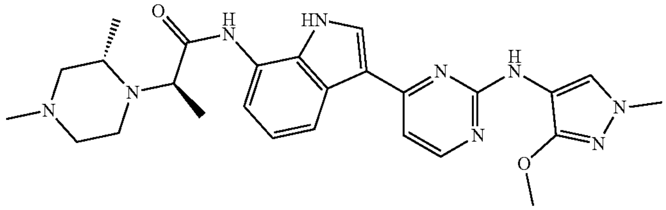 | (2R)-2-[(2S)-2,4-dimethylpiperazin-1-yl]-N-(3-{2-[(3-methoxy-1-methyl-1H-pyrazol-4-yl)amino]pyrimidin-4-yl}-1H-indol-7-yl)propanamide |

TABLE 1-continued

| Example No. | Chemical Structure | Name |
|---|---|---|
| Example 2 | 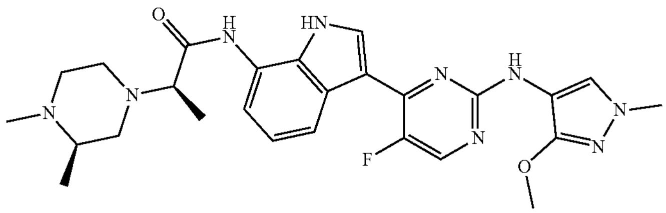 | (2R)-2-[(3R)-3,4-dimethylpiperazin-1-yl]-N-(3-{5-fluoro-2-[(3-methoxy-1-methyl-1H-pyrazol-4-yl)amino]pyrimidin-4-yl}-1H-indol-7-yl)propanamide |
| Example 3 | 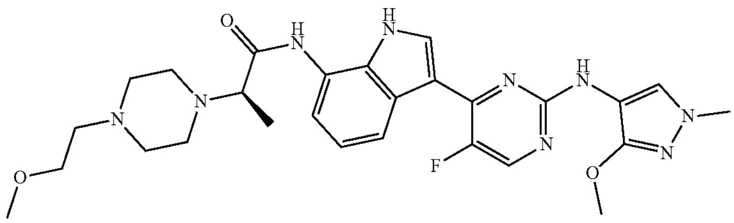 | (2R)-N-(3-{5-fluoro-2-[(3-methoxy-1-methyl-1H-pyrazol-4-yl)amino]pyrimidin-4-yl}-1H-indol-7-yl)-2-[4-(2-methoxyethyl)piperazin-1-yl]propanamide |
| Example 4 | 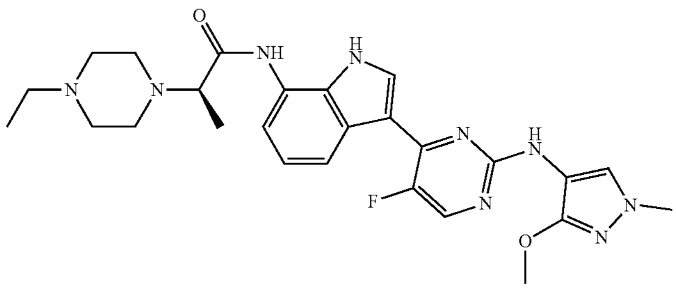 [SMILES: CCN1CCN([C@H](C)C(=O)Nc2cccc3c(-c4nc(Nc5cn(C)nc5OC)ncc4F)c[nH]c23)CC1] | (2R)-2-(4-ethylpiperazin-1-yl)-N-(3-{5-fluoro-2-[(3-methoxy-1-methyl-1H-pyrazol-4-yl)amino]pyrimidin-4-yl}-1H-indol-7-yl)propanamide |
| Example 5 | 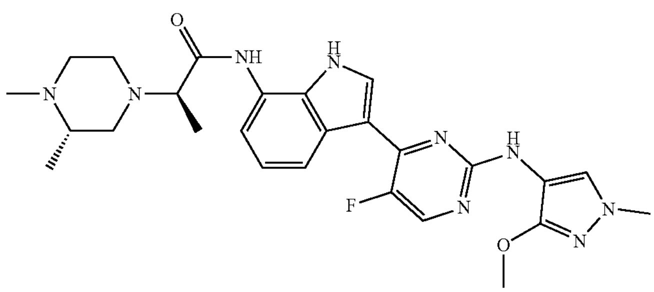 | (2R)-2-[(3S)-3,4-dimethylpiperazin-1-yl]-N-(3-{5-fluoro-2-[(3-methoxy-1-methyl-1H-pyrazol-4-yl)amino]pyrimidin-4-yl}-1H-indol-7-yl)propanamide |
| Example 6 | 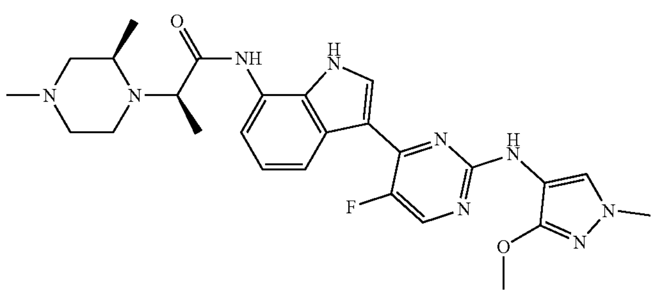 | (2R)-2-[(2R)-2,4-dimethylpiperazin-1-yl]-N-(3-{5-fluoro-2-[(3-methoxy-1-methyl-1H-pyrazol-4-yl)amino]pyrimidin-4-yl}-1H-indol-7-yl)propanamide |
| Example 7a | 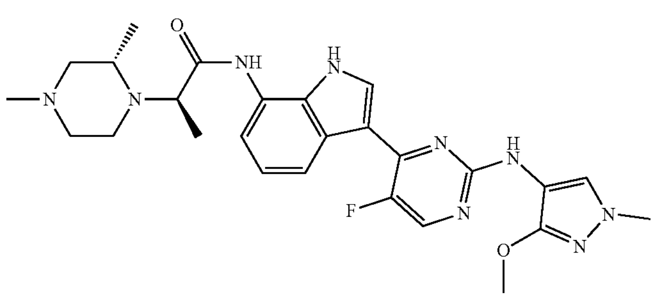 | (2R)-2-[(2S)-2,4-dimethylpiperazin-1-yl]-N-(3-{5-fluoro-2-[(3-methoxy-1-methyl-1H-pyrazol-4-yl)amino]pyrimidin-4-yl}-1H-indol-7-yl)propanamide |

TABLE 1-continued

| Example No. | Chemical Structure | Name |
|---|---|---|
| Example 7b | 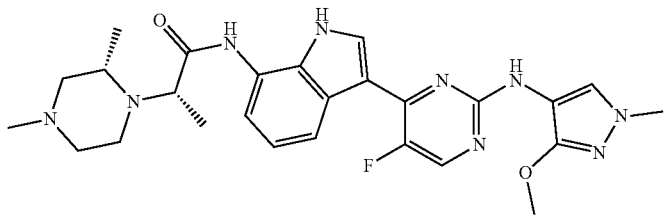 | (2S)-2-[(2S)-2,4-dimethylpiperazin-1-yl]-N-(3-{5-fluoro-2-[(3-methoxy-1-methyl-1H-pyrazol-4-yl)amino]pyrimidin-4-yl}-1H-indol-7-yl)propanamide |
| Example 8 | 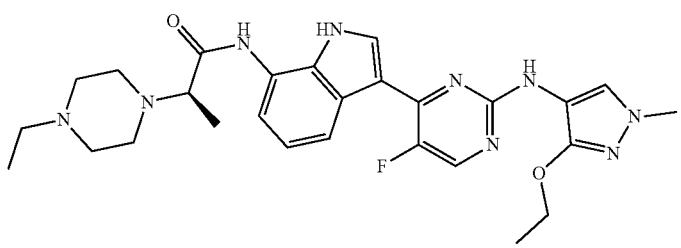 [SMILES: CCOc1nn(C)cc1Nc1ncc(F)c(-c2c[nH]c3c(NC(=O)[C@@H](C)N4CCN(CC)CC4)cccc23)n1] | (2R)-N-(3-{2-[(3-ethoxy-1-methyl-1H-pyrazol-4-yl)amino]-5-fluoropyrimidin-4-yl}-1H-indol-7-yl)-2-(4-ethylpiperazin-1-yl)propanamide |
| Example 9 | 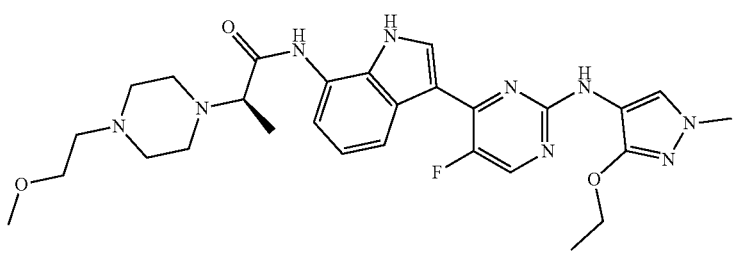 | (2R)-N-(3-{2-[(3-ethoxy-1-methyl-1H-pyrazol-4-yl)amino]-5-fluoropyrimidin-4-yl}-1H-indol-7-yl)-2-[4-(2-methoxyethyl)piperazin-1-yl]propanamide |
| Example 10a | 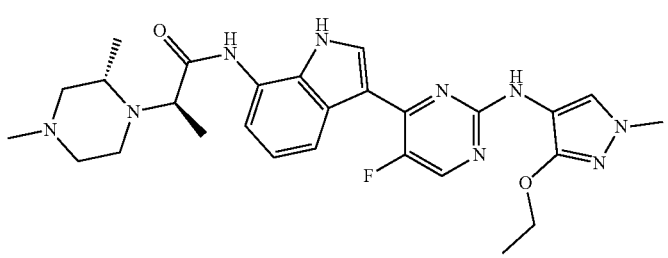 | (2R)-2-[(2S)-2,4-dimethylpiperazin-1-yl]-N-(3-{2-[(3-ethoxy-1-methyl-1H-pyrazol-4-yl)amino]-5-fluoropyrimidin-4-yl}-1H-indol-7-yl)propanamide |
| Example 10b | 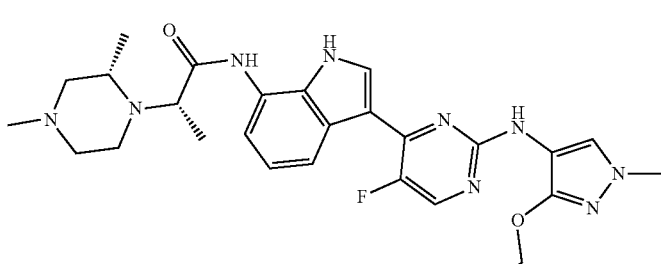 | (2S)-2-[(2S)-2,4-dimethylpiperazin-1-yl]-N-(3-{2-[(3-ethoxy-1-methyl-1H-pyrazol-4-yl)amino]-5-fluoropyrimidin-4-yl}-1H-indol-7-yl)propanamide |
| Example 11a | 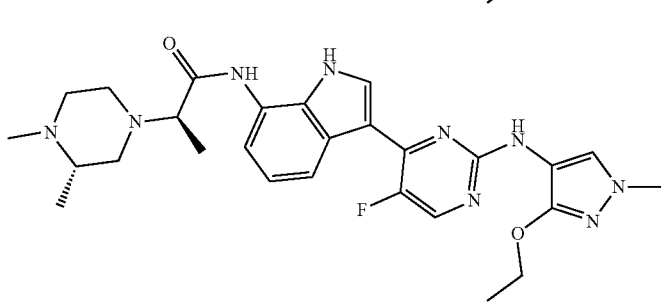 | (2R)-2-[(3S)-3,4-dimethylpiperazin-1-yl]-N-(3-{2-[(3-ethoxy-1-methyl-1H-pyrazol-4-yl)amino]-5-fluoropyrimidin-4-yl}-1H-indol-7-yl)propanamide |

TABLE 1-continued

| Example No. | Chemical Structure | Name |
|---|---|---|
| Example 11b | 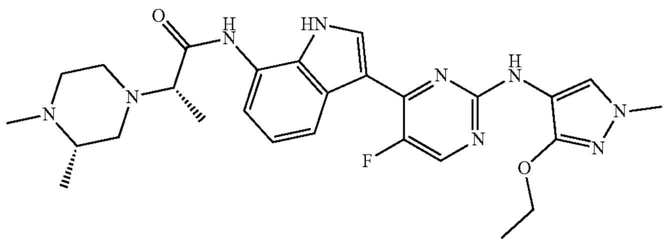 | (2S)-2-[(3S)-3,4-dimethylpiperazin-1-yl]-N-(3-{2-[(3-ethoxy-1-methyl-1H-pyrazol-4-yl)amino]-5-fluoropyrimidin-4-yl}-1H-indol-7-yl)propanamide |
| Example 12 | 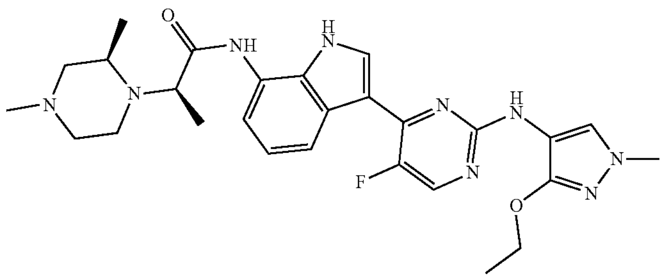 | (2R)-2-[(2R)-2,4-dimethylpiperazin-1-yl]-(3-{2-[(3-ethoxy-1-methyl-1H-pyrazol-4-yl)amino]-5-fluoropyrimidin-4-yl}-1H-indol-7-yl)propanamide |
| Example 13 | 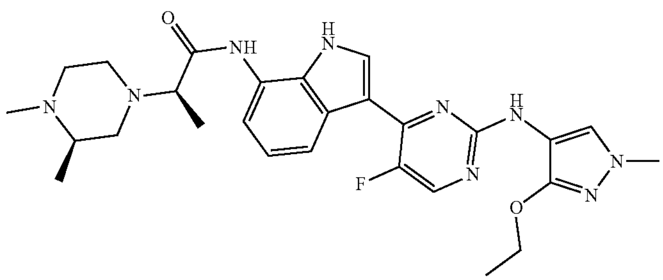 | (2R)-2-[(3R)-3,4-dimethylpiperazin-1-yl]-N-(3-{2-[(3-ethoxy-1-methyl-1H-pyrazol-4-yl)amino]-5-fluoropyrimidin-4-yl}-1H-indol-7-yl)propanamide |
| Example 14 | 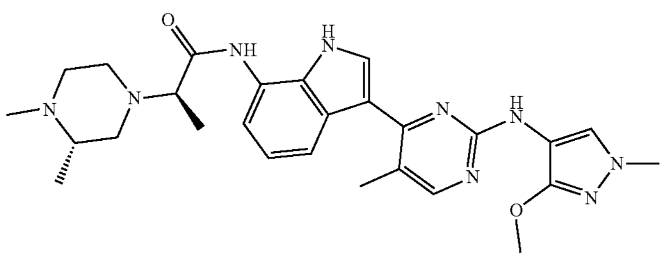 | (2R)-2-[(3S)-3,4-dimethylpiperazin-1-yl]-N-(3-{2-[(3-methoxy-1-methyl-1H-pyrazol-4-yl)amino]-5-methylpyrimidin-4-yl}-1H-indol-7-yl)propanamide |
| Example 15 | 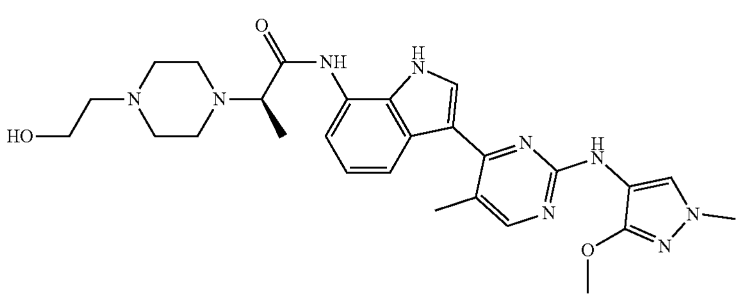 [SMILES: COc1nn(C)cc1Nc1ncc(C)c(-c2c[nH]c3c(NC(=O)[C@@H](C)N4CCN(CCO)CC4)cccc23)n1] | (2R)-2-[4-(2-hydroxyethyl)piperazin-1-yl]-N-(3-{2-[(3-methoxy-1-methyl-1H-pyrazol-4-yl)amino]-5-methylpyrimidin-4-yl}-1H-indol-7-yl)propanamide |
| Example 16 | 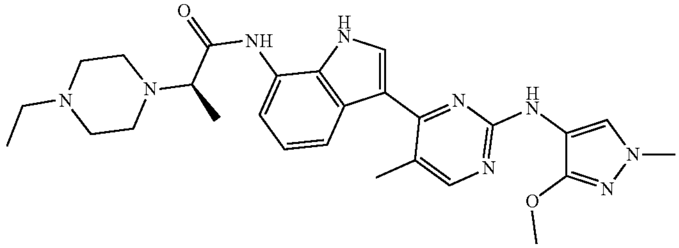 [SMILES: CCN1CCN([C@H](C)C(=O)Nc2cccc3c(-c4nc(Nc5cn(C)nc5OC)ncc4C)c[nH]c23)CC1] | (2R)-2-(4-ethylpiperazin-1-yl)-N-(3-{2-[(3-methoxy-1-methyl-1H-pyrazol-4-yl)amino]-5-methylpyrimidin-4-yl}-1H-indol-7-yl)propanamide |

TABLE 1-continued

| Example No. | Chemical Structure | Name |
|---|---|---|
| Example 17 | 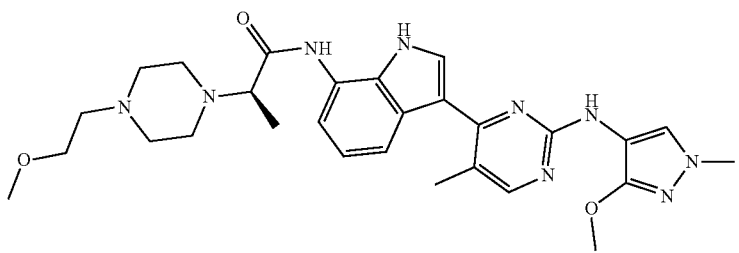 | (2R)-2-[4-(2-methoxyethyl)piperazin-1-yl]-N-(3-{2-[(3-methoxy-1-methyl-1H-pyrazol-4-yl)amino]-5-methylpyrimidin-4-yl}-1H-indol-7-yl)propanamide |
| Example 18 | 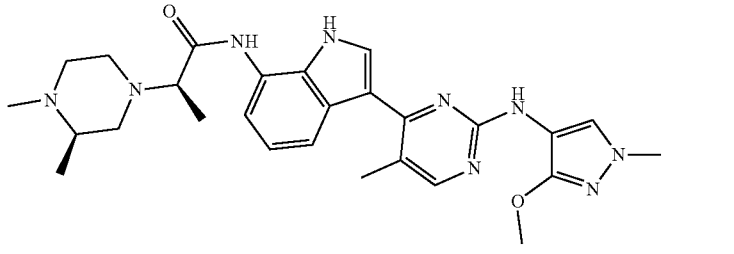 | (2R)-2-[(3R)-3,4-dimethylpiperazin-1-yl]-N-(3-{2-[(3-methoxy-1-methyl-1H-pyrazol-4-yl)amino]-5-methylpyrimidin-4-yl}-1H-indol-7-yl)propanamide |
| Example 19 | 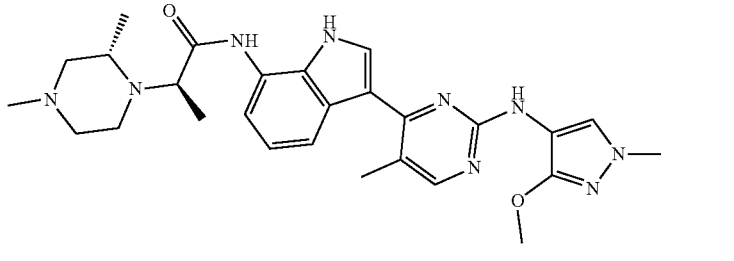 | (2R)-2-[(2S)-2,4-dimethylpiperazin-1-yl]-N-(3-{2-[(3-methoxy-1-methyl-1H-pyrazol-4-yl)amino]-5-methylpyrimidin-4-yl}-1H-indol-7-yl)propanamide |
| Example 20 | 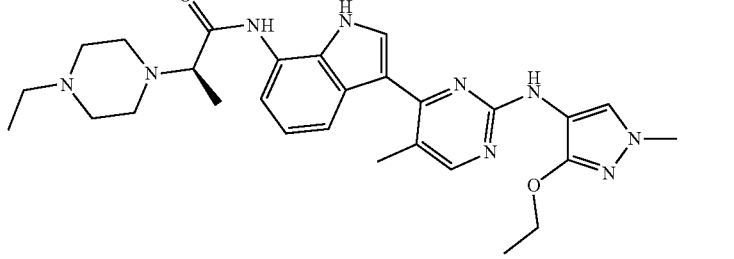 | (2R)-N-(3-{2-[(3-ethoxy-1-methyl-1H-pyrazol-4-yl)amino]-5-methylpyrimidin-4-yl}-1H-indol-7-yl)-2-(4-ethylpiperazin-1-yl)propanamide |
| Example 21 | 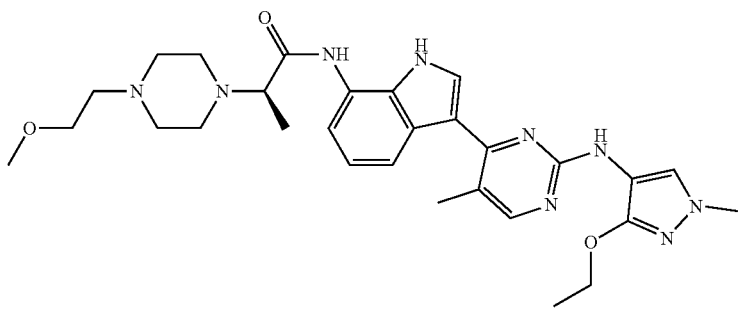 | (2R)-N-(3-{2-[(3-ethoxy-1-methyl-1H-pyrazol-4-yl)amino]-5-methylpyrimidin-4-yl}-1H-indol-7-yl)-2-[4-(2-methoxyethyl)piperazin-1-yl]propanamide |

TABLE 1-continued

| Example No. | Chemical Structure | Name |
|---|---|---|
| Example 22 | 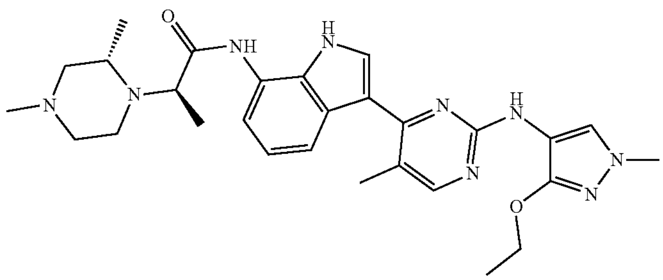 | (2R)-2-[(2S)-2,4-dimethylpiperazin-1-yl]-N-(3-{2-[(3-ethoxy-1-methyl-1H-pyrazol-4-yl)amino]-5-methylpyrimidin-4-yl}-1H-indol-7-yl)propanamide |
| Example 23 | 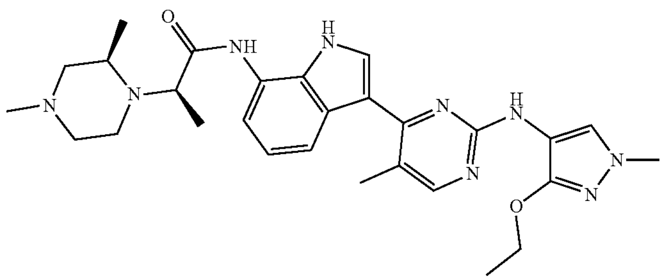 | (2R)-2-[(2R)-2,4-dimethylpiperazin-1-yl]-N-(3-{2-[(3-ethoxy-1-methyl-1H-pyrazol-4-yl)amino]-5-methylpyrimidin-4-yl}-1H-indol-7-yl)propanamide |
| Example 24 | 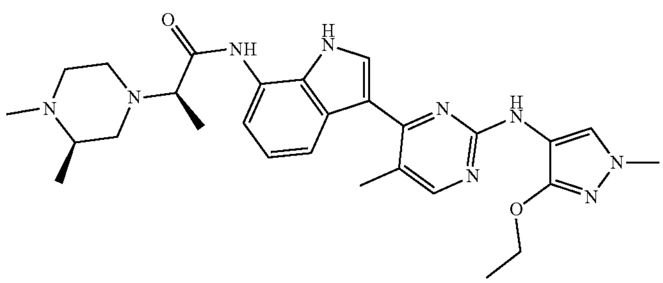 | (2R)-2-[(3R)-3,4-dimethylpiperazin-1-yl]-N-(3-{2-[(3-ethoxy-1-methyl-1H-pyrazol-4-yl)amino]-5-methylpyrimidin-4-yl}-1H-indol-7-yl)propanamide |
| Example 25 | 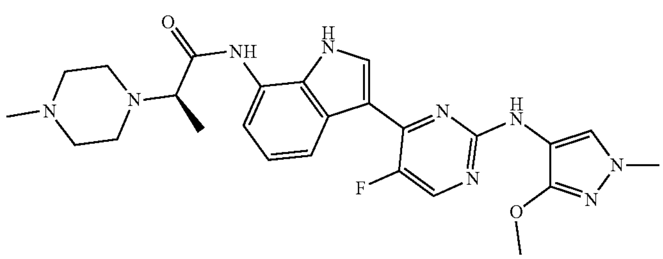 | (2R)-N-(3-{5-Fluoro-2-[(3-methoxy-1-methyl-1H-pyrazol-4-yl)amino]pyrimidin-4-yl}-1H-indol-7-yl)-2-(4-methylpiperazin-1-yl)propanamide |
| Example 26 | 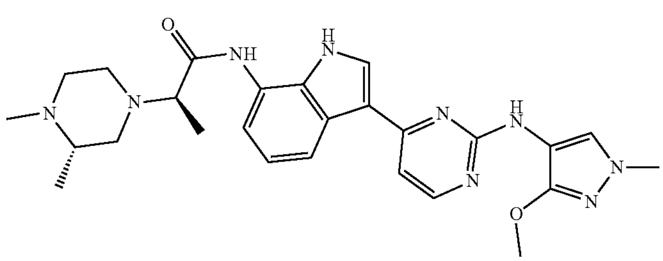 | (2R)-2-[(3S)-3,4-dimethylpiperazin-1-yl]-(3-{2-[(3-methoxy-1-methyl-1H-pyrazol-4-yl)amino]pyrimidin-4-yl}-1H-indol-7-yl)propanamide |

TABLE 1-continued

| Example No. | Chemical Structure | Name |
|---|---|---|
| Example 27 | 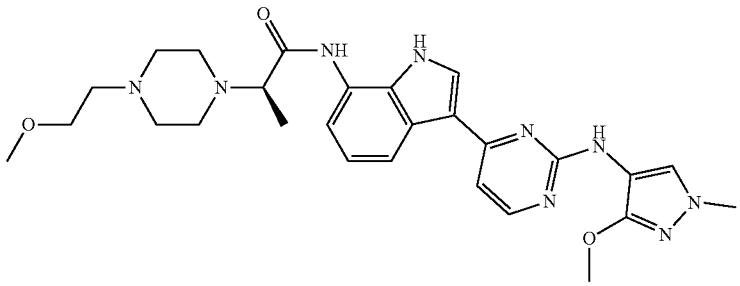 | (2R)-2-[4-(2-methoxyethyl)piperazin-1-yl]-N-(3-{2-[(3-methoxy-1-methyl-1H-pyrazol-4-yl)amino]pyrimidin-4-yl}-1H-indol-7-yl)propanamide |
| Example 28 | 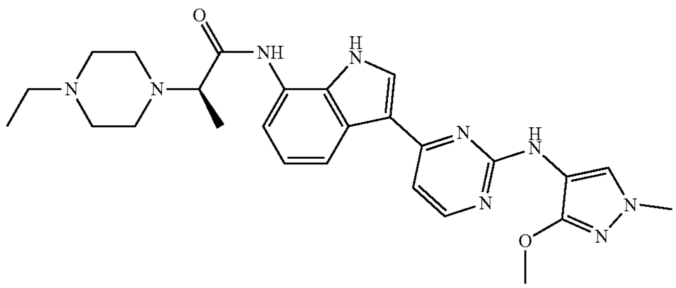 [SMILES: CCN1CCN([C@H](C)C(=O)Nc2cccc3c(-c4ccnc(Nc5cn(C)nc5OC)n4)c[nH]c23)CC1] | (2R)-2-(4-ethylpiperazin-1-yl)-N-(3-{2-[(3-methoxy-1-methyl-1H-pyrazol-4-yl)amino]pyrimidin-4-yl}-1H-indol-7-yl)propanamide |
| Example 29 | 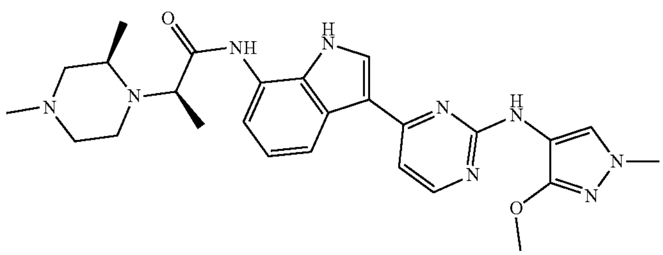 | (2R)-2-[(2R)-2,4-dimethylpiperazin-1-yl]-N-(3-{2-[(3-methoxy-1-methyl-1H-pyrazol-4-yl)amino]pyrimidin-4-yl}-1H-indol-7-yl)propanamide |
| Example 30 | 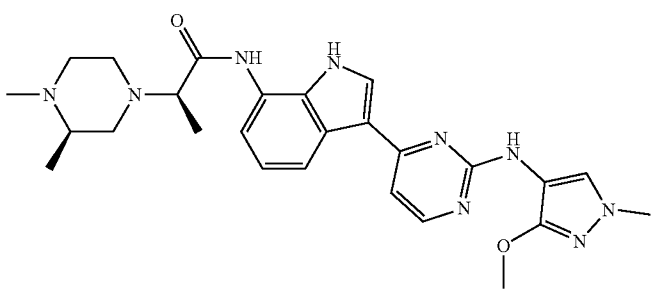 | (2R)-2-[(3R)-3,4-dimethylpiperazin-1-yl]-N-(3-{2-[(3-methoxy-1-methyl-1H-pyrazol-4-yl)amino]pyrimidin-4-yl}-1H-indol-7-yl)propanamide |
| Example 31a | 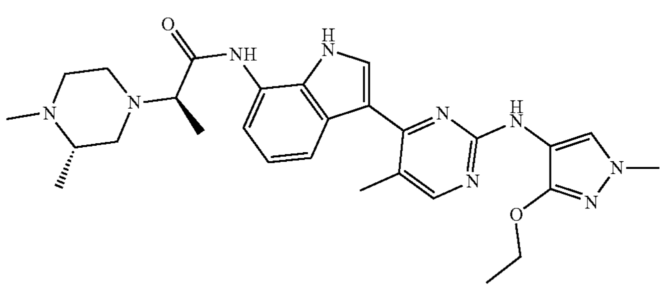 | (2R)-2-[(3S)-3,4-dimethylpiperazin-1-yl]-(3-{2-[(3-ethoxy-1-methyl-1H-pyrazol-4-yl)amino]-5-methylpyrimidin-4-yl}-1H-indol-7-yl)propanamide |

TABLE 1-continued

| Example No. | Chemical Structure | Name |
|---|---|---|
| Example 31b | 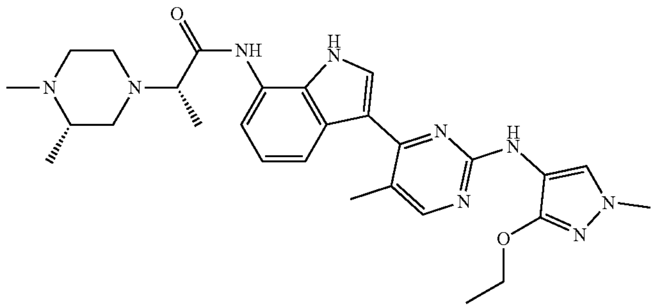 | (2S)-2-[(3S)-3,4-dimethylpiperazin-1-yl]-N-(3-{2-[(3-ethoxy-1-methyl-1H-pyrazol-4-yl)amino]-5-methylpyrimidin-4-yl}-1H-indol-7-yl)propanamide |
| Example 32 | 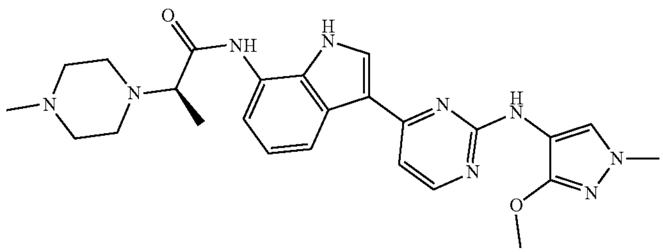 | (2R)-N-(3-{2-[(3-methoxy-1-methyl-1H-pyrazol-4-yl)amino]pyrimidin-4-yl}-1H-indol-7-yl)-2-(4-methylpiperazin-1-yl)propanamide |
| Example 33 | 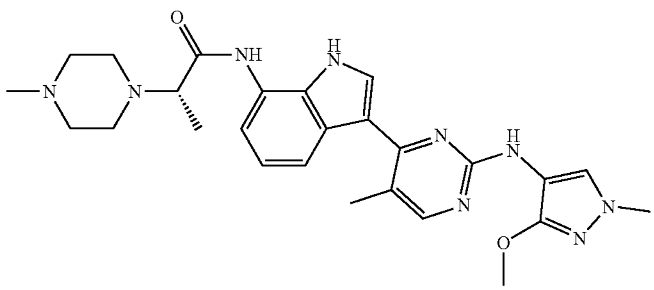 | (2S)-N-(3-{2-[(3-methoxy-1-methyl-1H-pyrazol-4-yl)amino]-5-methylpyrimidin-4-yl}-1H-indol-7-yl)-2-(4-methylpiperazin-1-yl)propanamide |
| Example 34 | 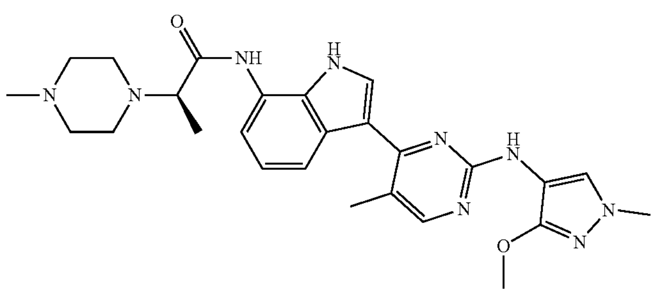 | (2R)-N-(3-{2-[(3-Methoxy-1-methyl-1H-pyrazol-4-yl)amino]-5-methylpyrimidin-4-yl}-1H-indol-7-yl)-2-(4-methylpiperazin-1-yl)propanamide |
| Example 35 | 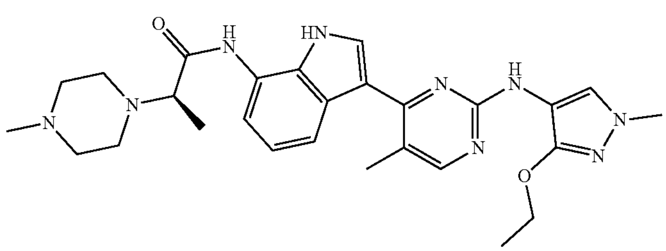 | (2R)-N-(3-{2-[(3-ethoxy-1-methyl-1H-pyrazol-4-yl)amino]-5-methylpyrimidin-4-yl}-1H-indol-7-yl)-2-(4-methylpiperazin-1-yl)propanamide |

TABLE 1-continued

| Example No. | Chemical Structure | Name |
|---|---|---|
| Example 36 | 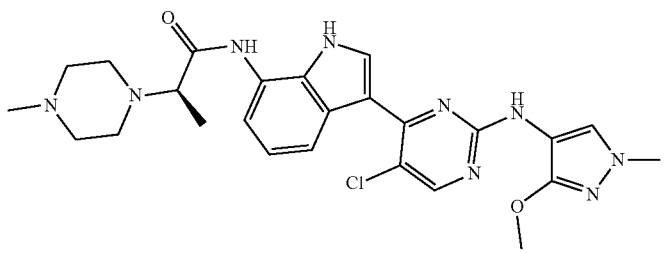 | (2R)-N-(3-{5-chloro-2-[(3-methoxy-1-methyl-1H-pyrazol-4-yl)amino]pyrimidin-4-yl}-1H-indol-7-yl)-2-(4-methylpiperazin-1-yl)propanamide |
| Example 37 | 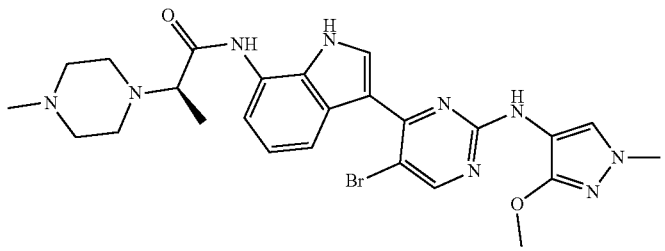 | (2R)-N-(3-{5-bromo-2-[(3-methoxy-1-methyl-1H-pyrazol-4-yl)amino]pyrimidin-4-yl}-1H-indol-7-yl)-2-(4-methylpiperazin-1-yl)propanamide |
| Example 38 | 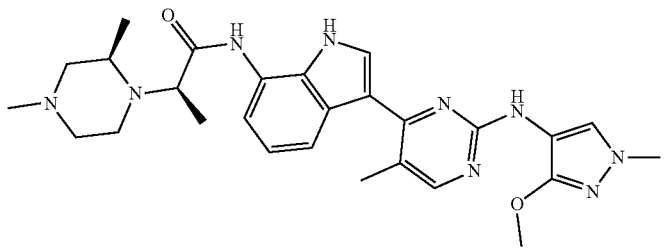 | (2R)-2-[(2R)-2,4-dimethylpiperazin-1-yl]-N-(3-{2-[(3-methoxy-1-methyl-1H-pyrazol-4-yl)amino]-5-methylpyrimidin-4-yl}-1H-indol-7-yl)propanamide |
| Example 39 | 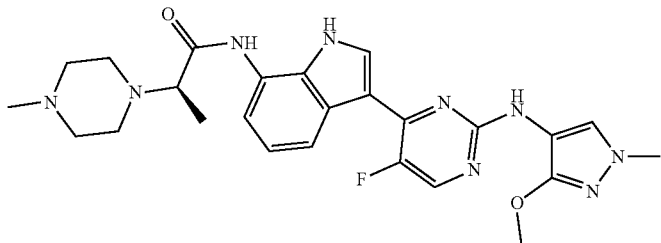 | (2R)-N-(3-{2-[(3-ethoxy-1-methyl-1H-pyrazol-4-yl)amino]-5-fluoropyrimidin-4-yl}-1H-indol-7-yl)-2-(4-methylpiperazin-1-yl)propanamide |
| Example 40 | 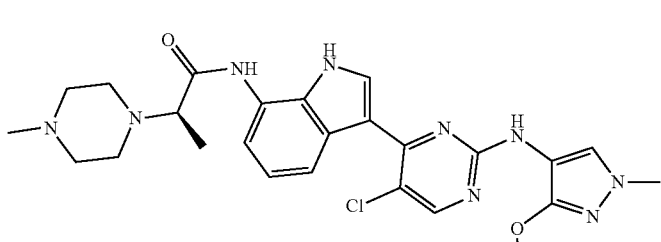 | (2R)-N-(3-{5-chloro-2-[(3-ethoxy-1-methyl-1H-pyrazol-4-yl)amino]pyrimidin-4-yl}-1H-indol-7-yl)-2-(4-methylpiperazin-1-yl)propanamide |
| Example 41 | 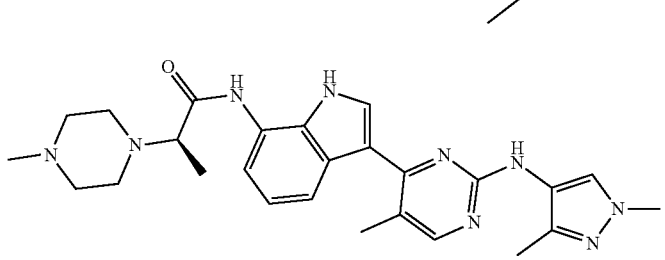 | (2R)-N-(3-{2-[(1,3-dimethyl-1H-pyrazol-4-yl)amino]-5-methylpyrimidin-4-yl}-1H-indol-7-yl)-2-(4-methylpiperazin-1-yl)propanamide |

TABLE 1-continued

| Example No. | Chemical Structure | Name |
|---|---|---|
| Example 42 | 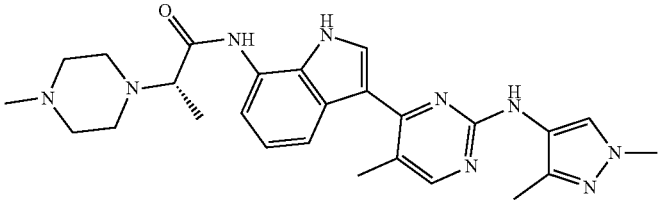 | (2S)-N-(3-{2-[(1,3-dimethyl-1H-pyrazol-4-yl)amino]-5-methylpyrimidin-4-yl}-1H-indol-7-yl)-2-(4-methylpiperazin-1-yl)propanamide |
| Example 43 | 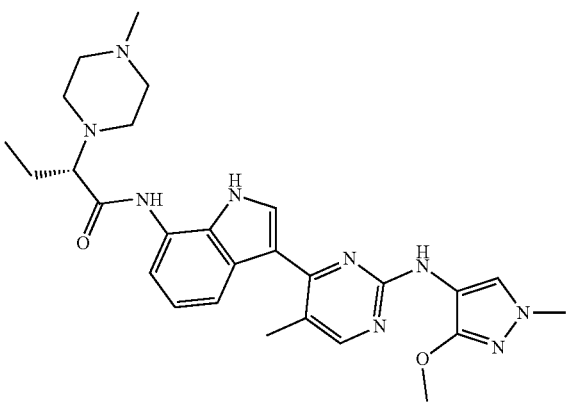 [SMILES: CC[C@@H](C(=O)Nc1cccc2c(-c3nc(Nc4cn(C)nc4OC)ncc3C)c[nH]c12)N1CCN(C)CC1] | (2S)-N-(3-{2-[(3-Methoxy-1-methyl-1H-pyrazol-4-yl)amino]-5-methylpyrimidin-4-yl}-1H-indol-7-yl)-2-(4-methylpiperazin-1-yl)butanamide |
| Example 44 | 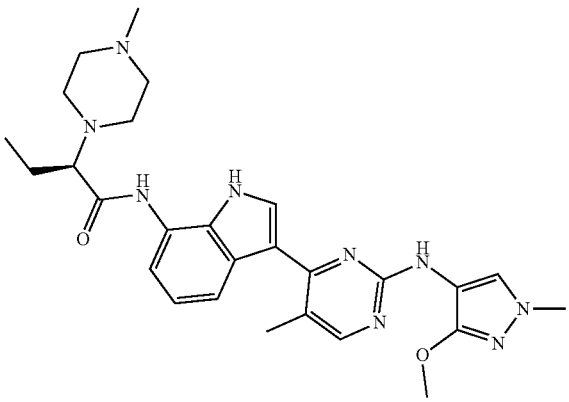 [SMILES: CC[C@H](C(=O)Nc1cccc2c(-c3nc(Nc4cn(C)nc4OC)ncc3C)c[nH]c12)N1CCN(C)CC1] | (2R)-N-(3-{2-[(3-Methoxy-1-methyl-1H-pyrazol-4-yl)amino]-5-methylpyrimidin-4-yl}-1H-indol-7-yl)-2-(4-methylpiperazin-1-yl)butanamide |
| Example 45 | 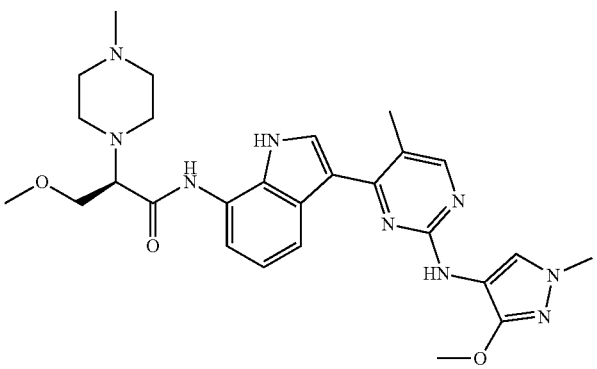 | (2R)-3-methoxy-N-(3-{2-[(3-methoxy-1-methyl-1H-pyrazol-4-yl)amino]-5-methylpyrimidin-4-yl}-1H-indol-7-yl)-2-(4-methylpiperazin-1-yl)propanamide |

TABLE 1-continued

| Example No. | Chemical Structure | Name |
|---|---|---|
| Example 46 | 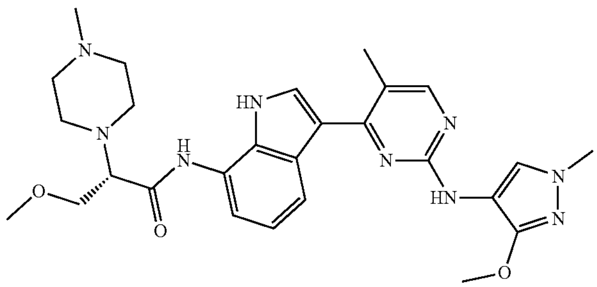 | (2S)-3-methoxy-N-(3-{2-[(3-methoxy-1-methyl-1H-pyrazol-4-yl)amino]-5-methylpyrimidin-4-yl}-1H-indol-7-yl)-2-(4-methylpiperazin-1-yl)propanamide |
| Example 47 | 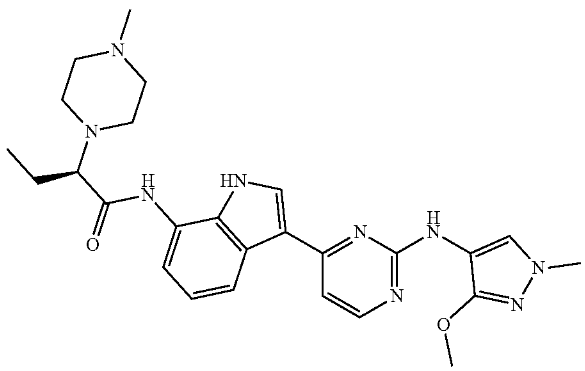 [SMILES: CC[C@H](C(=O)Nc1cccc2c(-c3ccnc(Nc4cn(C)nc4OC)n3)c[nH]c12)N1CCN(C)CC1] | (2R)-N-(3-{2-[(3-Methoxy-1-methyl-1H-pyrazol-4-yl)amino]pyrimidin-4-yl}-1H-indol-7-yl)-2-(4-methylpiperazin-1-yl)butanamide |
| Example 48 | 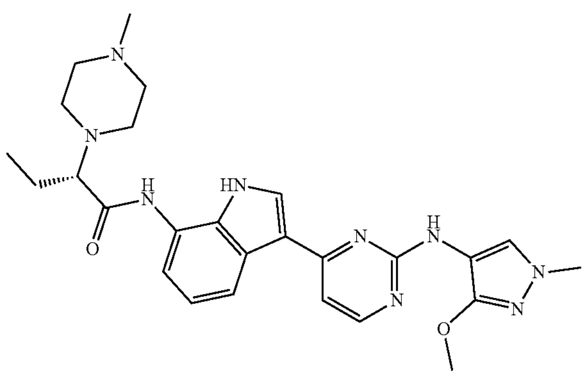 [SMILES: CC[C@@H](C(=O)Nc1cccc2c(-c3ccnc(Nc4cn(C)nc4OC)n3)c[nH]c12)N1CCN(C)CC1] | (2S)-N-(3-{2-[(3-Methoxy-1-methyl-1H-pyrazol-4-yl)amino]pyrimidin-4-yl}-1H-indol-7-yl)-2-(4-methylpiperazin-1-yl)butanamide |
| Example 49 | 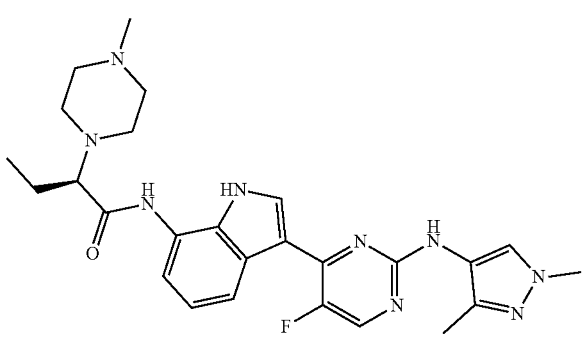 [SMILES: CC[C@H](C(=O)Nc1cccc2c(-c3nc(Nc4cn(C)nc4C)ncc3F)c[nH]c12)N1CCN(C)CC1] | (2R)-N-(3-{2-[(1,3-dimethyl-1H-pyrazol-4-yl)amino]-5-fluoropyrimidin-4-yl}-1H-indol-7-yl)-2-(4-methylpiperazin-1-yl)butanamide |

TABLE 1-continued

| Example No. | Chemical Structure | Name |
| --- | --- | --- |
| Example 50 | 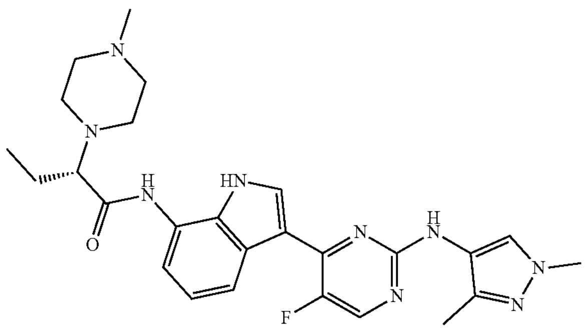 [SMILES: CC[C@@H](C(=O)Nc1cccc2c(-c3nc(Nc4cn(C)nc4C)ncc3F)c[nH]c12)N1CCN(C)CC1] | (2S)-N-(3-{2-[(1,3-dimethyl-1H-pyrazol-4-yl)amino]-5-fluoropyrimidin-4-yl}-1H-indol-7-yl)-2-(4-methylpiperazin-1-yl)butanamide |
| Example 51 | 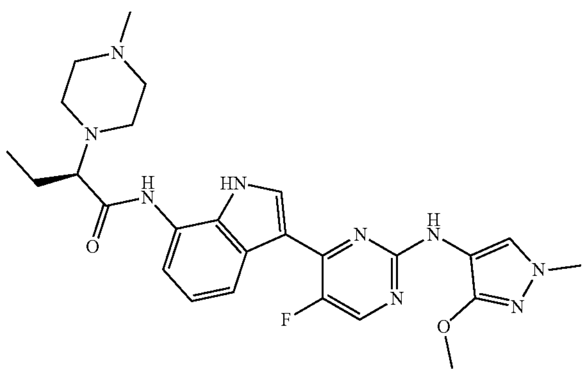 [SMILES: CC[C@H](C(=O)Nc1cccc2c(-c3nc(Nc4cn(C)nc4OC)ncc3F)c[nH]c12)N1CCN(C)CC1] | (2R)-N-(3-{5-fluoro-2-[(3-methoxy-1-methyl-1H-pyrazol-4-yl)amino]pyrimidin-4-yl}-1H-indol-7-yl)-2-(4-methylpiperazin-1-yl)butanamide |
| Example 52 | 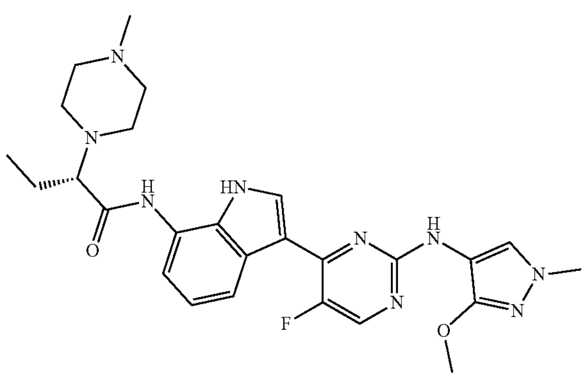 [SMILES: CC[C@@H](C(=O)Nc1cccc2c(-c3nc(Nc4cn(C)nc4OC)ncc3F)c[nH]c12)N1CCN(C)CC1] | (2S)-N-(3-{5-fluoro-2-[(3-methoxy-1-methyl-1H-pyrazol-4-yl)amino]pyrimidin-4-yl}-1H-indol-7-yl)-2-(4-methylpiperazin-1-yl)butanamide |
| Example 53 | 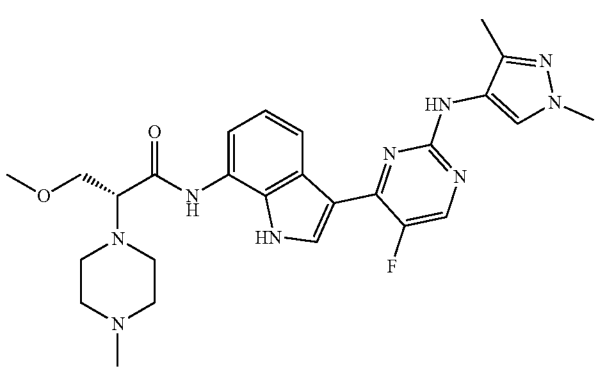 | (2R)-N-(3-{2-[(1,3-dimethyl-1H-pyrazol-4-yl)amino]-5-fluoropyrimidin-4-yl}-1H-indol-7-yl)-3-methoxy-2-(4-methylpiperazin-1-yl)propanamide |

TABLE 1-continued

| Example No. | Chemical Structure | Name |
|---|---|---|
| Example 54 | 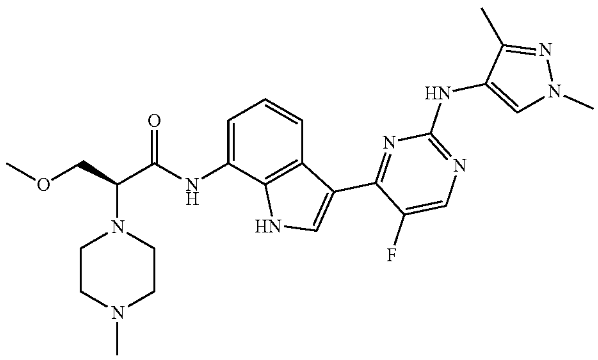 | (2S)-N-(3-{2-[(1,3-dimethyl-1H-pyrazol-4-yl)amino]-5-fluoropyrimidin-4-yl}-1H-indol-7-yl)-3-methoxy-2-(4-methylpiperazin-1-yl)propanamide |
| Example 55 | 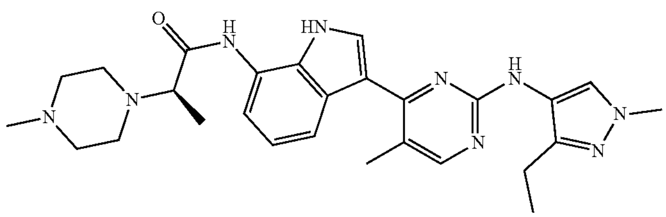 | (2R)-N-(3-{2-[(3-ethyl-1-methyl-1H-pyrazol-4-yl)amino]-5-methylpyrimidin-4-yl}-1H-indol-7-yl)-2-(4-methylpiperazin-1-yl)propanamide |
| Example 56 | 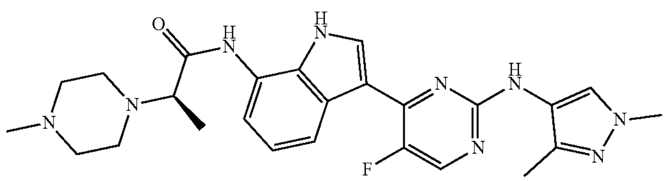 | (2R)-N-(3-{2-[(1,3-dimethyl-1H-pyrazol-4-yl)amino]-5-fluoropyrimidin-4-yl}-1H-indol-7-yl)-2-(4-methylpiperazin-1-yl)propanamide |
| Example 57 | 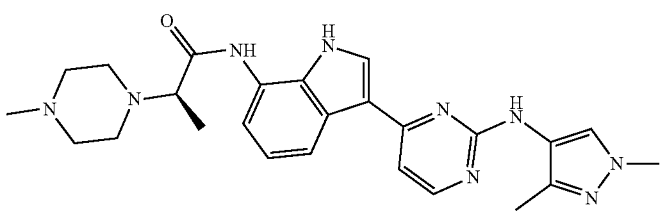 | (2R)-N-(3-{2-[(1,3-dimethyl-1H-pyrazol-4-yl)amino]pyrimidin-4-yl}-1H-indol-7-yl)-2-(4-methylpiperazin-1-yl)propanamide |
| Example 58 | 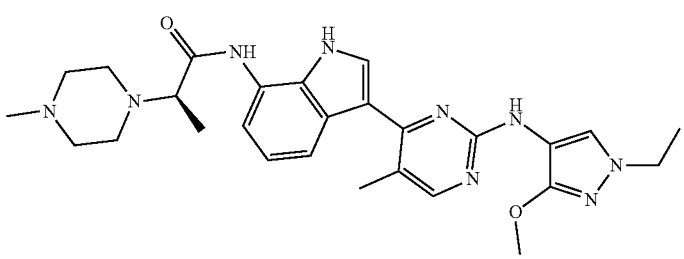 [SMILES: CCn1cc(Nc2ncc(C)c(-c3c[nH]c4c(NC(=O)[C@@H](C)N5CCN(C)CC5)cccc34)n2)c(OC)n1] | (2R)-N-(3-{2-[(1-ethyl-3-methoxy-1H-pyrazol-4-yl)amino]-5-methylpyrimidin-4-yl}-1H-indol-7-yl)-2-(4-methylpiperazin-1-yl)propanamide |
| Example 59 | 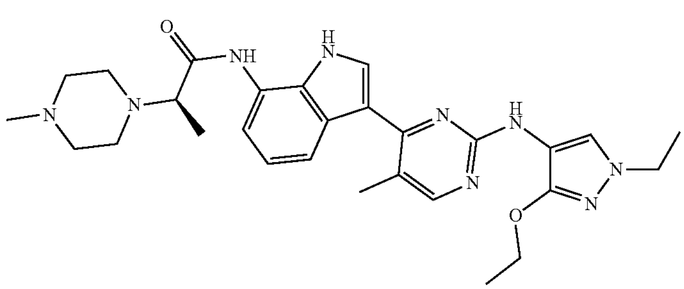 [SMILES: CCOc1nn(CC)cc1Nc1ncc(C)c(-c2c[nH]c3c(NC(=O)[C@@H](C)N4CCN(C)CC4)cccc23)n1] | (2R)-N-(3-{2-[(3-ethoxy-1-ethyl-1H-pyrazol-4-yl)amino]-5-methylpyrimidin-4-yl}-1H-indol-7-yl)-2-(4-methylpiperazin-1-yl)propanamide |

TABLE 1-continued

| Example No. | Chemical Structure | Name |
|---|---|---|
| Example 60 | 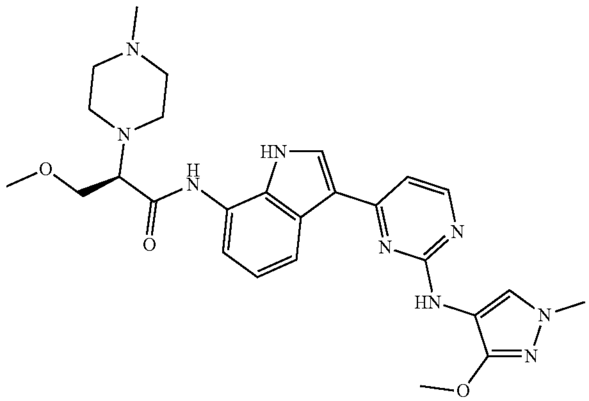 | (2R)-3-Methoxy-N-(3-{2-[(3-methoxy-1-methyl-1H-pyrazol-4-yl)amino]pyrimidin-4-yl}-1H-indol-7-yl)-2-(4-methylpiperazin-1-yl)propanamide |
| Example 61 | 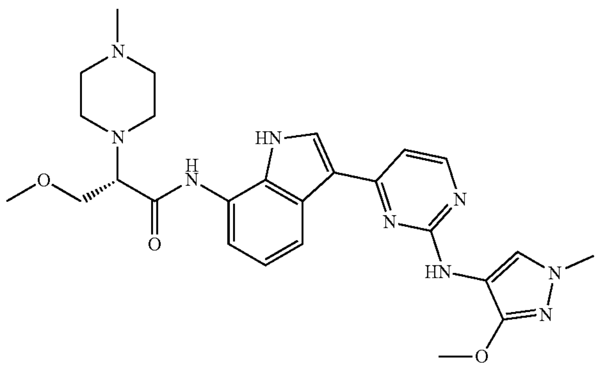 | (2S)-3-Methoxy-N-(3-{2-[(3-methoxy-1-methyl-1H-pyrazol-4-yl)amino]pyrimidin-4-yl}-1H-indol-7-yl)-2-(4-methylpiperazin-1-yl)propanamide |
| Example 62 | 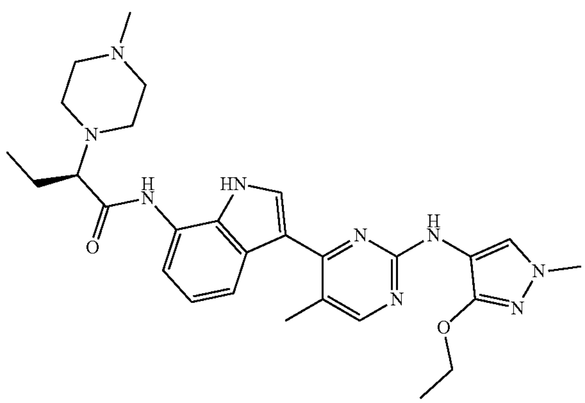 [SMILES: CCOc1nn(C)cc1Nc1ncc(C)c(-c2c[nH]c3c(NC(=O)[C@@H](CC)N4CCN(C)CC4)cccc23)n1] | (2R)-N-(3-{2-[(3-ethoxy-1-methyl-1H-pyrazol-4-yl)amino]-5-methylpyrimidin-4-yl}-1H-indol-7-yl)-2-(4-methylpiperazin-1-yl)butanamide |
| Example 63 | 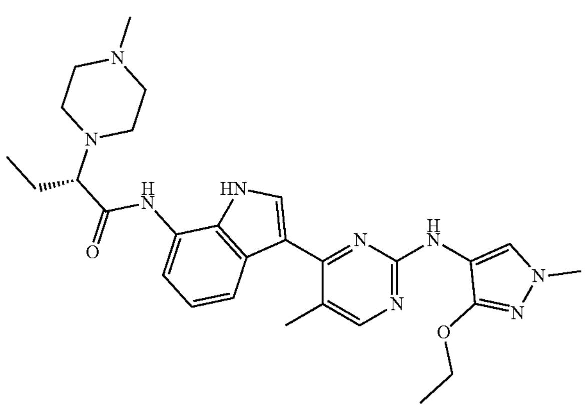 [SMILES: CCOc1nn(C)cc1Nc1ncc(C)c(-c2c[nH]c3c(NC(=O)[C@H](CC)N4CCN(C)CC4)cccc23)n1] | (2S)-N-(3-{2-[(3-ethoxy-1-methyl-1H-pyrazol-4-yl)amino]-5-methylpyrimidin-4-yl}-1H-indol-7-yl)-2-(4-methylpiperazin-1-yl)butanamide |

TABLE 1-continued

| Example No. | Chemical Structure | Name |
|---|---|---|
| Example 64 | 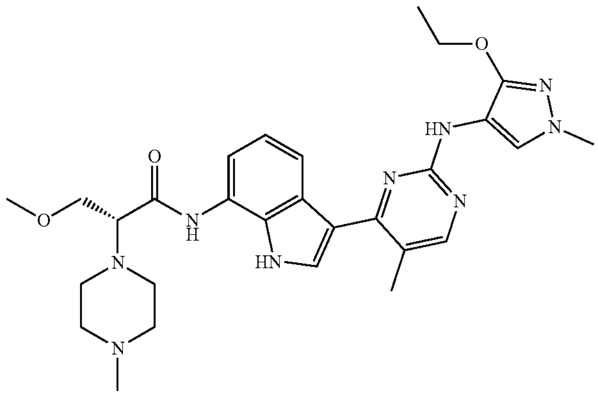 | (2R)-N-(3-{2-[(3-ethoxy-1-methyl-1H-pyrazol-4-yl)amino]-5-methylpyrimidin-4-yl}-1H-indol-7-yl)-3-methoxy-2-(4-methylpiperazin-1-yl)propanamide |
| Example 65 | 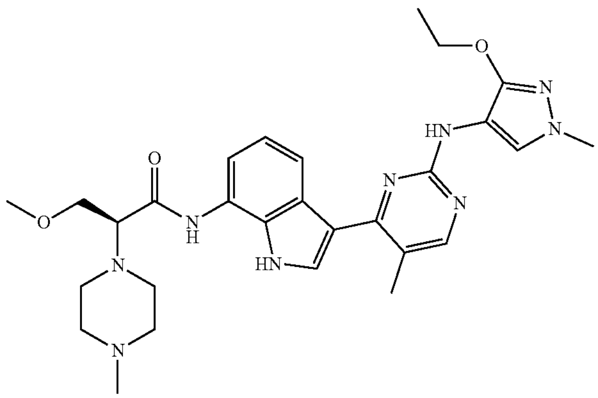 | (2S)-N-(3-{2-[(3-ethoxy-1-methyl-1H-pyrazol-4-yl)amino]-5-methylpyrimidin-4-yl}-1H-indol-7-yl)-3-methoxy-2-(4-methylpiperazin-1-yl)propanamide |

In one aspect, the disclosed compounds are obtainable by any process described in the Examples. In one embodiment, the disclosed are the intermediate compounds described in the Examples.

The language "pharmaceutically acceptable salt" includes acid addition or base salts that retain the biological effectiveness and properties of the compounds of Formula (I), (Ia), (Ib) and Table 1 and, which typically are not biologically or otherwise undesirable. In many cases, Formula (I), (Ia), (Ib) and Table 1 are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, napadisylate, naphthoate, napsylate, nicotinate, nitrate, octadecanoate, oleate, oxalate, palmitate, palmoate, phosphate/hydrogen phosphate/dihydrogen phosphate, polygalacturonate, propionate, stearate, succinate, subsalicylate, tartrate, tosylate, trimesate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, trimesic acid, citric acid, benzoic acid, mandelic acid, methanesulfonic acid, napadisylic acid, ethanesulfonic acid, toluenesulfonic acid, trifluoroacetic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the compounds Formula (I), (Ia), (Ib) and Table 1 can be synthesized from a basic or acidic moiety, by conventional chemical methods. Generally, such salts can be prepared by reacting free acid forms of these compounds with a stoichiometric amount of the appropriate base (such as $Na^+$, $Ca^{2+}$, $Mg^{2+}$, or $K^+$ hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences," 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms for the compounds of Formula (I), (Ia), (Ib) and Table 1. Isotopically labeled compounds have structures depicted by the formulas given herein except that one or more atoms are replaced by an atom having a selected atomic mass or mass number. Examples of isotopes that can be incorporated into the compounds of Formula (I), (Ia), (Ib) and Table 1 include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{16}F$, $^{31}P$, $^{32}P$, $^{35}S$, $^{36}Cl$ and $^{125}I$. The compounds of Formula (I), (Ia), (Ib) and Table 1 may include various isotopically labeled compounds into which radioactive isotopes, such as $^2H$, $^3H$, $^{13}C$ and $^{14}C$, are present. Isotopically labeled compounds of formula (I), (Ia) and (Ib) can generally be prepared by convention techniques known to those skilled in the art or by processes analogous to those described in the accompanying Examples using appropriate isotopically labeled reagents in place of the non-labeled reagents previously employed.

The compounds of formula (I), (Ia), (Ib) and Table 1 may have different isomeric forms. The language "optical isomer" or "stereoisomer" refers to any of the various stereoisomeric configurations which may exist for a given compound of formula (I), (Ia), (Ib) and Table 1. It is understood that a substituent may be attached at a chiral center of a carbon atom and, therefore, the disclosed compounds include enantiomers, diastereomers and racemates. The term "enantiomer" includes pairs of stereoisomers that are non-superimposable mirror images of each other. A 1:1 mixture of a pair of enantiomers is a racemic mixture. The term is used to designate a racemic mixture where appropriate. The terms "diastereomers" or "diastereoisomers" include stereoisomers that have at least two asymmetric atoms, but which are not mirror images of each other. The absolute stereochemistry is specified according to the Cahn-Ingold-Prelog R-S system. When a compound is a pure enantiomer, the stereochemistry at each chiral center may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds of Formula (I), (Ia), (Ib) and Table 1 contain one or more asymmetric centers or axes and may thus give rise to enantiomers, diastereomers or other stereoisomeric forms that may be defined, in terms of absolute stereochemistry, as (R)- or (S)-. The present disclosure is meant to include all such possible isomers, including racemic mixtures, optically pure forms and intermediate mixtures. Optically active (R)- and (S)-isomers may be prepared using chiral synthons or chiral reagents, or resolved using conventional techniques well known in the art, such as chiral HPLC.

Solid Forms

In some embodiments, disclosed are solid forms of the compounds of Formula (I), (Ia) and (Ib), or a pharmaceutically acceptable salt thereof. The term "solid form" includes polymorphs, crystalline salts, solvates, hydrates and amorphous forms of the compounds of Formula (I), (Ia) and (Ib). In some embodiments, disclosed are solid forms of (2R)—N-(3-{2-[(3-methoxy-1-methyl-1H-pyrazol-4-yl)amino]pyrimidin-4-yl}-indol-7-yl)-2-(4-methylpiperazin-1-yl)propanamide, or a pharmaceutically acceptable salt thereof. The term "polymorph" includes crystalline materials that have the same chemical composition but different molecular packing. The term language "crystalline salt" includes crystalline structures with the same chemical materials, but incorporating acid or base addition salts within the molecular packing of the crystalline structure. The term "solvate" includes crystalline structures of the same chemical material, but incorporating molecules of solvent within the molecular packing of the crystalline structure. The term "hydrates" includes crystalline structures of the same chemical material, but incorporating molecules of water within the molecular packing of the crystalline structure. The language "amorphous form" includes compounds of the same molecular material but without the molecular order of a crystalline structure (e.g., polymorph, crystalline salt, solvate or hydrate) of the same molecular material.

It is generally known that solid materials may be characterized using conventional techniques such as X-Ray Powder Diffraction (XRPD), Differential Scanning calorimetry (DSC), Thermal Gravimetric Analysis (TGA), Diffuse Reflectance Infrared Fourier Transform (DRIFT) spectroscopy, Near Infrared (NIR) spectroscopy, solution and/or solid state nuclear magnetic resonance spectroscopy. The water content of such solid materials may be determined by Karl Fischer analysis.

The solid forms described herein provide XRPD patterns substantially the same as the XRPD patterns shown in the Figures, and have the various 2-theta (2θ) values as shown in the Tables included herein. One skilled in the art will understand that an XRPD pattern or diffractogram may be obtained which has one or more measurement errors depending on the recording conditions, such as the equipment or machine used. Similarly, it is generally known that intensities in an XRPD pattern may fluctuate depending on measurement conditions or sample preparation as a result of preferred orientation. Persons skilled in the art of XRPD will further realize that the relative intensity of peaks can also be affected by, for example, grains above 30 μm in size and non-unitary aspect ratios. The skilled person understands that the position of reflections can be affected by the precise height at which the sample sits in the diffractometer, and also the zero calibration of the diffractometer. The surface planarity of the sample may also have a small effect.

As a result of these considerations, the diffraction pattern data presented are not to be taken as absolute values (Jenkins, R & Snyder, R. L. 'Introduction to X-Ray Powder Diffractometry' John Wiley & Sons 1996; Bunn, C. W. (1948), 'Chemical Crystallography', Clarendon Press, London; Klug, H. P. & Alexander, L. E. (1974), 'X-Ray Diffraction Procedures'). It should also be understood that the solid forms embodied herein are not limited to those that provide XRPD patterns that are identical to the XRPD pattern shown in the Figures, and any solid forms providing XRPD patterns substantially the same as those shown in the Figures fall within the scope of the corresponding embodiment. A person skilled in the art of XRPD is able to judge the substantial identity of XRPD patterns. Generally, a measurement error of a diffraction angle in an XRPD is approximately 2θ (±0.2°), and such degree of a measurement error should be taken into account when considering the X-ray powder diffraction pattern in the Figures and when reading data contained in the Tables included herein.

A person skilled in the art also understands that the value or range of values observed in a particular compound's DSC thermogram will show variation between batches of different purities. Therefore, whilst for one compound the range may be small, for others the range may be quite large. Generally, a measurement error of a diffraction angle in DSC thermal events is approximately plus or minus 5° C., and such degree of a measurement error should be taken into account when considering the DSC data included herein. TGA thermograms show similar variations, such that a person skilled in the art recognizes that measurement errors should be taken into account when judging substantial identity of TGA thermograms.

In some embodiments, disclosed is a solid form of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide, or a pharmaceutically acceptable salt thereof.

In some embodiments, disclosed is an amorphous form of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide, or a pharmaceutically acceptable salt thereof.

Form A

In some embodiments, disclosed is Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from the peaks listed in Table 17.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern substantially similar to FIG. 1.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram comprising an endotherm with a desolvation onset at about 110° C. and a peak at about 113° C.

Figure 2:
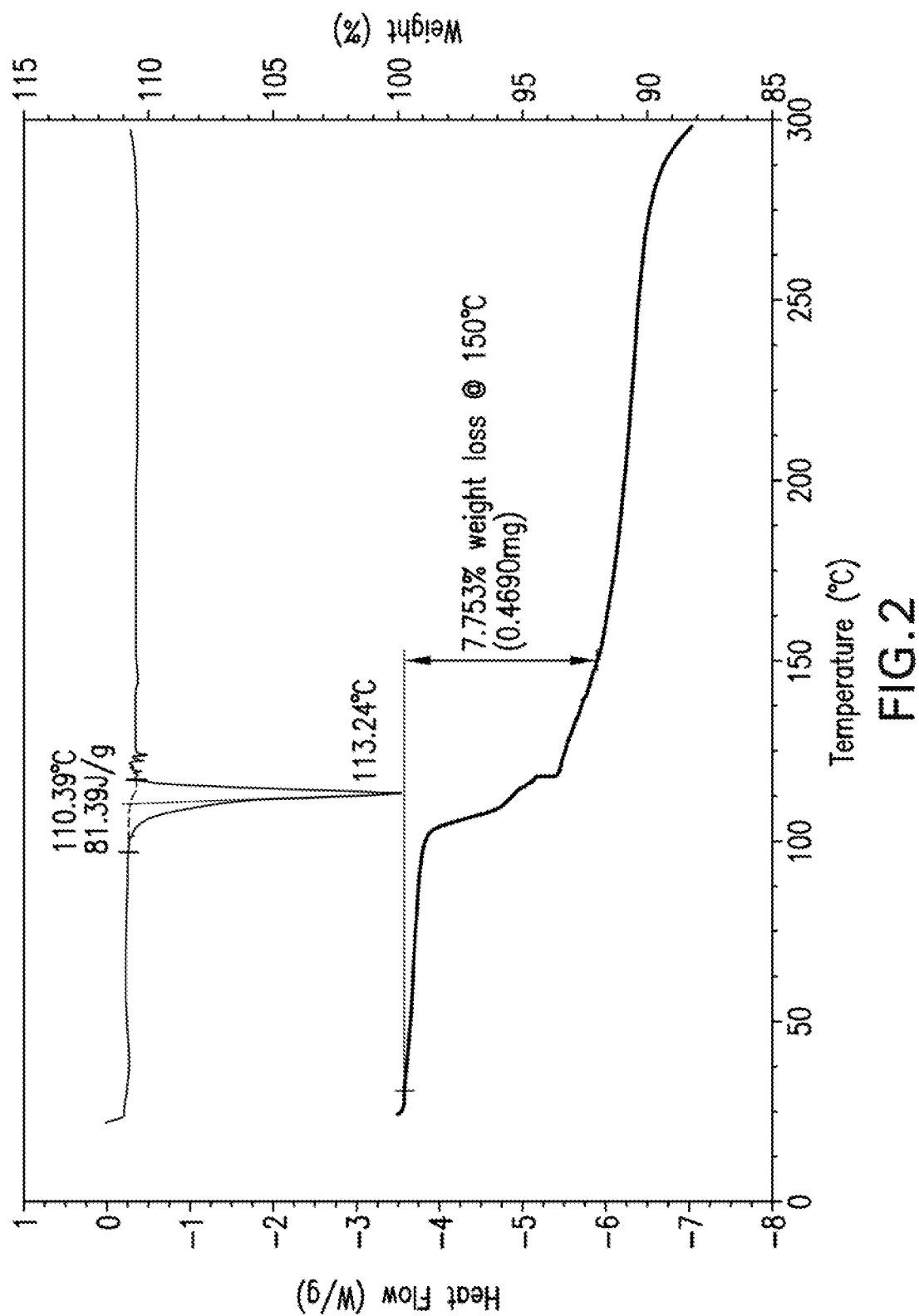
FIG. 2 illustrates the differential scanning calorimetry (DSC) and thermogravimetric analysis (TGA) traces of Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram substantially similar to FIG. 2.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram exhibiting a mass loss of about 7.8% upon heating from about 25° C. to about 150° C.

In some embodiments, Form A 2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram substantially similar to FIG. 2.

Form B

In some embodiments, disclosed is Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from the peaks listed in Table 18.

Figure 3:
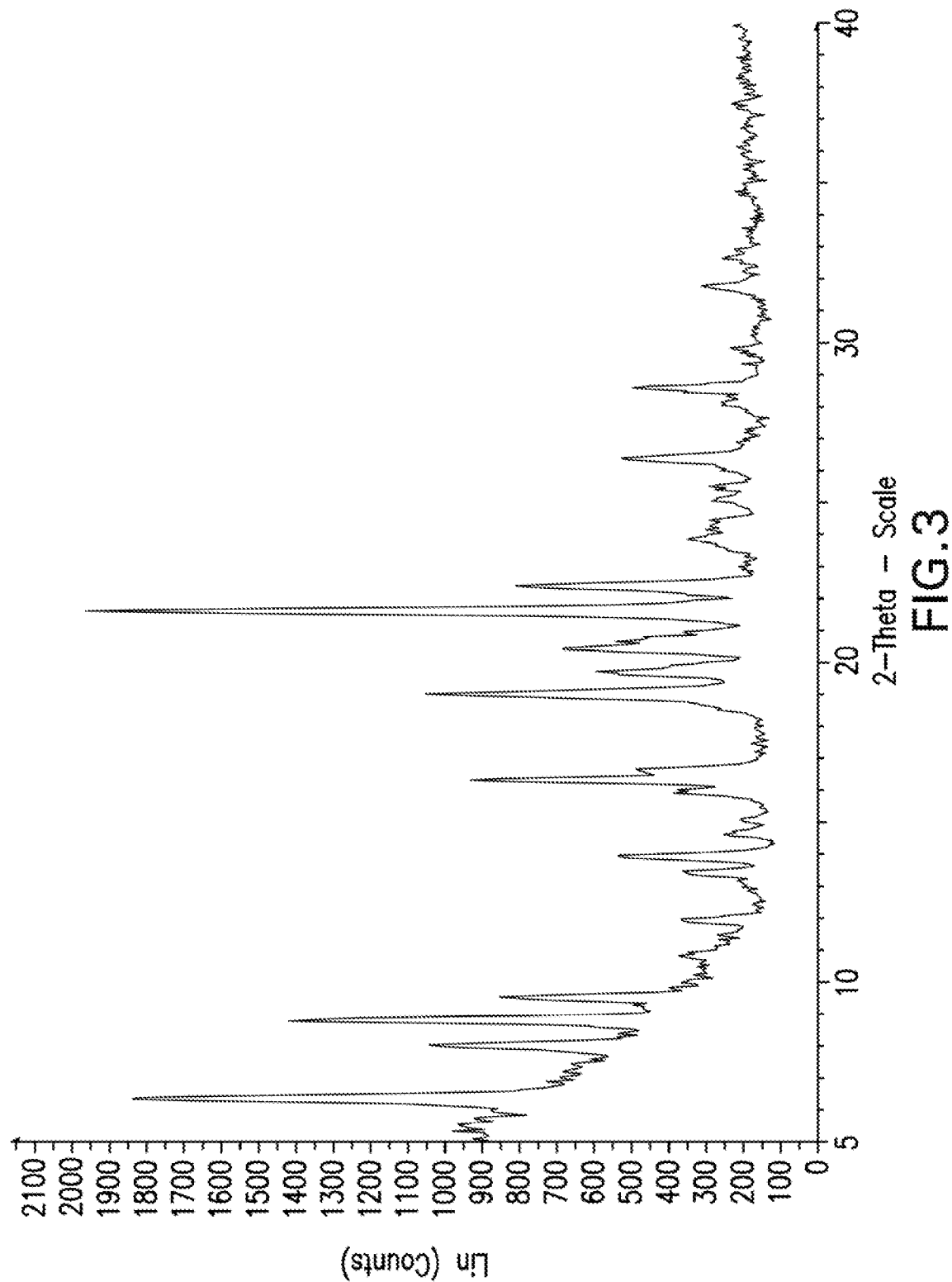
FIG. 3 illustrates the powder X-ray diffraction diagram of Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern substantially similar to FIG. 3.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram comprising an endotherm with a desolvation onset at about 112° C. and a peak at about 117° C.

Figure 4:
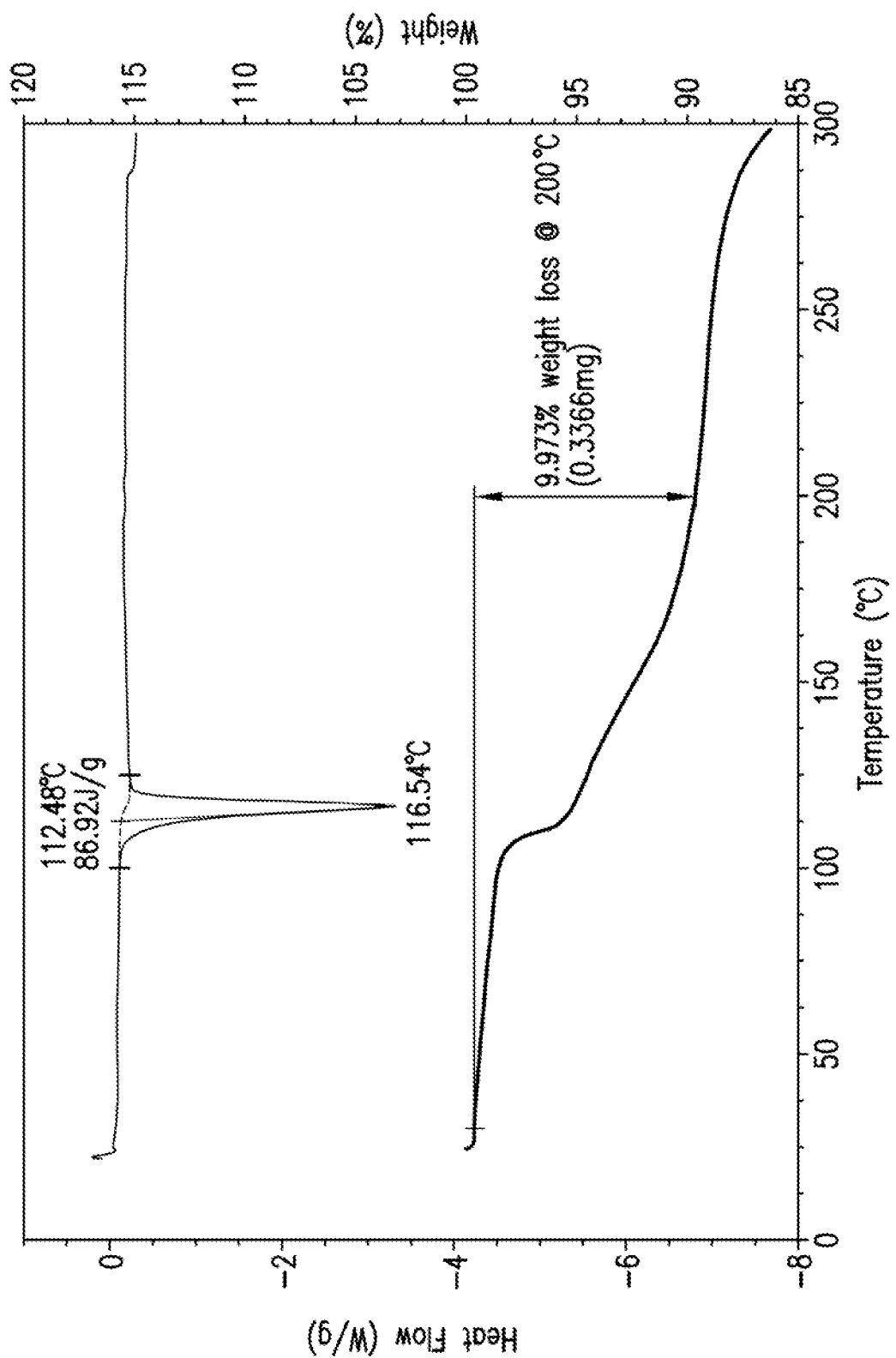
FIG. 4 illustrates the differential scanning calorimetry (DSC) and thermogravimetric analysis (TGA) traces of Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram substantially similar to FIG. 4.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram exhibiting a mass loss of about 10.0% upon heating from about 25° C. to about 200° C.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram substantially similar to FIG. 4.

Form C

In some embodiments, disclosed is Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from the peaks listed in Table 19.

Figure 5:
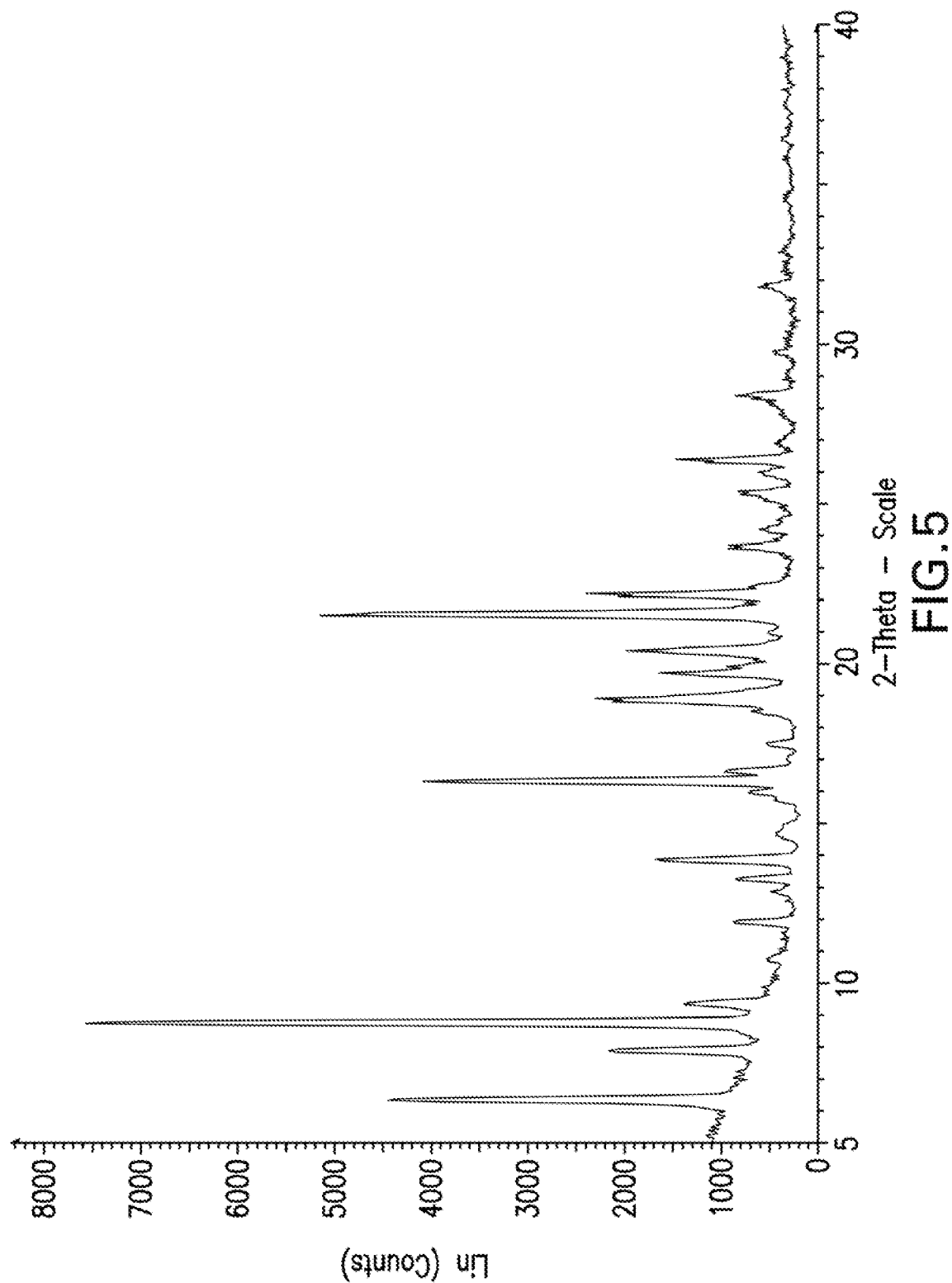
FIG. 5 illustrates the powder X-ray diffraction diagram of Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern substantially similar to FIG. 5.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram comprising an endotherm with a desolvation onset at about 112° C. and a peak at about 114° C.

Figure 6:
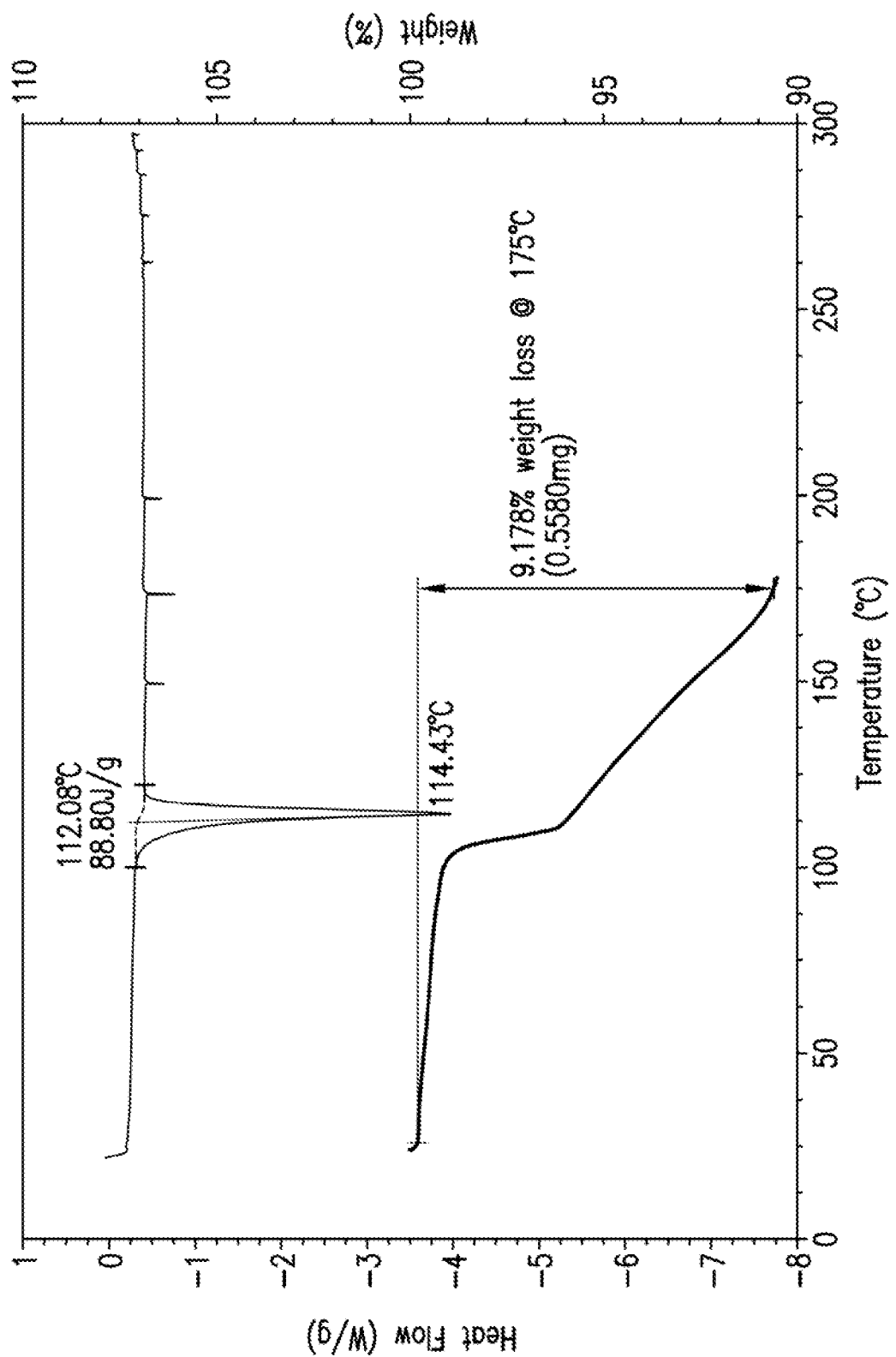
FIG. 6 illustrates the differential scanning calorimetry (DSC) and thermogravimetric analysis (TGA) traces of Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram substantially similar to FIG. 6.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram exhibiting a mass loss of about 9.2% upon heating from about 25° C. to about 175° C.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram substantially similar to FIG. 6.

Form D

In some embodiments, disclosed is Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) at about 21.8°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) at about 6.4°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) at about 16.6°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) at about 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) at about 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8° and 6.4°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8° and 16.6°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8° and 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 6.4° and 16.6°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 6.4° and 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 6.4° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 16.6° and 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 16.6° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 8.1° and 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 6.4° and 16.6°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 6.4° and 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 6.4° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 16.6° and 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 16.6° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 8.9° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 16.6°, 8.9° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 6.4°, 16.6° and 8.9°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 6.4°, 16.6° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 6.4°, 16.6°, 8.9° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from about 21.8°, 6.4°, 16.6°, 8.9° and 8.1°.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern comprising at least one peak expressed as 2θ (±0.2°) selected from the peaks listed in Table 20.

Figure 7:
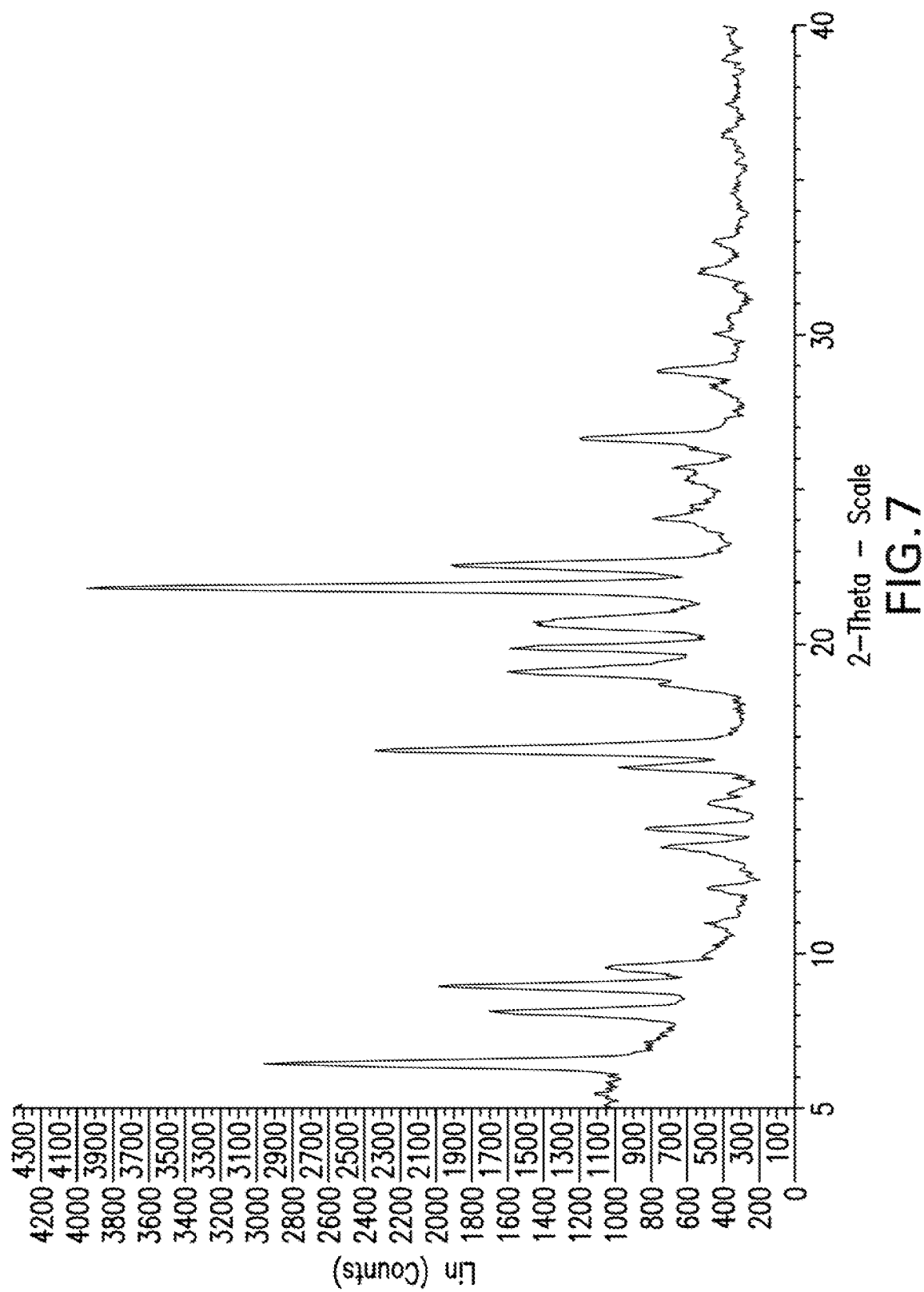
FIG. 7 illustrates the powder X-ray diffraction diagram of Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has an XRPD pattern substantially similar to FIG. 7.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram comprising an endotherm with a desolvation onset at about 116° C. and a peak at about 119° C.

Figure 8:
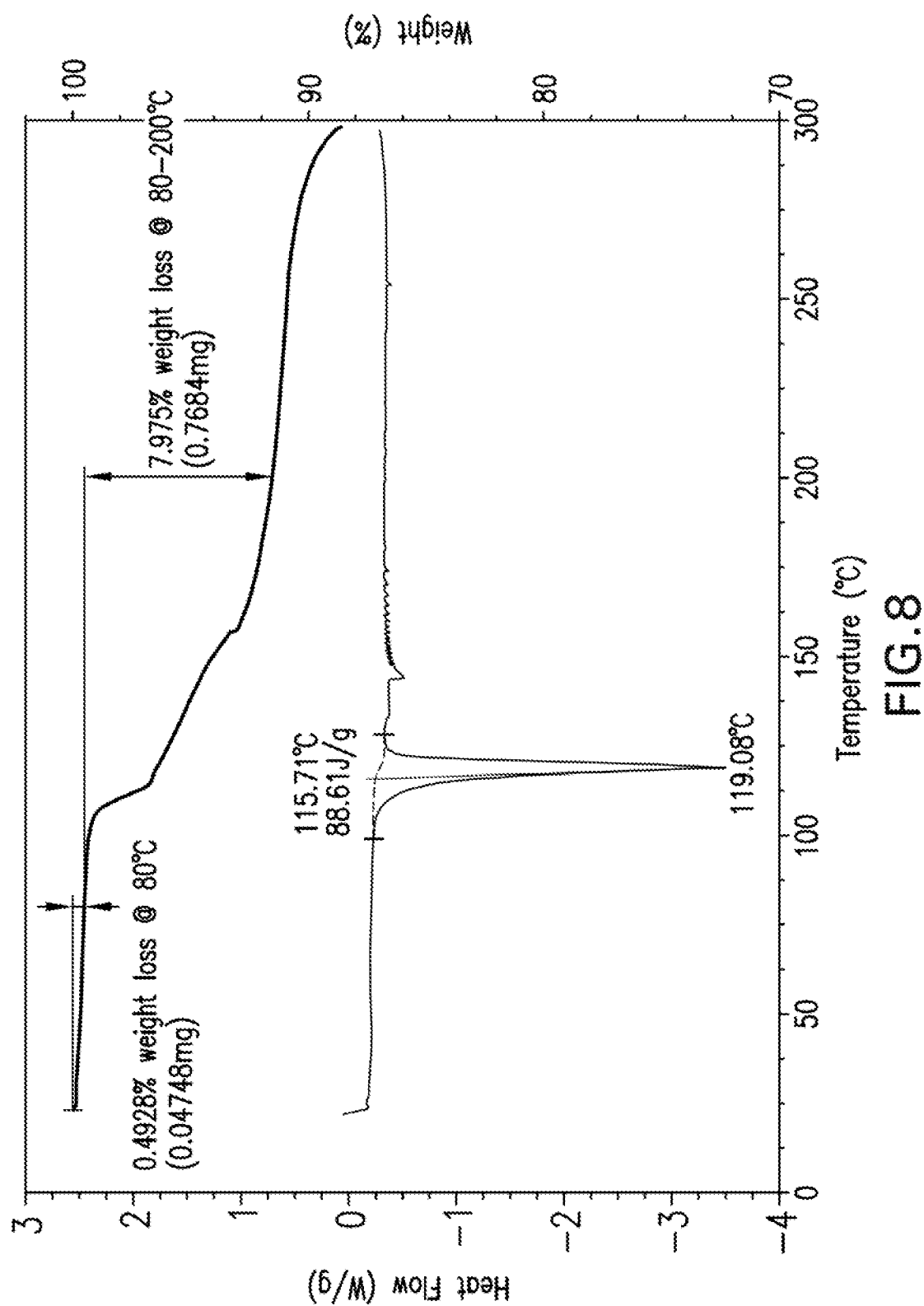
FIG. 8 illustrates the differential scanning calorimetry (DSC) and thermogravimetric analysis (TGA) traces of Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a DSC thermogram substantially similar to FIG. 8.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram exhibiting a mass loss of about 8.0% upon heating from about 25° C. to about 200° C.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide has a TGA thermogram substantially similar to FIG. 8.

Form A—Saccharine Salt

In some embodiments, disclosed is Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern comprising at least one peak expressed as 2θ (±0.2°) selected from the peaks listed in Table 21.

Figure 9:
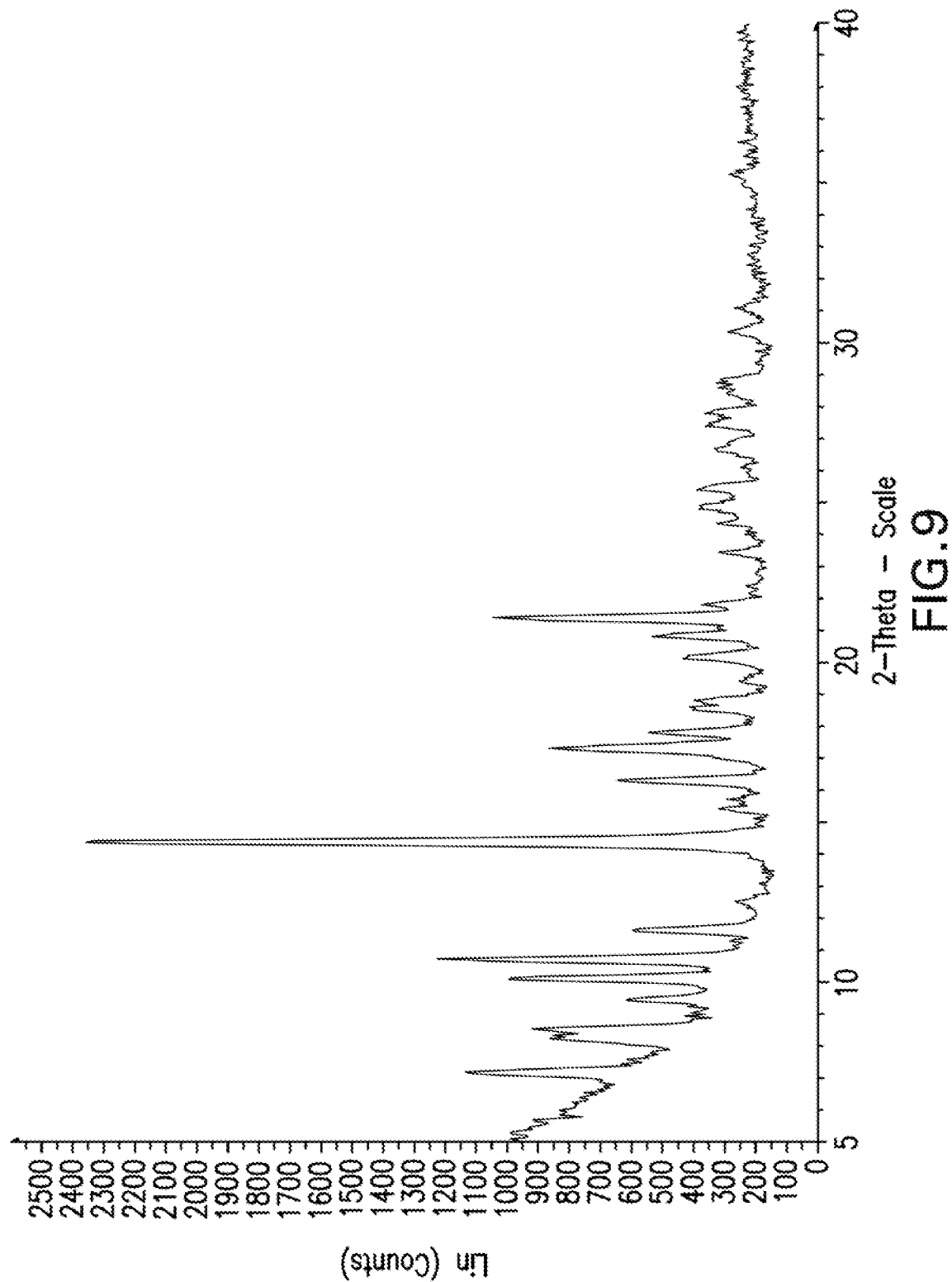
FIG. 9 illustrates the powder X-ray diffraction diagram of Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern substantially similar to FIG. 9.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a DSC thermogram comprising an endotherm with a melting point onset at about 163° C. and a peak at about 169° C.

Figure 10:
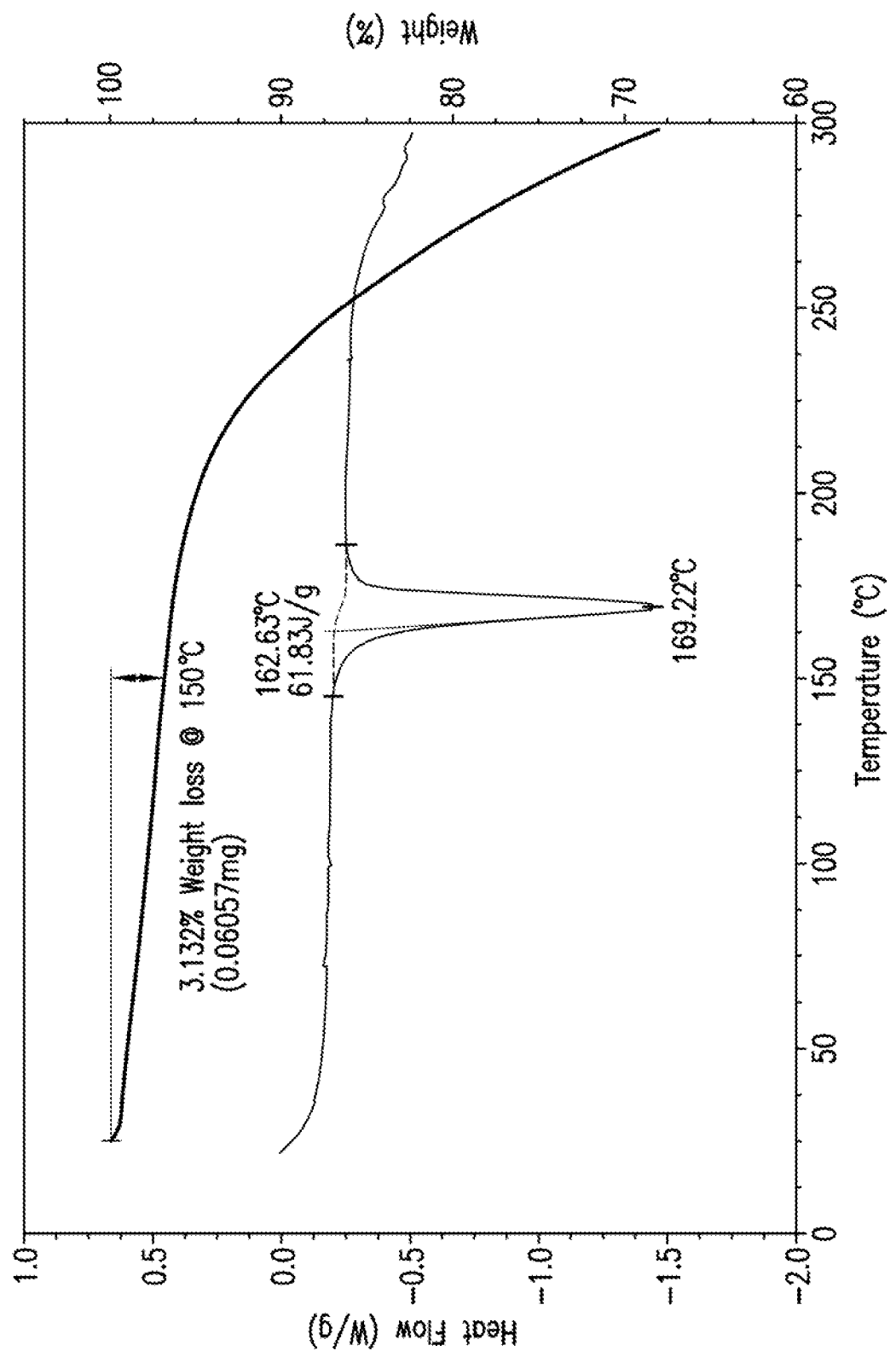
FIG. 10 illustrates the differential scanning calorimetry (DSC) and thermogravimetric analysis (TGA) traces of Form A (2R)—N-(3-{2-[(3-methoxy-1-methyl-1H-pyrazol- 4-yl)amino]pyrimidin-4-yl}-1H-indol-7-yl)-2-(4-methylpiperazin-1-yl)propanamide saccharine salt.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a DSC thermogram substantially similar to FIG. 10.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a TGA thermogram exhibiting a mass loss of about 3.1% upon heating from about 25° C. to about 150° C.

In some embodiments, Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a TGA thermogram substantially similar to FIG. 10.

Form B—Saccharine Salt

In some embodiments, disclosed is Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern comprising at least one peak expressed as 2θ (±0.2°) selected from the peaks listed in Table 22.

Figure 11:
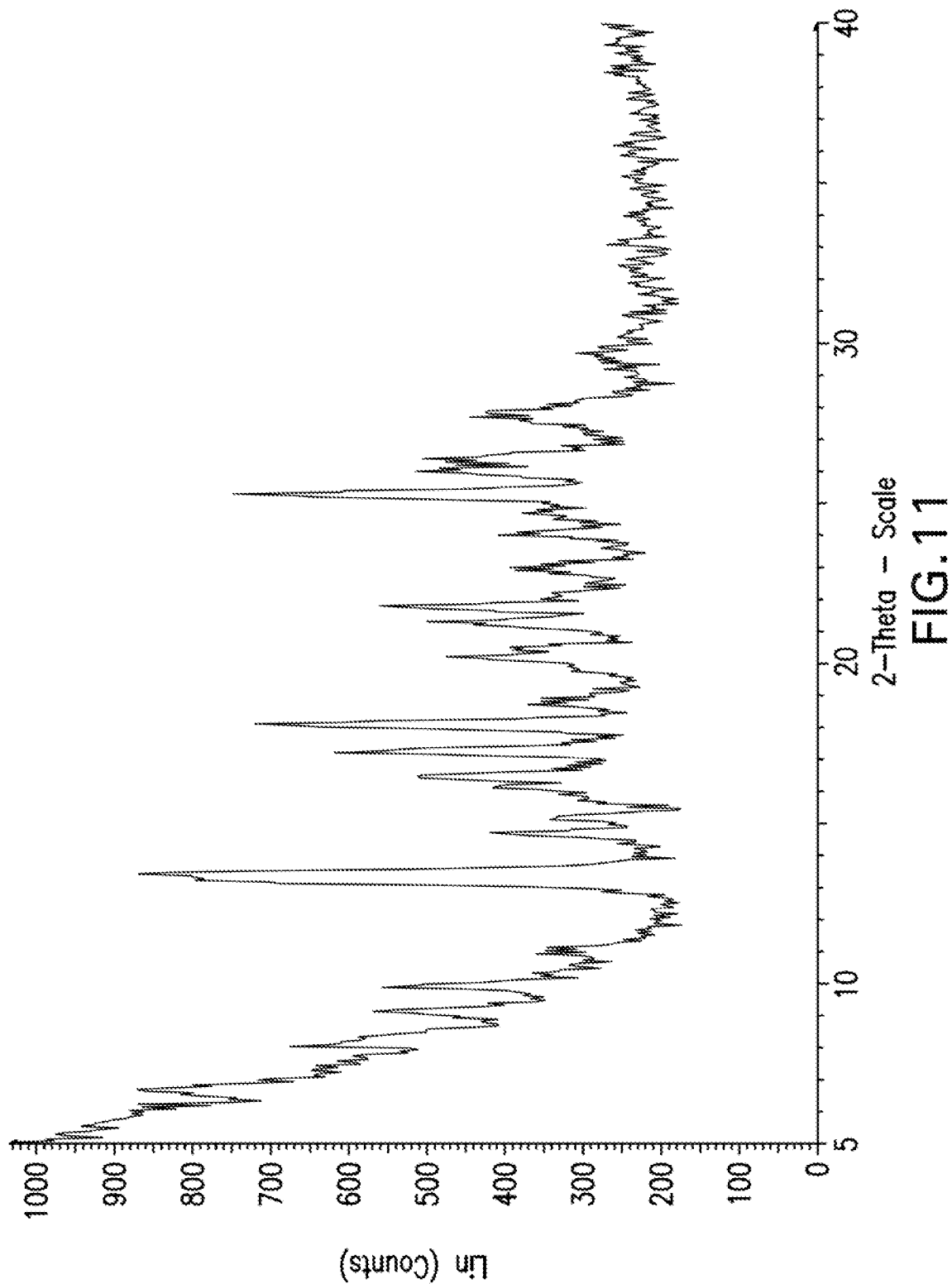
FIG. 11 illustrates the powder X-ray diffraction diagram of Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern substantially similar to FIG. 11.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a DSC thermogram comprising an endotherm with a broad desolvation peak at about 53° C. and two endotherm events with an onset at about 153° C. and a peak at 162° C. and an onset at about 176° C. and a peak at about 182° C.

Figure 12:
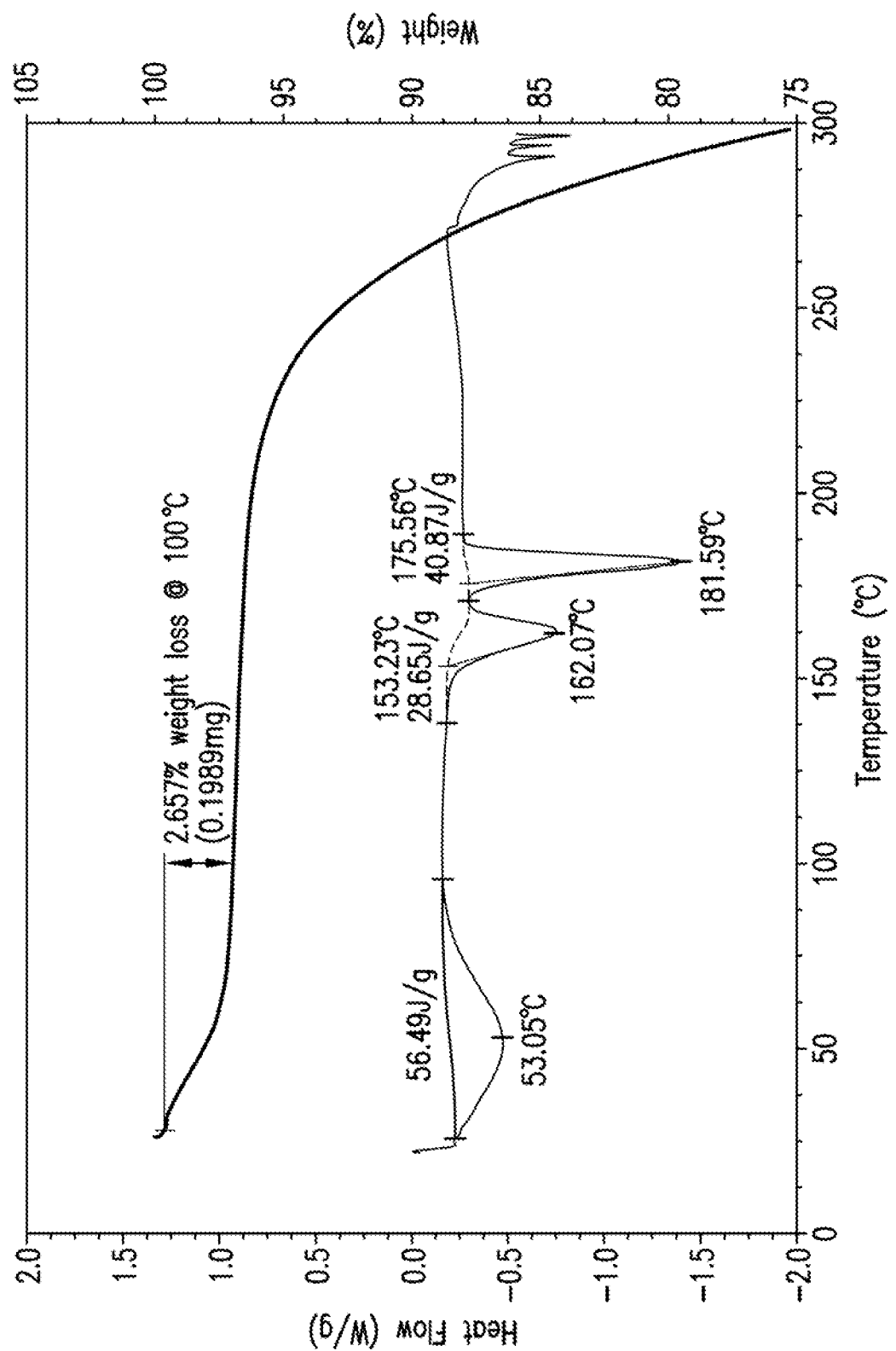
FIG. 12 illustrates the differential scanning calorimetry (DSC) and thermogravimetric analysis (TGA) traces of Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a DSC thermogram substantially similar to FIG. 12.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a TGA thermogram exhibiting a mass loss of about 2.7% upon heating from about 25° C. to about 100° C.

In some embodiments, Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has a TGA thermogram substantially similar to FIG. 12.

Form C—Saccharine Salt

In some embodiments, disclosed is Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern comprising at least one peak expressed as 2θ (±0.2°) selected from the peaks listed in Table 23.

Figure 13:
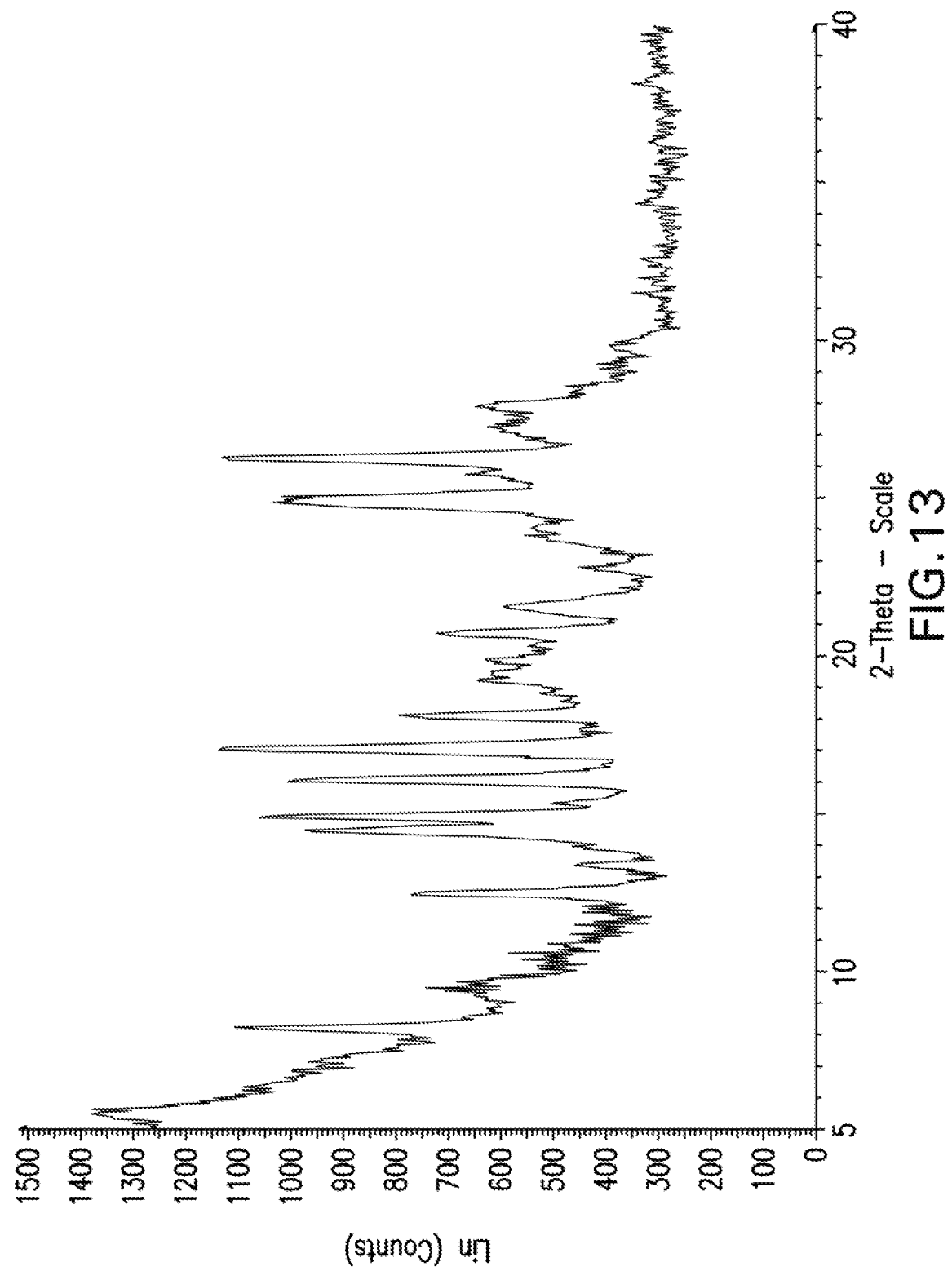
FIG. 13 illustrates the powder X-ray diffraction diagram of Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern substantially similar to FIG. 13.

Form D—Saccharine Salt

In some embodiments, disclosed is Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern comprising at least one peak expressed as 2θ (±0.2°) selected from the peaks listed in Table 24.

Figure 14:
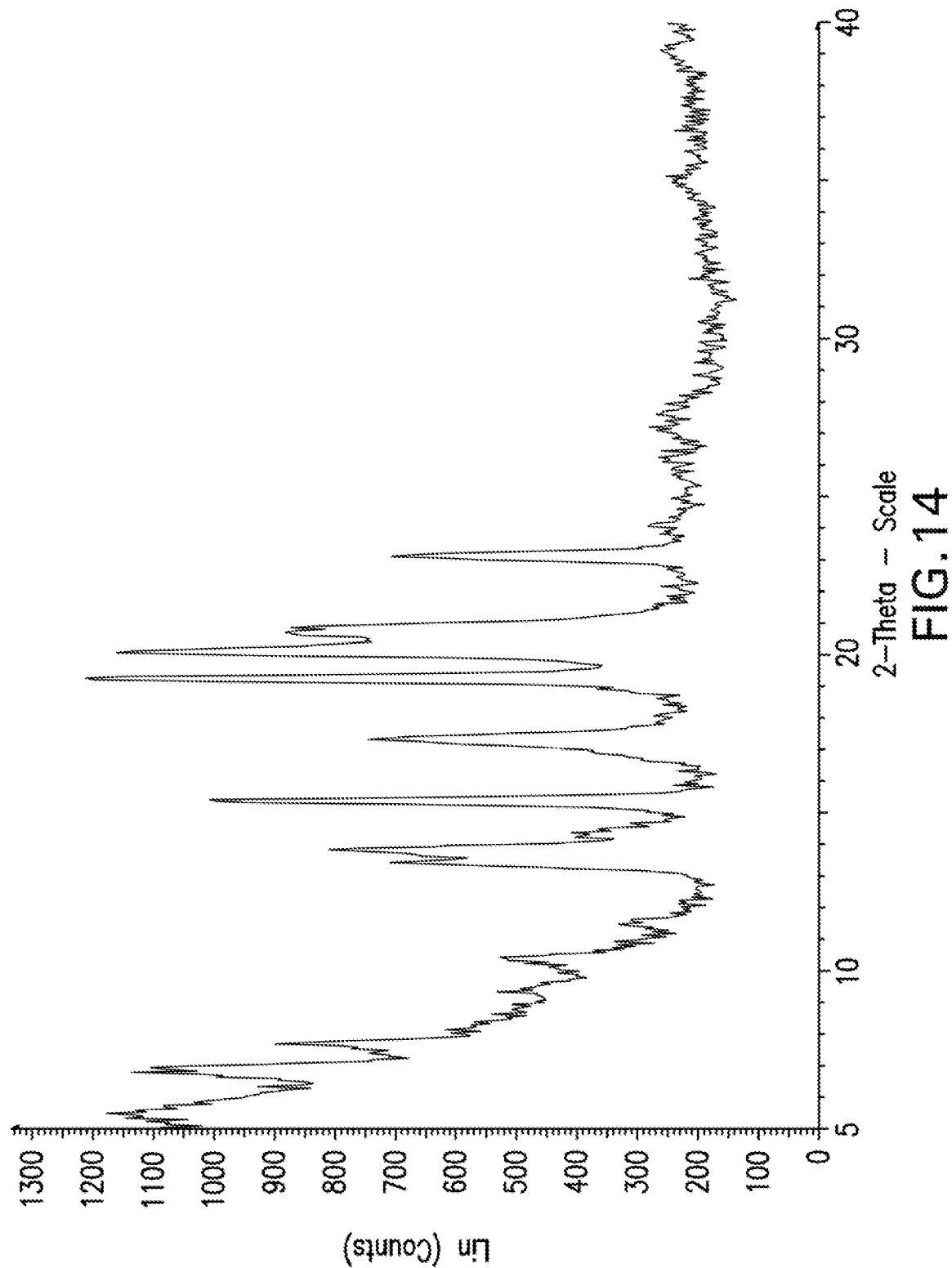
FIG. 14 illustrates the powder X-ray diffraction diagram of Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern substantially similar to FIG. 14.

Form E—Saccharine Salt

In some embodiments, disclosed is Form E (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form E (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern comprising at least one peak expressed as 2θ (±0.2°) selected from the peaks listed in Table 25.

Figure 15:
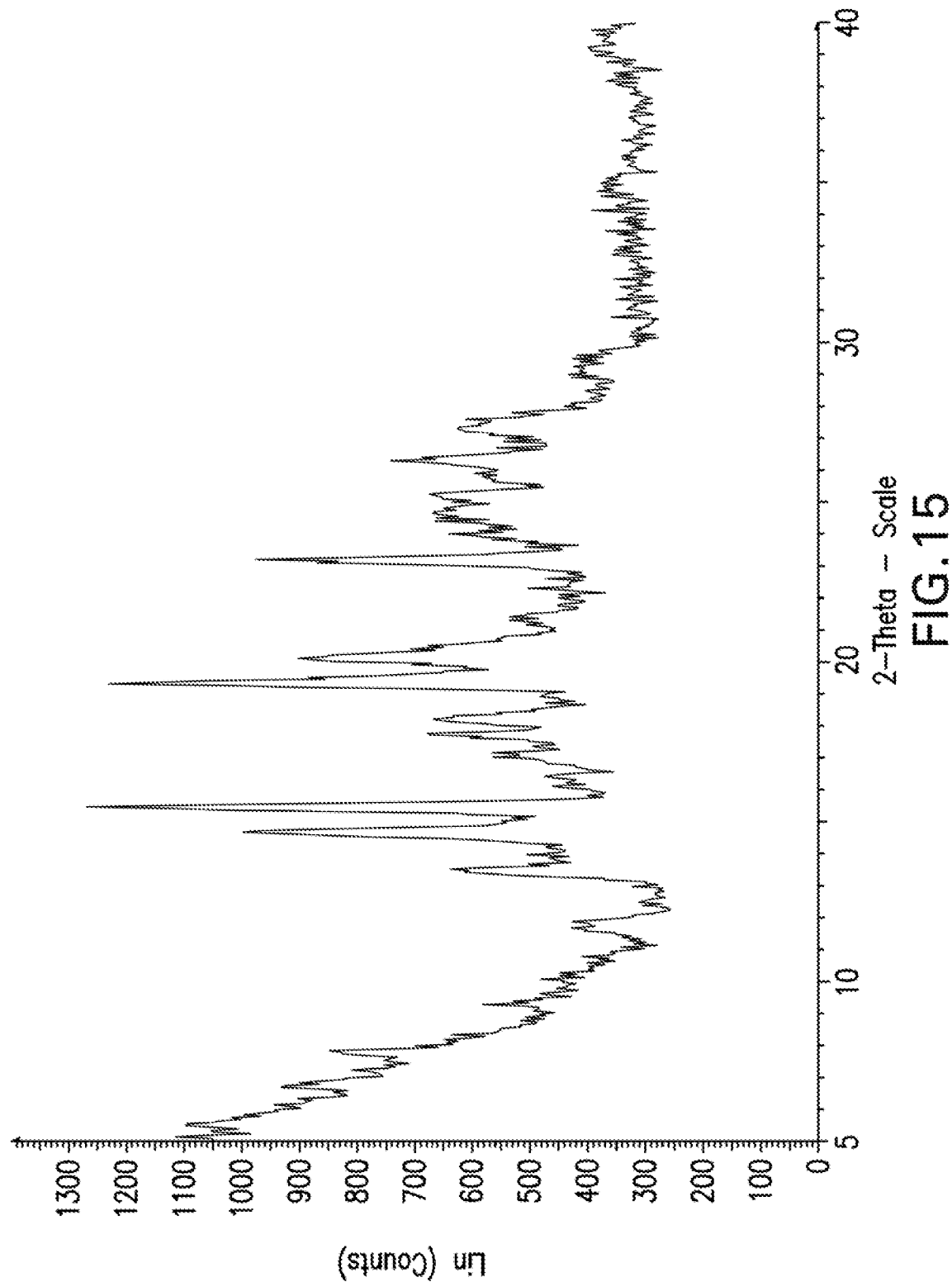
FIG. 15 illustrates the powder X-ray diffraction diagram of Form E (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt.

In some embodiments, Form E (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt has an XRPD pattern substantially similar to FIG. 15.

Hydrochloride Saccharine Salt

In some embodiments, disclosed is (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide hydrochloride saccharine salt.

In some embodiments, (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide hydrochloride saccharine salt has an XRPD pattern comprising at least one peak expressed as 2θ (±0.2°) selected from the peaks listed in Table 26.

Figure 16:
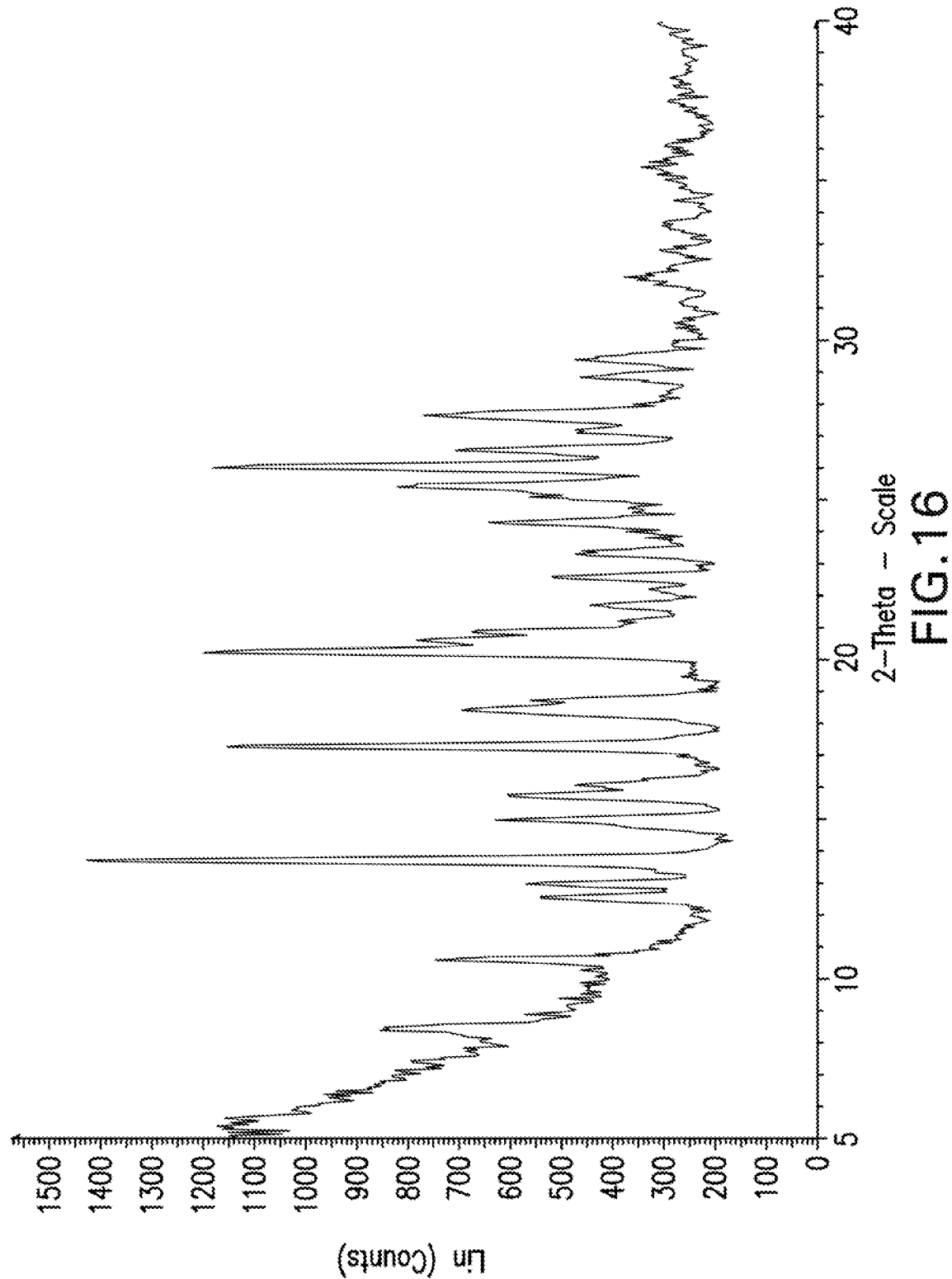
FIG. 16 illustrates the powder X-ray diffraction diagram of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine hydrochloride salt.

In some embodiments, (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide hydrochloride saccharine salt has an XRPD pattern substantially similar to FIG. 16.

Napadisylic Salt

In some embodiments, disclosed is (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide napadisylic salt.

In some embodiments, (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide hydrochloride napadisylic salt has an XRPD pattern comprising at least one peak expressed as 2θ (±0.2°) selected from the peaks listed in Table 27.

Figure 17:
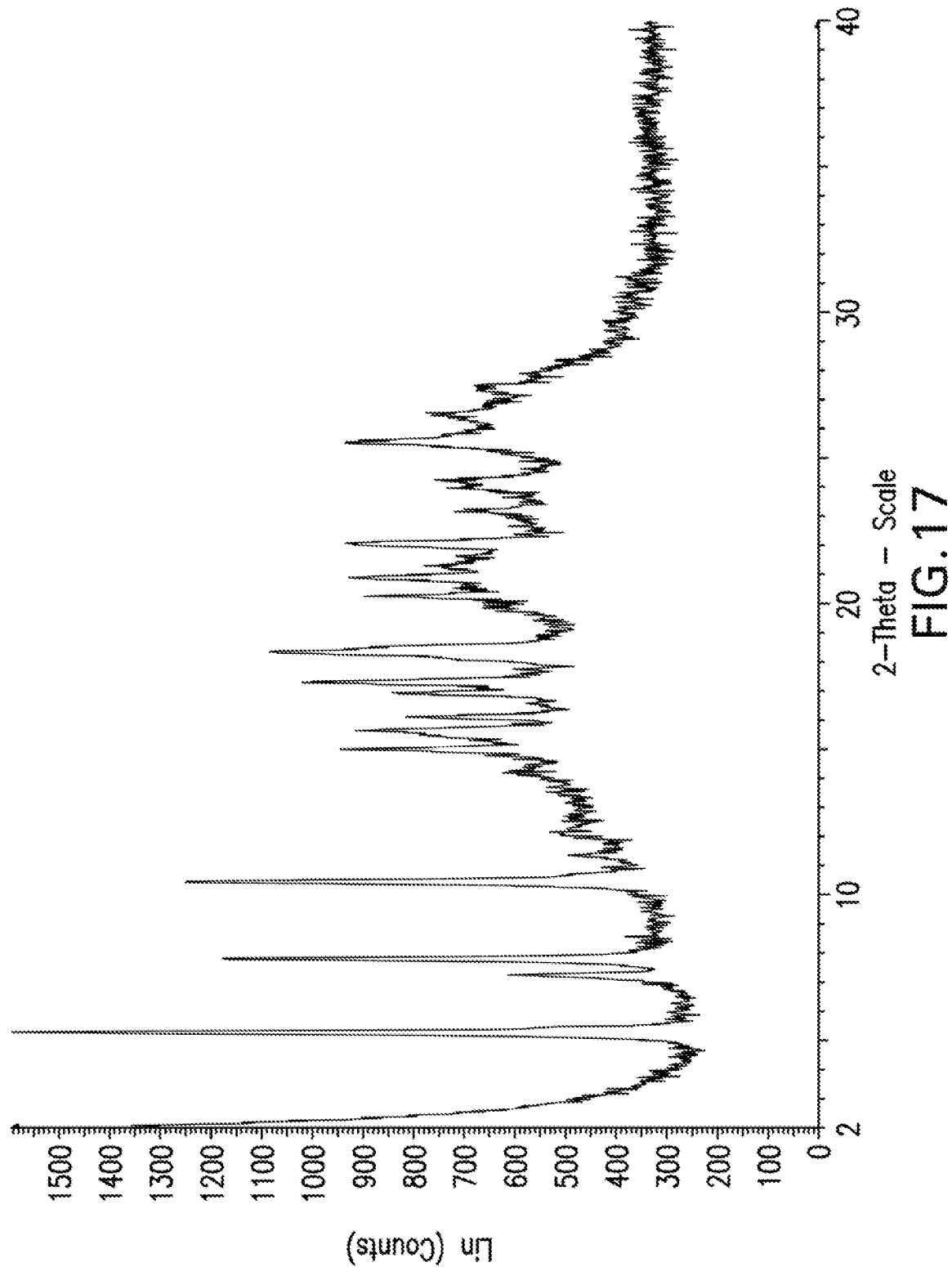
FIG. 17 illustrates the powder X-ray diffraction diagram of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide napadisylic salt.

In some embodiments, (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide napadisylic salt has an XRPD pattern substantially similar to FIG. 17.

Trimesic Salt

In some embodiments, disclosed is (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide trimesic salt.

In some embodiments, (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide hydrochloride trimesic salt has an XRPD pattern comprising at least one peak expressed as 2θ(±0.2°) selected from the peaks listed in Table 28.

Figure 18:
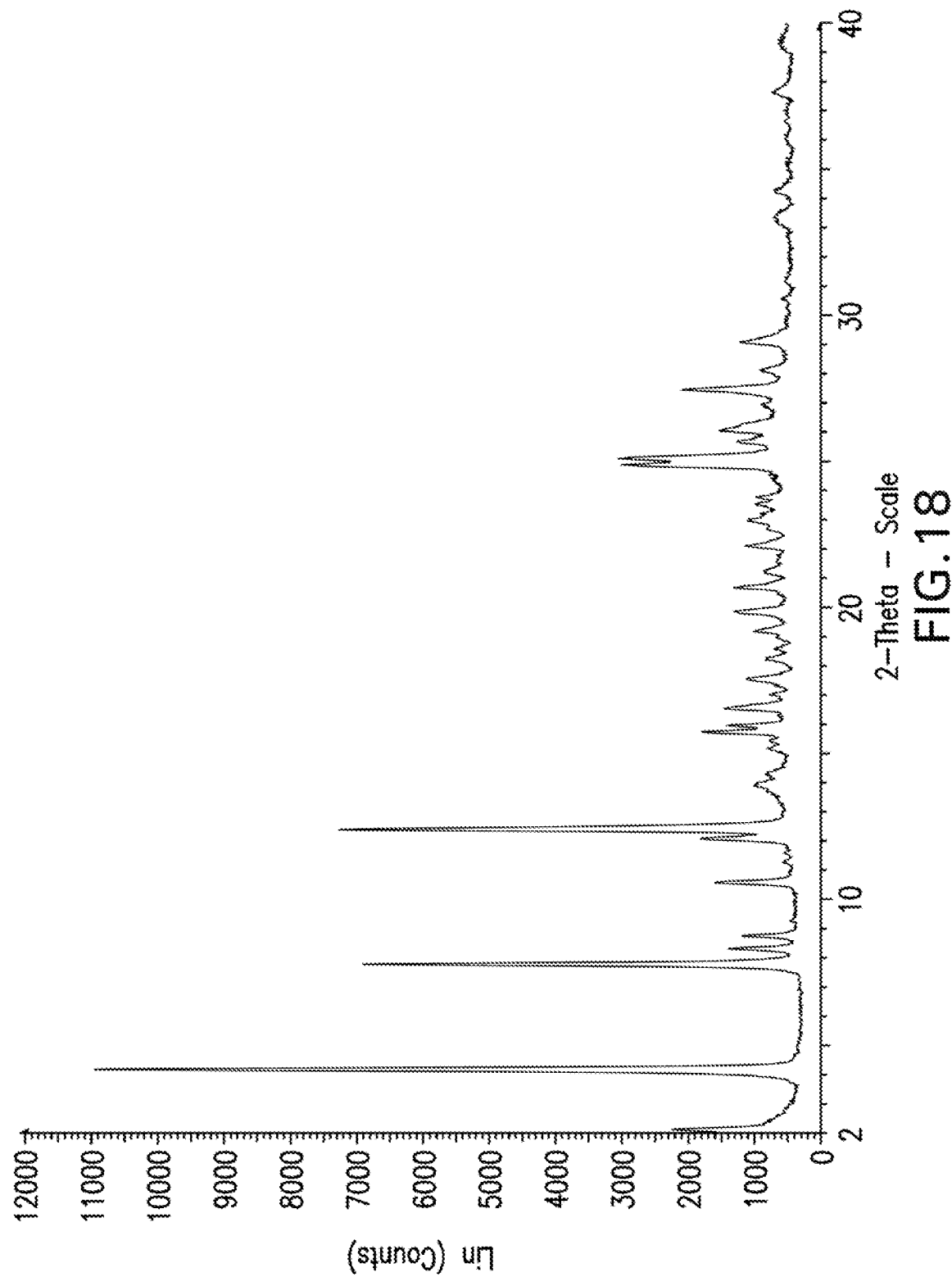
FIG. 18 illustrates the powder X-ray diffraction diagram of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide trimesic salt.

In some embodiments, (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide trimesic salt has an XRPD pattern substantially similar to FIG. 18.

Pharmaceutical Compositions

In some embodiments, disclosed are pharmaceutical compositions comprising a compound of formula (I), (Ia), (Ib) or of Table 1, and a pharmaceutically acceptable excipient, carrier or diluent.

The language "pharmaceutically acceptable excipient, carrier or diluent" includes compounds, materials, compositions, and/or dosage forms which are, within the scope of sound medical judgment, suitable for use in contact with the tissues of human beings and animals without excessive toxicity, irritation, allergic response, or other problem or complication, as ascertained by one of skill in the art.

The disclosed compositions may be in a form suitable for oral use (for example, as tablets, lozenges, hard or soft capsules, aqueous or oily suspensions, emulsions, dispersible powders or granules, syrups or elixirs), for topical use (for example, as creams, ointments, gels, or aqueous or oily solutions or suspensions), for administration by inhalation (for example, as a finely divided powder or a liquid aerosol), for administration by insufflation (for example, as a finely divided powder) or for parenteral administration (for example, as a sterile aqueous or oily solution for intravenous, subcutaneous, intramuscular or intramuscular dosing or as a suppository for rectal dosing).

The disclosed compositions may be obtained by conventional procedures using conventional pharmaceutical excipients well known in the art. Thus, compositions intended for oral use may contain, for example, one or more coloring, sweetening, flavoring and/or preservative agents.

Suitable pharmaceutically acceptable excipients for a tablet formulation include, for example, inert diluents such as lactose, sodium carbonate, calcium phosphate or calcium carbonate; granulating and disintegrating agents such as corn starch or algenic acid; binding agents such as starch; lubricating agents such as magnesium stearate, stearic acid or talc; preservative agents such as ethyl or propyl p-hydroxybenzoate; and anti-oxidants, such as ascorbic acid. Tablet formulations may be uncoated or coated either to modify their disintegration and the subsequent absorption of the active ingredient within the gastrointestinal tract, or to improve their stability and/or appearance using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil, such as peanut oil, liquid paraffin, or olive oil.

Aqueous suspensions generally contain the active ingredient in finely powdered form or in the form of nano or micronized particles together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives such as ethyl or propyl p-hydroxybenzoate; anti-oxidants such as ascorbic acid; coloring agents; flavoring agents; and/or sweetening agents such as sucrose, saccharine or aspartame.

Oily suspensions may be formulated by suspending the active ingredient in a vegetable oil such as arachis oil, olive oil, sesame oil or coconut oil or in a mineral oil such as liquid paraffin. The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compounds of Formula (I), (Ia), (Ib) and Table 1 may be administered once, twice, three times a day or as many times in a 24 hour period as medically necessary. One of skill in the art would readily be able to determine the amount of each individual dose based on the subject. In some embodiments, the compounds of Formula (I), (Ia), (Ib) or Table 1 are administered in one dosage form. In some embodiments, the compounds of formula (I), (Ia), (Ib) or Table are administered in multiple dosage forms.

Methods

In one aspect, disclosed are methods for treating a JAK-related disorder in a subject in need thereof, comprising administering to the subject an effective amount of a compound of Formula (I), (Ia), (Ib) or Table 1, or a pharmaceutically acceptable salt or solid form thereof.

In one aspect, disclosed is a compound of Formula (I), (Ia), (Ib) or Table 1, or a pharmaceutically acceptable salt or solid form thereof, for use in treating a JAK-related disorder.

In one aspect, disclosed is the use of a compound of Formula (I), (Ia), (Ib) or Table 1, or a pharmaceutically acceptable salt or solid form thereof, in the manufacture of a medicament for treating a JAK-related disorder.

In one aspect, disclosed are pharmaceutical compositions comprising a compound of Formula (I), (Ia), (Ib) or Table 1, or a pharmaceutically acceptable salt or solid form thereof, for use in treating a JAK-related disorder.

The language "JAK-related disorder" includes cancer, cancer cachexia and immune disorders.

The term "cancer" includes cancers with: (i) an EGFR-related etiology such as non-small cell lung cancer (NSCLC), head and neck: squamous cell cancer (HNSCC) and colorectal cancer; (ii) and activating RAS family mutations such as NSCLC, pancreatic cancer, colorectal cancer, prostate cancer, melanoma, thyroid cancer, bladder cancer, cholangiocarcinoma, and leukemia; (iii) a HER2 amplification or mutation such as breast cancer, gastric cancer, lung cancer; (iv) an ALK gene activation such as lung cancer, breast cancer, colorectal cancer, diffuse large B-cell lymphoma, anaplastic large cell lymphoma; (v) a MET amplification or mutation such as NSCLC, gastric cancer, colorectal cancer, papillary renal cell carcinoma; and (vi) an FGFR-related etiology such as breast cancer, gastric cancer, endometrial cancer, lung cancer. In some embodiments, the cancer is pancreatic cancer, gastrointestinal cancer, breast cancer, a gynecological cancer (e.g., ovarian cancer or cervical cancer), bladder cancer, SCHN, non-small cell lung cancer or small cell lung cancer. In some embodiments, the cancer has metastasized.

In one aspect, disclosed are methods for treating cancer in a subject in need thereof comprising administering to the subject an effective amount of a compound of Formula (I), (Ia), (Ib), or Table 1, or a pharmaceutically acceptable salt or solid form thereof in combination with an anti-cancer therapeutic agent, or a pharmaceutically acceptable salt thereof.

In one aspect, disclosed is a compound of Formula (I), (Ia), (Ib) or Table 1, or a pharmaceutically acceptable salt or solid form thereof in combination with anti-cancer therapeutic agent, or a pharmaceutically acceptable salt thereof, for use in treating a cancer.

In one aspect, disclosed is the use of a compound of Formula (I), (Ia), (Ib) or Table 1, or a pharmaceutically acceptable salt or solid form thereof, in combination with an anti-cancer therapeutic agent, or a pharmaceutically acceptable salt thereof, in the manufacture of a medicament for treating cancer.

In one aspect, disclosed are pharmaceutical compositions comprising a compound of Formula (I), (Ia), (Ib) or Table 1, or a pharmaceutically acceptable salt or solid form thereof, in combination with an anti-cancer therapeutic agent, or a pharmaceutically acceptable salt thereof, for use in treating cancer.

The language "in combination with" includes administering the compound of Formula (I), (Ia), (Ib) or Table 1, or a pharmaceutically acceptable salt thereof, and the anti-cancer therapeutic agent, or pharmaceutically acceptable salt thereof, sequentially, separately or simultaneously. In some aspects, the compound of Formula (I), (Ia), (Ib) or Table 1, or a pharmaceutically acceptable salt thereof, and the anti-cancer therapeutic agent, or pharmaceutically acceptable salt thereof, are administered in the same formulation, for example, in a fixed dose formulation. In some embodiments, the compound of Formula (I), (Ia), (Ib) or Table 1, or a pharmaceutically acceptable salt thereof, and the anti-cancer therapeutic agent, or pharmaceutically acceptable salt thereof, are administered in separate formulations, and are administered at substantially the same time, sequentially or separately. In some embodiments, the compound of Formula (I), (Ia), (Ib) or Table 1, or pharmaceutically acceptable salt thereof, is administered for one day, two days, three days, four days, five days, six days, seven days, eight days, nine days, ten days, 11 days, 12 days, 13 days, 14 days, three weeks or one month in a row. In some embodiments, compound of Formula (I), (Ia), (Ib) or Table 1, or pharmaceutically acceptable salt thereof, is administered intermittently, for example, for 7 days followed by a 7 day clearance period (e.g., 7 days on/7 days off), for 1 day followed by a 6 day clearance period (e.g., 1 day on/6 days off), for 2 days followed by a 5 day clearance period (2 days on/5 days off), for 3 days followed by a 4 day clearance period (e.g., 3 days on/4 days off), for 4 days followed by a 3 day clearance period (e.g., 4 days on/3 days off), for 5 days followed by a 2 day clearance period (5 days on/2 days off), or for 6 days followed by a 1 day clearance period (6 days on/1 day off).

The language "anti-cancer therapeutic agent" includes, for example, EGFR inhibitors, MAPK pathway inhibitors, Raf inhibitors, HER2 inhibitors, FGFR inhibitors, antimetabolites, alkylating agents and antimitotic agents, and pharmaceutically acceptable salts thereof.

In some embodiments, a compound of Formula (I), (Ia), (Ib) or Table 1 is administered in combination with one or more EGFR inhibitors. Examples of EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib), TAGRISSO™ (osimertinib or AZD9291), GILOTRIF® (afatinib), CO-1686, WZ4002, PD153035, PF 00299804 and the like. In some embodiments, a compound of Formula (I), (Ia), (Ib) or Table 1 is administered in combination with osimertinib. In some embodiments, a compound of Formula (I), (Ia), (Ib) or Table 1 is administered in combination with gefitinib.

In some embodiments, a compound of Formula (I), (Ia), (Ib) or Table 1 is administered in combination with one or more MAPK pathway inhibitors. MAPK pathway inhibitors include MEK inhibitors such as Selumetinib, Mekinist® (trametinib), Cobimetinib, PD0325901, Pimasertib, MEK162, Refametinib and the like; Raf and B-Raf inhibitors which include vemurafenib, dabrafenib, Encorafenib (LGX818) and the like.

In some embodiments, a compound of Formula (I), (Ia), (Ib) or Table 1 is administered in combination with one or more HER2 inhibitors. HER2 inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 bifunctional bispecific antibodies, mAB AR-209, mAB 2B-1 and the like.

In some embodiments, a compound of Formula (I), (Ia), (Ib) or Table 1 is administered in combination with one or more ALK inhibitors. ALK inhibitors include crizotinib, ceritinib, and the like.

In some embodiments, a compound of Formula (I), (Ia), (Ib) or Table 1 is administered in combination with one or more FGFR inhibitors. FGFR inhibitors include AZD4547, BJG398, Dovitinib, Lucitanib, MGFR1877S, FP-1039 and the like.

In some embodiments, a compound of Formula (I), (Ia), (Ib) or Table 1 is administered in combination with one or more MET inhibitors. MET inhibitors include Savolitinib, Onartuzumab, Rilotumumab, Cabozantinib, Tivantinib, LY2875358, Ficlatuzumab, Foretinib, Crizotinib, INC280, AMG337, MSC2156119J and the like In some embodiments, a compound of Formula (I), (Ia), (Ib) or Table 1 is administered in combination with one or more antimetabolites. Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, pemextred, raltitrexed, Ribavirin, triapine, trimetrexate, S-1, tiazofurin, tegafur, TS-1, vidarabine, UFT and the like.

In some embodiments, a compound of Formula (I), (Ia), (Ib) or Table 1 is administered in combination with one or more alkylating agents. Alkylating agents include altretamine, AMD-473, AP-5280, apaziquone, bendamustine, brostallicin, busulfan, cisplatin, carboplatin, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, nitrosoureas, oxaliplatin, ranimustine, temozolomide, thiotepa, TREANDA® (bendamustine), treosulfan, rofosfamide and the like.

In some embodiments, a compound of Formula (I), (Ia), (Ib) or Table 1 is administered in combination with one or more antimitotic agents. Antimitotic agents include batabulin, epothilone D (KOS-862), N-(24(4-hydroxyphenyl) amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

The language "cancer cachexia" includes a syndrome with symptoms that includes host tissue wasting, anorexia, asthenia and abnormal host intermediary metabolism. In some embodiments, the subject suffering from cancer cachexia has pancreatic cancer or an upper gastrointestinal cancer, for example, esophageal cancer, stomach cancer, gastric cancer, liver cancer, gall bladder cancer, neuroendocrine cancer or Barrett's esophagus. In some embodiments, the subject suffering from cancer cachexia has terminal cancer.

In one aspect, disclosed are methods for treating cancer cachexia in a subject in need thereof comprising administering to the subject an effective amount of a compound of Formula (I), (Ia), (Ib), or Table 1, or a pharmaceutically acceptable salt or solid form thereof.

In one aspect, disclosed is a compound of Formula (I), (Ia), (Ib) or Table 1, or a pharmaceutically acceptable salt or solid form thereof, for use in treating cancer cachexia.

In one aspect, disclosed is the use of a compound of Formula (I), (Ia), (Ib) or Table 1, or a pharmaceutically acceptable salt or solid form thereof, in the manufacture of a medicament for treating cancer cachexia.

In one aspect, disclosed are pharmaceutical compositions comprising a compound of Formula (I), (Ia), (Ib) or Table 1, or a pharmaceutically acceptable salt or solid form thereof, for use in treating cancer cachexia.

The language "immune disorder" includes, for example, bone marrow disorders (e.g., myelofibrosis and polycythemia vera), rheumatoid arthritis, psoriasis, irritable bowel disease (IBD), Crohn's disease, lupus, multiple sclerosis, asthma, autoimmune thyroid disorders (e.g., Hashimoto's thyroiditis, Graves' disease or post-partum thyroiditis), ulcerative colitis, Alopecia areata, vitiligo and myositis.

In one aspect, disclosed are methods for treating an immune disorder in a subject in need thereof comprising administering to the subject an effective amount of a compound of Formula (I), (Ia), (Ib), or Table 1, or a pharmaceutically acceptable salt or solid form thereof.

In one aspect, disclosed is a compound of Formula (I), (Ia), (Ib) or Table 1, or a pharmaceutically acceptable salt or solid form thereof, for use in treating an immune disorder.

In one aspect, disclosed is the use of a compound of Formula (I), (Ia), (Ib) or Table 1, or a pharmaceutically acceptable salt or solid form thereof, in the manufacture of a medicament for treating an immune disorder.

In one aspect, disclosed are pharmaceutical compositions comprising a compound of Formula (I), (Ia), (Ib) or Table 1, or a pharmaceutically acceptable salt or solid form thereof, for use in treating an immune disorder.

In one aspect, disclosed are methods for inhibiting JAK in a subject in need thereof, comprising administering to the subject an effective amount of a compound of Formula (I), (Ia), (Ib) or Table 1, or a pharmaceutically acceptable salt or solid form thereof.

In one aspect, disclosed is a compound of Formula (I), (Ia), (Ib) or Table 1, or a pharmaceutically acceptable salt or solid form thereof, for use in inhibiting JAK.

In one aspect, disclosed is the use of a compound of Formula (I), (Ia), (Ib) or Table 1, or a pharmaceutically acceptable salt or solid form thereof, in the manufacture of a medicament for inhibiting JAK.

In one aspect, disclosed are pharmaceutical compositions comprising a compound of Formula (I), (Ia), (Ib) or Table 1, or a pharmaceutically acceptable salt or solid form thereof, for use in inhibiting JAK.

The term "JAK" includes a family of Janus kinases that are intracellular, nonreceptor tyrosine kinases that transduce cytokine-mediated signals via the JAK-STAT pathway. The term JAK includes JAK1, JAK2 and JAK3. In some embodiments, the compounds of Formula (I), (Ia) and (Ib) are selective inhibitors of JAK1, JAK2 and/or JAK3. The language "selective inhibitor" includes compounds that have a greater inhibitory effect (as demonstrated, for example, by a lower $IC_{50}$) for one or two of the JAK family members over the other JAK family members. For example, a JAK1-selective inhibitor exhibits greater inhibitory effect on JAK1 over JAK2 and JAK3; a JAK2-selective inhibitor exhibits a greater inhibitory effect on JAK2 over JAK1 and JAK3; a JAK3-selective inhibitor exhibits a greater inhibitory effect on JAK3 over JAK1 and JAK2; a JAK1/2-selective inhibitor exhibits a greater inhibitory effect on JAK1 and JAK2 over JAK3; a JAK1/3-selective inhibitor exhibits a greater inhibitory effect on JAK1 and JAK3 over JAK2; and a JAK2/3-selective inhibitor exhibits a greater inhibitory effect on JAK2 and JAK3 over JAK1. In some embodiments, the compounds of Formula (I), (Ia) and (Ib) are JAK1-selective inhibitors. In some embodiments, the compounds of Formula (I), (Ia) and (Ib) are JAK1/2-selective inhibitors.

The language "effective amount" includes an amount of a compound of Formula (I), (Ia), (Ib) or Table 1 that will elicit a biological or medical response in a subject, for example, the reduction or inhibition of enzyme or protein activity related to JAK, cancer or an immune disorder; amelioration of symptoms of cancer or an immune disorder; or the slowing or delaying of progression of cancer or an immune disorder. In some embodiments, the language "effective amount" includes the amount of a compound of Formula (I), (Ia), (Ib) or Table 1, that when administered to a subject, is effective to at least partially alleviate, inhibit, and/or ameliorate cancer or an immune disorder or inhibit JAK, and/or reduce or inhibit the growth of a tumor or proliferation of cancerous cells in a subject.

The term "subject" includes warm blooded mammals, for example, primates, dogs, cats, rabbits, rats, and mice. In some embodiments, the subject is a primate, for example, a human. In some embodiments, the subject is suffering from cancer or an immune disorder. In some embodiments, the subject is in need of treatment (e.g., the subject would benefit biologically or medically from treatment). In some embodiments, the subject is suffering from cancer cachexia. In some embodiments, the subject is suffering from cancer. In some embodiments, the subject is suffering from cancer cachexia. In some embodiments, the subject is suffering from an immune disorder. In some embodiments, the subject may have elevated blood levels of inflammatory biomarkers e.g., serum systemic C-reactive protein (CRP), IL-6, TNFa, IL-1, procalcitonin and IL-8. In some embodiments, the subject may be suffering from a high STAT3-positive tumor. In some embodiments, the subject is suffering from a EGFR-M positive cancer (e.g., non-small cell lung cancer). In some embodiments, the EGFR-M positive cancer has a predominately T790M-positive mutation. In some embodiments, the EGFR-M positive cancer has a predominately T790M-negative mutation. In some embodiments, the subject is suffering from a KRAS mutant cancer (e.g., KRAS mutated non-small cell lung cancer). In some embodiments, the subject is suffering from metastatic pancreatic cancer, metastatic gastrointestinal cancer, metastatic breast cancer, a metastatic gynecologic cancer (e.g., metastatic ovarian cancer or metastatic cervical cancer), metastatic bladder cancer, metastatic squamous cell head and neck cancer (SCHN), metastatic non-small cell lung cancer, metastatic haematological cancers (e.g., non-Hodgkin's lymphoma) or metastatic small cell lung cancer. In some embodiments, the subject suffering from cancer may show evidence of immune inflammation, including, for example, the presence of PDL1, interferon gamma, tumor-infiltrating leukocytes and gene expression signatures indicating increased type I or type II interferon signaling, abnormal levels tumor suppressive cells, such as regulatory T lymphocytes or myeloid-derived cells, abnormal levels of granulocytes or proteins indicating the presence of granulocytes.

The language "inhibit," "inhibition" or "inhibiting" includes a decrease in the baseline activity of a biological activity or process. In some embodiments, the compounds of Formula (I), (Ia), (Ib) or Table 1 inhibit JAK.

The language "treat," "treating" and "treatment" includes the reduction or inhibition of enzyme or protein activity related to JAK, cancer or an immune disorder in a subject, amelioration of one or more symptoms of a cancer or an immune disorder in a subject, or the slowing or delaying of progression of cancer or an immune disorder in a subject.

The language "treat," "treating" and "treatment" also includes the reduction or inhibition of the growth of a tumor or proliferation of cancerous cells in a subject.

EXAMPLES

Aspects of the present disclosure can be further defined by reference to the following non-limiting examples, which describe in detail preparation of certain compounds and intermediates of the present disclosure and methods for using compounds of the present disclosure. It will be apparent to those skilled in the art that many modifications, both to materials and methods, can be practiced without departing from the scope of the present disclosure.

Unless stated otherwise:

(i) all syntheses were carried out at ambient temperature, i.e. in the range 17 to 25° C. and under an atmosphere of an inert gas such as nitrogen unless otherwise stated;

(ii) evaporations were carried out by rotary evaporation or utilising Genevac equipment or Biotage v10 evaporator in vacuo and work-up procedures were carried out after removal of residual solids by filtration;

(iii) flash chromatography purifications were performed on an automated Teledyne Isco CombiFlash® Rf or Teledyne Isco CombiFlash® Companion® using prepacked RediSep Rf Gold™ Silica Columns (20-40 μm, spherical particles), GraceResolv™ Cartridges (Davisil® silica) or Silicycle cartridges (40-63 μm).

(iv) preparative chromatography was performed on a Gilson prep HPLC instrument with UV collection; alternatively, preparative chromatography was performed on a Waters AutoPurification HPLC-MS instrument with MS- and UV-triggered collection;

(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection; alternatively, chiral preparative chromatography was performed on a Waters Prep 100 SFC-MS instrument with MS- and UV-triggered collection or a Thar MultiGram III SFC instrument with UV collection.

(vi) yields, where present, are not necessarily the maximum attainable;

(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz), Bruker Avance 400 (400 MHz), Bruker Avance 300 (300 MHz) or Bruker DRX (300 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal.

(viii) in general, end-products of the Formula I were also characterized by mass spectroscopy following liquid chromatography (LCMS or UPLC); UPLC was carried out using a Waters UPLC fitted with a Waters SQ mass spectrometer (Column temp 40° C., UV=220-300 nm or 190-400 nm, Mass Spec=ESI with positive/negative switching) at a flow rate of 1 mL/min using a solvent system of 97% A+3% B to 3% A+97% B over 1.50 min (total run time with equilibration back to starting conditions, etc., 1.70 min), where A=0.1% formic acid or 0.05% trifluoroacetic acid in water (for acidic work) or 0.1% ammonium hydroxide in water (for basic work) and B=acetonitrile. For acidic analysis the column used was a Waters Acquity HSS T3 (1.8 μm, 2.1×50 mm), for basic analysis the column used was a Waters Acquity BEH C18 (1.7 μm 2.1×50 mm). Alternatively, UPLC was carried out using a Waters UPLC fitted with a Waters SQ mass spectrometer (Column temp 30° C., UV=210-400 nm, Mass Spec=ESI with positive/negative switching) at a flow rate of 1 mL/min using a solvent gradient of 2 to 98% B over 1.5 mins (total run time with equilibration back to starting conditions 2 min), where A=0.1% formic acid in water and B=0.1% formic acid in acetonitrile (for acidic work) or A=0.1% ammonium hydroxide in water and B=acetonitrile (for basic work). For acidic analysis the column used was a Waters Acquity HSS T3 (1.8 μm, 2.1×30 mm), for basic analysis the column used was a Waters Acquity BEH C18 (1.7 μm, 2.1×30 mm); LCMS was carried out using a Waters Alliance HT (2795) fitted with a Waters ZQ ESCi mass spectrometer and a Phenomenex Gemini-NX C18 (5 μm, 110A, 2.1×50 mm column at a flow rate of 1.1 mL/min 95% A to 95% B over 4 min with a 0.5 min hold where A=0.1% formic acid and B=0.1% formic acid in acetonitrile (for acidic work) or A=0.1% ammonium hydroxide in water and B=acetonitrile (for basic work). Additionally, LCMS was carried out using a Shimadzu UFLC fitted with a Shimadzu LCMS-2020 mass spectrometer and a Waters HSS C18 (1.8 μm, 2.1×50 mm) or Shim-pack XR-ODS (2.2 μm, 3.0×50 mm) or Phenomenex Gemini-NX C18 (3 μm, 3.0×50 mm) column at a flow rate of 0.7 mL/min (for Waters HSS C18 column), 1.0 mL/min (for Shim-pack XR-ODS column) or 1.2 mL/min (for Phenomenex Gemini-NX C18), 95% A to 95% B over 2.2 min with a 0.6 min hold, where A=0.1% formic acid or 0.05% trifluoroacetic acid in water (for acidic work) or 0.1% ammonium hydroxide or 6.5 mM ammonium carbonate in water (for basic work) and B=acetonitrile. The reported molecular ion corresponds to the [M+H]+ unless otherwise specified; for molecules with multiple isotopic patterns (Br, Cl, etc.) the reported value is the one obtained for the lowest isotope mass unless otherwise specified.

(ix) ion exchange purification was generally performed using an SCX-2 (Biotage) cartridge.

(x) intermediate purity was assessed by thin layer chromatographic, mass spectroscopy, LCMS, UPLC/MS, HPLC (high performance liquid chromatography) and/or NMR analysis;

(xi) the following abbreviations have been used:—
ACN acetonitrile
BID twice a day
BSA bovine serum albumin
DCM dichloromethane
DMF N,N-dimethylformamide
DMSO dimethyl sulphoxide
dppf 1,1'-bis(diphenylphosphino)ferrocene
EA ethyl acetate
ee enantiomeric excess
equiv equivalents
e.r. enantiomeric ratio
EtOH ethanol
HATU (1-[Bis(dimethylamino)methylene]-1H-1,2,3-triazolo[4,5-b]pyridinium 3-oxid hexafluorophosphate)
HCl hydrochloric acid
HPMC hydroxypropyl methylcellulose
IPA Isopropanol
NaOH sodium hydroxide
NSCLC non-small cell lung cancer
QD four times a day
TBME tert-butyl methyl ether TEA triethylamine
TFA trifluoroacetic acid
THF tetrahydrofuran
Tos p-toluenesulfonyl
Xantphos 4,5-bis(diphenylphosphino)-9,9-dimethylxanthene Intermediate 1: 1-[(4-Methylphenyl)sulfonyl]-7-nitro-1H-indole

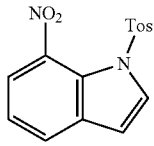

A solution of NaOH (599 g, 14986.55 mmol) in water (1500 mL) was added to a stirred mixture of 7-nitro-1H-indole (243 g, 1498.65 mmol) and tetrabutylammonium hydrogen sulfate (50.9 g, 149.87 mmol) in DCM (3000 mL) at 25° C., over a period of 5 minutes under air. The resulting mixture was stirred at 25° C. for 20 minutes. 4-methylphenylsulfonyl chloride (371 g, 1948.25 mmol) was added under air and the resulting mixture was stirred at 25° C. for 16 hours. The reaction mixture was diluted with DCM (2 L), and washed sequentially with water (500 mL×2), 10% aqueous $K_2CO_3$ (500 mL×2), and 1 M HCl (500 mL×2) and saturated NaCl (500 mL×2). The organic layer was dried over $Na_2SO_4$, filtered and evaporated. When approximately 200 mL DCM was left, 500 mL EA was added. The solvent was removed under reduced pressure. When approximately 200 mL EA was left, 1000 mL TBME was added. The precipitate was collected by filtration, washed with TBME (1 L) and dried under vacuum to afford 1-[(4-methylphenyl)sulfonyl]-7-nitro-1H-indole (402 g, 85%, Intermediate 1) as a white solid, which was used without further purification; 1H NMR δ (DMSO-d6, 300 MHz) 2.39 (3H, s), 7.09 (1H, d), 7.40-7.55 (3H, m), 7.75-7.85 (3H, m), 7.95-8.00 (1H, m), 8.06 (1H, d); m/z (ES+), [M+H]+=317.

Intermediate 2: 3-Bromo-1-[(4-methylphenyl)sulfonyl]-7-nitro-1H-indole

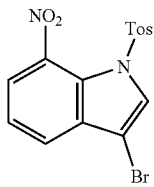

Bromine (81 mL, 1580 mmol) was added dropwise to 1-[(4-methylphenyl)sulfonyl]-7-nitro-1H-indole (50 g, 158 mmol, Intermediate 1) in $CCl_4$ (1000 mL) at 80° C. The resulting solution was stirred at 80° C. for 6 hours. The mixture was cooled to room temperature, concentrated and the residue was washed with ethyl acetate to afford 3-bromo-1-[(4-methylphenyl)sulfonyl]-7-nitro-1H-indole (53 g, 85%, Intermediate 2) as a brown solid; $^1$H NMR δ (DMSO-d6, 300 MHz) 2.41 (3H, s), 7.55-7.62 (2H, m), 7.57 (1H, t), 7.85-7.92 (3H, m), 7.96 (1H, d), 8.49 (1H, s); m/z (ES−), [M−H]−=393.

Intermediate 3: 1-[(4-Methylphenyl)sulfonyl]-7-nitro-3-(4,4,5,5-tetramethyl-1,3,2-dioxaborolan-2-yl)-1H-indole

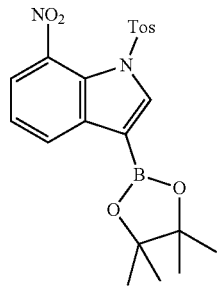

A solution of 3-bromo-1-[(4-methylphenyl)sulfonyl]-7-nitro-1H-indole (200 g, 506 mmol, Intermediate 2), 4,4,4',4',5,5,5',5'-octamethyl-2,2'-bi(1,3,2-dioxaborolane) (193 g, 759 mmol), potassium acetate (99 g, 1012 mmol) and $PdCl_2(dppf)$ (18.5 g, 25.3 mmol) in 1,4-dioxane (1500 mL) was degassed with nitrogen three times, then the reaction mixture was stirred at 90° C. for 8 hours. The mixture was cooled to room temperature and concentrated. The solids were treated with water and filtered. Washing with methanol and drying in vacuo afforded the 1-[(4-methylphenyl)sulfonyl]-7-nitro-3-(4,4,5,5-tetramethyl-1,3,2-dioxaborolan-2-yl)-1H-indole (150 g, 67%, Intermediate 3) as a grey solid; $^1$H NMR δ (Chloroform-d, 400 MHz) 1.41 (12H, s), 2.47 (3H, s), 7.38-7.43 (3H, m), 7.66 (1H, d), 7.87 (2H, d), 8.24 (1H, s), 8.29-8.32 (1H, d); m/z (ES+), [M+H]+=443.

Intermediate 4: 3-(2-Chloro-4-pyrimidinyl)-1-[(4-methylphenyl)sulfonyl]-7-nitro-1H-indole

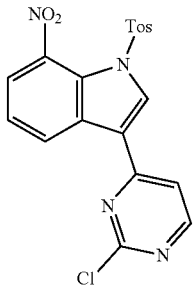

1-[(4-Methylphenyl)sulfonyl]-7-nitro-3-(4,4,5,5-tetramethyl-1,3,2-dioxaborolan-2-yl)-1H-indole (15 g, 33.9 mmol, Intermediate 3), 2,4-dichloropyrimidine (6.6 g, 44.1 mmol), potassium carbonate (14.1 g, 101.7 mmol) and $PdCl_2(dppf)$ (2.5 g, 3.4 mmol) in dioxane (200 mL) and water (40 mL) were stirred under nitrogen at 80° C. for 12 hours. The solvent was removed under reduced pressure. The aqueous layer was extracted with THF (4×100 mL) and concentrated to give 3-(2-chloro-4-pyrimidinyl)-1-[(4-methylphenyl)sulfonyl]-7-nitro-1H-indole (12 g, 83%, Intermediate 4) as a brown solid, which was used without further purification; $^1$H NMR δ (DMSO-d6, 300 MHz) 2.42 (3H, s), 7.52 (2H, d), 7.68 (1H, t), 7.98 (3H, m), 8.31 (1H, d), 8.85-8.90 (2H, m), 9.30 (1H, s); m/z (ES+), [M+H]+=429.

The procedure described above was repeated using the indicated dichloropyrimidine to give Intermediates 5-8 described in Table 2:

TABLE 2

| Intermediate | Dichloropyrimidine | NMR δ (300 MHz) | m/z [M + H]+ | Yield % |
|---|---|---|---|---|
| 5<br>3-(2-chloro-5-fluoro-4-pyrimidinyl)-1-[(4-methylphenyl)sulfonyl]-7-nitro-1H-indole | (2,4-dichloro-5-fluoropyrimidine) | DMSO-d6 2.43 (3H, s), 7.52 (2H, d), 7.70 (1H, t), 8.00 (3H, m), 8.76 (1H, s), 8.82 (1H, d), 9.04 (1H, d) | 447 | 76 |
| 6<br>3-(2-chloro-5-methyl-4-pyrimidinyl)-1-[(4-methylphenyl)sulfonyl]-7-nitro-1H-indole | (2,4-dichloro-5-methylpyrimidine) | DMSO-d6 2.47 (3H, s), 2.50 (3H, s), 7.56 (2H, d), 7.68 (1H, dd), 7.97 (2H, d), 8.04 (1H, d), 8.47 (1H, d), 8.68 (1H, s), 8.85 (1H, s) | 443 | 83 |
| 7<br>3-(2,5-dichloro-4-pyrimidinyl)-1-[(4-methylphenyl)sulfonyl]-7-nitro-1H-indole | (2,4,5-trichloropyrimidine) | DMSO-d6 2.40 (3H, s), 7.52 (2H, d), 7.65 (1H, d), 7.91 (2H, d), 8.00 (1H, d), 8.50 (1H, d), 8.88 (1H, s), 9.06 (1H, s) | 463 | 82 |
| 8<br>3-(5-bromo-2-chloro-4-pyrimidinyl)-1-[(4-methylphenyl)sulfonyl]-7-nitro-1H-indole | (5-bromo-2,4-dichloropyrimidine) | DMSO-d6 2.38 (3H, s), 7.46 (2H, d), 7.62 (1H, t), 7.88 (2H, d), 7.95 (1H, d), 8.35 (1H, d), 8.88 (1H, s), 9.16 (1H, s) | 509 | 51 |

Intermediate 9: 3-(2-Chloro-4-pyrimidinyl)-7-nitro-1H-indole

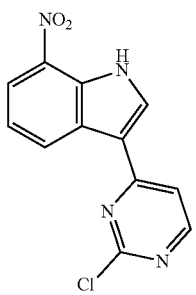 [SMILES: O=[N+]([O-])c1cccc2c(-c3ccnc(Cl)n3)c[nH]c12]

3-(2-Chloro-4-pyrimidinyl)-1-[(4-methylphenyl)sulfonyl]-7-nitro-1H-indole (1 g, 2.3 mmol, Intermediate 4) and sodium hydroxide (1.86 g, 46.6 mmol) in THF (10 mL) and water (5 mL) was stirred at 50° C. for 2 hours. The solvent was removed under reduced pressure. The crude product was purified by flash silica chromatography, elution gradient 0 to 10% methanol in ethyl acetate. Pure fractions were evaporated to dryness to afford 3-(2-chloro-4-pyrimidinyl)-7-nitro-1H-indole (0.52 g, 81%, Intermediate 9) as a yellow solid; $^1$H NMR δ (DMSO-d6, 300 MHz) 7.45 (1H, t), 8.10 (1H, s), 8.19 (1H, d), 8.60 (1H, d), 8.66 (1H, s), 8.94 (1H, d), 12.70 (1H, s); m/z (ES+), [M+H]+=275.

The procedure described above was repeated using the indicated Starting Intermediate to give Intermediates 10-13 described in Table 3:

TABLE 3

| Intermediate | Starting Intermediate | NMR δ (300 MHz) | m/z [M + H]+ | Yield % |
|---|---|---|---|---|
| 10<br>3-(2-chloro-5-fluoro-4-pyrimidinyl)-7-nitro-1H-indole | 5 | DMSO-d6 7.42 (1H, t), 8.14 (1H, d), 8.33 (1H, d), 8.69 (1H, d), 8.92 (1H, d) 12.72 (1H, s) | 293 | 89 |
| 11<br>3-(2-chloro-5-methyl-4-pyrimidinyl)-7-nitro-1H-indole | 6 | DMSO-d6 2.52 (3H, s), 7.46 (1H, t), 8.20 (1H, s), 8.24 (1H, d), 8.62 (1H, s), 8.89 (1H, d), 12.65 (1H, s) | 289 | 77 |
| 12<br>3-(2,5-dichloro-4-pyrimidinyl)-7-nitro-1H-indole | 7 | DMSO-d6 7.50 (1H, t), 8.24 (1H, d), 8.65 (1H, m), 8.89 (1H, s), 8.92 (1H, d), 12.78 (1H, s) | 309 | 70 |
| 13<br>3-(5-bromo-2-chloro-4-pyrimidinyl)-7-nitro-1H-indole | 8 | DMSO-d6 7.48 (1H, t), 8.25 (1H, d), 8.75 (1H, s), 8.83 (1H, d), 8.97 (1H, d), 12.77 (1H, s) | 355 | 80 |

Intermediate 14: N-(3-Methoxy-1-methyl-1H-pyrazol-4-yl)-4-(7-nitro-1H-indol-3-yl)pyrimidin-2-amine

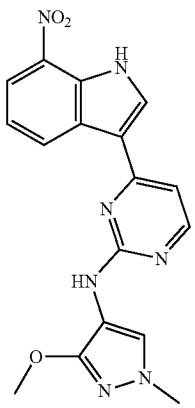

3-(2-Chloro-4-pyrimidinyl)-7-nitro-1H-indole (300 mg, 1.1 mmol, Intermediate 9), 3-methoxy-1-methyl-1H-pyrazol-4-amine dihydrochloride (328 mg, 1.64 mmol) and 4-methylbenzenesulfonic acid monohydrate (623 mg, 3.28 mmol) were dissolved in isopropanol (16 mL) and sealed into a microwave tube. The reaction was heated at 130° C. for 2 hours in the microwave reactor and cooled to room temperature. The reaction was concentrated under reduced pressure and then filtered to give N-(3-methoxy-1-methyl-1H-pyrazol-4-yl)-4-(7-nitro-1H-indol-3-yl)pyrimidin-2-amine (300 mg, 75%, Intermediate 14) as a yellow solid and was used in the next step directly without further purification; $^1$H NMR δ (DMSO-d6, 300 MHz) 3.77 (3H, s), 3.83 (3H, s), 7.39-7.49 (1H, m), 7.70 (1H, d), 7.83 (1H, s), 825-8.43 (2H, m), 8.71 (1H, d), 9.33 (1H, br s), 10.26 (1H, br s), 12.91 (1H, s); m/z (ES+), [M+H]+=366.

The procedure described above was repeated using the indicated aminopyrazole and Starting Intermediate to give Intermediates 15-22 described in Table 4:

TABLE 4

| Intermediate | Starting Intermediate | Aminopyrazole | NMR δ (300 MHz) | m/z [M + H]+ | Yield % |
|---|---|---|---|---|---|
| 15<br>5-fluoro-N-(3-methoxy-1-methyl-1H-pyrazol-4-yl)-4-(7-nitro-1H-indol-3-yl)pyrimidin-2-amine | 10 | | DMSO-d6 3.71 (3H, s), 3.78 (3H, s), 7.32 (1H, t), 7.68 (1H, s), 8.13 (1H, d), 8.17-8.27 (1H, m), 8.37 (1H, d), 8.55 (1H, s), 12.52 (1H, s) | 384 | 84 |
| 16<br>N-(3-methoxy-1-methyl-1H-pyrazol-4-yl)-5-methyl-4-(7-nitro-1H-indol-3-yl)-2-pyrimidinamine | 11 | | DMSO-d6 2.36 (3H, s), 3.68 (3H, s), 3.80 (3H, s7.26 (1H, t), 7.65 (1H, s), 8.01 (1H, s), 8.15-8.23 (2H, m)), 8.93 (1H, br s), 12.35 (1H, br s) | 380 | 95 |
| 17<br>5-chloro-N-(3-methoxy-1-methyl-1H-pyrazol-4-yl)-4-(7-nitro-1H-indol-3-yl)pyrimidin-2-amine | 12 | | Not obtained | 400 | 55 |
| 18<br>5-bromo-N-(3-methoxy-1-methyl-1H-pyrazol-4-yl)-4-(7-nitro-1H-indol-3-yl)pyrimidin-2-amine | 13 | | Not obtained | 444 | 80 |
| 19<br>N-(3-ethoxy-1-methyl-1H-pyrazol-4-yl)-5-fluoro-4-(7-nitro-1H-indol-3-yl)pyrimidin-2-amine | 10 | | DMSO-d6 1.25 (3H, t), 3.73 (3H, s), 4.18 (2H, q), 7.20-7.53 (1H, m), 7.68 (1H, s), 8.11-8.30 (2H, m), 8.35 (1H, d), 8.43 (1H, s), 9.04 (1H, s) | 398 | 74 |

TABLE 4-continued

| Intermediate | Starting Intermediate | Aminopyrazole | NMR δ (300 MHz) | m/z [M + H]+ | Yield % |
|---|---|---|---|---|---|
| 20 N-(3-ethoxy-1-methyl-1H-pyrazol-4-yl)-5-methyl-4-(7-nitro-1H-indol-3-yl)pyrimidin-2-amine | 11 | | DMSO-d6 1.25 (3H, t), 2.36 (3H, s), 3.68 (3H, s), 4.16 (2H, q), 7.27 (1H, t), 7.64 (1H, s), 7.95-8.15 (2H, m), 8.20 (2H, m), 8.94 (1H, br s), 12.35 (1H, s) | 394 | 74 |
| 21 N-(1,3-dimethyl-1H-pyrazol-4-yl)-5-methyl-4-(7-nitro-1H-indol-3-yl)pyrimidin-2-amine | 11 | | DMSO-d6 2.09 (3H, s), 2.47 (3H, s), 3.81 (3H, s), 7.38 (1H, s), 7.87 (1H, s), 8.19-8.33 (3H, m), 9.66 (1H, s), 12.79 (1H, s) | 364 | 62 |
| 22 5-chloro-N-(3-ethoxy-1-methyl-1H-pyrazol-4-yl)-4-(7-nitro-1H-indol-3-yl)pyrimidin-2-amine | 12 | | Not obtained | 414 | 100 |

Intermediate 23: 3-{2-[(3-Methoxy-1-methyl-1H-pyrazol-4-yl)amino]pyrimidin-4-yl}-1H-indol-7-amine

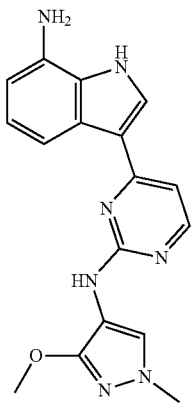 [SMILES: COc1nn(C)cc1Nc1nccc(-c2c[nH]c3c(N)cccc23)n1]

Iron (0.46 g, 8.2 mmol) was added to N-(3-methoxy-1-methyl-1H-pyrazol-4-yl)-4-(7-nitro-1H-indol-3-yl)pyrimidin-2-amine (0.6 g, 1.6 mmol, Intermediate 14) and ammonium chloride (0.88 g, 16.4 mmol) in THF (100 mL) and water (50 mL) at 25° C. under nitrogen. The resulting mixture was stirred at 80° C. for 2 hours. The reaction mixture was filtered through diatomaceous earth. The solvent was removed under reduced pressure and the crude product was purified by flash C18 silica chromatography, elution gradient 30 to 80% methanol in water. Pure fractions were evaporated to dryness to afford 3-{2-[(3-methoxy-1-methyl-1H-pyrazol-4-yl)amino]pyrimidin-4-yl}-1H-indol-7-amine (0.41 g, 74%, Intermediate 23) as a yellow solid; $^1$H NMR δ (DMSO-d6, 400 MHz) 3.68 (3H, s), 3.72 (3H, s), 5.10 (2H, s), 6.40 (1H, d), 6.82 (1H, t), 7.05 (1H, d), 7.60-7.73 (2H, m), 8.05 (1H, s), 8.10-8.21 (2H, m), 11.29 (1H, s); m/z (ES+), [M+H]+=336.

The procedure described above was repeated using the indicated Starting Intermediate to give Intermediates 24-31 described in Table 5:

TABLE 5

| Intermediate | Starting Intermediate | NMR δ (300 MHz) | m/z [M + H]+ | Yield % |
|---|---|---|---|---|
| 24 3-{5-fluoro-2-[(3-methoxy-1-methyl-1H-pyrazol-4-yl)amino]pyrimidin-4-yl}-1H-indol-7-amine | 15 | DMSO-d6 3.71 (3H, s), 3.79 (3H, s), 5.17 (2H, s), 6.44 (1H, d), (6.83 1H, t), 7.67 (1H, s), 7.79 (1H, s), 8.04-8.10 (1H, m), 8.19-8.26 (2H, m), 11.48 (1H, s) | 354 | 79 |
| 25 3-{2-[(3-methoxy-1-methyl-1H-pyrazol-4-yl)amino]-5-methylpyrimidin-4-yl}-1H-indol-7-amine | 16 | DMSO-d6 2.32 (3H, s), 3.66 (3H, s), 3.79 (3H, s), 5.10 (2H, br s), 6.40 (1H, dd), 6.79 (1H, t), 7.68 (2H, s), 7.81-7.92 (2H, m), 8.11 (1H, s), 11.23 (1H, s) | 350 | 61 |
| 26 3-{5-chloro-2-[(3-methoxy-1-methyl-1H-pyrazol-4-yl)amino]pyrimidin-4-yl}-1H-indol-7-amine | 17 | DMSO-d6 3.77 (3H, s), 3.81 (3H, s), 5.12 (2H, s), 6.40 (1H, d), 6.79 (1H, d), 6.88 (1H, s), 7.55-7.60 (1H, m), 8.26 (1H, s), 8.35 (2H, s), 11.41 (1H, s) | 370 | 67 |
| 27 3-{5-bromo-2-[(3-methoxy-1-methyl-1H-pyrazol-4-yl)amino]pyrimidin-4-yl}-1H-indol-7-amine | 18 | DMSO-d6 3.63 (3H, s), 3.78 (3H, s), 5.12 (2H, s), 6.40 (1H, d), 6.90 (1H, t), 7.60-7.65 (2H, m), 8.37 (2H, s), 8.43 (1H, d), 11.37 (1H, s) | 414 | 92 |
| 28 3-{2-[(1,3-dimethyl-1H-pyrazol-4-yl)amino]-5-methylpyrimidin-4-yl}-1H-indol-7-amine | 21 | Not obtained | 334 | 70 |

TABLE 5-continued

| Intermediate | Starting Intermediate | NMR δ (300 MHz) | m/z [M + H]+ | Yield % |
|---|---|---|---|---|
| 29 3-{2-[(3-ethoxy-1-methyl-1H-pyrazol-4-yl)amino]-5-fluoropyrimidin-4-yl}-1H-indol-7-amine | 19 | DMSO-d6 1.25 (3H, t), 3.68 (3H, s), 4.14 (2H, q), 5.15 (2H, s), 6.43 (1H, d), 6.82 (1H, t), 7.64 (1H, s), 7.78 (1H, s), 8.01-8.17 (2H, m), 8.22 (1H, d), 11.46 (1H, s) | 368 | 67 |
| 30 3-{2-[(3-ethoxy-1-methyl-1H-pyrazol-4-yl)amino]-5-methylpyrimidin-4-yl}-1H-indol-7-amine | 20 | Methanol-d4 1.38 (3H, t), 2.39 (3H, s), 3.72 (3H, s), 4.26 (2H, q), 6.64 (1H, d), 6.96 (1H, t), 7.74 (3H, m), 8.14 (1H, s)—four exchangeable protons not observed | 364 | 93 |
| 31 3-{5-chloro-2-[(3-ethoxy-1-methyl-1H-pyrazol-4-yl)amino]pyrimidin-4-yl}-1H-indol-7-amine | 22 | Not obtained | 384 | 56 |

Intermediate 32: (2S)-2-Bromo-N-(3-{2-[(3-methoxy-1-methyl-1H-pyrazol-4-yl)amino]pyrimidin-4-yl}-1H-indol-7-yl)propanamide

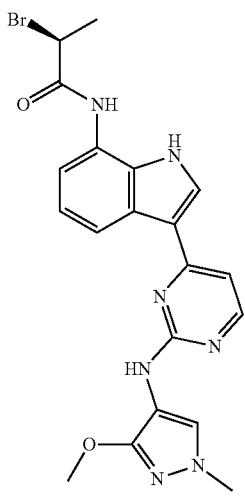 [SMILES: COc1nn(C)cc1Nc1nccc(-c2c[nH]c3c(NC(=O)[C@H](C)Br)cccc23)n1]

1-Propanephosphonic acid cyclic anhydride (25.6 g, 40.3 mmol) was added dropwise to 3-{2-[(3-methoxy-1-methyl-1H-pyrazol-4-yl)amino]pyrimidin-4-yl}-1H-indol-7-amine (4.5 g, 13.4 mmol, Intermediate 23), (S)-2-bromopropanoic acid (4.1 g, 26.8 mmol) and pyridine (3.3 mL, 40.3 mmol) in ethyl acetate (100 mL) at −50° C. over a period of 30 minutes under nitrogen. The resulting mixture was stirred at −50° C. for 1 hour. The reaction was allowed to warm up to −15° C. and stirred for 16 hour. The reaction mixture was quenched with ice water (100 mL), extracted with ethyl acetate (3×200 mL), the organic layer was dried, filtered and evaporated to afford a tan solid. The crude product was purified by flash silica chromatography, elution gradient 100 to 0% petroleum ether in ethyl acetate. Pure fractions were evaporated to dryness to afford (2S)-2-bromo-N-(3-{2-[(3-methoxy-1-methyl-1H-pyrazol-4-yl)amino]pyrimidin-4-yl}-1H-indol-7-yl)propanamide (4.9 g, 78%, Intermediate 32) as a yellow solid; $^1$H NMR δ (DMSO-d6, 400 MHz) 1.76 (3H, d), 3.60 (1H, m), 3.62 (3H, s), 3.71 (3H, s), 4.83 (1H, q), 7.01-7.16 (2H, m), 7.41 (1H, d), 7.71 (1H, s), 8.20 (1H, d), 8.26 (1H, d), 8.27 (1H, s), 10.12 (1H, s), 11.26 (1H, s); m/z (ES+), [M+H]+=470.

The procedure described above was repeated using the indicated Starting Intermediate to give Intermediates 33-36 described in Table 6:

TABLE 6

| Intermediate | Starting Intermediate | NMR δ (300 MHz) | m/z [M + H]+ | Yield % |
|---|---|---|---|---|
| 33 (2S)-2-bromo-N-(3-{5-fluoro-2-[(3-methoxy-1-methyl-1H-pyrazol-4-yl)amino]pyrimidin-4-yl}-1H-indol-7-yl)propanamide | 24 | DMSO-d6 1.85 (3H, d), 3.72 (3H, s), 3.79 (3H, s), 4.81 (1H, q), 7.09 (1H, t), 7.50 (1H, d), 7.67 (1H, s), 8.19 (1H, t), 8.29 (1H, d), 8.39 (2H, d), 10.22 (1H, s), 11.43 (1H, s) | 490 | 94 |
| 34 (2S)-2-bromo-N-(3-{2-[(3-methoxy-1-methyl-1H-pyrazol-4-yl)amino]-5-methylpyrimidin-4-yl}-1H-indol-7-yl)propanamide | 25 | DMSO-d6 1.84 (3H, d), 2.33 (3H, s), 3.68 (3H, s), 3.78 (3H, s), 4.80 (1H, q), 7.03 (1H, t), 7.45 (1H, d), 7.66 (1H, s), 7.99 (1H, s), 8.00 (1H, s), 8.15 (1H, s), 8.26 (1H, s), 10.14 (1H, s), 11.22 (1H, s) | 484 | 66 |
| 35 (2S)-2-bromo-N-(3-{2-[(3-ethoxy-1-methyl-1H-pyrazol-4-yl)amino]-5-fluoropyrimidin-4-yl}-1H-indol-7-yl)propanamide | 29 | DMSO-d6 1.24 (3H, t), 1.84 (3H, d), 3.70 (3H, s), 4.14 (2H, q), 4.80 (1H, q), 7.07 (1H, t), 7.49 (1H, d), 7.65 (1H, s), 8.18 (1H, t), 8.28 (3H, d), 10.21 (1H, s), 11.27-11.63 (1H, m) | 502 | 86 |
| 36 (2S)-2-bromo-N-(3-{2-[(3-ethoxy-1-methyl-1H-pyrazol-4-yl)amino]-5-methylpyrimidin-4-yl}-1H-indol-7-yl)propanamide | 30 | DMSO-d6 1.30 (3H, t), 1.86 (3H, d), 2.35 (3H, s), 3.60-3.65 (1H, m), 3.68 (3H, s), 4.11 (2H, q), 4.84 (1H, q), 7.03 (1H, t), 7.47 (1H, d), 7.66 (1H, s), 7.95 (1H, s), 8.17 (1H, s), 8.28 (1H, s), 10.15 (1H, s), 11.23 (1H, s) | 500 (Br isotope value) | 62 |

Intermediate 37: (R)-2-(4-Methylpiperazin-1-yl)propanoic Acid Dihydrochloride

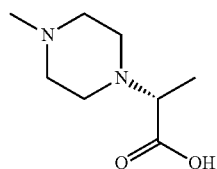

Trifluoromethanesulfonic anhydride (53.6 mL, 317 mmol) was added dropwise to (S)-methyl 2-hydroxypropanoate (30 g, 288 mmol) and 2,6-lutidine (37 mL, 317 mmol) in DCM (500 mL) at −78° C. over a period of 1 hour. The resulting solution was stirred at −78° C. for 0.5 hours. The solution was then warmed to room temperature for 1 hour. The organic phase was washed with 1N HCl (aq.) (2×100 mL) and dried over sodium sulfate, then filtered and evaporated. The residue was dissolved in DCM (500 mL), cooled to 0° C., then 1-methylpiperazine (65 g, 646 mmol) was added slowly. Potassium carbonate (212 g, 1537 mmol) in water (700 mL) was added dropwise at 0° C. The solution was stirred at 25° C. overnight, then washed with brine, dried over sodium sulfate, filtered and evaporated to give a yellow oil. 6N (aq.) HCl (270 mL, 1625 mmol) was added in one portion at 25° C. and the resulting mixture was stirred at 110° C. for 18 hours. The solution was evaporated and the product washed with acetonitrile (200 mL) to afford an off-white solid. This solid was suspended in isopropanol (1000 mL) and was stirred for 3 hours at 100° C. and then stirred for 16 hours at room temperature. The precipitate was collected by filtration, washed with isopropanol (150 mL) and dried under vacuum to afford (2R)-2-(4-methylpiperazin-1-yl)propanoic acid dihydrochloride (15 g, 48%, Intermediate 37) as a white solid; $^1$H NMR δ (D2O, 400 MHz) 1.51 (3H, d), 2.94 (3H, s), 3.48-4.13 (9H, m); m/z (ES+), [M+H]+=173.

The procedure described above was repeated using the indicated 2-hydroxypropanoate and piperazine to give the Intermediates 38 and 39 described in Table 7:

ethyl)trimethylsilane (4.1 mL, 23 mmol) was added rapidly dropwise. After 5 minutes the cooling bath was removed and the reaction left to stir at ambient temperature for 1.5 hours. Additional sodium hydride (60% dispersion in mineral oil) (130 mg, 3.3 mmol) and (2-(chloromethoxy)ethyl)trimethylsilane (0.4 mL, 2.3 mmol) were added. The reaction was stirred for an additional 40 minutes then quenched with saturated aqueous NaHCO₃ and the pale yellow mixture was diluted with ether. The layers were separated and the aqueous layer extracted with ether. The combined organic layer was washed with brine, dried over magnesium sulfate, filtered and evaporated. The residue was dissolved in chloroform and was subject to silica gel chromatography using 5-45% ethyl acetate-hexane as eluent to afford 3-(2-chloro-5-methyl-4-pyrimidinyl)-7-nitro-1-{[2-(trimethylsilyl)ethoxy]methyl}-1H-indole (9.2 g, 100%, Intermediate 40) as a yellow solid; $^1$H NMR δ (DMSO-d6, 400 MHz) −0.16 (9H, s), 0.60-0.73 (2H, m), 2.51-2.52 (3H, m), 3.11-3.22 (2H, m), 5.72 (2H, s), 7.48 (1H, t), 7.94 (1H, dd), 8.57 (1H, s), 8.64 (1H, s), 8.84 (1H, dd); m/z (ES+), [M+H]+=419.

TABLE 7

| Intermediate | Piperazine | Hydroxy-propanoate | NMR δ (300 MHz) | m/z [M + H]+ | Yield % |
|---|---|---|---|---|---|
| 38 (2S)-2-(4-methylpiperazin-1-yl)propanoic acid dihydrochloride | | (R)-methyl 2-hydroxypropanoate | DMSO-d6 1.54 (3H, d), 2.83 (3H, s), 3.69 (8H, d), 4.30 (1H, s), 11.84 (1H, s) | 173 | 100 |
| 39 (2R)-2-[(2R)-2,4-dimethylpiperazin-1-yl]propanoic acid dihydrochloride | | (S)-methyl 2-hydroxypropanoate | Methanol-d4 1.26 (3H, d), 1.43 (3H, d), 2.90 (4H, s), 3.05-3.21 (2H, m), 3.34-3.40 (2H, m), 3.42-3.49 (1H, m), 3.53 (1H, br s), 4.07 (1H, q) | 187 | 95 |

Intermediate 40: 3-(2-Chloro-5-methyl-4-pyrimidinyl)-7-nitro-1-{[2-(trimethylsilyl)ethoxy]methyl}-1H-indole

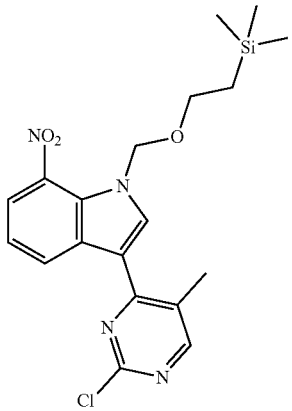 [SMILES: Cc1cnc(Cl)nc1-c1cn(COCC[Si](C)(C)C)c2c([N+](=O)[O-])cccc12]

Sodium hydride (60% dispersion in mineral oil) (1.3 g, 33 mmol) was added portion-wise to a stirred suspension of 3-(2-chloro-5-methyl-4-pyrimidinyl)-7-nitro-1H-indole (6.4 g, 22 mmol, Intermediate 11) in anhydrous THF (150 mL) at 0° C. After stirring for 25 minutes, (2-(chloromethoxy)

Intermediate 41: N-(3-Methoxy-1-methyl-1H-pyrazol-4-yl)-5-methyl-4-(7-nitro-1-{[2-(trimethylsilyl)ethoxy]methyl}-1H-indol-3-yl)pyrimidin-2-amine

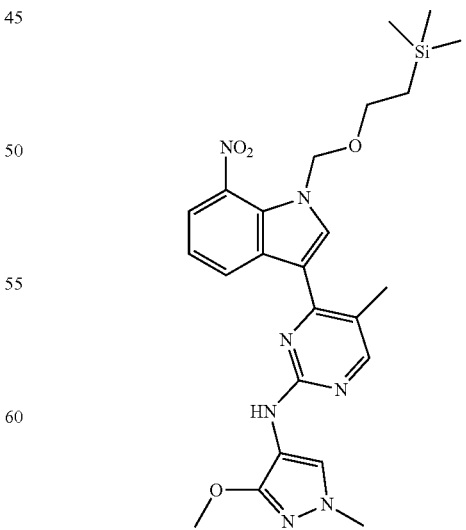

A mixture of dioxane and water (10:1, 44 mL) was added to a mixture of 3-(2-chloro-5-methyl-4-pyrimidinyl)-7-nitro-1-{[2-(trimethylsilyl)ethoxy]methyl}-1H-indole (1.59 g, 3.8 mmol, Intermediate 40), 3-methoxy-1-methyl-1H-pyrazol-4-amine dihydrochloride (1.7 g, 10.4 mmol), palladium (II) acetate (0.085 g, 0.4 mmol), Xantphos (0.22 g, 0.4 mmol) and cesium carbonate (4.95 g, 15.2 mmol) under nitrogen. The mixture was then heated at 110° C. for 3.5 hours under nitrogen. The mixture was allowed to cool to ambient temperature, diluted with ethyl acetate, filtered through diatomaceous earth and concentrated. The resultant gum was subject to silica gel chromatography using 30-100% ethyl acetate-hexane as eluent to afford N-(3-methoxy-1-methyl-1H-pyrazol-4-yl)-5-methyl-4-(7-nitro-1-{[2-(trimethylsilyl)ethoxy]methyl}-1H-indol-3-yl)pyrimidin-2-amine (1.3 g, 67%, Intermediate 41) as a pale yellow solid; $^1$H NMR δ (DMSO-d6, 400 MHz) −0.17 (9H, s), 0.60-0.74 (2H, m), 2.35 (3H, s), 3.05-3.20 (2H, m), 3.68 (3H, s), 3.79 (3H, s), 5.69 (2H, s), 7.23-7.36 (1H, m), 7.65 (1H, s), 7.86 (1H, d), 8.19 (1H, br s), 8.23 (1H, s), 8.35 (1H, s), 8.67-9.02 (1H, m); m/z (ES+), [M+H]+=510.

Intermediate 42: 3-{2-[(3-Methoxy-1-methyl-1H-pyrazol-4-yl)amino]-5-methylpyrimidin-4-yl}-1-{[2-(trimethylsilyl)ethoxy]methyl}-1H-indol-7-amine

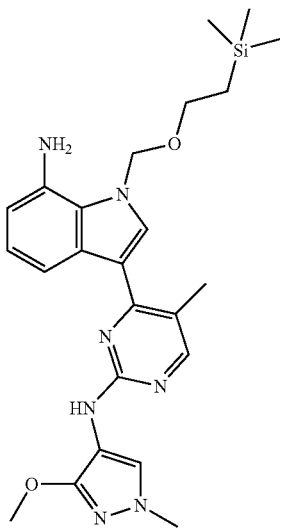 [SMILES: COc1nn(C)cc1Nc1ncc(C)c(-c2cn(COCC[Si](C)(C)C)c3c(N)cccc23)n1]

A mixture of N-(3-methoxy-1-methyl-1H-pyrazol-4-yl)-5-methyl-4-(7-nitro-1-{[2-(trimethylsilyl)ethoxy]methyl}-1H-indol-3-yl)pyrimidin-2-amine (1.26 g, 2.5 mmol, Intermediate 41) in methanol-ethyl acetate (1:1, 20 mL) was subject to hydrogenation at atmospheric pressure in the presence of 10% palladium on carbon (w/w) (0.26 g, 0.25 mmol) at ambient temperature for 23 hours. The slurry was diluted with ethyl acetate and filtered through diatomaceous earth, then concentrated to afford 3-{2-[(3-methoxy-1-methyl-1H-pyrazol-4-yl)amino]-5-methylpyrimidin-4-yl}-1-{[2-(trimethylsilyl)ethoxy]methyl}-1H-indol-7-amine (1.1 g, 93%, Intermediate 42) as a pale yellow solid; $^1$H NMR δ (DMSO-d6, 400 MHz) −0.05 (9H, s), 0.86-0.96 (2H, m), 2.30 (3H, s), 3.51-3.62 (2H, m), 3.65 (3H, s), 3.79 (3H, s), 4.97-5.05 (2H, m), 5.72 (2H, s), 6.53 (1H, d), 6.83 (1H, t), 7.65 (1H, s), 7.70 (1H, br s), 7.90 (1H, s), 7.95 (1H, s), 8.13 (1H, s); m/z (ES+), [M+H]+=480.

Intermediate 43: 2-(4-Methylpiperazin-1-yl)butanoic Acid

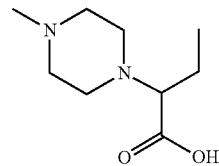

Ethyl 2-bromobutanoate (30 g, 154 mmol) was added dropwise to 1-methylpiperazine (61.6 g, 615 mmol) in THF (500 mL) at 0° C. over a period of 30 minutes under nitrogen. The resulting mixture was stirred at 25° C. for 12 hours. The solvent was removed under reduced pressure. The mixture was made basic with saturated aqueous potassium carbonate and extracted with ethyl acetate (3×150 mL). The combined organic layers were evaporated to give a yellow oil which was added dropwise to 6N (aq.) HCl (200 mL, 1200 mmol) at 0° C. over a period of 10 minutes under air. The resulting mixture was stirred at 100° C. for 16 hours. The reaction mixture was cooled to room temperature before being washed with ethyl acetate (100 mL). The water was removed under reduced pressure to give 2-(4-methylpiperazin-1-yl)butanoic acid hydrochloride (35 g, 96%, Intermediate 43) as a white solid that was used in the next step directly without further purification; $^1$H NMR δ (DMSO-d6, 300 MHz) 0.93 (3H, t), 1.76-2.09 (2H, m), 2.80 (3H, s), 3.29-3.69 (8H, m), 3.99 (1H, br s), 11.84 (1H, s); m/z (ES+), [M+H]+=187.

Intermediate 44: Methyl 3-methoxy-2-(4-methylpiperazin-1-yl)propanoate

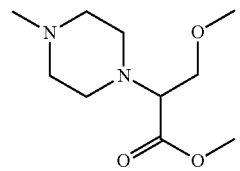

Potassium carbonate (1.38 g, 10.1 mmol) was added to a stirred solution of 1-methylpiperazine (0.93 mL, 8.3 mmol) and methyl 2-bromo-3-methoxypropanoate (1.7 g, 8.6 mmol) in acetonitrile (20 mL) under a nitrogen atmosphere. The pale yellow mixture was then warmed to 60° C. for 21 hours. The reaction was cooled to ambient temperature, diluted with ethyl acetate and filtered. Concentration afforded methyl 3-methoxy-2-(4-methylpiperazin-1-yl)propanoate (1.69 g, 94%) as an orange oil which was used without further purification; $^1$H NMR δ (DMSO-d6, 400 MHz) 2.12 (3H, s), 2.20-2.36 (4H, m), 2.48-2.56 (5H, m), 3.21-3.25 (3H, s), 3.39 (1H, dd), 3.48-3.53 (1H, m), 3.63 (3H, s); m/z (ES+), [M+H]+=217.

Intermediate 45: Lithium 3-methoxy-2-(4-methylpiperazin-1-yl)propanoate

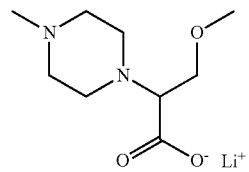

A solution of lithium hydroxide (52 mg, 2.2 mmol) in water (3 mL) was added to a stirred solution of methyl 3-methoxy-2-(4-methylpiperazin-1-yl)propanoate (0.47 g, 2.2 mmol, Intermediate 44) in THF (3 mL) at ambient temperature. After stirring for 21 hours the reaction was warmed to 40° C. for 22 hours. A few drops of methanol were added, clarifying the pale yellow solution and heating continued. After 2 hours, additional lithium hydroxide (16 mg, 0.7 mmol) was added and the reaction left to stir for 4 days. The solvent was removed under reduced pressure and the aqueous solution lyophilized to afford the lithium 3-methoxy-2-(4-methylpiperazin-1-yl)propanoate (0.45 g, 98%) as an off-white solid; $^1$H NMR δ (DMSO-d6, 400 MHz) 2.10 (3H, s), 2.27 (4H, br s), 2.51-2.60 (4H, m), 2.87 (1H, t), 3.19 (3H, s), 3.50-3.60 (2H, m); m/z (ES+), [M+H]+ =203.

The procedure described for Example 32 was repeated using the indicated Starting Intermediates to give Intermediates 46 and 47 described in Table 8:

TABLE 8

| Intermediate | Starting Intermediates | NMR δ (400 MHz) | m/z [M + H]+ | Yield % |
| --- | --- | --- | --- | --- |
| 46 N-(3-{2-[(3-methoxy-1-methyl-1H-pyrazol-4-yl)amino]-5-methylpyrimidin-4-yl}-1-{2-[2-(trimethylsilyl)ethoxy]ethyl}-1H-indol-7-yl)-2-(4-methylpiperazin-1-yl)butanamide | 42 and 43 | DMSO-d6 −0.07 (9H, s), 0.86 (2H, dd), 0.98 (3H, t), 1.68-1.84 (2H, m), 2.33 (4H, s), 2.80 (2H, br s), 3.07 (3H, m), 3.17 (4H, s), 3.40-3.52 (4H, m), 3.67 (3H, s), 3.79 (3H, s), 5.66-5.75 (2H, m), 7.10 (1H, t), 7.34 (1H, d), 7.65 (1H, s), 8.05 (1H, br s), 8.11 (1H, s), 8.18 (1H, s), 9.33 (1H, br s), 9.72 (1H, s) | 648 | 81 |
| 47 3-methoxy-N-(3-{2-[(3-methoxy-1-methyl-1H-pyrazol-4-yl)amino]-5-methylpyrimidin-4-yl}-1-{[2-(trimethylsilyl)ethoxy]methyl}-1H-indol-7-yl)-2-(4-methylpiperazin-1-yl)propanamide | 42 and 45 | DMSO-d6 −0.08 (9H, s), 0.83-0.94 (2H, m), 2.33 (3H, s), 2.58-3.14 (11H, m), 3.41-3.51 (3H, m), 3.67 (3H, s), 3.70-3.86 (6H, m), 5.64-5.86 (3H, m), 7.09 (1H, t), 7.30 (1H, d), 7.64 (1H, s), 8.05 (1H, s), 8.10 (1H, s), 8.18 (1H, s), 8.30(1H, br s), 9.36 (1H, br s), 9.84 (1H, s) | 664 | 82 |

Intermediate 48:
3-(2-Chloropyrimidin-4-yl)-1H-indol-7-amine

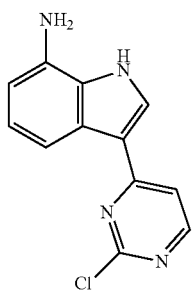 [SMILES: Nc1cccc2c(-c3ccnc(Cl)n3)c[nH]c12]

Ammonium chloride (7.8 g, 146 mmol) was added to 3-(2-chloro-4-pyrimidinyl)-7-nitro-1H-indole (4 g, 14.6 mmol, Intermediate 9) and iron (4.1 g, 72 mmol) in THF (200 mL) and water (100 mL) at 25° C. under nitrogen. The resulting mixture was stirred at 80° C. for 12 hours. The reaction mixture was filtered through diatomaceous earth. The organic phase was separated and the aqueous phase was extracted with THF (2×100 mL). The organic phases were combined and concentrated to afford 3-(2-chloropyrimidin-4-yl)-1H-indol-7-amine (3 g, 84%, Intermediate 48) as a green solid; $^1$H NMR δ (DMSO-d6, 400 MHz) 5.42 (2H, s), 6.44 (1H, d), 6.91 (1H, m), 7.60 (1H, d), 7.78-7.91 (1H, m), 8.36 (1H, s), 8.45 (1H, d)-NH proton obscured; m/z (ES+), [M+MeCN]+=286.

The procedure described above for Intermediate 48 was repeated using the indicated Starting Intermediate to give Intermediates 49 and 50 described in Table 9:

TABLE 9

| Intermediate | Starting Intermediate | NMR δ (400 MHz) | m/z [M + H]+ | Yield % |
| --- | --- | --- | --- | --- |
| 49 3-(2-chloro-5-methylpyrimidin-4-yl)-1H-indol-7-amine | 11 | DMSO-d6 2.50 (3H, s), 5.26 (2H, s), 6.47 (1H, dd), 6.92 (1H, t), 7.76 (1H, d), 8.12 (1H, d), 8.45 (1H, s), 11.71 (1H, d) | 259 | 80 |
| 50 3-(2-chloro-5-fluoropyrimidin-4-yl)-1H-indol-7-amine | 10 | Methanol-d4 6.68 (1H, dd), 7.06 (1H, t), 8.04 (1H, dd), 8.18(1H, d), 8.39 (1H, d)—three exchangeable protons not observed | 263 | 79 |

Intermediate 51: N-[3-(2-Chloropyrimidin-4-yl)-1H-indol-7-yl]-2-(4-methylpiperazin-1-yl)butanamide

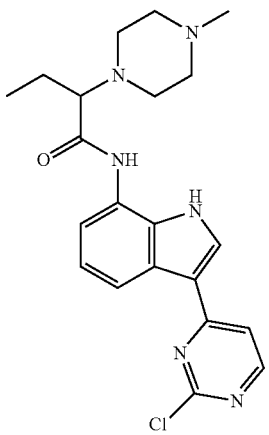 [SMILES: CCC(C(=O)Nc1cccc2c(-c3ccnc(Cl)n3)c[nH]c12)N1CCN(C)CC1]

1-Propanephosphonic acid cyclic anhydride (7.8 g, 12.3 mmol) was added dropwise to 3-(2-chloropyrimidin-4-yl)-1H-indol-7-amine (1 g, 4.1 mmol, Intermediate 48), 2-(4-methylpiperazin-1-yl)butanoic acid dihydrochloride (1.3 g, 4.9 mmol, Intermediate 43) and pyridine (2 mL, 25 mmol) in DMF (100 mL) at 0° C. over a period of 10 minutes under nitrogen. The resulting mixture was stirred at 25° C. for 2 hours. The solvent was removed under reduced pressure and the crude product purified by reverse phase silica (C18) gel chromatography using 0-100% methanol in water to give N-[3-(2-chloropyrimidin-4-yl)-1H-indol-7-yl]-2-(4-methylpiperazin-1-yl)butanamide (0.24 g, 14%, Intermediate 51) as a yellow solid; $^1$H NMR δ (Methanol-d4, 300 MHz) 1.08 (3H, t), 1.79-2.02 (2H, m), 2.32 (3H, s), 2.58 (4H, s), 2.84 (4H, m), 3.10-3.27 (1H, m), 7.25 (2H, m), 7.77 (1H, d), 8.27 (1H, s), 8.37 (1H, dd), 8.44 (1H, d)-two exchangeable protons not observed; m/z (ES+), [M+H]+=413.

The procedure described above for Intermediate 51 was repeated using the indicated Starting Intermediates to give Intermediates 52-55 described in Table 10:

TABLE 10

| Intermediate | Starting Intermediates | NMR δ (300 MHz) | m/z [M + H]+ | Yield % |
|---|---|---|---|---|
| 52 N-[3-(2-chloro-5-fluoropyrimidin-4-yl)-1H-indol-7-yl]-2-(4-methylpiperazin-1-yl)butanamide | 50 and 43 | Not obtained | 431 | 89 |
| 53 N-[3-(2-chloro-5-fluoropyrimidin-4-yl)-1H-indol-7-yl]-3-methoxy-2-(4-methylpiperazin-1-yl)propanamide | 50 and 45 | DMSO-d6 2.27 (3H, s), 2.41 (4H, br s), 2.64 (2H, m), 2.77 (2H, m), 3.29 (3H, s), 3.50-3.73 (2H, m), 3.79 (1H, dd), 7.23 (1H, t), 7.59 (1H, dd), 8.29-8.44 (2H, m), 8.71 (1H, d), 9.97 (1H, s), 11.85 (1H, s) | 447 | 47 |
| 54[1, 2] (R)-N-[3-(2-chloro-5-methylpyrimidin-4-yl)-1H-indol-7-yl]-2-(4-methylpiperazin-1-yl)propanamide | 49 and 37 | DMSO-d6 1.28 (3H, d), 2.24 (3H, s), 2.51-2.71 (11H, m), 3.39 (1H, m), 7.18 (1H, t), 7.50 (1H, d), 8.19 (1H, s), 8.31 (1H, d), 8.52 (1H, s), 9.76 (1H, s), 11.69 (1H, s) | 413 | 81 |
| 55[3] (R)-N-[3-(2-chloro-5-fluoropyrimidin-4-yl)-1H-indol-7-yl]-2-(4-methylpiperazin-1-yl)propanamide | 50 and 37 | DMSO-d6 1.27 (3H, d), 2.27 (3H, s), 2.35-2.68 (8H, m), 3.39 (1H, q), 7.24 (1H, t), 7.53 (1H, d), 8.34-8.37 (2H, m), 8.72 (1H, d), 9.83 (1H, s), 11.90 (1H, s) | 417 | 79 |

[1]$^1$H NMR analysis was performed using a Bruker Avance 400 (400 MHz) spectrometer.
[2]The indicated amino acid (1.5 equiv) and 7-amino-indole intermediates were reacted in the presence of HATU (2 equiv) and diisopropylethylamine (4 equiv) in DMF at room temperature.
[3]The indicated amino acid (1.3 equiv) and 7-amino-indole intermediates were reacted in the presence of HATU (1.5 equiv) and diisopropylethylamine (5 equiv) in DMF at room temperature.

Intermediate 56: 3-(2-Chloropyrimidin-4-yl)-7-nitro-1-{[2-(trimethylsilyl)ethoxy]methyl}-1H-indole

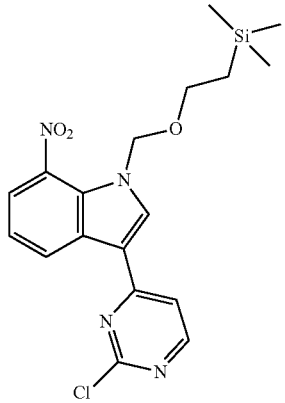 [SMILES: C[Si](C)(C)CCOCn1cc(-c2ccnc(Cl)n2)c2cccc([N+](=O)[O-])c21]

3-(2-Chloropyrimidin-4-yl)-7-nitro-1H-indole (4.4 g, 16 mmol, Intermediate 9) was dissolved in THF (60 mL) and cooled to 0° C. Sodium hydride (1.2 g, 29 mmol) was then added and the reaction mixture was warmed to room temperature. (2-(Chloromethoxy)ethyl)trimethylsilane (4.3 mL, 24 mmol) was then slowly added and the reaction mixture was allowed to stir for 1.5 hours. The reaction mixture was quenched with aqueous sodium bicarbonate, and extracted with ethyl acetate. The organic layers were dried over sodium sulfate, filtered, and concentrated giving the crude product as a red oil which was purified via silica gel column chromatography using 0-40% ethyl acetate-hexanes as eluent to give 3-(2-chloropyrimidin-4-yl)-7-nitro-1-{[2-(trimethylsilyl)ethoxy]methyl}-1H-indole (5.7 g, 88%, Intermediate 56) as a yellow solid; $^1$H NMR δ (DMSO-d6, 300 MHz) −0.16 (9H, s), 0.67 (2H, t), 3.19 (2H, t), 5.66 (2H, s), 7.51 (1H, s), 7.88-8.01 (2H, m), 8.71 (1H, d), 8.88 (1H, s), 8.91 (1H, s); m/z (ES+), [M+H]+=405.

Intermediate 57: 3-(2-Chloropyrimidin-4-yl)-1-{[2-(trimethylsilyl)ethoxy]methyl}-1H-indol-7-amine

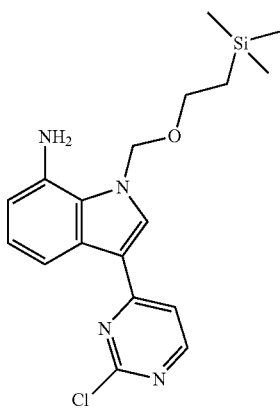 [SMILES: C[Si](C)(C)CCOCn1cc(-c2ccnc(Cl)n2)c2cccc(N)c21]

3-(2-Chloropyrimidin-4-yl)-7-nitro-1-{[2-(trimethylsilyl)ethoxy]methyl}-1H-indole (5.7 g, 14.1 mmol, Intermediate 56) was dissolved in methanol (47 mL), THF (47 mL) and water (47 mL). The solution was then heated to 60° C. and ammonium chloride (32.8 g, 612 mmol) was added, followed by iron (34.4 g, 617 mmol). The solution was then allowed to stir for 2 hours at 60° C. The reaction mixture was partitioned between water and diethyl ether. The organic layers were extracted and combined, dried over sodium sulfate, filtered, and concentrated to give 3-(2-chloropyrimidin-4-yl)-1-{[2-(trimethylsilyl)ethoxy]methyl}-1H-indol-7-amine (5.2 g, 98%, Intermediate 57) as a yellow oil; $^1$H NMR δ (DMSO-d6, 300 MHz) −0.04 (9H, m), 0.92 (2H, t), 3.60 (2H, t), 5.15 (2H, s), 5.71 (2H, s), 6.59-6.62 (1H, m), 7.00 (1H, t), 7.70 (1H, dd), 7.80 (1H, d), 8.50 (1H, s), 8.55 (1H, d); m/z (ES+), [M+H]+=375.

Intermediate 58: (2R)—N-[3-(2-Chloropyrimidin-4-yl)-1-{[2-(trimethylsilyl)ethoxy]methyl}-1H-indol-7-yl]-2-(4-methylpiperazin-1-yl)propanamide

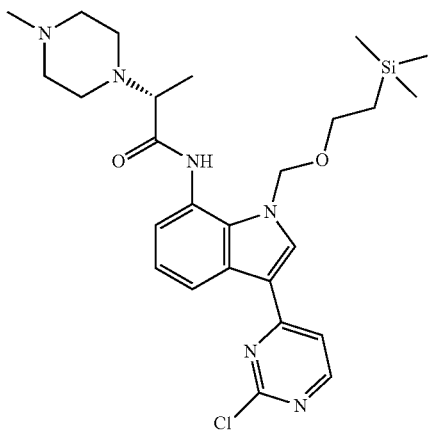

(R)-2-(4-Methylpiperazin-1-yl)propanoic acid dihydrochloride (2.45 g, 10 mmol, Intermediate 37) was dissolved in DMF (15 mL) and di(1H-imidazol-1-yl)methanone (1.3 g, 8 mmol) was added. Gas evolved, and the reaction mixture was allowed to stir under nitrogen at room temperature until the reaction mixture became homogeneous. 3-(2-Chloropyrimidin-4-yl)-1-{[2-(trimethylsilyl)ethoxy]methyl}-1H-indol-7-amine (1.5 g, 4 mmol, Intermediate 57) in DMSO (11 mL) was then added and the reaction mixture was stirred overnight. The reaction was quenched with 10% potassium carbonate solution and extracted with ethyl acetate. The organic layers were combined, dried over sodium sulfate, filtered, and concentrated. The crude product was purified via silica gel column chromatography using 100% ethyl acetate then 0-20% methanol-DCM as eluent to give (2R)—N-[3-(2-chloropyrimidin-4-yl)-1-{[2-(trimethylsilyl)ethoxy]methyl}-1H-indol-7-yl]-2-(4-methylpiperazin-1-yl)propanamide (0.92 g, 43%, Intermediate 58) as a yellow solid; $^1$H NMR δ (Chloroform-d, 300 MHz) −0.10 (9H, s), 0.96-1.08 (2H, m), 1.40 (3H, d), 2.36 (3H, m), 2.47-2.92 (8H, m), 3.27 (1H, q), 3.51-3.64 (2H, m), 5.54-5.79 (2H, m), 7.36 (1H, t), 7.58 (1H, d), 7.79 (1H, d), 7.96 (1H, s), 8.12 (1H, d), 8.54 (1H, d), 9.72 (1H, br s); m/z (ES+), [M+H]+=529.

Intermediate 59: (2R)—N-[3-(2-Chloropyrimidin-4-yl)-1H-indol-7-yl]-2-(4-methylpiperazin-1-yl)propanamide (2R)—N-[3-(2-Chloropyrimidin-4-yl)-1-{[2-(trimethylsilyl)ethoxy]methyl}-1H-indol-7-yl]-2-(4-methylpiperazin-1-yl)propanamide (0.38 g, 0.7 mmol, Intermediate 58) was dissolved in DMSO (7 mL) and cesium fluoride (0.32 g, 2.1 mmol) was added. The reaction mixture was then heated at 100° C. and allowed to stir for 2 hours. The reaction mixture was diluted with ethyl acetate and water. The organic layer was separated and the aqueous layer was extracted with ethyl acetate. The organic layers were combined, dried over sodium sulfate, filtered, and concentrated to give (2R)—N-[3-(2-chloropyrimidin-4-yl)-1H-indol-7-yl]-2-(4-methylpiperazin-1-yl)propanamide (0.17 g, 59%) as a yellow solid; $^1$H NMR δ (Chloroform-d, 300 MHz) 1.43 (3H, d), 2.32-3.02 (11H, m), 3.39 (1H, m), 6.84 (1H, m), 7.22-7.25 (1H, m), 7.52 (1H, d), 8.03 (1H, d), 8.34 (1H, d), 8.47 (1H, d), 9.81 (1H, br. s), 11.58 (1H, br s); m/z (ES+), [M+H]+=399.

Example 1: (2R)-2-[(2S)-2,4-Dimethylpiperazin-1-yl]-N-(3-{2-[(3-methoxy-1-methyl-1H-pyrazol-4-yl)amino]pyrimidin-4-yl}-1H-indol-7-yl)propanamide

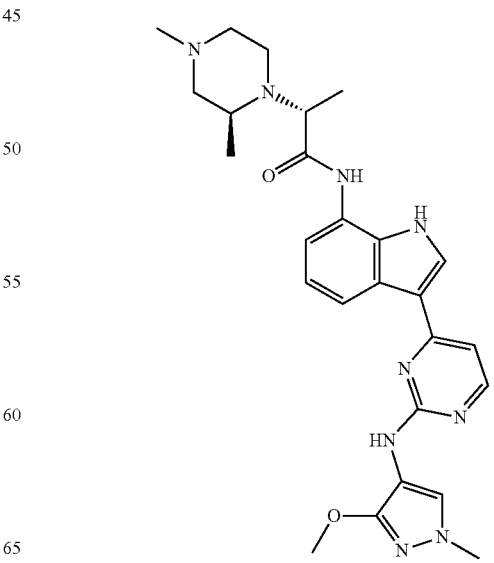

(S)-1,3-Dimethylpiperazine dihydrochloride (0.16 g, 0.85 mmol) was added in one portion to (2S)-2-bromo-N-(3-{2-[(3-methoxy-1-methyl-1H-pyrazol-4-yl)amino]pyrimidin-4-yl}-1H-indol-7-yl)propanamide (0.2 g, 0.43 mmol, Intermediate 32) and potassium carbonate (0.24 g, 1.7 mmol) in DMF (2 mL) at 0° C. The resulting solution was stirred at 25° C. for 16 hours. The crude product was purified by preparative HPLC (X Bridge C18, 5 μm, 19×150 mm; Mobile Phase A: water/0.05% TFA, Mobile Phase B: acetonitrile; Flow rate: 20 mL/min; Gradient: 20% B to 70% B in 10 min; 254 nm) to afford (2R)-2-[(2S)-2,4-dimethylpiperazin-1-yl]-N-(3-{2-[(3-methoxy-1-methyl-1H-pyrazol-4-yl)amino]pyrimidin-4-yl}-1H-indol-7-yl)propanamide (49 mg, 23%, Example 1) as a white solid; 1H NMR δ (Methanol-d4, 400 MHz) 1.15 (3H, d), 1.43 (3H, d), 2.06 (1H, t), 2.32 (3H, s), 2.41 (1H, m), 2.75-2.92 (3H, m), 3.01 (2H, m), 3.79-3.83 (4H, m), 3.94 (3H, s), 7.12-7.19 (3H, dt), 7.73 (1H, s), 8.09 (1H, s), 8.19 (1H, d), 8.27 (1H, s); m/z (ES+), [M+H]+=504; chiral HPLC (ChiralPak ADH, 5 μm, 0.46×10 cm, mobile phase: 1:1 hexanes (modified with 0.1% TEA) and ethanol at 1.0 mL/min) indicates 99:1 e.r., retention time=9.24 min.

The procedure described above for Example 1 was repeated using the indicated piperazine and Starting Intermediate to give the compounds described in Table 11:

TABLE 11

| Example | Starting Intermediate | Piperazine | NMR δ (300 MHz) | m/z [M + H]+ | Yield % |
|---|---|---|---|---|---|
| 2 | 33 | (2-methylpiperazine, N-methyl) | Methanol-d4 1.14 (3H, d), 1.42 (3H, d), 2.26-2.38 (5H, m), 2.52 (2H, m), 2.86-3.01 (3H, m), 3.39 (1H, m), 3.79 (3H, s), 3.92 (3H, s), 7.10-7.22 (2H, m), 7.68 (1H, s), 8.14 (2H, dd), 8.42 (1H, s) | 522 | 47 |
| 3[1] | 33 | (4-(2-methoxyethyl)piperazine) | Methanol-d4 1.42 (3H, d), 2.61-2.84 (10H, m), 3.36 (4H, s), 3.58 (2H, t), 3.79 (3H, s), 3.91 (3H, s), 7.10-7.22 (2H, m), 7.68 (1H, s), 8.14 (2H, dd), 8.42 (1H, s) | 552 | 70 |
| 4[1] | 33 | (1-ethylpiperazine) | Methanol-d4 1.15 (3H, t), 1.43 (3H, d), 2.51 (2H, q), 2.56-2.90 (8H, m), 3.34-3.45 (1H, m), 3.79 (3H, s), 3.92 (3H, s), 7.10-7.22 (2H, m), 7.68 (1H, s), 8.14 (2H, dd), 8.42 (1H, s) | 522 | 62 |
| 5 | 33 | (N-methyl-2-methylpiperazine) | Methanol-d4 1.14 (3H, d), 1.42 (3H, dd), 2.18 (1H, t), 2.36 (4H, s), 2.50 (1H, m), 2.61-2.72 (1H, m), 2.86-3.00 (3H, m), 3.33-3.44 (1H, m), 3.79 (3H, s), 3.92 (3H, s), 7.10-7.22 (2H, m), 7.68 (1H, s), 8.14 (2H, dd), 8.42 (1H, s) | 522 | 60 |
| 6 | 33 | (N-methyl-2-methylpiperazine) | Methanol-d4 1.23 (3H, d), 1.30 (3H, d), 2.20 (1H, m), 2.35 (3H, s), 2.42 (1H, m), 2.68 (1H, m), 2.79 (1H, m), 2.85 (3H, m), 3.80 (3H, s), 3.92 (3H, s), 4.06 (1H, m), 7.07-7.20 (2H, m), 7.68 (1H, s), 8.14 (2H, dd), 8.43 (1H, s) | 522 | 22 |
| 7a[2] | 33 | (N-methyl-3-methylpiperazine) | Methanol-d4 1.17 (3H, d), 1.45 (3H, d), 2.10 (1H, t), 2.33 (3H, s), 2.41 (1H, s), 2.72-2.96 (3H, m), 3.02 (2H, m), 3.73-3.87 (4H, m), 3.92 (3H, s), 7.16 (2H, d), 7.69 (1H, s), 8.15 (2H, dd), 8.43 (1H, s) | 522 | 35 |

TABLE 11-continued

| Example | Starting Intermediate | Piperazine | NMR δ (300 MHz) | m/z [M + H]+ | Yield % |
|---|---|---|---|---|---|
| 7b[2] | 33 | (4-methyl-2-methylpiperazine) | Methanol-d4 1.23 (3H, d), 1.31 (3H, d), 2.17 (1H, m), 2.34 (4H, m), 2.60-2.94 (5H, m), 3.80 (3H, s), 3.92 (3H, s), 4.07 (1H, d), 7.13 (2H, m), 7.69 (1H, s), 8.15 (2H, dd), 8.44 (1H, s) | 522 | 15 |
| 8[1] | 35 | (4-ethylpiperazine) | Methanol-d4 1.13 (3H, t), 1.32 (3H, t), 1.42 (3H, d), 2.49 (2H, d), 2.55-2.94 (8H, m), 3.40 (1H, m), 3.77 (3H, s), 4.23 (2H, q), 7.08-7.21 (2H, m), 7.66 (1H, s), 8.13 (2H, dd), 8.41 (1H, d) | 536 | 62 |
| 9[1] | 35 | (4-(2-methoxyethyl)piperazine) | Methanol-d4 1.32 (3H, t), 1.41 (3H, d), 2.52-2.95 (10H, m), 3.33-3.44 (4H, m), 3.56 (2H, t), 3.77 (3H, s), 4.23 (2H, q), 7.04-7.26 (2H, m), 7.66 (1H, s), 8.12 (2H, dd), 8.41 (1H, m) | 566 | 57 |
| 10a[3] | 35 | (4-methyl-2-methylpiperazine) | Methanol-d4 1.19 (3H, d), 1.34 (3H, t), 1.46 (3H, d), 2.25 (1H, t), 2.44 (3H, s), 2.58 (1H, m), 2.85-3.02 (3H, m), 3.03-3.13 (2H, m), 3.80 (3H, s), 3.82-3.90 (1H, m), 4.25 (2H, q), 7.09-7.20 (2H, m), 7.69 (1H, s), 8.15 (2H, dd), 8.43 (1H, s) | 536 | 51 |
| 10b[3] | 35 | (4-methyl-2-methylpiperazine) | Methanol-d4 1.19-1.40 (9H, m), 2.17 (1H, t), 2.34 (4H, s), 2.60-2.91 (5H, m), 3.79 (3H, s), 4.06 (1H, m), 4.25 (2H, q), 7.06-7.22 (2H, m), 7.69 (1H, s), 8.14 (2H, dd), 8.44 (1H, d) | 536 | 12 |
| 11a[4] | 35 | (4-methyl-3-methylpiperazine) | Methanol-d4 1.13 (3H, d), 1.32 (3H, t), 1.41 (3H, d), 2.16 (1H, t), 2.33 (4H, s), 2.47 (1H, td), 2.65 (1H, td), 2.81-2.99 (3H, m), 3.32-3.43 (1H, m), 3.77 (3H, s), 4.23 (2H, q), 7.07-7.22 (2H, m), 7.67 (1H, s), 8.13 (2H, dd), 8.41 (1H, d) | 536 | 84 |
| 11b[4] | 35 | (4-methyl-3-methylpiperazine) | Methanol-d4 1.11 (3H, d), 1.32 (3H, t), 1.40 (3H, d), 2.22-2.37 (5H, m), 2.42-2.59 (2H, m), 2.84-3.02 (3H, m), 3.31-3.44 (1H, m), 3.77 (3H, s), 4.23 (2H, q), 7.07-7.22 (2H, m), 7.67 (1H, s), 8.13 (2H, dd), 8.41 (1H, s) | 536 | 12 |
| 12 | 35 | (4-methyl-2-methylpiperazine) | Methanol-d4 1.21 (3H, d), 1.26-1.38 (6H, m), 2.16 (1H, t), 2.33 (4H, s), 2.57-2.95 (5H, m), 3.77 (3H, s), 4.04 (1H, q), 4.23 (2H, q), 6.91-7.22 (2H, m), 7.67 (1H, s), 8.12 (2H, dd), 8.42 (1H, d) | 536 | 33 |

TABLE 11-continued

| Example | Starting Intermediate | Piperazine | NMR δ (300 MHz) | m/z [M + H]+ | Yield % |
|---|---|---|---|---|---|
| 13 | 35 | 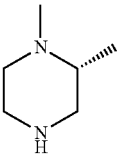 | Methanol-d4 1.11 (3H, d), 1.32 (3H, t), 1.40 (3H, d), 2.22-2.40 (5H, m), 2.42-2.59 (2H, m), 2.90 (3H, dd), 3.35-3.42 (1H, m), 3.77 (3H, s), 4.23 (2H, q), 7.06-7.21 (2H, m), 7.67 (1H, s), 8.13 (2H, dd), 8.42 (1H, br s) | 536 | 88 |
| 14[5] | 34 | 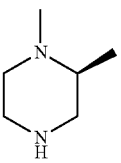 | Methanol-d4 1.13 (3H, d), 1.41 (3H, d), 2.16 (1H, t), 2.36 (6H, d), 2.54-2.41 (1H, m), 2.66 (1H, t), 2.91 (3H, q), 3.72 (3H, s), 3.92 (3H, s), 7.21-7.04 (2H, m), 7.70 (1H, s), 7.87 (1H, s), 8.14 (1H, s), 8.20 (1H, d) | 518 | 19 |
| 15 | 34 | 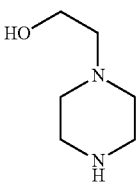 | DMSO-d6 1.26 (3H, d), 2.33 (3H, s), 2.35-2.78 (10H, m), 3.33-3.35 (1H, m), 3.42-3.65 (2H, m), 3.67 (3H, s), 3.79 (3H, s), 4.36 (1H, s), 7.00 (1H, t), 7.41 (1H, d), 7.66 (1H, s), 7.95 (1H, s), 7.97 (1H, s), 8.14 (1H, s), 8.16 (1H, br s), 9.65 (1H, s), 11.28 (1H, s) | 534 | 39 |
| 16 | 34 | 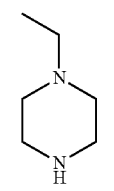 | Chloroform-d 1.17 (3H, t), 1.40 (3H, d), 2.35 (3H, s), 2.39-3.02 (10H, m), 3.37 (1H, d), 3.70 (3H, s), 3.98 (3H, s), 6.52 (1H, s), 6.81 (1H, d), 7.12 (1H, t), 7.66 (1H, d), 7.82 (1H, s), 8.14-8.30 (2H, m), 9.78 (1H, s), 11.17 (1H, s) | 518 | 75 |
| 17 | 34 | 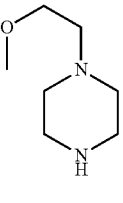 | Methanol-d4 1.40 (3H, d), 2.35 (3H, s), 2.75 (10H, m), 3.37 (4H, s), 3.57 (2H, t), 3.70 (3H, s), 3.98 (3H, s), 6.54 (1H, s), 6.81 (1H, d), 7.12 (1H, t), 7.66 (1H, d), 7.81 (1H, s), 8.17-8.32 (2H, m), 9.80 (1H, s), 11.17 (1H, s) | 548 | 78 |
| 18 | 34 | 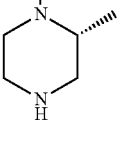 | Methanol-d4 1.25 (3H, s), 1.39 (3H, d), 2.35 (3H, s), 2.48 (4H, d), 2.62 (3H, s), 2.94 (3H, s), 3.45 (1H, s), 3.70 (3H, s), 3.98 (3H, s), 6.53 (1H, s), 6.82-7.19 (2H, m), 7.64 (1H, d), 7.81 (1H, s), 8.13-8.37 (2H, m), 9.68 (1H, s), 11.19 (1H, s) | 518 | 22 |
| 19 | 34 | 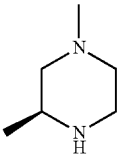 | Methanol-d4 1.11 (3H, d), 1.39 (3H, d), 1.95-2.11 (1H, m), 2.31 (7H, d), 2.61-2.89 (3H, m), 2.92-3.07 (2H, m), 3.68 (4H, s), 3.88 (3H, s), 6.98-7.17 (2H, m), 7.66 (1H, s), 7.82 (1H, s), 8.09 (2H, s) | 518 | 6 |
| 20 | 36 | 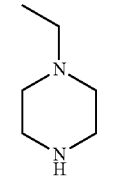 | DMSO-d6 0.98 (3H, t), 1.20-1.31 (6H, m), 2.31-2.78 (13H, m), 3.31 (1H, s), 3.65 (3H, s), 4.15 (2H, q), 7.00 (1H, t), 7.41 (1H, d), 7.64 (1H, s), 7.86-7.98 (2H, m), 8.14 (1H, s), 8.22 (1H, s), 9.66 (1H, s), 11.30 (1H, s) | 532 | 44 |

TABLE 11-continued

| Example | Starting Intermediate | Piperazine | NMR δ (300 MHz) | m/z [M + H]+ | Yield % |
|---|---|---|---|---|---|
| 21 | 36 | 2-methoxyethyl piperazine | DMSO-d6 1.20-1.31 (6H, m), 2.33 (3H, s), 2.45-2.70 (10 H, m), 3.21 (3H, s), 3.26-3.30 (1H, m), 3.41 (2H, t), 3.65 (3H, s), 4.15 (2H, q), 7.00 (1H, t), 7.41 (1H, d), 7.64 (1H, s), 7.86-7.99 (2H, m), 8.14 (1H, s), 8.22 (1H, s), 9.65 (1H, s), 11.29 (1H, s) | 562 | 62 |
| 22 | 36 | (S)-1,3-dimethylpiperazine | Chloroform-d 1.13 (3H, d), 1.44-1.62 (6H, m), 2.13-2.24 (1H, m), 2.25-2.63 (6H, m), 2.64-2.68 (2H, m), 2.71-2.83 (1H, m), 2.84-2.98 (3H, m), 3.53 (1H, s), 3.72 (3H, s), 4.32 (2H, q), 6.63 (1H, s), 6.83 (1H, s), 7.17 (1H, t), 7.34 (1H, s), 7.68 (1H, d), 7.87 (1H, s), 8.25 (2H, t), 11.18 (1H, s) | 532 | 28 |
| 23 | 36 | (R)-1,3-dimethylpiperazine | Methanol-d4 1.20-1.43 (9H, m), 2.19 (1H, t), 2.38 (7H, d), 2.66-2.90 (5H, m), 3.73 (3H, s), 4.02-4.14 (1H, m), 4.26 (2H, q), 7.12 (2H, d), 7.73 (1H, s), 7.88 (1H, s), 8.13-8.27 (2H, m) | 532 | 12 |
| 24 | 36 | (R)-1,2-dimethylpiperazine | Methanol-d4 1.14 (3H, d), 1.29-1.47 (6H, m), 2.28-2.45 (8H, m), 2.52 (2H, t), 2.86-3.04 (3H, m), 3.40 (1H, d), 3.73 (3H, d), 4.26 (2H, q), 7.15 (2H, dt), 7.73 (1H, d), 7.89 (1H, s), 8.13-8.27 (2H, m) | 532 | 46 |
| 25 | 33 | 1-methylpiperazine | Methanol-d4 1.42 (3H, d), 2.34 (3H, s), 2.48-2.89 (8H, m), 3.40 (1H, m), 3.79 (3H, s), 3.91 (3H, s), 7.10-7.22 (2H, m), 7.68 (1H, s), 8.14 (2H, dd), 8.42 (1H, br s) | 508 | 72 |
| 26 | 32 | (S)-1,2-dimethylpiperazine | Methanol-d4 1.14 (3H, d), 1.41 (3H, d), 2.15-2.18 (1H, m), 2.36 (4H, m), 2.50-2.53 (1H, m), 2.64-2.71 (1H, m), 2.88-2.94 (3H, m), 3.40 (1H, m), 3.79 (3H, s), 3.94 (3H, s), 7.12-7.17 (3H, m), 7.73 (1H, s), 8.09 (1H, s), 8.19 (1H, d), 8.29 (1H, br s) | 504 | 56 |

TABLE 11-continued

| Example | Starting Intermediate | Piperazine | NMR δ (300 MHz) | m/z [M + H]+ | Yield % |
|---|---|---|---|---|---|
| 27[1] | 32 | 4-(2-methoxyethyl)piperazine | Methanol-d4 1.38 (3H, d), 2.59-2.78 (10H, m), 3.33 (3H, s), 3.38 (1H, m), 3.52 (2H, m), 3.75 (3H, s), 3.90 (3H, s), 7.09-7.13 (3H, m), 7.69 (1H, s), 8.05 (1H, s), 8.15 (1H, d), 8.25 (1H, br s) | 534 | 45 |
| 28 | 32 | 1-ethylpiperazine | Methanol-d4 1.08 (3H, t), 1.38 (3H, d), 2.43-2.51 (1H, q), 2.61-2.77 (8H, m), 3.37 (1H, m), 3.75 (3H, s), 3.90 (3H, s), 7.08-7.13 (3H, m), 7.68 (1H, s), 8.04 (1H, s), 8.14 (1H, d), 8.24 (1H, br s) | 504 | 54 |
| 29 | 32 | (S)-1,3-dimethylpiperazine | Methanol-d4 1.14 (3H, d), 1.19 (3H, d), 2.08-2.15 (1H, m), 2.29-2.41 (4H, m), 2.60-2.83 (5H, m), 3.75 (3H, s), 3.90 (3H, s), 4.02 (1H, m), 7.08-7.14 (3H, m), 7.68 (1H, s), 8.04 (1H, s), 8.14 (1H, d), 8.24 (1H, d) | 504 | 43 |
| 30[6] | 32 | (R)-1,2-dimethylpiperazine | Methanol-d4 1.12 (3H, d), 1.40 (3H, d), 2.27-2.48 (5H, m), 2.51-2.57 (2H, m), 2.88-2.99 (3H, m), 3.40 (2H, m), 3.79 (3H, s), 3.94 (3H, s), 7.12-7.17 (3H, m), 7.73 (1H, s), 8.09 (1H, s), 8.19 (1H, d), 8.29 (1H, s) - two exchangeable protons not observed | 504 | 42 |
| 31a[7] | 36 | (R)-1,2-dimethylpiperazine | Methanol-d4 1.15 (3H, d), 1.31-1.48 (6H, m), 2.16-2.24 (1H, m), 2.38 (6H, d), ), 2.52-2.56 (1H, m), 2.65-2.69 (1H, m), 2.92-2.99 (3H, m), 3.33 (2H, m), 3.73 (3H, s), 4.86 (2H, q), 7.17 (2H, m), ), 7.73 (1H, s), 7.89 (1H, s), 8.16 (1H, s), 8.21 (1H, d)-)- two exchangeable protons not observed | 532 | 22 |
| 31b[7] | 36 | (R)-1,2-dimethylpiperazine | Methanol-d4 1.14 (d, 3H), 1.30-1.50 (m, 6H), 2.25-2.38 (m, 4H), 2.41 (s, 3H), 2.45-2.60 (m, 2H), 2.85-3.10 (m, 3H), 3.35-3.46 (m, 2H), 3.73 (s, 3H), 4.25 (q, 2H), 7.05-7.25 (m, 2H), 7.73 (s, 1H), 7.89 (s, 1H), 8.16 (s, 1H), 8.25 (d, 1H) | 532 | 33 |

[1] The appropriate piperazine and 2-bromo-acetamide intermediate were combined in DMF according to the procedure of Example 1. Potassium carbonate was not used.
[2] The indicated piperazine and 2-bromo-acetamide intermediate were reacted under the conditions described by the procedure for Example 1. Chiral purification on a preparative chiral-HPLC using a Lux Cellulose-4 column (isocratic elution with 50% EtOH in isohexane modified with 0.2% IPA) to afford Example 7a (isolated as the second eluting peak, retention time = 9.45 min) and Example 7b (isolated as the first eluting peak, retention time = 7.54 min). Stereochemical assignment of the enantiomers was made based on the major product formation of the reaction and validated by biological activity against JAK1 in the Enzyme Inhibition Studies, as shown in Example 66.
[3] The indicated piperazine and 2-bromo-acetamide intermediate were reacted under the conditions described by the procedure for Example 1. The crude product was purified by preparative chiral-HPLC on a Lux Cellulose-4 column, isocratic with 25% EtOH in isohexane (modified with 0.2% IPA) as eluent to afford Example 10a (first eluting peak, retention time = 5.02 min) and Example 10b, (second eluting peak, retention time = 6.68 min). Stereochemical assignment of the enantiomers was made based on the major product formation of the reaction and validated by biological activity against JAK1 in the Enzyme Inhibition Studies, as shown in Example 66.
[4] The indicated piperazine and 2-bromo-acetamide intermediate were reacted under the conditions described by the procedure for Example 1. The crude product was purified by preparative chiral-HPLC (ADH column, isocratic with 50% EtOH in isohexane (modified with 0.2%? IPA) as eluent) to give Example 11a (first eluting peak, retention time = 3.61 min) and Example 11b (second eluting peak, retention time = 4.60 min). Stereochemical assignment of the enantiomers was made based on the major product formation of the reaction and validated by biological activity against JAK1 in the Enzyme Inhibition Studies, as shown in Example 66.

TABLE 11-continued

| Example | Starting Intermediate | Piperazine | NMR δ (300 MHz) | m/z [M + H]+ | Yield % |
|---|---|---|---|---|---|

[5]The appropriate piperazine (2 equiv) and racemic 2-bromo-acetamide intermediate (1 equiv) were combined in 1,4-dioxane in the presence of silver oxide (4 equiv). Chiral-HPLC separation (ChiralPak IA column, isocratic with 50% EtOH in n-hexane (modified with 0.1% diethylamine) as eluent) was performed to afford Example 14 (retention time = 3.99 min). Stereochemical assignment of the enantiomers was made based on the biological activity against JAK1 in the Enzyme Inhibition Studies, as shown in Example 66.
[6]The e.r. was determined to be 94:6 by chiral-HPLC analysis (ChiralPak IA-3, 3μm, 0.46x5 cm, mobile phase: 50% ethanol in hexanes (modified with 0.2% IPA) at 1.0mL/min), retention time = 2.99 min.
[7]The indicated piperazine and racemic 2-bromo-acetamide intermediate were reacted in the presence of silver oxide (8.0 equivalents) in 1,4-dioxane at room temperature for 2 hours. The crude product was purified by preparative chiral-HPLC (Chiralpak IB column, isocratic with 50% Hexanes in EtOH (modified with 0.1% TEA) as eluent) to afford Example 31a (analytical chiral-HPLC: Chiralpak IA, 5μ silica, 0.46x25 cm column, hexanes (0.1% TEA): EtOH (60:40) at 1.0 mL/min as the eluent, retention time = 8.18 min) isolated as the first eluting peak and Example 31b (analytical chiral-HPLC: Chiralpak IA, 5μ silica, 0.46x25 cm column, hexanes (0.1% TEA): EtOH (60:40) at 1.0 mL/min as the eluent, retention time = 9.55 min) isolated as the second eluting peak. Stereochemical assignment of the enantiomers was made based on the biological activity against JAK1 in the Enzyme Inhibition Studies, as shown in Example 66.

Example 32: (2M-N-(3-{2-[(3-Methoxy-1-methyl-1H-pyrazol-4-yl)amino]pyrimidin-4-yl}-1H-indol-7-yl)-2-(4-methylpiperazin-1-yl)propanamide

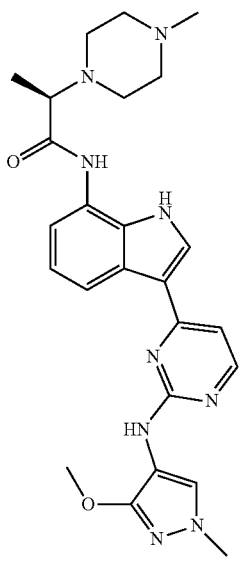 [SMILES: COc1nn(C)cc1Nc1nccc(-c2c[nH]c3c(NC(=O)[C@@H](C)N4CCN(C)CC4)cccc23)n1]

3-{2-[(3-Methoxy-1-methyl-1H-pyrazol-4-yl)amino]pyrimidin-4-yl}-1H-indol-7-amine (180 mg, 0.54 mmol, Intermediate 23), (R)-2-(4-methylpiperazin-1-yl)propanoic acid dihydrochloride (158 mg, 0.64 mmol, Intermediate 37) and HATU (408 mg, 1.1 mmol) in THF (5 mL) were stirred together to give an orange solution. Diisopropylethylamine (0.38 mL, 2.2 mmol) was added at 25° C. The resulting suspension was stirred at 25° C. for 3 hours. The reaction mixture was diluted with ethyl acetate (100 mL), and washed with saturated aqueous $Na_2CO_3$ (50 mL), water (50 mL) and brine (50 mL). The organic layer was dried, filtered and evaporated to afford crude product. The crude product was purified by preparative HPLC (XSelect CSH Prep C18 OBD column, 5 μm, 19x150 mm), employing a gradient of 30-70% acetonitrile in 0.03% aqueous ammonia as eluents. Fractions containing the desired compound were evaporated to dryness to afford (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide (125 mg, 48%, Example 32) as a white solid; $^1$H NMR δ (DMSO, 400 MHz) 1.26 (3H, d), 2.16 (3H, s), 2.25-2.45 (4H, m), 2.51-2.70 (4H, m), 3.71 (3H, s), 3.80 (3H, s), 7.05 (1H, t), 7.13 (1H, d), 7.38 (1H, d), 7.70 (1H, s), 8.16-8.31 (4H, m), 9.62 (1H, s), 11.35 (1H, s)—the α-proton to the amide is masked by the residual water peak; m/z (ES+), [M+H]+=490.

The procedure described above for Example 32 was repeated using the indicated Intermediates to give Examples 33-42 described in Table 12:

TABLE 12

| Example | Starting Intermediates | NMR δ (400 MHz) | m/z [M + H]+ | Yield % |
|---|---|---|---|---|
| 33 | 25 and 38 | DMSO-d6 with D2O 1.28 (3H, d), 2.27 (3H, s), 2.73 (3H, s), 2.85-3.34 (8H, m), 3.44 (1H, q), 3.63 (3H, s), 374 (3H, s), 7.04 (1H, t), 7.19 (1H, d), 7.55 (1H, s), 7.91 (1H, s), 8.08 (2H, s), 8.26 (1H, s)—two exchangeable protons not observed | 504 | 13 |
| 34 | 25 and 37 | DMSO-d6 1.26 (3H, d), 2.16 (3H, s), 2.33 (3H, s), 2.38 (4H, s), 2.57-2.62 (4H, m), 3.33 (1H, q), 3.67 (3H, s), 3.79 (3H, s), 7.00 (1H, t), 7.41 (1H, d), 7.66 (1H, s), 7.96 (2H, t), 8.14 (1H, s), 8.22 (1H, s), 9.65 (1H, s), 11.28 (1H, s) | 504 | 72 |
| 35 | 30 and 37 | Methanol-d4 1.34 (3H, t), 1.40 (3H, d), 2.32 (3H, s), 2.37 (3H, s), 2.50-2.80 (8H, m), 3.38 (1H, q), 3.69 (3H, s), 4.34 (2H, q), 7.05-7.20 (2H, m), 7.69 (1H, s), 7.85 (1H, s), 8.23 (1H, s), 8.17 (1H, d)—three exchangeable protons not observed | 518 | 16 |
| 36 | 26 and 37 | DMSO-d6 1.26 (3H, d), 2.27 (3H, s), 2.24-2.52 (4H, m), 2.53-2.70 (4H, m), 3.30-3.36 (1H, m), 3.69 (3H, s), 3.78 (3H, s), 7.02 (1H, s), 7.40 (1H, d), 7.65 (1H, s), 8.32 (1H, s), 8.48 (1H, s), 9.69 (1H, s), 11.42 (1H, s) | 524 | 48 |
| 37 | 27 and 37 | DMSO-d6 1.26 (3H, d), 2.17 (3H, s), 2.23-2.45 (4H, m), 2.46-2.71 (4H, m), 3.30-3.32 (1H, m), 3.68 (3H, s), 3.78 (3H, s), 7.01 (1H, s), 7.37 (1H, d), 7.64 (1H, s), 8.42 (1H, s), 8.45-8.56 (2H, m), 9.70 (1H, s), 11.36 (1H, s) | 568 | 49 |
| 38 | 25 and 39 | Chloroform-d 1.19 (3H, d), 1.35 (3H, d), 2.10 (1H, m), 2.26 (1H, m), 2.38 (6H, m), 2.69 (2H, t), 2.89 (3H, m), | 518 | 19 |

TABLE 12-continued

| Example | Starting Intermediates | NMR δ (400 MHz) | m/z [M + H]+ | Yield % |
|---|---|---|---|---|
| | | 3.72 (3H, s), 3.91 (1H, q), 4.00 (3H, s), 6.57 (1H, s), 6.80 (1H, d), 7.15 (1H, t), 7.68 (1H, d), 7.84 (1H, s), 8.06-8.36 (2H, m), 9.88 (1H, s), 11.15 (1H, s) | | |
| 39 | 29 and 37 | Methanol-d4 1.34 (3H, t), 1.43 (3H, d), 2.35 (3H, s), 2.50-2.85 (8H, m), 3.41 (1H, q), 3.79 (3H, s), 4.24 (2H, q), 7.10-7.22 (2H, m), 7.68 (1H, s), 8.13 (1H, d), 8.16 (1H, d), 8.43 (1H, s)—three exchangeable protons not observed | 522 | 25 |
| 40 | 31 and 37 | Methanol-d4 1.33 (3H, t), 1.42 (3H, d), 2.35 (3H, s), 2.63-2.71 (4H, m), 2.77-2.81 (4H, m), 3.42 (1H, q), 3.76 (3H, s), 4.26 (2H, q), 7.10-7.20 (2H, m), 7.70 (1H, s), 8.28 (2H, m), 8.48 (1H, m)—three exchangeable protons not observed | 538 | 22 |
| 41 | 28 and 37 | Chloroform-d 1.41 (3H, d), 2.29 (3H, s), 2.36 (3H, s), 2.42 (3H, s), 2.67-2.80 (8H, m), 3.38 (1H, q), 3.80 (3H, s), 6.42 (1H, s), 6.82 (1H, d), 7.12 (1H, t), 7.69 (1H, d), 7.88 (1H, s), 8.21 (2H, m), 9.74 (1H, s), 11.18 (1H, s) | 488 | 36 |
| 42 | 28 and 38 | DMSO-d6 1.27 (3H, d), 2.12 (3H, s), 2.17 (3H, s), 2.35 (3H, s), 2.40 (4H, s), 2.57-2.63 (4H, m), 3.72 (3H, s), 7.03 (1H, t), 7.43 (1H, d), 7.81 (1H, s), 7.97 (1H, d), 8.19 (2H, m), 8.37 (1H, s), 9.68 (1H, s), 11.33 (1H, s) | 488 | 4 |

Examples 43 and 44: (2S)—N-(3-{2-[(3-Methoxy-1-methyl-1H-pyrazol-4-yl)amino]-5-methylpyrimidin-4-yl}-1H-indol-7-yl)-2-(4-methylpiperazin-1-yl)butanamide and (2R)—N-(3-(2-{[(3-Methoxy-1-methyl-1H-pyrazol-4-yl)amino]-5-methylpyrimidin-4-yl}-1H-indol-7-yl)-2-(4-methylpiperazin-1-yl)butanamide Example 43

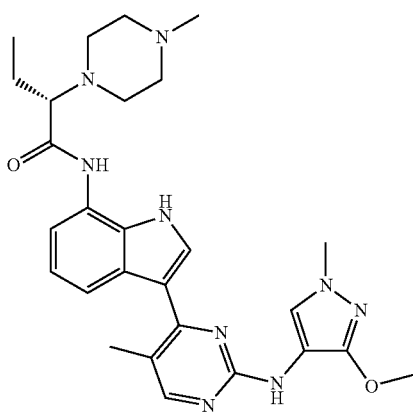

Example 44

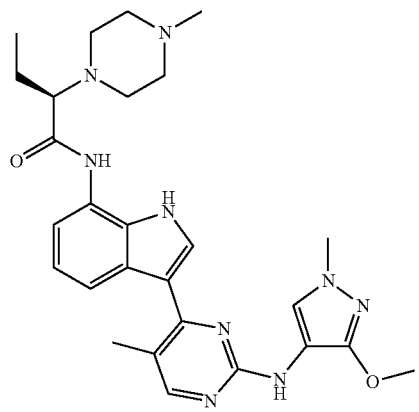

Cesium fluoride (143 mg, 0.94 mmol) was added to a stirring solution of N-(3-{2-[(3-methoxy-1-methyl-1H-pyrazol-4-yl)amino]-5-methylpyrimidin-4-yl}-1-{2-[2-(trimethylsilyl)ethoxy]ethyl}-1H-indol-7-yl)-2-(4-methylpiperazin-1-yl)butanamide (203 mg, 0.31 mmol, Intermediate 46) in anhydrous DMSO (3 mL). The mixture was heated at 80° C. under nitrogen for 4 hours then allowed to cool to ambient temperature. The reaction was diluted with ethyl acetate then water and the phases separated. The aqueous phase was extracted with ethyl acetate then the combined organic phase was washed with brine, dried over magnesium sulfate, and concentrated. The resultant residue was subject to silica gel chromatography using 5-20% methanol-DCM as eluent to afford a pale tan solid (101 mg). Chiral separation was performed by chiral-HPLC: Chiralpak ID, 4.6×50 mm, 3, 50% hexane 50% 1:1 methanol-ethanol (modified with 0.1% diethylamine) to give (2S)—N-(3-{2-[(3-methoxy-1-methyl-1H-pyrazol-4-yl)amino]-5-methylpyrimidin-4-yl}-1H-indol-7-yl)-2-(4-methylpiperazin-1-yl)butanamide (17 mg, 11%, Example 43); Chiral HPLC: >99:1 e.r., retention time=2.34 min; $^1$H NMR δ (Dichloromethane-d2, 400 MHz) 1.09 (3H, t), 1.84-1.93 (2H, m), 2.29 (3H, s), 2.36 (3H, s), 2.51 (4H, br s), 2.67 (2H, br s), 2.75 (2H, m), 3.03 (1H, t), 3.67 (3H, s), 3.93 (3H, s), 6.49 (1H, s), 6.82 (1H, d), 7.12 (1H, t), 7.72 (1H, d), 7.79 (1H, s), 8.20 (1H, s), 8.24 (1H, d), 9.62 (1H, s), 11.06 (1H, br s); m/z (ES+) [M+H]+=518; followed by (2R)—N-(3-{2-[(3-methoxy-1-methyl-1H-pyrazol-4-yl)amino]-5-methylpyrimidin-4-yl}-1H-indol-7-yl)-2-(4-methylpiperazin-1-yl)butanamide (18 mg, 11%, Example 44); Chiral HPLC: −99:5 e.r., retention time=2.78 min; $^1$H NMR δ (Dichloromethane-d2, 400 MHz) 1.09 (3H, t), 1.84-1.93 (2H, m), 2.29 (3H, s), 2.36 (3H, s), 2.51 (4H, br s), 2.67 (2H, br s), 2.75 (2H, m), 3.03 (1H, t), 3.67 (3H, s), 3.93 (3H, s), 6.49 (1H, s), 6.82 (1H, d), 7.12 (1H, t), 7.72 (1H, d), 7.79 (1H, s), 8.20 (1H, s), 8.24 (1H, d), 9.62 (1H, s), 11.06 (1H, br s); m/z (ES+), [M+H]+=518. Stereochemical assignment of the enantiomers was made based on the biological activity against JAK1 in the Enzyme Inhibition Studies, as shown in Example 66.

The procedure described above for Examples 43 and 44 was repeated using the indicated Starting Intermediates to give Examples 45 and 46 described in Table 13:

TABLE 13

| Example | Starting Intermediate | NMR δ (400 MHz) | m/z [M + H]+ | Yield % |
|---|---|---|---|---|
| 45[1] | 47 | Methanol-d4 2.31 (3H, s), 2.37 (3H, s), 2.58 (4H, br s), 2.81 (2H, br s), 2.86-2.99 (2H, m), 3.41 (3H, s), 3.49 (1H, t), 3.70 (3H, s), 3.79-3.87 (1H, m), 3.88-3.96 (4H, m), 7.06-7.12 (1H, m), 7.13-7.18 (1H, m), 7.69 (1H, s), 7.86 (1H, s), 8.12 (1H, s), 8.19 (1H, d)—three exchangeable protons not observed | 534 | 26 |
| 46[1] | 47 | Methanol-d4 2.31 (3H, s), 2.37 (3H, s), 2.58 (4H, br s), 2.81 (2H, br s), 2.86-2.99 (2H, m), 3.41 (3H, s), 3.49 (1H, t), 3.70 (3H, s), 3.79-3.87 (1H, m), 3.88-3.96 (4H, m), 7.06-7.12 (1H, m), 7.13-7.18 (1H, m), 7.69 (1H, s), 7.86 (1H, s), 8.12 (1H, s), 8.19 (1H, d)—three exchangeable protons not observed | 534 | 28 |

[1]Chiral separation was performed by preparative chiral-SFC (Chiralcel OD, 5 μm, 4.6 × 100 mm) with 35% MeOH (modified with 0.1% dimethylethylamine) as eluent at 5 mL/min at 40° C., to afford Example 46 (first eluting peak, retention time = 2.54 min) and Example 45 (second eluting peak, retention time = 3.10 min). Stereochemical assignment of the enantiomers was made based on the biological activity against JAK1 in the Enzyme Inhibition Studies, as shown in Example 66.

Examples 47 and 48: (2M-N-(3-{2-[(3-Methoxy-1-methyl-1H-pyrazol-4-yl)amino]pyrimidin-4-yl}-1H-indol-7-yl)-2-(4-methylpiperazin-1-yl)butanamide and (2S)—N-(3-{2-[3-Methoxy-1-methyl-1H-pyrazol-4-yl)amino]pyrimidin-4-yl}-1H-indol-7-yl)-2-(4-methylpiperazin-1-yl)butanamide Example 47

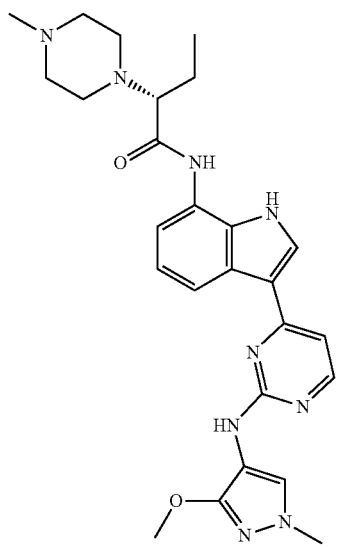

Example 48

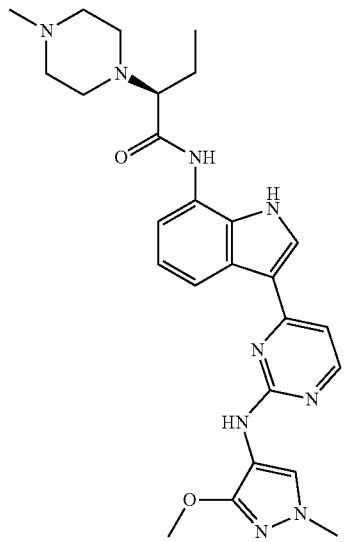

N-[3-(2-Chloropyrimidin-4-yl)-1H-indol-7-yl]-2-(4-methylpiperazin-1-yl)butanamide (0.22 g, 0.53 mmol, Intermediate 51), 3-methoxy-1-methyl-1H-pyrazol-4-amine dihydrochloride (0.16 g, 0.8 mmol) and 4-methylbenzenesulfonic acid monohydrate (0.2 g, 1.1 mmol) were dissolved in isopropanol (6 mL) and sealed into a microwave tube. The reaction was heated at 120° C. for 2 hours in the microwave reactor and cooled to room temperature. The crude product was purified by preparative HPLC (XBridge Prep C18 OBD column, 5p silica, 19×150 mm), using decreasingly polar mixtures of water (containing 0.2% formic acid) and acetonitrile as eluents. Fractions containing the desired compound were evaporated to dryness to afford racemic N-(3-{2-[(3-methoxy-1-methyl-1H-pyrazol-4-yl)amino]pyrimidin-4-yl}-1H-indol-7-yl)-2-(4-methylpiperazin-1-yl) butanamide (90 mg, 34%) as a white solid; m/z (ES+), [M+H]+=504. The product was purified by preparative chiral-HPLC on an IC-3 column, isocratica with 30% ethanol in isohexane (modified with 0.2% isopropanol) as eluent. The fractions containing the desired compound were evaporated to dryness to afford firstly (2S)—N-(3-{2-[(3-methoxy-1-methyl-1H-pyrazol-4-yl)amino]pyrimidin-4-yl}-1H-indol-7-yl)-2-(4-methylpiperazin-1-yl)butanamide (32 mg, 35%, Example 48) as a white solid; $^1$H NMR δ (Methanol-d4, 300 MHz) 1.08 (3H, t), 1.89 (2H, dt), 2.33 (3H, s), 2.59 (4H, br s), 2.83 (4H, br s), 3.21 (1H, dd), 3.80 (3H, s), 3.94 (3H, s), 7.10-7.27 (3H, m), 7.74 (1H, s), 8.11 (1H, s), 8.21 (1H, d), 8.30 (1H, s)—three exchangeable protons not observed; m/z (ES+), [M+H]+=504; chiral HPLC: 100% ee, retention time=4.48 min; followed by (2R)—N-(3-{2-[(3-methoxy-1-methyl-1H-pyrazol-4-yl) amino]pyrimidin-4-yl}-1H-indol-7-yl)-2-(4-methylpiperazin-1-yl)butanamide (32 mg, 35%, Example 47) as a white solid; $^1$H NMR δ (Methanol-d4, 300 MHz) 1.08 (3H, t), 1.89 (2H, dt), 2.33 (3H, s), 2.59 (4H, br s), 2.83 (4H, br s), 3.21 (1H, dd), 3.80 (3H, s), 3.94 (3H, s), 7.10-7.27 (3H, m), 7.74 (1H, s), 8.11 (1H, s), 8.21 (1H, d), 8.30 (1H, s)—three exchangeable protons not observed; m/z (ES+), [M+H]+=504; Chiral HPLC: 100% ee, retention time=5.69 min. Stereochemical assignment of the enantiomers was made based on the biological activity against JAK1 in the Enzyme Inhibition Studies, as shown in Example 66.

The procedure described above for Examples 47 and 48 was repeated using the indicated Starting Intermediates and aminopyrazole to give Examples 49-59 described in Table 14:

TABLE 14

| Example | Starting Intermediate | Aminopyrazole | NMR δ (400 MHz) | m/z [M + H]+ | Yield % |
|---|---|---|---|---|---|
| 49[1] | 52 | (1-methyl-3-methyl-1H-pyrazol-4-amine) | Methanol-d4 1.07 (3H, t), 1.89 (2H, m), 2.21 (3H, s), 2.33 (3H, d), 2.59 (4H, s), 2.83 (4H, d), 3.20 (1H, dd), 3.88 (3H, s), 7.12 (1H, t), 7.21 (1H, d), 7.74 (1H, s), 8.16 (2H, d), 8.37 (1H, s)-three exchangeable protons not observed | 506 | 38 |
| 50[1] | 52 | (1-methyl-3-methyl-1H-pyrazol-4-amine) | Methanol-d4 1.07 (3H, t), 1.89 (2H, m), 2.21 (3H, s), 2.33 (3H, d), 2.59 (4H, s), 2.83 (4H, d), 3.20 (1H, dd), 3.88 (3H, s), 7.12 (1H, t), 7.21 (1H, d), 7.74 (1H, s), 8.16 (2H, d), 8.37 (1H, s)-three exchangeable protons not observed | 506 | 38 |
| 51[2,3] | 52 | (1-methyl-3-methoxy-1H-pyrazol-4-amine) | DMSO-d6 0.92 (3H, t), 1.65-1.82 (2H, m), 2.14 (3H, s), 2.34 (4H, m), 2.65 (4H, m), 3.16 (1H, t), 3.71 (3H, s), 3.78 (3H, s), 7.05 (1H, t), 7.54 (1H, d), 7.66 (1H, s), 8.16 (1H, t), 8.23-8.35 (3H, m), 9.75 (1H, s), 11.36 (1H, s) | 522 | 48 |
| 52[2,3] | 52 | (1-methyl-3-methoxy-1H-pyrazol-4-amine) | DMSO-d6 0.92 (3H, t), 1.65-1.82 (2H, m), 2.14 (3H, s), 2.34 (4H, m), 2.65 (4H, m), 3.16 (1H, t), 3.71 (3H, s), 3.78 (3H, s), 7.05 (1H, t), 7.54 (1H, d), 7.66 (1H, s), 8.16 (1H, t), 8.23-8.35 (3H, m), 9.75 (1H, s), 11.36 (1H, s) | 522 | 47 |
| 53[4] | 53 | (1-methyl-3-methyl-1H-pyrazol-4-amine) | Methanol-d4 2.21 (3H, s), 2.34 (3H, s), 2.61 (4H, m), 2.83 (2H, s), 2.93 (2H, s), 3.43 (3H, s), 3.51 (1H, t), 3.80-3.92 (4H, m), 3.95 (1H, m), 7.08-7.21 (2H, m), 7.74 (1H, s), 8.15 (2H, t), 8.38 (1H, s)-three exchangeable protons not observed | 522 | 26 |
| 54[4] | 53 | (1-methyl-3-methyl-1H-pyrazol-4-amine) | Methanol-d4 2.21 (3H, s), 2.34 (3H, s), 2.61 (4H, m), 2.83 (2H, s), 2.93 (2H, s), 3.43 (3H, s), 3.51 (1H, t), 3.80-3.92 (4H, m), 3.95 (1H, m), 7.08-7.21 (2H, m), 7.74 (1H, s), 8.15 (2H, t), 8.38 (1H, s)-three exchangeable protons not observed | 522 | 26 |
| 55[3,5] | 54 | (1-methyl-3-ethyl-1H-pyrazol-4-amine) | Methanol-d4 1.31 (3H, t), 1.42 (3H, d), 2.26 (3H, s), 2.35 (3H, s), 2.52-2.70 (6H, m), 2.73-2.88 (4H, m), 3.40-3.42 (1H, m), 3.85 (3H, s), 7.06-7.18 (2H, m), 7.77 (1H, s), 7.91 (1H, s), 8.14-8.19 (2H, m)-three exchangeable protons not observed | 502 | 19 |

TABLE 14-continued

| Example | Starting Intermediate | Aminopyrazole | NMR δ (400 MHz) | m/z [M + H]+ | Yield % |
|---|---|---|---|---|---|
| 56[5] | 55 | 4-amino-1,3-dimethylpyrazole | Methanol-d4 1.43 (3H, d), 2.21 (3H, s), 2.34 (3H, s), 2.51-2.91 (8H, m), 3.41 (1H, q), 3.88 (3H, s), 7.07-7.21 (2H, m), 7.74 (1H, s), 8.15 (2H, dd), 8.37 (1H, s)- three exchangeable protons not observed | 492 | 17 |
| 57[5] | 59 | 4-amino-1,3-dimethylpyrazole | DMSO-d6 1.27 (3H, d), 2.14 (3H, s), 2.18 (3H, s), 2.26-2.75 (8H, m), 3.25-3.41 (1H, m), 3.77 (3H, s), 7.07 (1H, t), 7.14 (1H, d), 7.40 (1H, d), 7.83 (1H, s), 8.08-8.36 (3H, m), 8.47 (1H, s), 9.63 (1H, s), 11.36 (1H, br s) | 474 | 60 |
| 58[5] | 54 | 4-amino-1-ethyl-3-methoxypyrazole | Dichloromethane-d2 1.17-1.44 (6H, m), 2.36 (3H, s), 2.39 (3H, s), 2.57-2.90 (8H, m), 3.37 (1H, q), 3.80-4.08 (5H, m), 6.65 (1H, s), 6.86 (1H, d), 7.18 (1H, t), 7.75 (1H, d), 7.87 (1H, s), 8.24 (1H, s), 8.32 (1H, d), 9.62 (1H, s), 11.23 (1H, s) | 518 | 50 |
| 59[5] | 54 | 4-amino-1-ethyl-3-ethoxypyrazole | Chloroform-d 1.36-1.50 (9H, m), 2.36 (3H, s), 2.39 (3H, s), 2.55-2.90 (8H, m), 3.36 (1H, m), 3.95 (2H, q), 4.32 (2H, q), 6.73 (1H, s), 6.84 (1H, d), 7.13 (1H, t), 7.67 (1H, d), 7.90 (1H, s), 8.13-8.40 (2H, m), 9.78 (1H, s), 11.17 (1H, br s) | 532 | 82 |

[1]Chiral separation was performed by chiral-HPLC (Chiralcel OD-H column, isocratic with 10% IPA in hexanes) to give Example 50 (analytical chiral-HPLC: Chiralpak OD-H 5μ silica, 0.46x10 cm column, hexanes (modified with 0.2% IPA): EtOH (90:10) at 1.0 mL/min as the eluent, retention time = 9.02 min) isolated as the first eluting peak and Example 49 (analytical chiral-HPLC: Chiralpak OD-H 5μ silica, 0.46x10 cm column, hexanes (modified with 0.2% IPA): EtOH (90:10) at 1.0 mL/min as the eluent, retention time = 11.35 min) isolated as the second eluting peak. Stereochemical assignment of the enantiomers was made based on the biological activity against JAK1 in the Enzyme Inhibition Studies, as shown in Example 66.

[2]Chiral separation was performed by preparative chiral-HPLC (Chiralcel OD-H, 20x250 mm column, isocratic with 10% ethanol in hexanes (modified with 0.2% diethylamine) at 20 mL/min as an eluent) to afford Example 52 (first eluting peak, retention time = 15.87 min) and Example 51 (second eluting peak, retention time = 21.29 min). Stereochemical assignment of the enantiomers was made based on the biological activity against JAK1 in the Enzyme Inhibition Studies, as shown in Example 66.

[3]1H NMR analysis was performed using a Bruker Avance 300 (300 MHz) spectrometer.

[4]Chiral separation was performed by preparative chiral-HPLC (Chiralcel IC column, isocratic with 40% ethanol in hexanes as an eluent) to afford Example 54 (analytical chiral-HPLC: Lux Cellulose-4 3μ silica, 0.46x5 cm column, hexanes (modified with 0.1% TEA): EtOH (60:40) at 1.0 mL/min as the eluent, retention time = 2.69 min) isolated as the first eluting peak and Example 53 (analytical chiral-HPLC: Lux Cellulose-4 3μ silica, 0.46x5 cm column, hexanes (modified with 0.1% TEA): EtOH (60:40) at 1.0 mL/min as the eluent, retention time = 3.62 min) isolated as the second eluting peak. Stereochemical assignment of the enantiomers was made based on the biological activity against JAK1 in the Enzyme Inhibition Studies, as shown in Example 66.

[5]Enantiopure starting material utilized-final product not subject to chiral-HPLC purification.

Examples 60 and 61: (2R)-3-Methoxy-N-(3-{2-[(3-methoxy-1-methyl-1H-pyrazol-4-yl)amino]pyrimidin-4-yl}-1H-indol-7-yl)-2-(4-methylpiperazin-1-yl)propanamide and (2S)-3-Methoxy-N-(3-{2-[(3-methoxy-1-methyl-1H-pyrazol-4-yl)amino]pyrimidin-4-yl}-1H-indol-7-yl)-2-(4-methylpiperazin-1-yl)propanamide

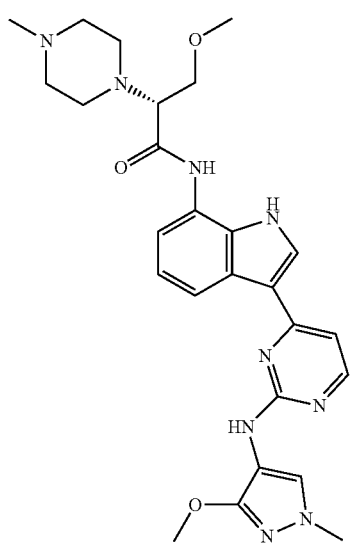

Example 60

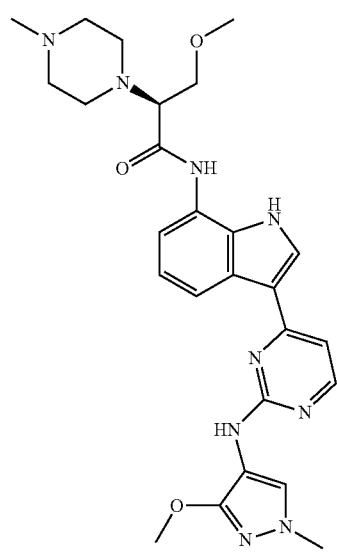

Example 61

Diisopropylethylamine (1.25 mL, 7.2 mmol) was added to 3-(24(3-methoxy-1-methyl-1H-pyrazol-4-yl)amino)pyrimidin-4-yl)-1H-indol-7-amine (0.4 g, 1.2 mmol, Intermediate 23), lithium 3-methoxy-2-(4-methylpiperazin-1-yl)propanoate (0.72 g, 3.6 mmol, Intermediate 45) and HATU (1.4 g, 3.6 mmol) in DMF (18 mL) at 25° C. under nitrogen. The resulting mixture was stirred at 25° C. for 1 hour. The crude product was purified by preparative HPLC (XBridge Prep C18 OBD column, 5p silica, 19 mm diameter, 150 mm length), using decreasingly polar mixtures of water (containing 0.2% ammonia) and acetonitrile as eluents. Fractions containing the desired compound were evaporated to dryness to afford racemic 3-methoxy-N-(3-(2-((3-methoxy-1-methyl-1H-pyrazol-4-yl)amino)pyrimidin-4-yl)-1H-indol-7-yl)-2-(4-methylpiperazin-1-yl)propanamide (0.15 g, 24%) as a white solid; m/z (ES+), [M+H]+=520. The crude product was purified by preparative chiral-HPLC on a Lux Cellulose-4 column, eluting isocratically with 50% ethanol in isohexane (modified with 0.1% triethylamine) as eluent. The fractions containing the desired compound were evaporated to dryness to afford firstly (2S)-3-methoxy-N-(3-{2-[(3-methoxy-1-methyl-1H-pyrazol-4-yl)amino]pyrimidin-4-yl}-1H-indol-7-yl)-2-(4-methylpiperazin-1-yl)propanamide (53 mg, 35%, Example 61) as a white solid; $^1$H NMR δ (Methanol-d4, 300 MHz) 2.33 (3H, s), 2.60 (4H, s), 2.78-2.99 (4H, m), 3.43 (3H, s), 3.51 (1H, t), 3.76-4.00 (8H, m), 7.08-7.22 (3H, m), 7.72 (1H, s), 8.09 (1H, s), 8.19 (1H, d), 8.30 (1H, s)—three exchangeable protons not observed; m/z (ES+), [M+H]+=520; Chiral HPLC: 100% ee, $R_t$=4.072 min; followed by (2R)-3-methoxy-N-(3-{2-[(3-methoxy-1-methyl-1H-pyrazol-4-yl)amino]pyrimidin-4-yl}-1H-indol-7-yl)-2-(4-methylpiperazin-1-yl)propanamide (57 mg, 36%, Example 60) as a white solid; $^1$H NMR δ (Methanol-d4, 300 MHz) 2.30 (3H, s), 2.57 (4H, s), 2.87-2.80 (4H, m), 3.39 (3H, s), 3.47 (1H, t), 3.75-3.98 (8H, m), 7.04-7.18 (3H, m), 7.68 (1H, s), 8.05 (1H, s), 8.15 (1H, d), 8.26 (1H, s)—three exchangeable protons not observed; m/z (ES+), [M+H]+=520; Chiral HPLC: 99.2% ee, $R_t$=5.376 min. Stereochemical assignment of the enantiomers was made based on the biological activity against JAK1 in the Enzyme Inhibition Studies, as shown in Example 66.

The procedure described above for Examples 60 and 61 was repeated using the indicated Starting Intermediates to give the compounds described in Table 15:

TABLE 15

| Example | Starting Intermediates | NMR δ (300 MHz) | m/z [M + H]+ | Yield % |
|---|---|---|---|---|
| 62[1] | 30 and 43 | DMSO-d6 0.86 (3H, t), 1.20 (3H, t), 1.38-1.88 (2H, m), 2.07 (3H, s), 2.26 (7H, m), 2.45-2.74 (4H, m), 3.12 (1H, t), 3.59 (3H, s), 4.09 (2H, q), 6.93 (1H, t), 7.47 (1H, d), 7.58 (1H, s), 7.77 (1H, s), 7.92 (1H, s), 8.08 (1H, s), 8.18 (1H, br s), 9.58 (1H, s), 11.13 (1H, s) | 532 | 24 |
| 63[1] | 30 and 43 | DMSO-d6 0.86 (3H, t), 1.20 (3H, t), 1.45-1.76 (2H, m), 2.07 (3H, s), 2.26 (7H, s) 2.54-2.73 (4H, m), 3.10 (1H, t), 3.59 (3H, s), 4.09 (2H, q), 6.94 (1H, s), 7.45 (1H, d), 7.58 (1H, s), 7.78 (1H, s), 7.91 (1H, s), 8.08 (1H, s), 8.18 (1H, br s) 9.55 (1H, s), 11.10 (1H, s) | 532 | 16 |
| 64[2] | 30 and 45 | DMSO-d6 1.19 (3H, t), 2.10 (3H, s), 2.33-2.38 (7H, m), 2.56-2.72 (4H, m), 3.34 (3H, s), 3.64 (1H, t), 3.69-3.73 (5H, m), 4.09 (2H, q), 6.94 (1H, t), 7.39 (1H, d), 7.58 (1H, s), 7.80 (1H, s), 7.91(1H, d), 8.08 (1H, s), 8.18 (1H, br s), 9.69 (1H, s), 11.08 (1H, br s) | 548 | 32 |
| 65[2] | 30 and 45 | DMSO-d6 1.27 (3H, t), 2.15 (3H, s), 2.34-2.38 (7H, m), 2.60-2.76 (4H, m), 3.33 (3H, s), 3.69 (1H, | 548 | 30 |

TABLE 15-continued

| Example | Starting Intermediates | NMR δ (300 MHz) | m/z [M + H]+ | Yield % |
|---|---|---|---|---|
| | | t), 3.68-3.73 (5H, m), 4.16 (2H, q), 6.96 (1H, t), 7.45 (1H, d), 7.60 (1H, s), 7.83 (1H, s), 7.90 (1H, s), 8.10 (1H, s), 8.18 (1H, br s), 9.71 (1H, br s), 11.10 (1H, br s) | | |

[1] Chiral separation was performed by preparative chiral-SFC (Chiralcel OD, 5 µm, 21 × 250 mm) eluting isocratically with 20% MeOH (modified with 0.1% dimethylethylamine) at 75 mL/min at 40° C., to afford Example 63 (first eluting peak, retention time = 7.89 min) and Example 62 (second eluting peak, retention time = 8.81 min). Stereochemical assignment of the enantiomers was made based on the biological activity against JAK1 in the Enzyme Inhibition Studies, as shown in Example 66.

[2] Chiral separation was performed by preparative chiral-SFC (Chiralcel OD, 5 µm, 21 × 250 mm) eluting isocratically with 25% MeOH (modified with 0.1% dimethylethylamine) at 75 mL/min at 40° C., to afford Example 65 (first eluting peak, retention time = 4.84 min) and Example 64 (second eluting peak, retention time = 5.95 min). Stereochemical assignment of the enantiomers was made based on the biological activity against JAK1 in the Enzyme Inhibition Studies, as shown in Example 66.

Example 66: Enzyme Inhibition Studies

Enzyme inhibition studies were performed using recombinant JAK1 (amino acids 866-1154, Life Technologies, #PV4774, Carlsbad, CA), JAK2 (amino acids 831-1132), or JAK3 (amino acids 781-1124) under buffer conditions of 50 mM HEPES pH 7.3, 1 mM DTT, 0.01% Tween® 20, 50 µg/mL BSA, and 10 mM $MgCl_2$. JAK enzyme was expressed as an N-terminal GST fusion in insect cells and purified by glutathione-affinity and size-exclusion chromatographies. Enzymes were assayed both at their respective ATP Km (JAK1: 55 µM, JAK2: 15 µM, JAK3: 3 µM) and the approximated high end of physiological ATP concentration of 5 mM, in the presence of inhibitor dosed at 30, 3, 0.3, 0.03, 0.003 and 0 µM final test concentrations. For JAK1, 6 nM of enzyme (for Km ATP assay) or 4 nM enzyme (for high ATP assay) was incubated with 1.5 µM peptide substrate (FITC-C6-KKHTDDGYMPMSPGVA-NH2 (SEQ ID NO:1), Intonation, Boston, MA). For JAK2, 0.8 nM of enzyme (for Km ATP assay) or 0.3 nM enzyme (for high ATP assay) was incubated with 1.5 µM peptide substrate (5FAM-GEEPLYWSFPAKKK-NH2 (SEQ ID NO:2), Intonation, Boston, MA). For JAK3, 0.2 nM of enzyme (for Km ATP assay) or 0.1 nM enzyme (for high ATP assay) was incubated with 1.5 µM peptide substrate (5FAM-GEEP-LYWSFPAKKK-NH2 (SEQ ID NO:2), Intonation, Boston, MA). Phosphorylated and unphosphorylated peptides were separated and quantified by a Caliper LC3000 system (Caliper Life Sciences, MA) for calculating percent inhibition. The results of this assay are shown in Table 16 and indicate that the compounds of Formula (I), (Ia), (Ib) and Table 1 exhibit preferential inhibition of JAK1 over JAK2 (in many cases demonstrating over 100 times selectivity for inhibition of JAK1 vs. JAK2).

Example 67: Cellular pSTAT3 Assay

NCI-H1975 cells were plated onto Costar #3701 96 or 384 well tissue-culture treated plates at 5,000 cells/well in 30 uL medium (RPMI, 10% FBS, supplemented with L-glutamine) and incubated overnight at 37° C. in 5% $CO_2$. Phospho STAT3 signal was quantitated utilizing Cell Signaling Technology #7146B Pathscan 97hosphor STAT3 antibody pair kit, following manufacturer's instructions.

Cells were dosed with compound and incubated at 37° C. in 5% $CO_2$ for 2 hours, after which medium and compound were aspirated and cells lysed with 35 uL cold 1× Cell Signaling Lysis buffer and chilled at 4° C. for 1-2 hours. Lysate was incubated on STAT3 capture plates at 4° C. overnight, washed 3× with Tris-Buffered Saline with 0.05% Tween® 20 (TBST), then 98 phosphor STAT3 detection antibody was applied for 2 hours. Following washing with TBST (3×), HRP-secondary antibody was applied for 2 hours. After additional washing, signal was detected using TMB and Stop solution and read at 450 nm using Tecan Infinite M100. $IC_{50}$ values (the concentration that causes 50% inhibition) were calculated by plotting percent inhibition of the phosphor-signal relative to untreated sample (maximum signal) and positive control treated sample (maximum inhibition/minimum signal), using Xlfit4 version 4.2.2 for Microsoft Excel. The results of this assay, shown in Table 16, demonstrate good correlation between cellular inhibition of STAT3 phosphorylation in NCI-H1975 cells and JAK1 enzyme inhibition.

TABLE 16

| Example | JAK1 ($IC_{50}$, µM) | JAK2 ($IC_{50}$, µM) | JAK3 ($IC_{50}$, µM) | NCI-H1975 pSTAT3 ($IC_{50}$, µM) |
|---|---|---|---|---|
| 1 | 0.847 | >30 | >30 | 0.643 |
| 2 | 0.085 | 12.8 | >30 | 0.227 |
| 3 | 0.191 | 26.8 | >30 | 0.302 |
| 4 | 0.043 | 6.57 | >30 | 0.0986 |
| 5 | 0.024 | 10.4 | >30 | 0.0872 |
| 6 | 0.030 | 9.62 | >30 | 0.111 |
| 7a | 0.359 | >30 | >30 | 0.509 |
| 7b | 3.60 | >30 | >30 | >3 |
| 8 | 0.110 | 23.6 | >30 | 0.191 |
| 9 | 0.426 | >30 | >30 | 0.594 |
| 10a | 0.846 | >30 | >30 | 0.531 |
| 10b | 7.60 | >30 | >30 | >3 |
| 11a | 0.040 | >30 | >30 | 0.209 |
| 11b | 1.85 | >30 | >30 | 2.28 |
| 12 | 0.068 | 22.6 | >30 | 0.246 |
| 13 | 0.166 | >30 | >30 | 0.222 |
| 14 | 0.009 | 6.39 | >30 | 0.0703 |
| 15 | 0.007 | 2.53 | >30 | 0.131 |
| 16 | 0.019 | 6.24 | >30 | 0.105 |
| 17 | 0.107 | 18.1 | >30 | 0.229 |
| 18 | 0.057 | 17.3 | >30 | 0.175 |
| 19 | 0.296 | >30 | >30 | 0.470 |
| 20 | 0.051 | 17.2 | >30 | 0.184 |
| 21 | 0.184 | >30 | >30 | 0.703 |
| 22 | 0.490 | >30 | >30 | 0.550 |
| 23 | 0.029 | 25.7 | >30 | 0.410 |
| 24 | 0.113 | >30 | >30 | 0.370 |
| 25 | 0.019 | 6.62 | >30 | 0.115 |
| 26 | 0.069 | 16.7 | >30 | 0.256 |
| 27 | 0.575 | >30 | >30 | 0.609 |
| 28 | 0.106 | 11.8 | >30 | 0.100 |
| 29 | 0.097 | 20.4 | >30 | 0.227 |
| 30 | 0.304 | >30 | >30 | 0.359 |
| 31a | 0.015 | 19.8 | >30 | 0.153 |
| 31b | 0.454 | >30 | >30 | 0.330 |
| 32 | 0.073 | >14.7 | >30 | 0.161 |
| 33 | 0.272 | >30 | >30 | 0.308 |
| 34 | 0.010 | 5.37 | >30 | 0.128 |
| 35 | 0.020 | 17.0 | >30 | 0.153 |
| 36 | 0.007 | 1.76 | 19.1 | 0.0579 |
| 37 | 0.008 | 1.58 | 15.4 | 0.0942 |
| 38 | 0.013 | 6.48 | >30 | 0.108 |
| 39 | 0.055 | 25.5 | >30 | 0.191 |
| 40 | 0.024 | 8.93 | >30 | 0.160 |
| 41 | <0.005 | 2.58 | >30 | 0.0923 |
| 42 | 0.106 | 21.1 | >30 | 0.172 |
| 43 | 0.079 | 21.1 | >30 | 0.176 |
| 44 | <0.003 | 1.95 | >30 | 0.0577 |
| 45 | <0.003 | 0.790 | >30 | 0.0603 |
| 46 | 0.986 | >30 | >30 | 1.28 |
| 47 | 0.013 | 6.95 | >30 | 0.136 |
| 48 | 1.21 | >30 | >30 | 0.863 |
| 49 | <0.004 | 1.77 | >30 | 0.0751 |

TABLE 16-continued

| Example | JAK1 (IC$_{50}$, µM) | JAK2 (IC$_{50}$, µM) | JAK3 (IC$_{50}$, µM) | NCI-H1975 pSTAT3 (IC$_{50}$, µM) |
|---|---|---|---|---|
| 50 | 0.265 | 24.1 | >30 | 0.999 |
| 51 | <0.003 | 3.19 | >30 | 0.111 |
| 52 | 0.296 | >30 | >30 | 0.548 |
| 53 | <0.003 | 0.322 | >30 | 0.0566 |
| 54 | 1.67 | >30 | >30 | >3 |
| 55 | 0.027 | 4.22 | >30 | 0.116 |
| 56 | 0.028 | 5.15 | >30 | 0.126 |
| 57 | 0.069 | 9.26 | >30 | 0.155 |
| 58 | 0.017 | 8.85 | >30 | 0.106 |
| 59 | 0.069 | >30 | >30 | 0.245 |
| 60 | 0.004 | 1.53 | >30 | 0.0973 |
| 61 | 2.90 | >30 | >30 | 1.27 |
| 62 | <0.006 | 5.01 | >30 | 0.104 |
| 63 | 0.192 | >30 | >30 | 0.433 |
| 64 | <0.005 | 2.04 | >30 | 0.112 |
| 65 | 2.53 | >30 | >30 | 1.03 |

Example 68: Solid Forms of (2R)—N-(3-{2-[(3-methoxy-1-methyl-1H-pyrazol-4-yl)amino]pyrimidin-4-vl}-1H-indol-7-v1)-2-(4-methylpiperazin-1-yl)propanamide Methods X-Ray Powder Diffraction (XRPD) Analysis XRPD analysis was performed using a Bruker D4 (or D8) diffractometer, which is commercially available from Bruker AXS Inc™ (Madison, Wisconsin). The XRPD spectra were obtained by mounting a sample (approximately 20 mg) of the material for analysis on a single silicon crystal wafer mount (e.g., a Bruker silicon zero background X-ray diffraction sample holder) and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5406 angstroms (i.e., about 1.54 angstroms). The sample was exposed for 1 second per 0.02 degree 2-theta increment (continuous scan mode) over the range 5 degrees (or 2 degrees) to 40 degrees 2-theta in theta-theta mode. The running time was ~17 min for D4 and ~15 min for D8.

XRPD 2θ values may vary with a reasonable range, e.g., in the range ±0.2° and that XRPD intensities may vary when measured for essentially the same crystalline form for a variety of reasons including, for example, preferred orientation. Principles of XRPD are described in publications, such as, for example, Giacovazzo, C. et al. (1995), Fundamentals of Crystallography, Oxford University Press; Jenkins, R. and Snyder, R. L. (1996), Introduction to X-Ray Powder Diffractometry, John Wiley & Sons, New York; and Klug, H. P. & Alexander, L. E. (1974), X-ray Diffraction Procedures, John Wiley and Sons, New York.

DSC Analysis

DSC analysis was performed on samples prepared according to standard methods using a Q SERIES™ Q1000 DSC calorimeter available from TA INSTRUMENTS® (New Castle, Delaware). A sample (approximately 2 mg) was weighed into an aluminum sample pan and transferred to the DSC. The instrument was purged with nitrogen at 50 mL/min and data collected between 22° C. and 300° C., using a dynamic heating rate of 10° C./minute. Thermal data was analyzed using standard software, e.g., Universal v.4.5A from TA INSTRUMENTS®.

Thermogravimetry Analysis (TGA)

TGA was performed on samples prepared according to standard methods using a Q SERIES™ Q5000 thermogravimetry analyzer available from TA Instruments INSTRUMENTS® (New Castle, Delaware). A sample (approximately 5 mg) was placed into an aluminum sample pan and transferred to the TGA furnace. The instrument was purged with nitrogen at 50 mL/min and data collected between 25° C. and 300° C., using a dynamic heating rate of 10° C./minute. Thermal data was analyzed using standard software, e.g., Universal v.4.5A from TA INSTRUMENTS®.

Example 68A: Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Method 1: 50 mg of off-white amorphous (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was dissolved in 0.4 ml of TBME in a 4 mL vial. The solid precipitated out from the solution after 30 minutes. The slurry was stirred under ambient conditions overnight. The resulting white solid material was identified as Form A by XRPD analysis.

Method 2: 500 mg of amorphous (2R)— N-(3-{2-[(3-methoxy-1-methyl-1H-pyrazol-4-yl)amino]pyrimidin-4-yl}-1H-indol-7-yl)-2-(4-methylpiperazin-1-yl)propanamide and approximately 50 mg of crystalline seeds obtained from Method 1 were mixed in a 20 mL vial. To the mixture, 5 mL of TBME was added to form a slurry. The slurry was stirred under ambient conditions overnight and a homogenous slurry formed. The slurry was filtered, and the resulting solid was washed with TBME and dried in air. 498 mg of a white crystalline solid was obtained and identified as Form A by XRPD analysis.

Form A (Method 2) was analyzed by XRPD and the results are tabulated below (Table 17) and shown in FIG. 1.

TABLE 17

| Angle (2θ ± 0.2°) | Intensity (%) |
|---|---|
| 21.6 | 100.0 |
| 6.4 | 74.9 |
| 16.4 | 56.5 |
| 8.7 | 54.2 |
| 20.4 | 45.8 |
| 7.9 | 42.8 |
| 22.2 | 36.2 |
| 18.8 | 34.6 |
| 16.8 | 29.6 |
| 9.3 | 29.2 |
| 20.1 | 26.3 |
| 16.1 | 24.5 |
| 19.8 | 23.2 |
| 26.5 | 22.1 |
| 13.8 | 20.9 |
| 19.2 | 20.8 |
| 13.2 | 19.5 |
| 12.0 | 17.2 |
| 23.8 | 16.9 |
| 21.1 | 15.4 |
| 25.4 | 14.3 |
| 28.5 | 14.3 |
| 12.9 | 13.7 |
| 8.3 | 12.7 |
| 10.9 | 11.7 |
| 25.9 | 11.7 |
| 24.4 | 11.5 |
| 22.7 | 11.4 |
| 32.0 | 10.9 |

TABLE 17-continued

| Angle (2θ ± 0.2°) | Intensity (%) |
|---|---|
| 15.7 | 10.7 |
| 14.8 | 10.1 |
| 25.0 | 9.2 |
| 27.0 | 8.7 |
| 9.9 | 8.2 |
| 11.6 | 8.2 |
| 29.2 | 7.7 |
| 29.9 | 7.6 |
| 17.4 | 7.4 |
| 17.8 | 7.4 |
| 27.8 | 7.2 |
| 30.2 | 6.8 |
| 32.6 | 6.2 |
| 31.1 | 5.5 |

Form A (Method 2) was analyzed by thermal techniques. DSC analysis indicated that Form A has an endotherm event of desolvation with an onset at 110° C. and a peak at 113° C. TGA indicated that Form A exhibits a mass loss of about 7.8% upon heating from about 25° C. to about 150° C. A representative DSC/TGA thermogram of Form A is shown in FIG. 2.

Example 68B: Form 8 (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Approximately 100 mg of light yellow amorphous (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was suspended 0.5 mL of toluene with Form B seeds. The slurry was stirred at room temperature overnight. The slurry was evaporated and dried in the ambient condition. A white crystalline solid was obtained and identified as Form B by XRPD.

Form B was analyzed by XRPD and the results are tabulated below (Table 18) and shown in FIG. 3.

TABLE 18

| Angle (2θ ± 0.2°) | Intensity (%) |
|---|---|
| 21.6 | 100.0 |
| 6.3 | 93.7 |
| 8.8 | 72.2 |
| 19.0 | 53.5 |
| 8.0 | 53.1 |
| 16.3 | 47.3 |
| 9.5 | 43.4 |
| 22.4 | 41.2 |
| 20.4 | 34.8 |
| 19.7 | 30.2 |
| 13.9 | 27.1 |
| 26.4 | 26.7 |
| 28.6 | 25.2 |
| 16.7 | 24.7 |
| 15.9 | 19.5 |
| 10.8 | 19.0 |
| 11.9 | 18.5 |
| 13.4 | 18.4 |
| 23.9 | 17.6 |
| 31.8 | 15.8 |
| 24.4 | 14.7 |
| 25.5 | 14.6 |
| 25.1 | 14.3 |
| 28.1 | 13.5 |
| 32.7 | 12.9 |
| 14.6 | 12.6 |
| 29.8 | 11.9 |
| 37.5 | 11.7 |

TABLE 18-continued

| Angle (2θ ± 0.2°) | Intensity (%) |
|---|---|
| 29.3 | 10.6 |
| 15.0 | 10.4 |

Single crystals of Form B were obtained from slow evaporation of a toluene solution. Single crystal structure analysis confirmed that Form B is a hemi-toluene solvate form. Crystallographic data: Space group triclinic P1, unit cell dimensions: a=14.1919(8) Å, b=14.2964(8) Å, c=14.7632(8) Å, α=82.283(1)°, β=77.596(1)°, γ=85.567(1)°, V=2895.3(3) Å$^3$.

Form B was analyzed by thermal techniques. DSC analysis indicated that Form B has an endotherm event of desolvation with an onset at 112° C. and a peak at 117° C. TGA indicated that Form B exhibits a mass loss of about 10.0% upon heating from about 25° C. to about 200° C. A representative DSC/TGA thermogram of Form B is shown in FIG. 4.

Example 68C: Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Approximately 100 mg of amorphous (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was dissolved in 1 mL of isopropyl acetate to yield a clear solution. The solution was placed in the freezer overnight and a solid precipitated out. The slurry was stirred at room temperature for 4 hours to obtain a white solid in the slurry. The slurry was evaporated and dried under ambient condition. A white crystalline solid was obtained and was identified as Form C by XRPD.

Form C was analyzed by XRPD and the results are tabulated below (Table 19) and shown in FIG. 5.

TABLE 19

| Angle (2θ ± 0.2°) | Intensity (%) |
|---|---|
| 8.7 | 100.0 |
| 21.5 | 68.0 |
| 6.3 | 58.6 |
| 16.3 | 53.8 |
| 22.2 | 31.5 |
| 18.9 | 30.3 |
| 7.9 | 28.3 |
| 20.4 | 26.3 |
| 13.8 | 22.0 |
| 19.7 | 21.5 |
| 26.4 | 19.3 |
| 9.3 | 18.1 |
| 16.6 | 12.6 |
| 23.6 | 12.1 |
| 19.9 | 11.8 |
| 11.9 | 11.3 |
| 13.2 | 11.1 |
| 28.4 | 11.1 |
| 25.3 | 10.7 |
| 16.0 | 9.3 |
| 18.4 | 8.9 |
| 31.8 | 8.1 |
| 26.0 | 8.0 |
| 24.2 | 7.9 |
| 10.7 | 6.8 |
| 17.5 | 6.8 |
| 20.9 | 6.6 |
| 12.8 | 6.3 |
| 29.8 | 6.0 |

TABLE 19-continued

| Angle (2θ ± 0.2°) | Intensity (%) |
|---|---|
| 15.7 | 5.8 |
| 26.9 | 5.8 |
| 14.7 | 5.5 |

Form C was analyzed by thermal techniques. DSC analysis indicated that Form C has an endotherm event of desolvation with an onset at 112° C. and a peak at 114° C. TGA indicated that Form C exhibits a mass loss of about 9.2% upon heating from about 25° C. to about 175° C. A representative DSC/TGA thermogram of Form C is shown in FIG. 6.

Example 68D: Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Method 1: Approximately 100 mg of light yellow amorphous (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was dissolved in 1 ml of EtOAC to get a clear solution. The solution was placed in the freezer overnight and solid was precipitated out. The slurry was stirred at room temperature for 4 hours to get a white solid in the slurry. The slurry was evaporated and dried under ambient conditions. An off-white crystalline solid was obtained and identified as Form D by XRPD analysis.

Method 2: 5.01 g of light brown amorphous (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was dissolved in 10 mL of EtOAC to yield a light brown solution and a brown gel. 0.10 g of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide-Form D seed from Method 1 was added and the solution became a wet cake within 5 minutes. 10 mL of EtOAc was added to form a slurry. The slurry was stirred under ambient conditions overnight. The brown gel disappeared to obtain a slurry of an off-white solid with brown solution. The slurry was filtered, and the solid was washed twice with EtOAc. The off-white solid was dried under ambient conditions. 4.78 g of an off-white crystalline solid was obtained and identified as Form D by XRPD analysis.

Form D (Method 2) was analyzed by XRPD and the results are tabulated below (Table 20) and shown in FIG. 7.

| Angle (2θ ± 0.2°) | Intensity (%) |
|---|---|
| 21.8 | 100.0 |
| 6.4 | 74.8 |
| 16.6 | 59.2 |
| 8.9 | 50.1 |
| 22.5 | 48.3 |
| 8.1 | 43.0 |
| 19.1 | 40.4 |
| 19.9 | 40.0 |
| 20.6 | 36.8 |
| 26.6 | 30.2 |
| 9.5 | 26.6 |
| 16.0 | 24.8 |
| 14.0 | 20.9 |
| 24.1 | 19.8 |
| 28.9 | 19.2 |
| 18.6 | 19.0 |
| 13.4 | 18.8 |
| 25.8 | 17.1 |
| 25.4 | 15.4 |
| 26.3 | 14.8 |
| 32.1 | 13.5 |
| 10.9 | 12.6 |
| 12.1 | 12.2 |
| 14.8 | 12.2 |
| 28.4 | 11.9 |
| 30.0 | 11.4 |
| 33.0 | 11.4 |
| 38.9 | 10.2 |
| 36.5 | 10.1 |
| 15.2 | 9.3 |

Single crystals of Form D were obtained from slow evaporation of an EtOAc solution. Single crystal structure analysis confirmed that Form D is a hemi-EtOAc solvate form. Crystallographic data: Space group triclinic P1, unit cell dimensions: a=14.051(2) Å, b=14.289(2) Å, c=14.756(2) Å, α=81.174(5)°, β=77.476(5)°, γ=85.331(6)°, V=2854.5(8) Å$^3$.

Form D was analyzed by thermal techniques. DSC analysis indicated that Form D has an endotherm event of desolvation with an onset at 116° C. and a peak at 119° C. TGA indicated that Form D exhibits a mass loss of about 8.0% upon heating from about 25° C. to about 200° C. A representative DSC/TGA thermogram of Form D is shown in FIG. 8.

Example 68E: Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Saccharine Salt 25.1 mg of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide (0.05 mmol) was dissolved in 1 mL of MeOH, and 2.0 mL (0.10 mmol) of 0.05 M of saccharin MeOH solution was added to yield a light yellow solution. To the solution, 1 mL of ACN was added and the resulting solution was evaporated under ambient conditions. A partial yellow crystalline material was obtained. Approximately 10 mg of the resulting material was dissolved in 2 mL of ACN and the resulting yellow solution was evaporated slowly to obtain yellow needle crystals identified as Form A (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharin salt by XRPD analysis.

Form A of the saccharin salt was analyzed by XRPD and the results are tabulated below (Table 21) and shown in FIG. 9.

TABLE 21

| Angle (2θ ± 0.2°) | Intensity (%) |
|---|---|
| 14.4 | 100.0 |
| 10.7 | 52.0 |
| 7.1 | 48.1 |
| 21.4 | 44.3 |
| 10.1 | 42.1 |
| 8.5 | 38.9 |
| 8.2 | 36.5 |
| 17.3 | 36.5 |
| 16.3 | 27.3 |
| 9.4 | 26.0 |

TABLE 21-continued

| Angle (2θ ± 0.2°) | Intensity (%) |
|---|---|
| 11.6 | 25.2 |
| 17.8 | 23.0 |
| 20.8 | 22.5 |
| 20.1 | 18.2 |
| 18.5 | 16.8 |
| 18.8 | 16.7 |
| 25.4 | 16.3 |
| 24.9 | 15.9 |
| 21.8 | 15.6 |
| 27.4 | 15.2 |
| 27.8 | 15.2 |
| 26.7 | 13.9 |
| 24.4 | 13.6 |
| 23.4 | 13.4 |
| 15.4 | 13.3 |
| 28.9 | 13.1 |
| 30.4 | 12.2 |
| 35.3 | 11.9 |
| 31.1 | 11.2 |
| 12.5 | 11.1 |
| 19.4 | 10.5 |

Form A of the saccharin salt was analyzed by thermal techniques. DSC analysis indicated that Form A has an endotherm event of melting point with an onset at 163° C. and a peak at 169° C. TGA indicated that Form A exhibits a mass loss of about 3.1% upon heating from about 25° C. to about 150° C. A representative DSC/TGA thermogram of Form D is shown in FIG. 10.

Example 68F: Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Saccharine Salt 246 mg of light yellow (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide (0.5 mmol) and 184 mg (1.0 mmol) of saccharine was dissolved in 3 mL of acetonitrile and 1 mL of MeOH to yield a clear yellow solution. The solution was evaporated to have about 1.0 mL of solvent and a yellow crystalline material precipitated. The suspension was stirred for 30 minutes and filtered. The solid was dried under ambient conditions. A yellow crystal material was obtained and identified as Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharin salt by XRPD.

Form B of the saccharin salt was analyzed by XRPD and the results are tabulated below (Table 22) and shown in FIG. 11.

TABLE 22

| Angle (2θ ± 0.2°) | Intensity (%) |
|---|---|
| 6.6 | 100.0 |
| 13.4 | 99.8 |
| 25.3 | 85.8 |
| 18.1 | 82.7 |
| 8.0 | 76.8 |
| 17.2 | 71.0 |
| 9.1 | 65.3 |
| 21.8 | 64.2 |
| 9.9 | 64.0 |
| 26.0 | 58.9 |
| 16.4 | 58.7 |
| 26.4 | 57.9 |
| 21.3 | 57.3 |
| 20.2 | 54.5 |
| 27.9 | 48.6 |
| 14.7 | 48.1 |
| 16.2 | 47.6 |
| 24.1 | 46.8 |
| 20.4 | 45.0 |
| 23.0 | 45.0 |
| 24.7 | 43.3 |
| 18.7 | 42.4 |
| 11.0 | 39.9 |
| 15.2 | 39.2 |
| 15.7 | 35.1 |
| 29.7 | 34.4 |

Form B of the saccharin salt was analyzed by thermal techniques. DSC analysis indicated that Form B has a broad endotherm event of desolvation with a peak at 53° C., followed by two endotherm events, one with an onset at 153° C. and a peak at 162° C. and the other with an onset at 176° C. and a peak at 182° C. TGA indicated that Form B exhibits a mass loss of about 2.7% upon heating from about 25° C. to about 100° C. A representative DSC/TGA thermogram of Form B is shown in FIG. 12.

Example 68G: Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl) propanamide Saccharine Salt Approximately 200 mg of Form B (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharin salt was slurried in acetone for 3 days, and the resulting slurry was evaporated under ambient conditions. A yellow crystal material was obtained and identified as Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine salt by XRPD.

Form C of the saccharin salt was analyzed by XRPD and the results are tabulated below (Table 23) and shown in FIG. 13.

TABLE 23

| Angle (2θ ± 0.2°) | Intensity (%) |
|---|---|
| 5.5 | 100.0 |
| 17.0 | 82.5 |
| 26.3 | 82.0 |
| 8.2 | 80.3 |
| 14.9 | 76.9 |
| 24.9 | 73.4 |
| 16.0 | 72.9 |
| 14.4 | 70.6 |
| 18.1 | 57.6 |
| 12.4 | 55.8 |
| 9.4 | 53.0 |
| 20.7 | 52.4 |
| 28.0 | 46.8 |
| 19.2 | 46.6 |
| 19.8 | 45.3 |
| 21.5 | 43.0 |
| 23.8 | 40.2 |
| 15.4 | 36.7 |
| 13.4 | 33.1 |
| 22.8 | 32.6 |
| 29.8 | 28.0 |

Example 68H: Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Saccharine Salt Approximately 15 mg of Form B or Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharin salt was slurried in 0.5 mL of water. The resulting slurry was dried in the sample holder and was measured by XRPD analysis and Form D (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharin salt was identified.

Form D of the saccharin salt was analyzed by XRPD and the results are tabulated below (Table 24) and shown in FIG. 14.

TABLE 24

| Angle (2θ ± 0.2°) | Intensity (%) |
|---|---|
| 19.2 | 100.0 |
| 5.4 | 96.7 |
| 20.1 | 95.7 |
| 6.8 | 93.7 |
| 15.4 | 83.0 |
| 7.7 | 74.1 |
| 20.8 | 72.1 |
| 13.8 | 66.8 |
| 17.3 | 61.4 |
| 13.4 | 58.5 |
| 23.1 | 58.3 |
| 10.4 | 43.4 |
| 9.3 | 42.5 |
| 14.3 | 33.4 |
| 16.9 | 30.9 |
| 11.5 | 27.2 |
| 27.2 | 22.8 |
| 26.2 | 21.1 |

Example 68I: Form E (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Saccharine Salt About 15 mg of Form C (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharin salt was slurried in 0.5 mL of EtOH. The resulting slurry was evaporated under ambient conditions. A yellow powder was obtained and was identified as Form E (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharin salt by XRPD analysis.

Form E of the saccharin salt was analyzed by XRPD and the results are tabulated below (Table 25) and shown in FIG. 15.

TABLE 25

| Angle (2θ ± 0.2°) | Intensity (%) |
|---|---|
| 15.4 | 100.0 |
| 19.3 | 96.9 |
| 5.5 | 86.4 |
| 14.7 | 78.5 |
| 23.2 | 76.8 |
| 6.7 | 73.3 |
| 20.1 | 71.0 |
| 7.8 | 66.8 |
| 26.3 | 58.4 |
| 17.7 | 53.3 |
| 25.2 | 53.0 |
| 18.2 | 52.5 |
| 24.6 | 52.0 |
| 24.0 | 50.3 |
| 13.5 | 50.1 |
| 27.3 | 49.4 |
| 9.3 | 45.7 |
| 17.1 | 44.5 |
| 21.4 | 42.1 |
| 16.4 | 37.2 |
| 29.2 | 33.9 |
| 11.8 | 33.5 |

Example 68J: (2R)—N-(3-{2-[3-methoxy-1-methyl-1H-pyrazol-4-yl)amino]pyrimidin-4-yl}-1H-indol-7-yl)-2-(4-methylpiperazin-1-yl)propanamide Saccharine Hydrochloride Salt 249 mg (0.50 mmol) of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was dissolved in 4 mL of MeOH to yield a light brown solution. 0.5 ml of 1N HCl aqueous solution (0.50 mmol) was added and the color of the solution turned to yellow. To the yellow solution, 0.5 mmol of saccharine was added, and the saccharine gradually dissolved in the solution to yield a yellow solution. The solution was evaporated under ambient conditions to dry. The resulting solid was slurried in 4 mL of acetone overnight, then filtered and washed with acetone. The yellow solid was dried in air and identified as (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide saccharine hydrochloride salt by XRPD analysis.

The saccharin hydrochloride salt was analyzed by XRPD and the results are tabulated below (Table 26) and shown in FIG. 16.

TABLE 26

| Angle (2θ ± 0.2°) | Intensity (%) |
|---|---|
| 13.7 | 100.0 |
| 20.2 | 84.0 |
| 26.0 | 82.7 |
| 17.3 | 80.8 |
| 8.4 | 59.9 |
| 25.4 | 57.4 |
| 20.6 | 54.8 |
| 27.6 | 53.9 |
| 10.6 | 52.1 |
| 26.6 | 49.4 |
| 18.4 | 48.5 |
| 20.9 | 47.1 |
| 24.3 | 44.8 |
| 15.0 | 43.9 |
| 15.7 | 42.3 |
| 12.9 | 39.7 |
| 25.1 | 39.3 |
| 18.8 | 39.2 |
| 12.5 | 37.7 |
| 22.6 | 36.2 |
| 16.1 | 33.1 |
| 29.4 | 33.1 |
| 23.3 | 32.9 |
| 27.2 | 32.9 |
| 28.9 | 32.3 |

TABLE 26-continued

| Angle (2θ ± 0.2°) | Intensity (%) |
|---|---|
| 21.7 | 31.0 |
| 21.2 | 27.1 |
| 32.0 | 26.3 |
| 22.2 | 22.9 |
| 32.8 | 21.5 |
| 33.6 | 21.1 |
| 29.9 | 19.7 |
| 30.5 | 19.6 |
| 31.2 | 18.8 |

Example 68K: (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Napadosylic Salt 35.8 mg of off-white amorphous (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was dissolved in 0.8 mL of EtOH:water mixture (70:30), and 29.02 mg of napadisylic acid tetrahydrate was dissolved in 0.5 mL of the same solvent. The counter ion solution was added to the solution of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide dropwise and a yellow precipitate was obtained. The slurry was stirred at the ambient condition for overnight. The slurry was filtered to obtain a crystalline material.

The napadisylic acid salt was analyzed by XRPD and the results are tabulated below (Table 27) and shown in FIG. 17.

TABLE 27

| Angle (2θ ± 0.2°) | Intensity (%) |
|---|---|
| 5.2 | 100.0 |
| 10.4 | 78.5 |
| 7.8 | 74.0 |
| 18.3 | 68.1 |
| 17.3 | 64.1 |
| 15.0 | 59.3 |
| 22.1 | 58.7 |
| 25.6 | 58.7 |
| 20.9 | 58.2 |
| 15.6 | 57.4 |
| 20.3 | 56.3 |
| 16.9 | 52.9 |
| 16.1 | 51.1 |
| 26.5 | 46.9 |
| 24.2 | 46.6 |
| 21.2 | 46.6 |
| 24.0 | 44.2 |
| 27.5 | 42.7 |
| 23.2 | 42.5 |
| 19.9 | 41.6 |
| 14.2 | 39.0 |
| 7.2 | 38.4 |
| 12.1 | 32.2 |
| 13.5 | 32.2 |
| 11.3 | 31.0 |
| 30.6 | 24.3 |
| 31.2 | 23.8 |

Example 68L: (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide Trimesic Salt 30 mg of off-white amorphous (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide was dissolved in 0.5 mL of EtOH:water mixture (70:30), and 14.16 mg of trimesic acid was dissolved in 0.6 mL of the same solvent. The counter ion solution was added to the solution of (2R)—N-(3-{2-[(3-methoxy-1-methyl-1H-pyrazol-4-yl)amino]pyrimidin-4-yl}-1H-indol-7-yl)-2-(4-methylpiperazin-1-yl)propanamide dropwise. The resulting solution was subjected to slow evaporation and isolated by centrifugation.

The trimesic acid salt was analyzed by XRPD and the results are tabulated below (Table 28) and shown in FIG. 18.

TABLE 28

| Angle (2θ ± 0.2°) | Intensity (%) |
|---|---|
| 4.2 | 100.0 |
| 12.4 | 66.3 |
| 7.8 | 63.0 |
| 25.1 | 27.8 |
| 24.9 | 27.3 |
| 2.1 | 20.6 |
| 27.5 | 19.1 |
| 12.1 | 16.3 |
| 15.7 | 16.2 |
| 10.6 | 14.4 |
| 26.1 | 13.8 |
| 16.5 | 13.2 |
| 15.9 | 12.8 |
| 8.3 | 12.6 |
| 19.8 | 11.8 |
| 20.7 | 11.8 |
| 25.7 | 11.4 |
| 29.1 | 11.0 |
| 8.7 | 10.7 |
| 22.1 | 10.4 |
| 17.5 | 10.0 |
| 23.0 | 9.9 |
| 19.2 | 9.0 |
| 13.9 | 9.0 |
| 23.5 | 8.9 |
| 23.8 | 8.9 |
| 28.1 | 8.2 |
| 26.9 | 8.1 |
| 21.2 | 7.6 |
| 14.3 | 7.4 |
| 18.2 | 7.4 |
| 22.7 | 7.4 |
| 15.2 | 7.3 |
| 17.0 | 6.9 |
| 37.7 | 6.5 |
| 18.6 | 6.3 |
| 33.2 | 6.1 |
| 34.3 | 6.1 |
| 39.3 | 5.6 |
| 39.3 | 5.4 |
| 30.6 | 5.3 |
| 11.3 | 5.0 |
| 31.2 | 4.9 |

Example 69: Example 32 In Combination with Osimertinib—In Vivo Efficacy and Pharmacodynamics in the H1975 Xenograft Model SUMMARY: NCI-H1975 tumor xenografts were grown subcutaneously in female nude mice. The mice were treated by oral dosing with vehicle, Example 32, the EGFR inhibitor osimertinib (AZD9291, TAGRISSO™), an irreversible inhibitor of T790M mutant EGFR, or combinations of Example 32 and osimertinib. Average tumor size at the start of treatment (10 days after implant) was 189 mm$^3$. Tumor volume was measured twice a week. Additional mice were treated with the same doses of Example 32 and osimertinib, and tumors and plasma harvested after one day of treatment, for analysis of pSTAT3 (Y705) levels in tumors and drugs levels in plasma.

The combination of Example 32 with osimertinib resulted in enhanced antitumor activity, compared to treatment with osimertinib alone. There was no significant antitumor activity observed after treatment with Example 32 alone. The enhanced antitumor activity of the combination correlated with pSTAT3 knockdown by Example 32, consistent with a role for JAK/STAT signaling in escape from pEGFR inhibition.

Osimertinib, an irreversible inhibitor of T790M mutant EGFR, overcomes T790M-mediated resistance to EGFR inhibitors such as gefitinib and erlotinib in lung cancer. This study was carried out to evaluate the ability of Example 32 to enhance the antitumor response to osimertinib in mice bearing subcutaneous NCI-H1975 tumor xenografts. The EGFR gene in the NCI-H1975 tumors is mutated at L858R and also contains the T790M resistance mutation.

MATERIALS AND METHODS: NCI-H1975 cells (a human NSCLC cell line with L858R and T790M mutations in the EGFR gene) tumor cells were implanted subcutaneously in female NCr nude mice (Taconic Laboratories), $3 \times 10^6$ cells/mouse. Ten days after cell implantation, mice were randomized into 10 groups (6-8 mice/group, average tumor volume 189 mm$^3$, range 152-250 mm$^3$), and were dosed orally with either vehicle (20% captisol), Example 32 as a single agent (12.5 mg/kg, 25 mg/kg, 50 mg/kg), osimertinib as a single agent (2.5 mg/kg), or combinations of Example 32 and osimertinib (osimertinib at 2.5 mg/kg and Example 32 at 12.5 mg/kg, 25 mg/kg and 50 mg/kg) for 18 days. Some of the mice from the tumor implant that were not randomized into these groups were treated for a single day with these compounds for pharmacokinetic and pharmacodynamic analysis (tumor and plasma collected for analysis of drug levels in plasma and pSTAT3 (Y705) levels in tumor lysates, samples collected 2, 8 and 24 hours after the AM dose). Tumor length and width were measured by caliper, and tumor volume calculated using the formula volume= (length×width$^2$)*π/6. Example 32 was formulated in water, adjusted to pH 2 with methane sulfonic acid. Osimertinib was formulated in 0.5% HPMC in water. All formulations were administered by oral gavage, at a volume of 5 ml/kg. Osimertinib was dosed QD (AM), Example 32 was dosed BID (AM and PM, 8 hours apart). In the groups that were dosed with osimertinib in combination with Example 32, the AM dosing of osimertinib occurred 3 hours before Example 32 to minimize exposure interactions. AZD1480 (5-chloro-N2-[(1S)-1-(5-fluoro-2-pyrimidinyl)ethyl]-N4-(5-methyl-1H-pyrazol-3-yl)-2,4-pyrimidinediamine, see U.S. Patent Application Publication No. US20080287475), a JAK1/2 inhibitor and a positive control for 100% pSTAT3 knockdown in the pharmacokinetic/pharmacodynamic experiment was formulated in 0.5% HPMC/0.1% Tween® 80 in water, and administered by oral gavage at a volume of 5 ml/kg. Y705 phosphorylated STAT3 (pSTAT3) levels were measured in tumor lysates using a sandwich ELISA (PathScan Phospho-STAT3 Sandwich ELISA Kit, CST #7146B). Drug levels in plasma were measured by LC/MS, using a Linear Ion Trap Quadrupole LC/MS/MS Mass Spectrometer (QTRAP 5500 model 1024945-BB, AB Sciex Instruments), with separation on a Waters Xbridge C18 column.

Figure 19:
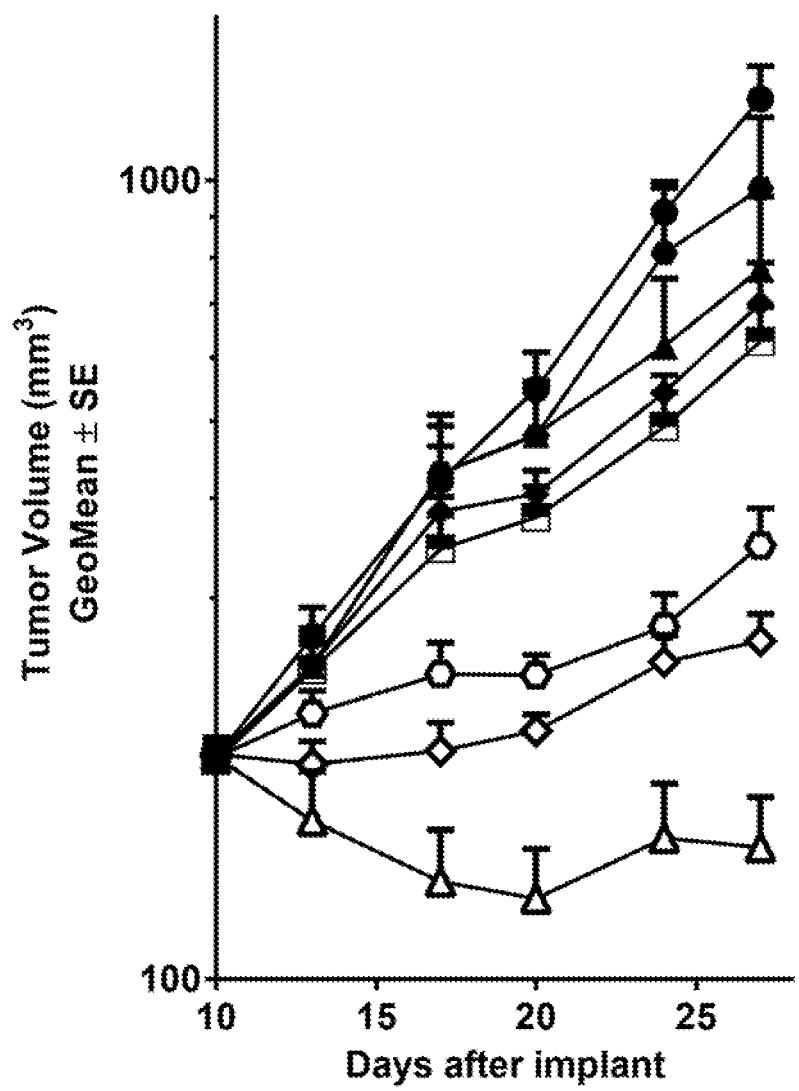
FIG. 19 illustrates NCI-H1975 tumor volumes after treatment with vehicle, osimertinib (2.5 mg/kg QD) administered as a single agent, Example 32 (12.5 mg/kg BID, 25 m/kg BID or 50 mg/kg BID) as a single agent, and osimertinib (2.5 mg/kg QD) in combination with Example 32 (12.5 mg/kg BID, 25 mg/kg BID or 50 mg/kg BID). represents vehicle; represents osimertinib administered as a single agent; represents 50 mg/kg BID Example 32 administered as a single agent; represents 25 mg/kg BID Example 32 administered as a single agent; represents 12.5 mg/kg BID Example 32 administered as a single agent; represents osimertinib administered in combination with 50 mg/kg BID Example 32; represents osimertinib administered in combination with 25 mg/kg BID Example 32; and represents osimertinib administered in combination with 12.5 mg/kg BID Example 32.
Figure 20:
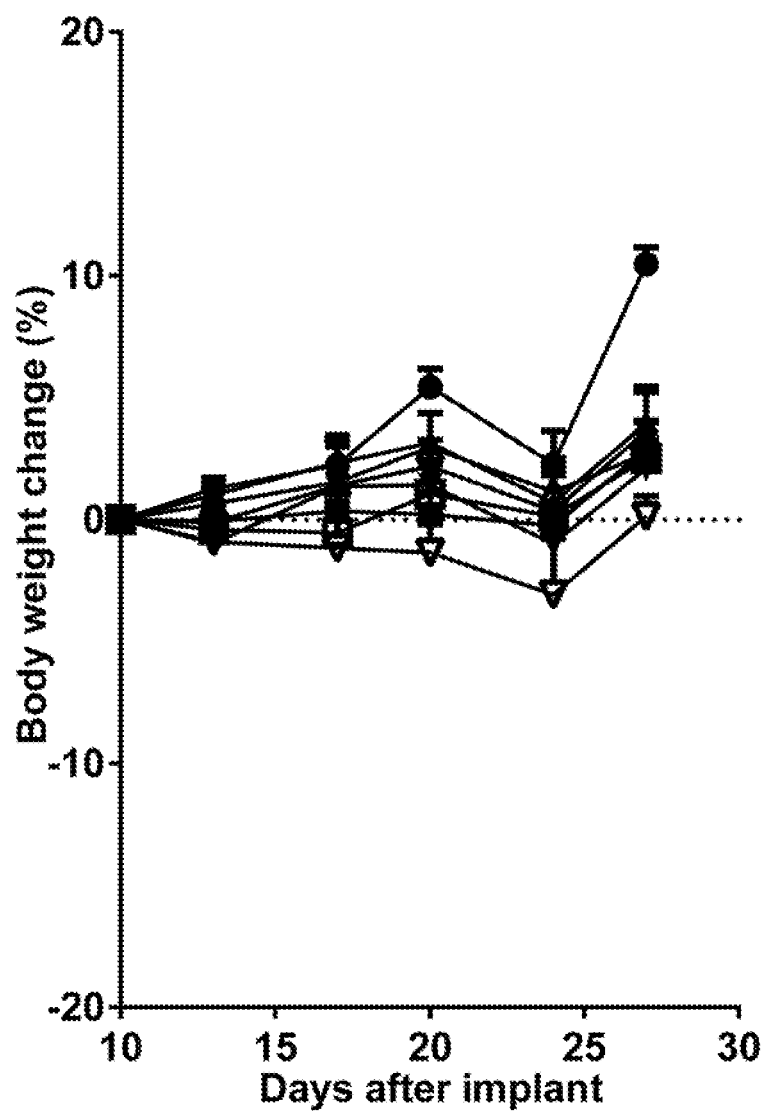
FIG. 20 illustrates body weights after treatment with vehicle, osimertinib (2.5 mg/kg QD) as a single agent, Example 32 (12.5 mg/kg BID, 25 mg/kg BID or 50 mg/kg BID) as a single agent, and osimertinib (2.5 mg/kg QD) in combination with Example 32 (12.5 mg/kg BID, 25 mg/kg BID or 50 mg/kg BID). represents vehicle; represents osimertinib administered as a single agent; represents 50 mg/kg BID Example 32 administered as a single agent; represents 25 mg/kg BID Example 32 administered as a single agent; represents 12.5 mg/kg BID Example 32 administered as a single agent; represents 50 mg/kg BID Example 32 administered in combination with osimertinib; represents 25 mg/kg BID Example 32 administered in combination with osimertinib; and represents 12.5 mg/kg BID Example 32 administered in combination with osimertinib.
Figure 21:
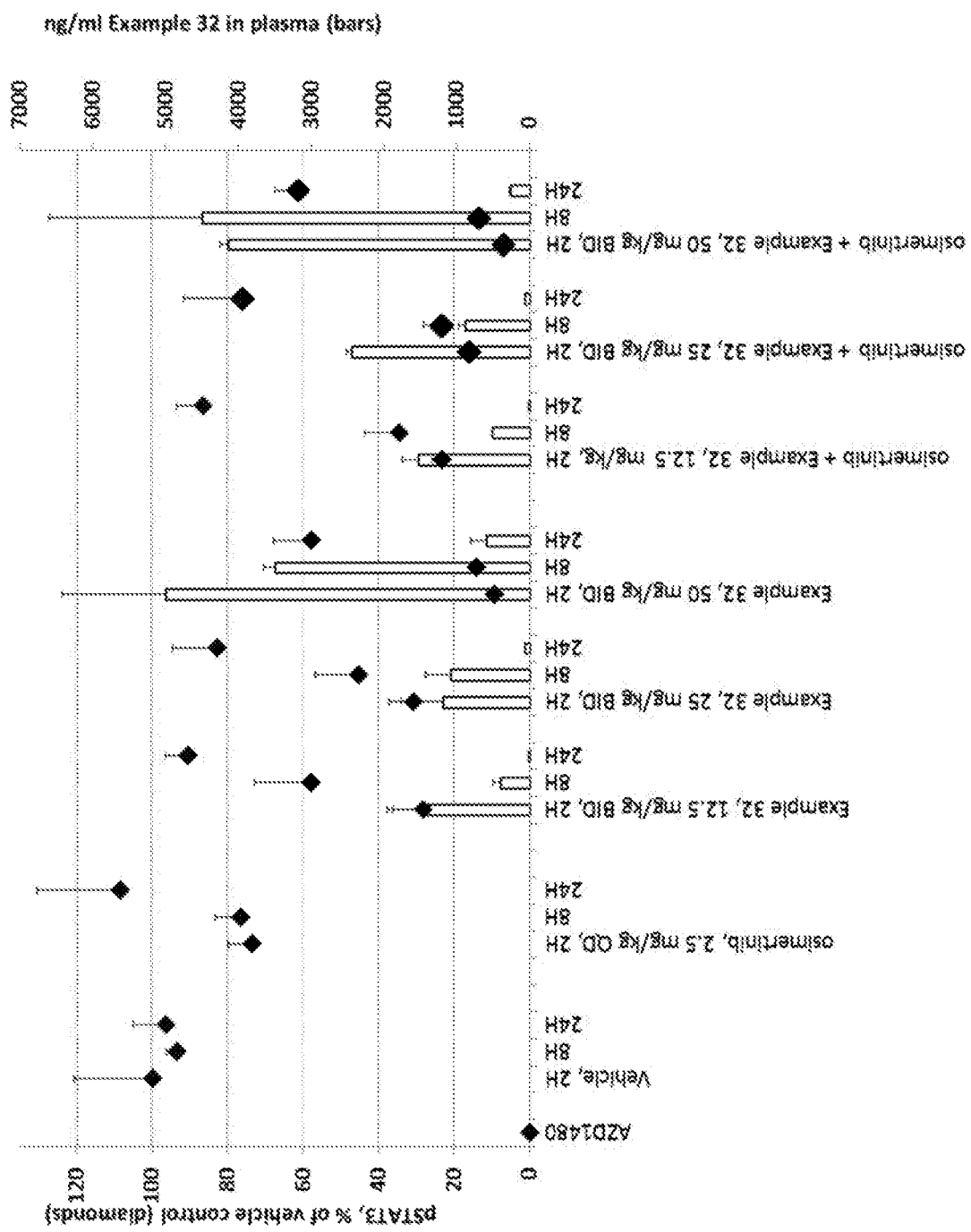
FIG. 21 illustrates knockdown of pSTAT3 in NCI-H1975 tumors after treatment with vehicle, AZD1480 as a single agent, osimertinib (2.5 mg/kg QD) as a single agent, Example 32 (12.5 mg/kg BID, 25 mg/kg BID or 50 mg/kg BID) as a single agent, and osimertinib (2.5 mg/kg QD) administered in combination with Example 32 (12.5 mg/kg BID, 25 mg/kg BID or 50 mg/kg BID). ♦ represents pSTAT3 and bars represent plasma levels of Example 32.

RESULTS: The addition of Example 32 enhanced the antitumor activity of osimertinib, compared to treatment with osimertinib alone. Example 32 administered as a single agent had only weak antitumor activity relative to vehicle control treatment (FIG. 19). The enhancement of antitumor activity increased with increasing dose of Example 32 (12.5 mg/kg up to 50 mg/kg). At the last day of treatment, the inhibition of tumor growth of all of the combination treatments was statistically significant (p<0.05), compared to single agent osimertinib (Table 29). All treatments were well tolerated, with no significant weight loss (FIG. 20) or other outward signs observed over the course of treatment. A dose dependent increase in pSTAT3 knockdown was observed with increasing dose of Example 32 (FIG. 21), which correlated with an increasing level of Example 32 in plasma.

TABLE 29 p values For Antitumor Activity of Osimertinib and Example 32 combinations, After 18 Days of Treatment

| Treatment | vs. Osimertinib Single Agent[a] | vs. Vehicle Control[b] |
|---|---|---|
| osimertinib, 2.5 mg/kg QD | — | 0.0002 |
| osimertinib, 2.5 mg/kg QD + Example 32, 12.5 mg/kg BID | 0.0027 | <0.0001 |
| osimertinib, 2.5 mg/kg QD + Example 32, 25 mg/kg BID | <0.0001 | <0.0001 |
| osimertinib, 2.5 mg/kg QD + Example 32, 50 mg/kg BID | <0.0001 | <0.0001 |

[a]Two-sided test
[b]One-sided test

CONCLUSION: The increased antitumor activity of the osimertinib in combination with Example 32 compared to single agent osimertinib, and the correlation with pSTAT3 knockdown by Example 32, is consistent with a role for STAT3 signaling in escape from, or resistance to, EGFR inhibition in this model of non-small cell lung cancer. This conclusion is further supported by the correlation of increased pSTAT3 knockdown with increased combination antitumor activity over the dose range of Example 32. The results support the hypothesis that inhibition of STAT3 signaling can enhance the antitumor activity of an EGFR inhibitor in T790M EGFR mutant NSCLC.

Example 70: Example 32 In Combination with Gefitinib—In Vivo Efficacy and Pharmacodynamics in the PC-9 Xenograft Model SUMMARY: PC9 tumor xenografts were grown subcutaneously in female nude mice. The mice were treated, by oral dosing, with vehicle, Example 32, the EGFR inhibitor gefitinib, or combinations of Example 32 and gefitinib. Average tumor size at the start of treatment was 240 mm$^3$. Tumor volume was measured twice a week. At the end of treatment (21 days), tumors were harvested for analysis of pSTAT3 (Y705) levels.

The combination of Example 32 and gefitinib resulted in enhanced antitumor activity, compared to treatment with gefitinib alone. The enhanced antitumor activity of the combination correlated with pSTAT3 knockdown by Example 32, consistent with a role for JAK/STAT signaling in escape from pEGFR inhibition.

Gefitinib is an inhibitor of mutant EGFR, with activity in non-small cell lung cancer patients bearing the del19 and L858R mutations in EGFR. This study was carried out to evaluate the ability of Example 32 to enhance the antitumor response to gefitinib in mice bearing subcutaneous PC-9 tumor xenografts. The EGFR gene in PC-9 tumors contains the del19 mutation.

MATERIALS AND METHODS: PC-9 cells (a human NSCLC cell line with the EGFR del19 mutation), were implanted subcutaneously in female CB17-SCID mice (Charles River Laboratories), $2 \times 10^6$ cells/mouse. Thirty-two days after cell implantation, the mice were randomized into 5 groups (7 mice/group, average tumor volume 240 mm$^3$, range 204-298 mm$^3$). Mice were dosed orally with either vehicle (1% Tween® 80, QD), gefitinib as a single agent or combinations of gefitinib and Example 32, for 21 days at the doses and schedules indicated in FIGS. 22 and 23. On the last day of treatment, tumors were collected (2, 8 and 24 hours after the AM dose) for analysis of pSTAT3 (Y705) levels in tumor lysates. Tumor length and width were measured by caliper, and tumor volume calculated using the formula volume=(length×width$^2$)*π/6. Example 32 was formulated in water, adjusted to pH 2 with methane sulfonic acid. Gefitnib was formulated in 1% Tween® 80 in water. All formulations were administered by oral gavage, at a volume of 5 ml/kg. Gefitnib was dosed QD (AM), Example 32 was dosed BID (AM and PM, 8 hours apart). In the groups that were dosed with gefitnib in combination with Example 32, the AM dosing of gefitinib occurred before Example 32 (less than 10 minutes between the two). Y705 phosphorylated STAT3 (pSTAT3) levels were measured in tumor lysates (collected 2, 8 and 24 hours after the AM dose) by Western Blot analysis (4-12% tris-gly PAGE gels and semi-dry transfer to PVDF membrane; immunoblotting for pSTAT3 with Cell Signaling Technologies (CST) #9145 primary antibody and CST #7074 goat anti-rabbit HRP-linked secondary antibody; immunoblotting for beta-actin with CST #3700 primary antibody and CST #7076 goat anti-mouse HRP-linked secondary antibody), with electro-chemiluminescence captured using ImageQuant LAS 4000 and analysis with ImageQuant TL software.

Figure 22:
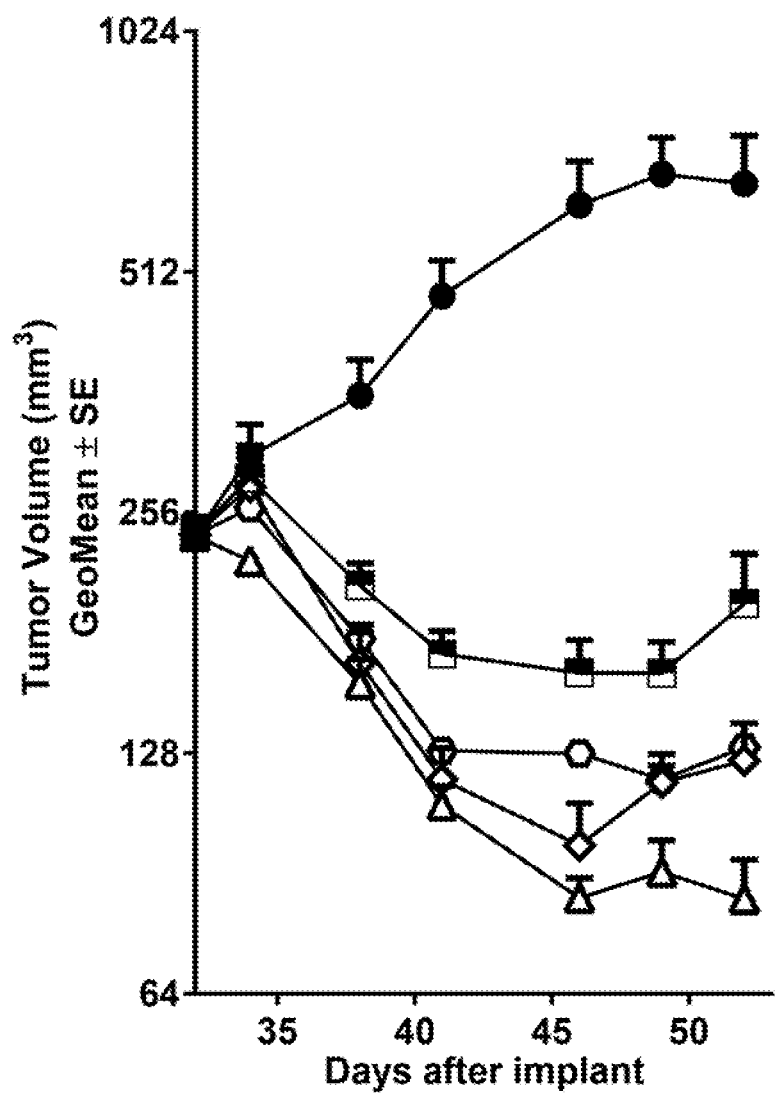
FIG. 22 illustrates PC-9 tumor volumes after treatment with vehicle, gefitinib (IRESSA®, 6.25 mg/kg QD) administered as a single agent and gefitinib (IRESSA®, 6.25 mg/kg QD) administered in combination with Example 32 (12.5 mg/kg BID, 50 mg/kg BID and 50 mg/kg BID dosed 2 days on/5 days off/wk). represents vehicle; represents gefitinib (IRESSA®) administered as a single agent; represents gefinitib (IRESSA®) administered in combination with 50 mg/kg BID Example 32; represents gefitinib (IRESSA®) administered in combination with 12.5 mg/kg BID Example 32; and represents gefinitib (IRESSA®) administered in combination with 50 mg/kg BID with Example 32 dosed 2 days on/5 days off/wk.
Figure 23:
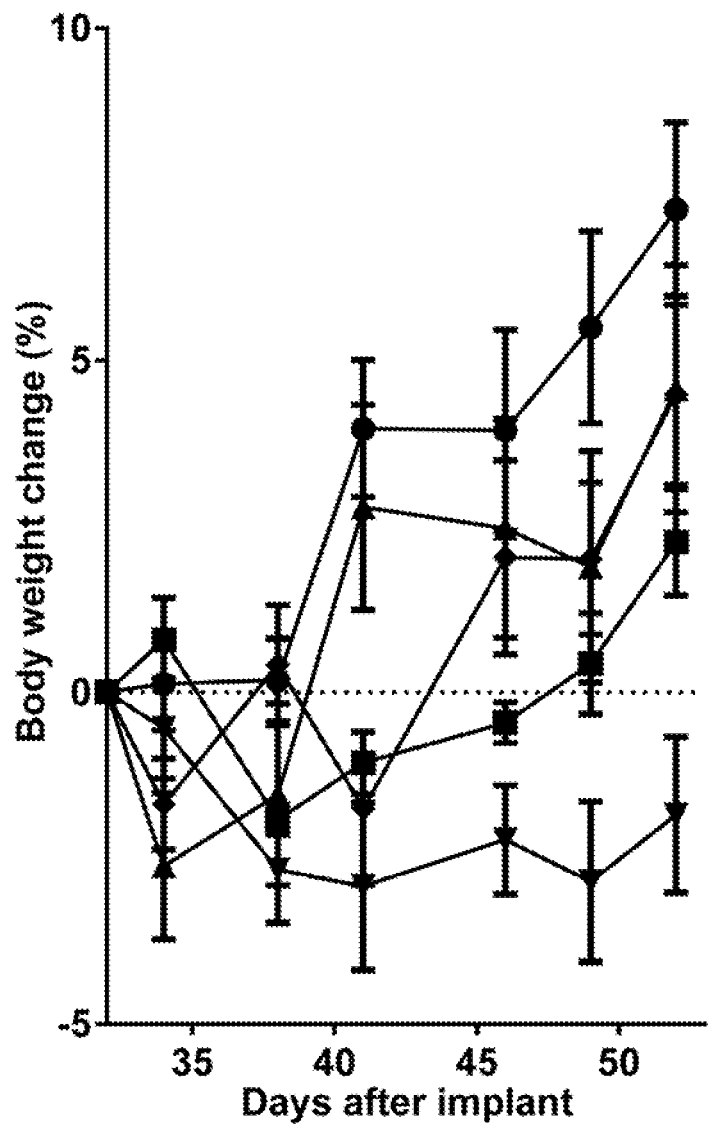
FIG. 23 illustrates body weights after treatment with vehicle, gefitinib (IRESSA®, 6.25 mg/kg QD) administered as a single agent and gefitinib (IRESSA®, 6.25 mg/kg QD) administered in combination with Example 32 (12.5 mg/kg BID, 50 mg/kg BID and 50 mg/kg 2 dosed days on/5 days off/wk). represents vehicle; represents gefitinib (IRESSA®) administered as a single agent; represents gefinitib (IRESSA®) administered in combination with 50 mg/kg BID Example 32; represents gefitinib (IRESSA®) administered in combination with 12.5 mg/kg BID Example 32; and represents gefinitib (IRESSA®) administered in combination with 50 mg/kg BID Example 32 dosed 2 days on/5 days off/wk.
Figure 24:
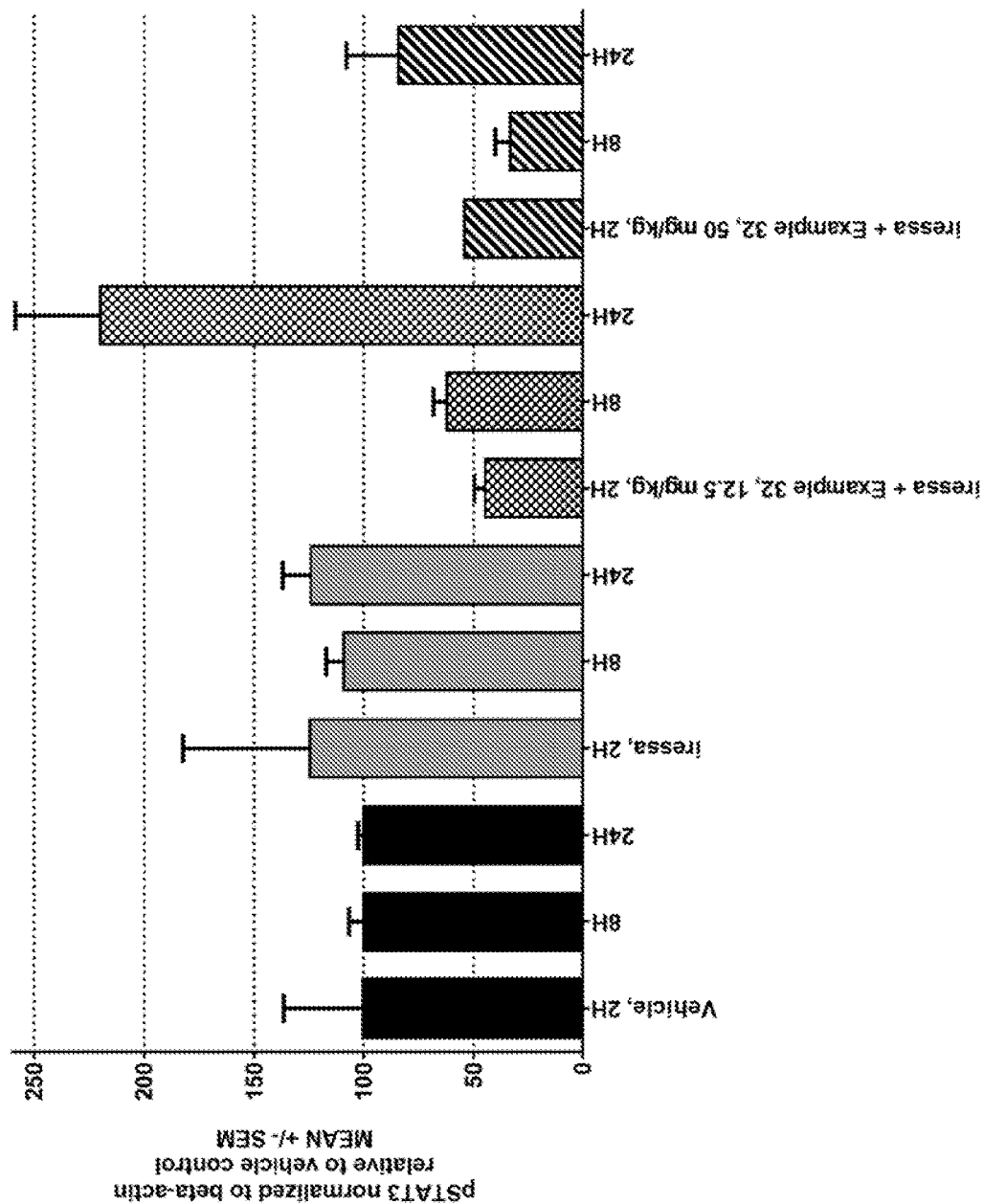
FIG. 24 illustrates knockdown of pSTAT3 in PC-9 tumors after treatment with vehicle, gefitinib (IRESSA®, 6.25 mg/kg QD) administered as a single agent and gefitinib (IRESSA®, 6.25 mg/kg QD) administered in combination with Example 32 (12.5 mg/kg BID and 50 mg/kg BID).

RESULTS: The addition of Example 32 enhanced the antitumor activity of gefitinib (iressa), compared to treatment with gefitinib (FIG. 22). For treatment with gefitinib in combination with Example 32, the enhancement of antitumor activity increased with increasing dose of Example 32, from 12.5 mg/kg to 50 mg/kg. When Example 32 was dosed 2 days on/5 days of on a weekly cycle, in combination with daily gefitinib, the antitumor activity was similar to that of Example 32 at 12.5 mg/kg administered 7 days a week in combination with gefitinib. On the last day of treatment, the inhibition of tumor growth with gefinitib in combination with 50 mg/kg of Example 32 was statistically significant (p<0.05), compared to single agent gefitinib (Table 30). Gefitinib in combination with 12.5 mg/kg of Example 32 daily and with 50 mg/kg Example 32 dosed 2 days on/5 days off had greater activity than single agent gefitinib, but did not quite achieve statistical significance. All treatments were well tolerated, with no significant weight loss (FIG. 23) or other outward signs observed over the course of treatment. A dose dependent increase in the duration of pSTAT3 knockdown was observed with increasing dose of Example 32 (FIG. 24).

TABLE 30 p values for Antitumor Activity of Gefitinib in Combination with Example 32, After 36 Days of Treatment

| Treatment | vs. gefitinib single agent[a] | vs. vehicle control[b] |
|---|---|---|
| gefitinib, 6.25 mg/kg QD | — | <0.0001 |
| gefitinib, 6.25 mg/kg QD + Example 32, 12.5 mg/kg BID | 0.1263 | <0.0001 |
| gefitinib, 6.25 mg/kg QD + Example 32, 50 mg/kg BID | 0.0006 | <0.0001 |
| gefitinib, 6.25 mg/kg QD + Example 32, 50 mg/kg BID, 2 days on/5 days off/week | 0.0685 | <0.0001 |

[a]Two-sided test
[b]One-sided test

CONCLUSION: The increased antitumor activity of Example 32 in combination with gefitinib compared to single agent gefitinib, and the correlation with pSTAT3 knockdown by Example 32, is consistent with a role for STAT3 signaling in escape from, or resistance to, EGFR inhibition in this model of non-small cell lung cancer. This conclusion is further supported by the correlation of increased pSTAT3 knockdown with increased combination antitumor activity over the dose range of Example 32 (12.5 to 50 mg/kg). The results support the hypothesis that inhibition of STAT3 signaling can enhance the antitumor activity of an EGFR inhibitor in NSCLC tumors bearing the exon 19 deletion in the EGFR gene.

Example 71: Example 32 Plus Gefitinib Combination—In Vivo Efficacy and Pharmacodynamics in the H1650 Xenograft Model SUMMARY: NCI-H1650 tumor xenografts were grown subcutaneously in female nude mice. The mice were treated, by oral dosing, with vehicle, Example 32, the EGFR inhibitor gefitinib, or combinations of Example 32 plus gefitinib. Average tumor size at the start of treatment was 257 mm$^3$. Tumor volume was measured twice a week. Additional tumor bearing mice were treated with the same doses of Example 32 and gefitinib, and tumors and plasma were harvested after one day of treatment for analysis of pSTAT3 levels in tumors and drug levels in plasma.

The combination of Example 32 plus gefitinib resulted in enhanced antitumor activity, compared to treatment with gefitinib alone. The enhanced antitumor activity of the combination correlated with pSTAT3 knockdown by Example 32, consistent with a role for JAK/STAT signaling in escape from pEGFR inhibition.

Gefitinib is an inhibitor of mutant EGFR, with activity in non-small cell lung cancer patients bearing the del19 and L858R mutations in EGFR. This study was carried out to evaluate the ability of Example 32 to enhance the antitumor response to gefitinib in mice bearing subcutaneous NCI-H1650 tumor xenografts. The EGFR gene in NCI-H1650 tumors contains the del19 mutation.

MATERIALS AND METHODS: NCI-H1650 cells (a human NSCLC cell line with the EGFR del19 mutation), were implanted subcutaneously in female CB17-SCID mice (Charles River Laboratories), 5×10$^6$ cells/mouse. Twenty-three days after cell implantation, the mice were randomized into 6 groups (9 mice/group, average tumor volume 257 mm$^3$, range 205-303 mm$^3$). Mice were dosed orally with either vehicle (1% Tween® 80, QD), gefitinib as a single agent, Example 32 as a single agent, or combinations of gefitinib plus Example 32, at the doses and schedules indicated in FIGS. 25 and 26 for 21 days. Tumor length and width were measured by caliper, and tumor volume calculated using the formula volume=(length×width$^2$)*π/6. Example 32 was formulated in water, adjusted to pH 2 with methane sulfonic acid. Gefitnib was formulated in 1% Tween® 80 in water. All formulations were administered by oral gavage, at a volume of 5 ml/kg. Gefitnib was dosed QD (AM), Example 32 was dosed BID (AM and PM, 8 hours apart). In the groups that were dosed with gefitnib in combination with Example 32, the AM dosing of gefitinib occurred before dosing with Example 32 (less than 10 minutes between the two). Additional tumor bearing mice were treated with the same doses of Example 32 and gefitinib, and tumors and plasma were harvested after one day of treatment for analysis of pSTAT3 levels in tumors and drug levels in plasma. AZD1480 (5-chloro-N2-[(1 S)-1-(5-fluoro-2-pyrimidinyl)ethyl]-N4-(5-methyl-1H-pyrazol-3-yl)-2,4-pyrimidinediamine, see U.S. Patent Application Publication No. US20080287475), a JAK1/2 inhibitor and a positive control for 100% pSTAT3 knockdown in the pharmacokinetic/pharmacodynamic experiment was formulated in 0.5% HPMC/0.1% Tween® 80 in water, and administered by oral gavage at a volume of 5 ml/kg. Y705 phosphorylated STAT3 (pSTAT3) levels were measured in tumor lysates (collected 2, 8 and 24 hours after the AM dose) by Western Blot analysis (4-12% tris-gly PAGE gels and semi-dry transfer to PVDF membrane; immunoblotting for pSTAT3 with Cell Signaling Technologies (CST) #9145 primary antibody and CST #7074 goat anti-rabbit HRP-linked secondary antibody; immunoblotting for GAPDH with CST #2118 primary antibody and CST #7074 goat anti-rabbit HRP-linked secondary antibody), with electrochemiluminescence captured using ImageQuant LAS 4000 and analysis with ImageQuant TL software. Drug levels in plasma were measured by LC/MS, using a Linear Ion Trap Quadrupole LC/MS/MS Mass Spectrometer (QTRAP 5500 model 1024945-BB, AB Sciex Instruments), with separation on a Waters Xbridge C18 column.

Figure 25:
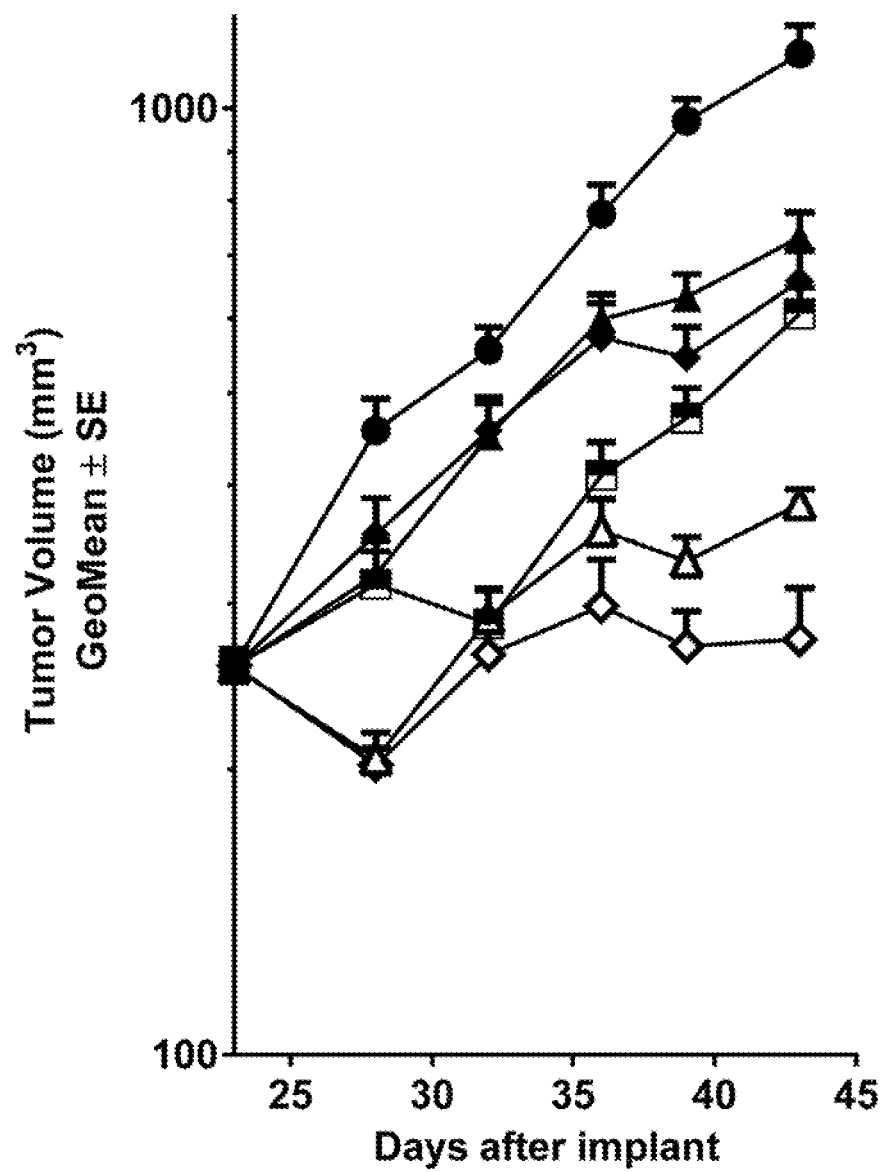
FIG. 25 illustrates NCI-H1650 tumor volumes after treatment with vehicle, gefitinib (IRESSA®, 6.25 mg/kg QD) administered as a single agent, Example 32 (25 mg/kg BID or 50 mg/kg BID) as a single agent and gefitinib (IRESSA®, 6.25 mg/kg QD) administered in combination with Example 32 (25 mg/kg BID or 50 mg/kg BID). represents vehicle; represents gefitinib (IRESSA®) administered as a single agent; represents 25 mg/kg BID Example 32 administered as a single agent; represents 50 mg/kg BID Example 32 administered as a single agent; represents gefinitib (IRESSA®) administered in combination with 25 mg/kg BID Example 32; and represents gefinitib (IRESSA®) administered in combination with 50 mg/kg BID Example 32.
Figure 26:
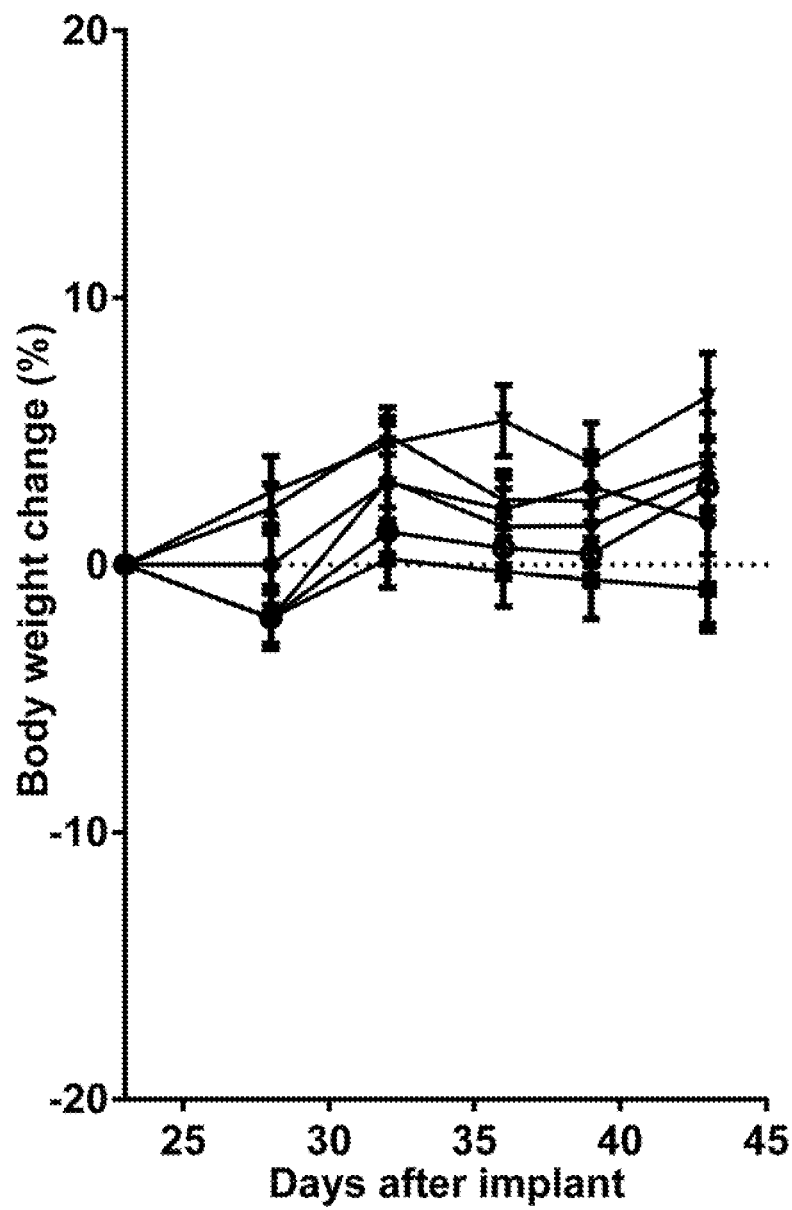
FIG. 26 illustrates body weights after treatment with vehicle, gefitinib (IRESSA®, 6.25 mg/kg QD) administered as a single agent, Example 32 (25 mg/kg BID or 50 mg/kg BID) administered as a single agent and gefitinib (IRESSA®, 6.25 mg/kg QD) administered in combination with Example 32 (25 mg/kg BID or 50 mg/kg BID). represents vehicle; represents gefitinib (IRESSA®) administered as a single agent; represents 25 mg/kg BID Example 32 administered as a single agent; represents 50 mg/kg BID Example 32 administered as a single agent; ◆ represents gefinitib (IRESSA®) administered in combination with 25 mg/kg BID Example 32; and ◆ represents gefinitib (IRESSA®) administered in combination with 50 mg/kg BID Example 32.
Figure 27:
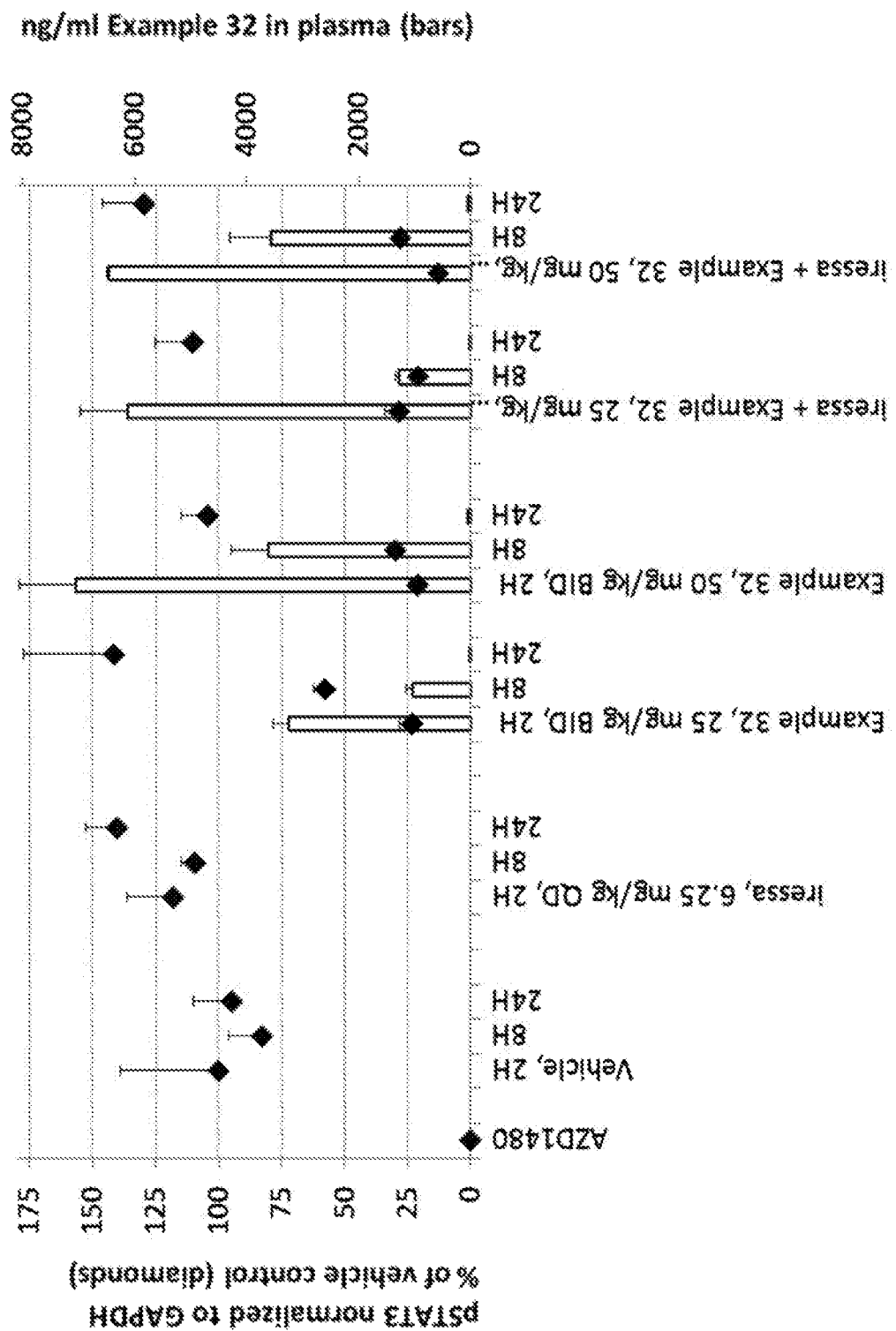
FIG. 27 illustrates knockdown of pSTAT3 in NCI-H1650 tumors after treatment with vehicle, AZD1408 administered as a single agent, gefitinib (IRESSA®, 6.25 mg/kg QD) administered as a single agent, Example 32 (25 mg/kg BID or 50 mg/kg BID) administered as a single agent and gefitinib (IRESSA®, 6.25 mg/kg QD) administered in combination with Example 32 (25 mg/kg BID or 50 mg/kg BID). ◆ represents pSTAT and bars represent plasma levels of Example 32.

RESULTS: The addition of Example 32 enhanced the antitumor activity of gefitinib, compared to single agent gefitinib (FIG. 25). Example 32 administered as a single agent had only modest antitumor activity. For the treatment of gefitinib in combination with Example 32, enhancement of antitumor activity increased with increasing dose of Example 32, from 25 mg/kg to 50 mg/kg. At the last day of treatment, the inhibition of tumor growth with gefinitib in combination with 25 or 50 mg/kg of Example 32 was statistically significant (p<0.05), compared to single agent gefitinib (Table 31). All treatments were well tolerated, with no significant weight loss (FIG. 26) or other outward signs observed over the course of treatment. Knockdown of pSTAT3 was observed with Example 32 as single agent and in combination (FIG. 27), measured after one day of treatment.

TABLE 31 p values for Antitumor Activity of Gefitinib Plus Example 32 Combination, After 21 Days of Treatment

| Treatment | vs. gefitinib single agent[a] | vs. vehicle control[b] |
|---|---|---|
| gefitinib, 6.25 mg/kg QD | — | <0.0001 |
| Example 32, 25 mg/kg BID | 0.0314 | 0.0002 |
| Example 32, 50 mg/kg BID | 0.282 | <0.0001 |
| gefitinib, 6.25 mg/kg QD + Example 32, 25 mg/kg BID | <0.0001 | <0.0001 |
| gefitinib, 6.25 mg/kg QD + Example 32, 50 mg/kg BID | <0.0001 | <0.0001 |

[a]Two-sided test
[b]One-sided test

CONCLUSIONS: The increased antitumor activity of Example 32 in combination with gefitinib compared to single agent gefitinib and the correlation with pSTAT3 knockdown by Example 32 is consistent with a role for STAT3 signaling in escape from, or resistance to, EGFR inhibition in this model of non-small cell lung cancer. The results support the hypothesis that inhibition of STAT3 signaling can enhance the antitumor activity of an EGFR inhibitor in NSCLC tumors bearing the del19 mutation in the EGFR gene.

Example 72: Example 32 in Combination with Osimertinib—In Vivo Efficacy and Pharmacodynamics in the LG1049 Xenograft PDX Model SUMMARY: LG1049 non-small cell lung cancer PDX tumor xenografts were grown subcutaneously in female NSG mice. The mice were treated, by oral dosing, with vehicle, Example 32 as a single agent, the EGFR inhibitor osimertinib (an irreversible inhibitor of T790M mutant EGFR) as a single agent, or combinations of Example 32 with osimertinib. Average tumor size at the start of treatment was 189 mm$^3$. Tumor volume was measured twice a week. A separate set of mice bearing LG1049 tumors were treated for 5 days and tumors harvested for analysis of pSTAT3 (Y705) and pEGFR levels.

The combination of Example 32 with osimertinib resulted in enhanced tumor regression, compared to treatment with osimertinib alone. There was no significant antitumor activity observed after treatment with Example 32 alone. When treatment was stopped after 28 days, tumors rapidly regrew in mice that had been treated with osimertinib as a single agent or with osimertinib in combination with Example 32. When Example 32 treatment was continued, tumors also regrew, but more slowly. Analysis of tumors taken from mice treated for 5 days confirmed robust knockdown of pSTAT3 and pEGFR by Example 32 and osimertinib, respectively.

Osimertinib, an irreversible inhibitor of T790M mutant EGFR, overcomes T790M-mediated resistance to EGFR inhibitors such as gefitinib and erlotinib in lung cancer. This study was carried out to evaluate the ability of Example 32 to enhance the antitumor response to osimertinib in mice bearing subcutaneous LG1049 tumor xenografts. LG1049 is a non-small cell lung cancer (NSCLC) primary tumor xenograft (PDX) model, in which the EGFR gene contains the T790M resistance mutation.

MATERIALS AND METHODS: LG1049 tumor fragments were implanted subcutaneously in female NSG mice (JAX Stock No. 005557). Once tumor volumes reached ~125-275 mm$^3$, mice were randomized into 5 groups (10 mice/group, average tumor volume 189 mm$^3$, range 138-253 mm$^3$). Mice were dosed orally with either vehicle, Example 32 as a single agent, osimertinib as a single agent, or combinations of Example 32 with osimertinib, at the doses and schedules indicated in FIGS. 28 and 29 for 28 days (18 days for single agent Example 32). In one of the two groups that received Example 32 in combination with osimertinib, treatment with Example 32 was continued for an additional 14 days. A separate set of tumor bearing mice were treated with vehicle, Example 32 as a single agent, osimertinib as a single agent, or a combination of Example 32 and osimertinib for 5 days, and tumors collected for analysis of pSTAT3 (Y705) and pEGFR levels in tumor lysates. Tumor length and width were measured by caliper, and tumor volume calculated using the formula volume=(length×width$^2$)*π/6.

Example 32 was formulated in water, adjusted to pH 2 with methane sulfonic acid. Osimertinib was formulated in 0.5% HPMC in water. All formulations were administered by oral gavage, at a volume of 5 ml/kg. Osimertinib was dosed QD (AM), Example 32 was dosed BID (AM and PM, 8 hours apart). In the groups that were dosed with Example 32 in combination with osimertinib, the AM dosing of osimertinib occurred before the dosing of Example 32 (less than 10 minutes between the two). Phosphorylated STAT3 and phosphorylated EGFR levels were measured in tumor lysates by Western Blot analysis (4-12% tris-gly PAGE gels and semi-dry transfer to PVDF membrane; immunoblotting for pSTAT3 with Cell Signaling Technologies (CST) #9145 primary antibody and CST #7074 goat anti-rabbit HRP-linked secondary antibody; immunoblotting for pEGFR pY1173 with Epitomics #1124 primary antibody and CST #7074 goat anti-rabbit HRP-linked secondary antibody; immunoblotting for GAPDH with CST #2118 primary antibody and CST #7074 goat anti-rabbit HRP-linked secondary antibody), with electrochemiluminescence captured using ImageQuant LAS 4000 and analysis with ImageQuant TL software.

Figure 28:
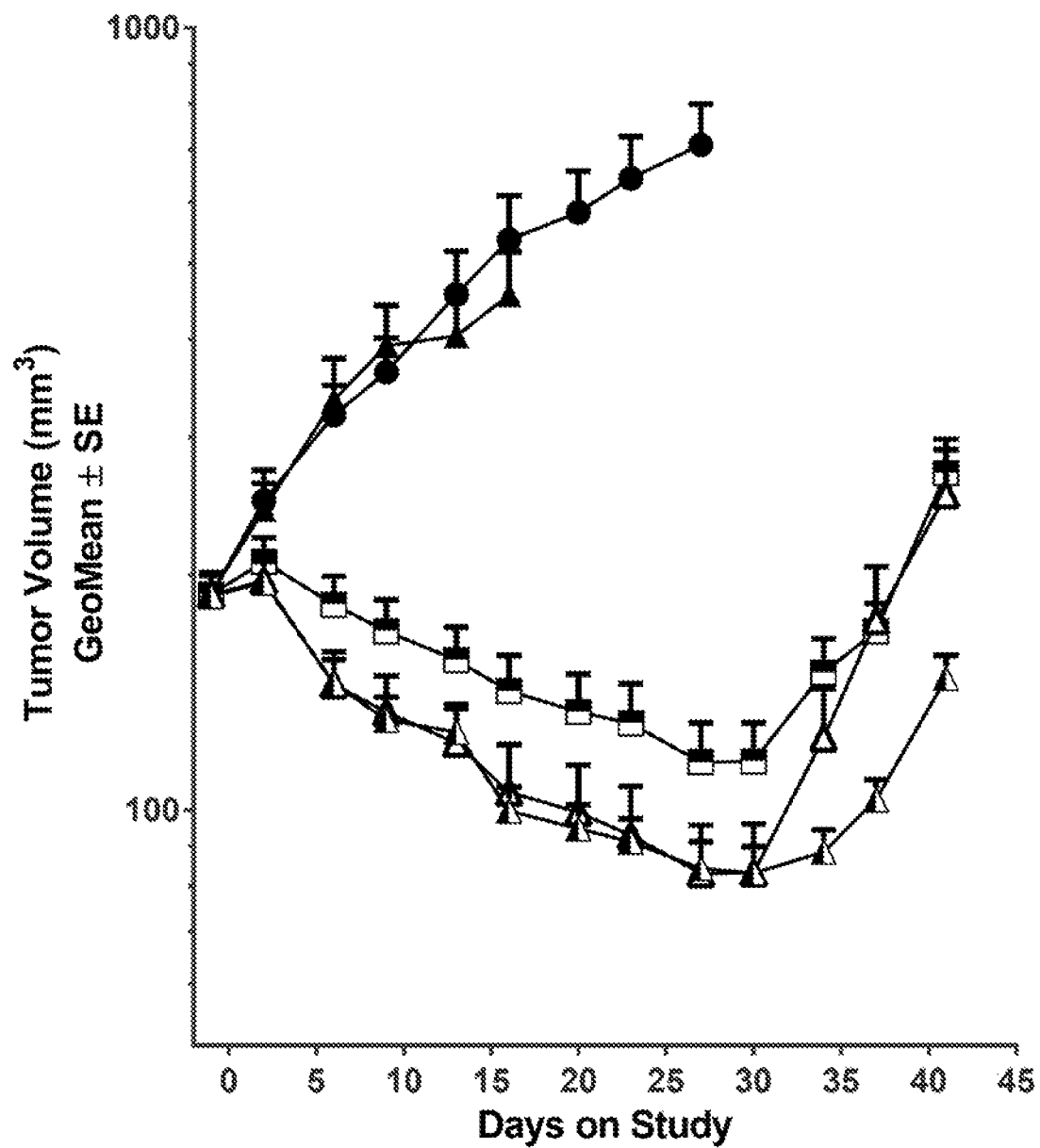
FIG. 28 illustrates LG1049 tumor volumes after treatment with vehicle (◆); osimertinib (25 mg/kg QD) administered as a single agent for 28 days (▬), Example 32 (25 mg/kg BID) administered as a single agent for 18 days (▲); osimertinib (25 mg/kg QD) administered in combination with Example 32 (25 mg/kg BID) dosed 7 days, then 3 days on/4 days off/wk until day 28 (△). ☆ represents mice treated with the combination for 28 days, then with Example 32 (25 mg/kg BID) alone for 3 days on/4 days off/wk until the end of the study.
Figure 29:
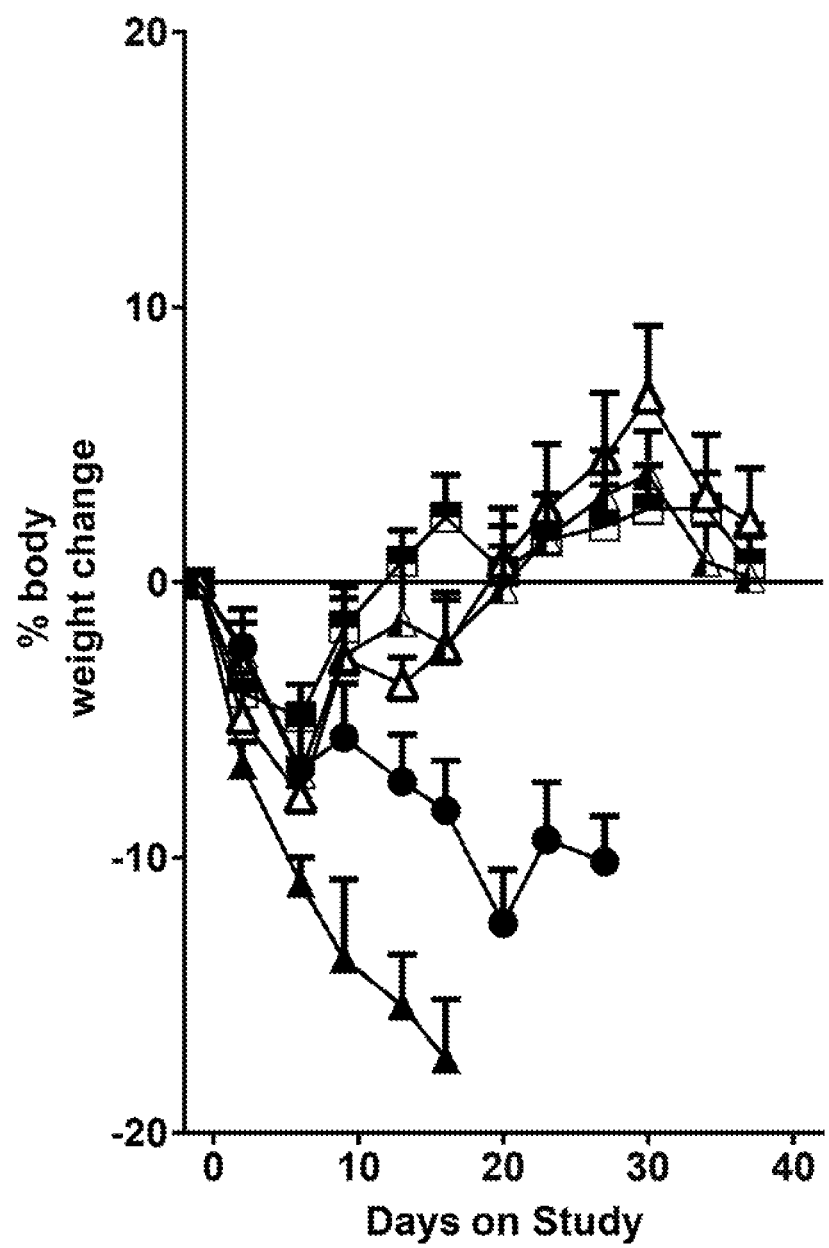
FIG. 29 illustrates body weights after treatment LG1049 tumor volumes after treatment with vehicle (◆), osimertinib (25 mg/kg QD) administered as a single agent for 28 days (▬), Example 32 (25 mg/kg BID) administered as a single agent (▲), osimertinib (25 mg/kg QD) administered in combination with Example 32 (25 mg/kg BID) dosed 7 days, then 3 days on/4 days off until day 28 (△). ☆ represents mice treated with the combination for 28 days, then with Example 32 (25 mg/kg BID) alone for 3 days on/4 days off/wk until the end of the study

RESULTS: Addition of Example 32 enhanced the tumor regression induced by osimertinib, compared to treatment with osimertinib alone. Example 32 administered as a single agent had no significant activity relative to vehicle control treatment (FIG. 28). When treatment was stopped, after 28 days of dosing (osimertinib and Example 32 in combination with osimertinib groups), tumors regrew. When osimertinib treatment was continued for an additional 14 days (one of the combination groups) tumors also regrew, but more slowly. Mice treated with vehicle or Example 32 alone experienced significant weight loss (FIG. 29), suggesting that the weight loss was the result of tumor growth. The Example 32 single agent group was terminated early due to excessive weight loss. Tumor dependent weight loss was seen in other experiments with this model. The lack of significant weight loss in treatment groups in which tumors regressed (osimertinib as a single agent, and Example 32 in combination with osimertinib), is consistent with weight loss being dependent on tumor growth.

Figure 30:
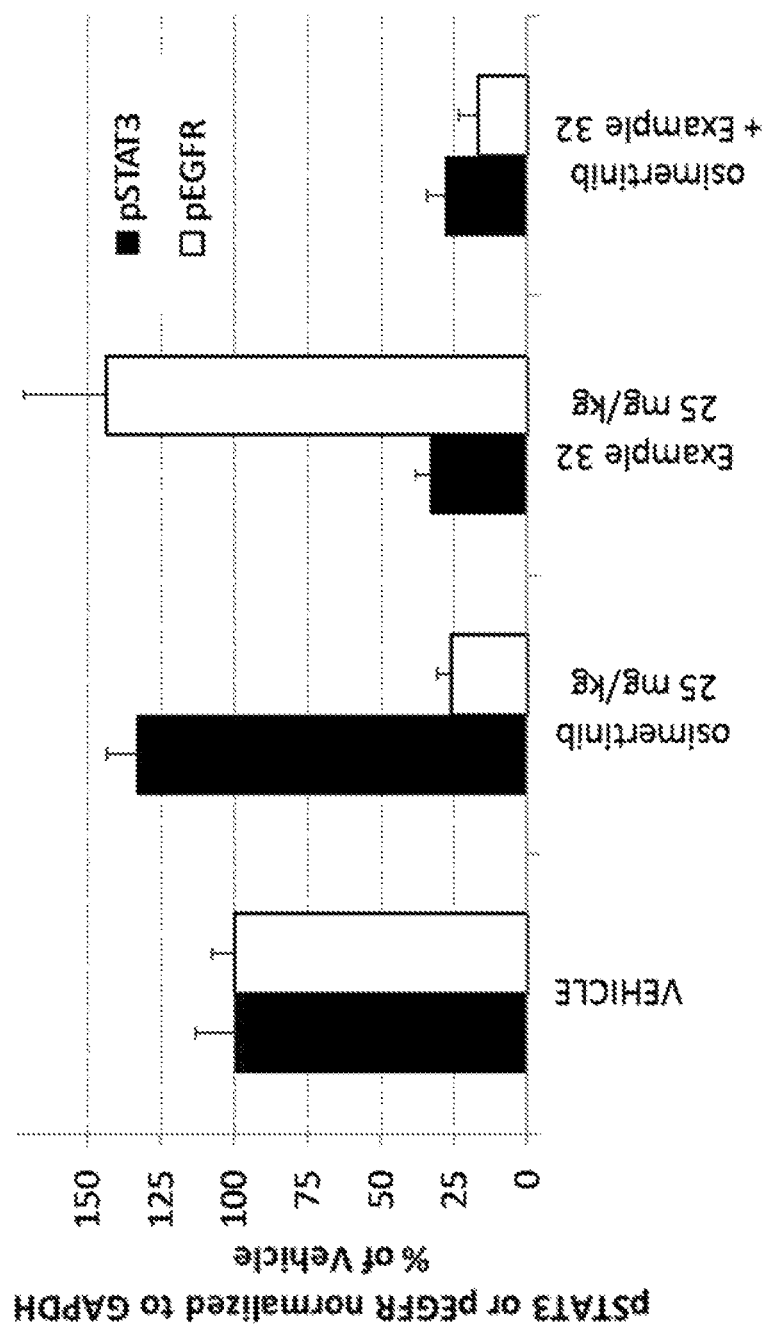
FIG. 30 illustrates knockdown of pSTAT3 and pEGFR in LG1049 tumors after five days of treatment with vehicle, osimertinib (25 mg/kg QD) administered as a single agent, Example 32 (25 mg/kg BID) administered as a single agent and osimertinib (25 mg/kg QD) administered in combination with Example 32 (25 mg/kg BID).
Figure 31A:
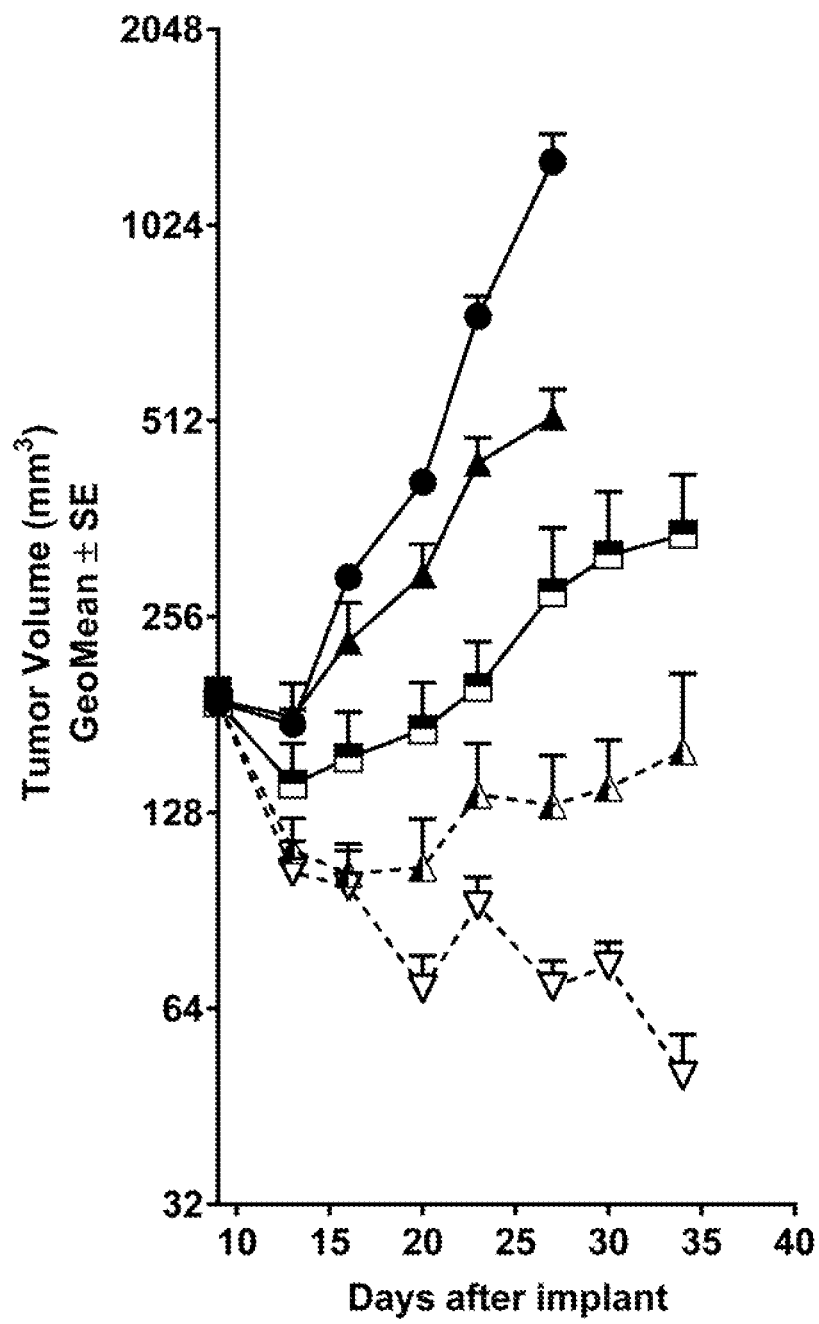
FIGS. 31A-E illustrate NCI-H1975 tumor volumes after treatment with vehicle, Example 32 administered as a single agent, osimertinib administered as a single agent, and Example 32 administered in combination with osimertinib.
Figure 31B:
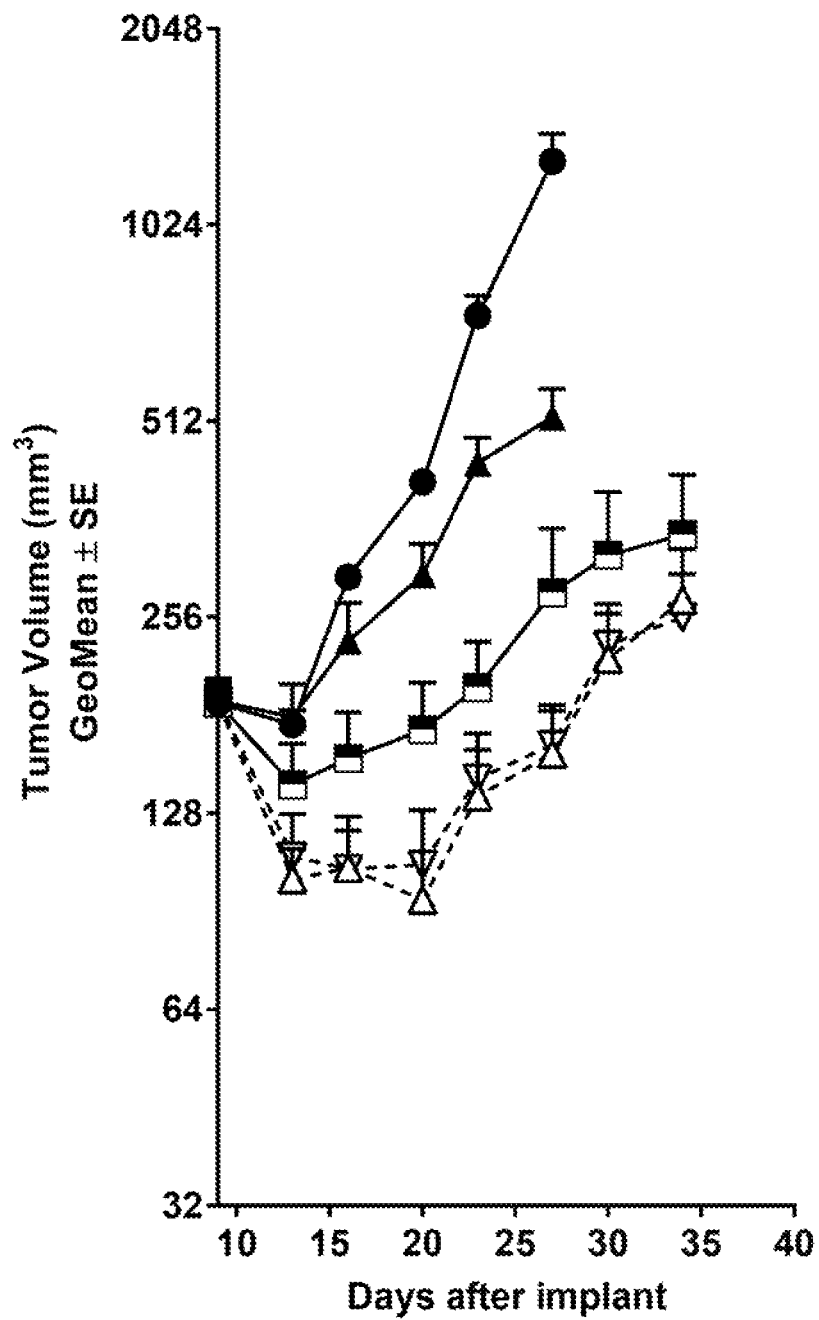
Figure 31C:
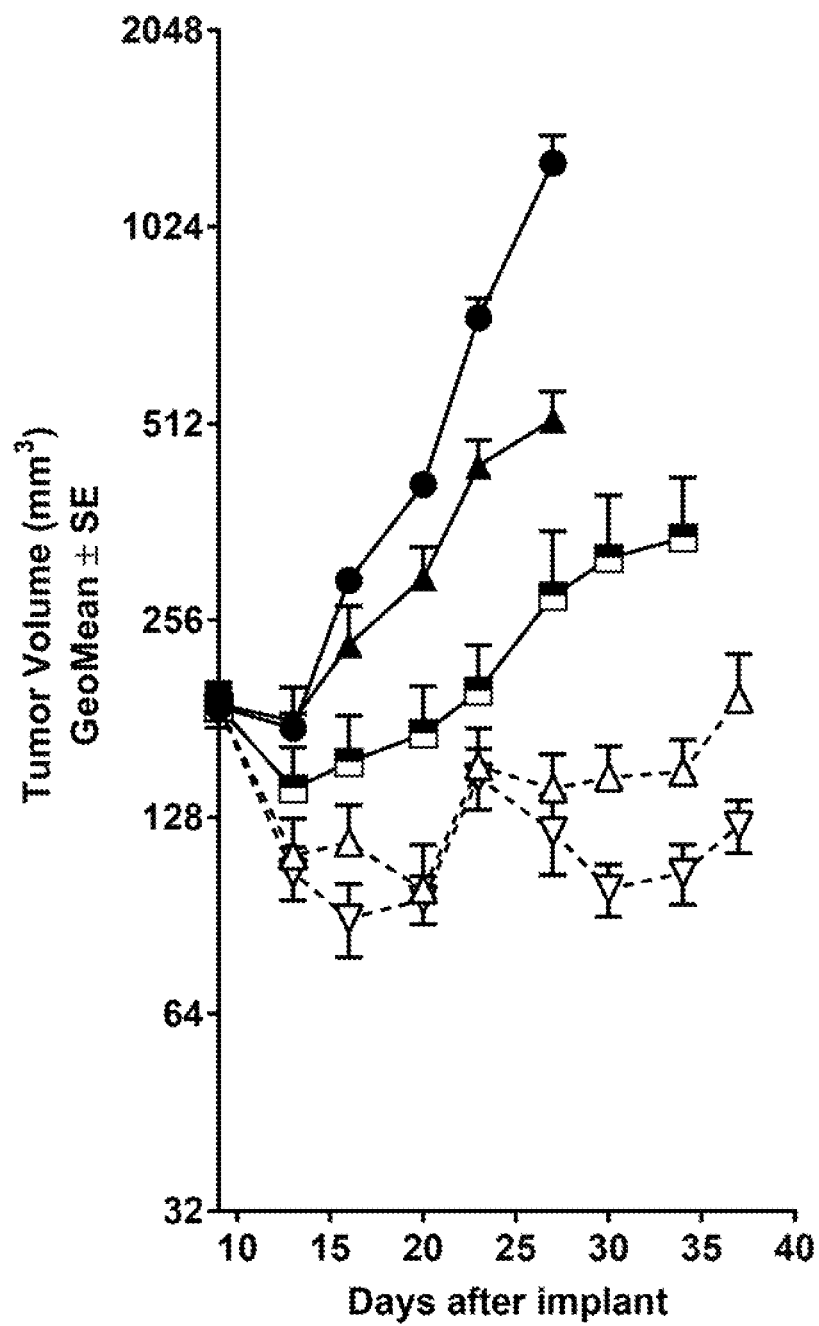
Figure 31D:
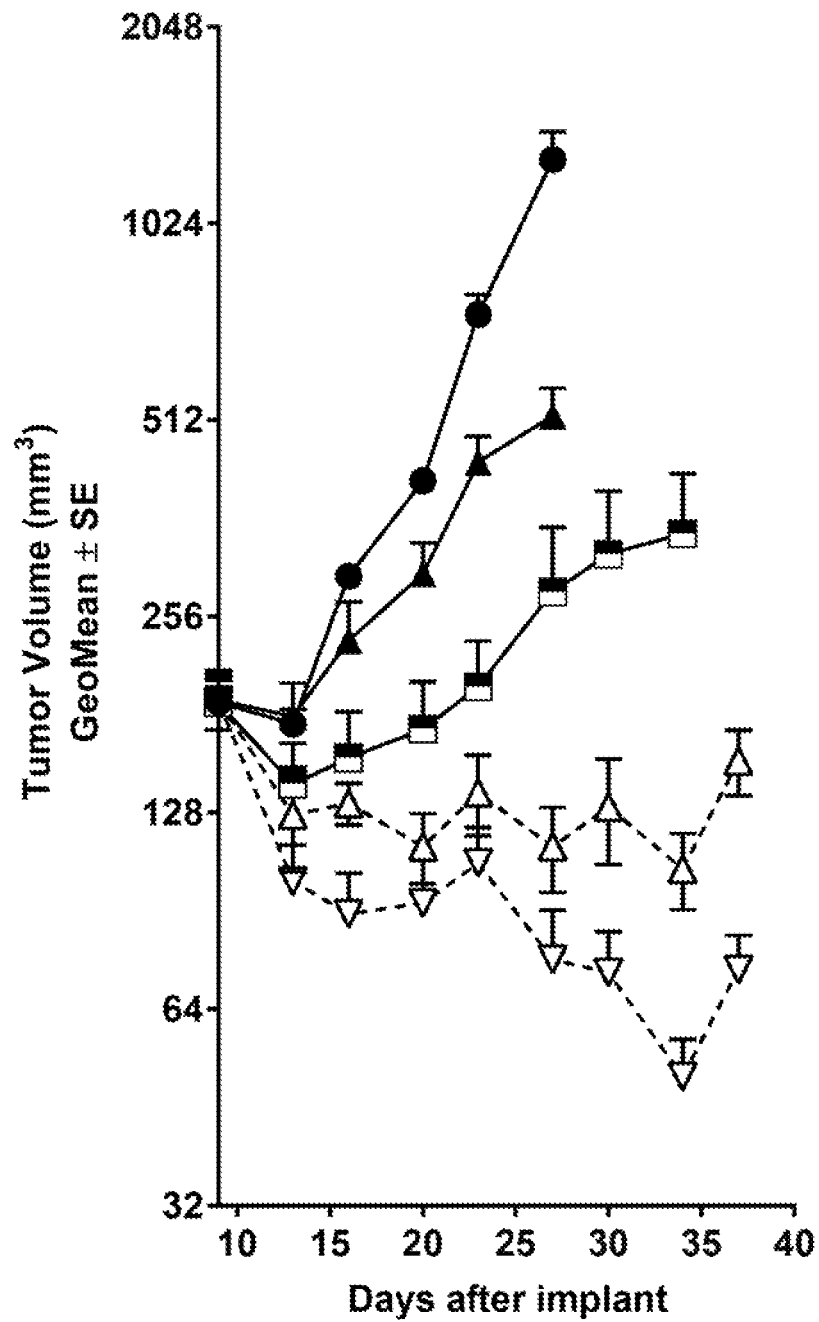
Figure 31E:
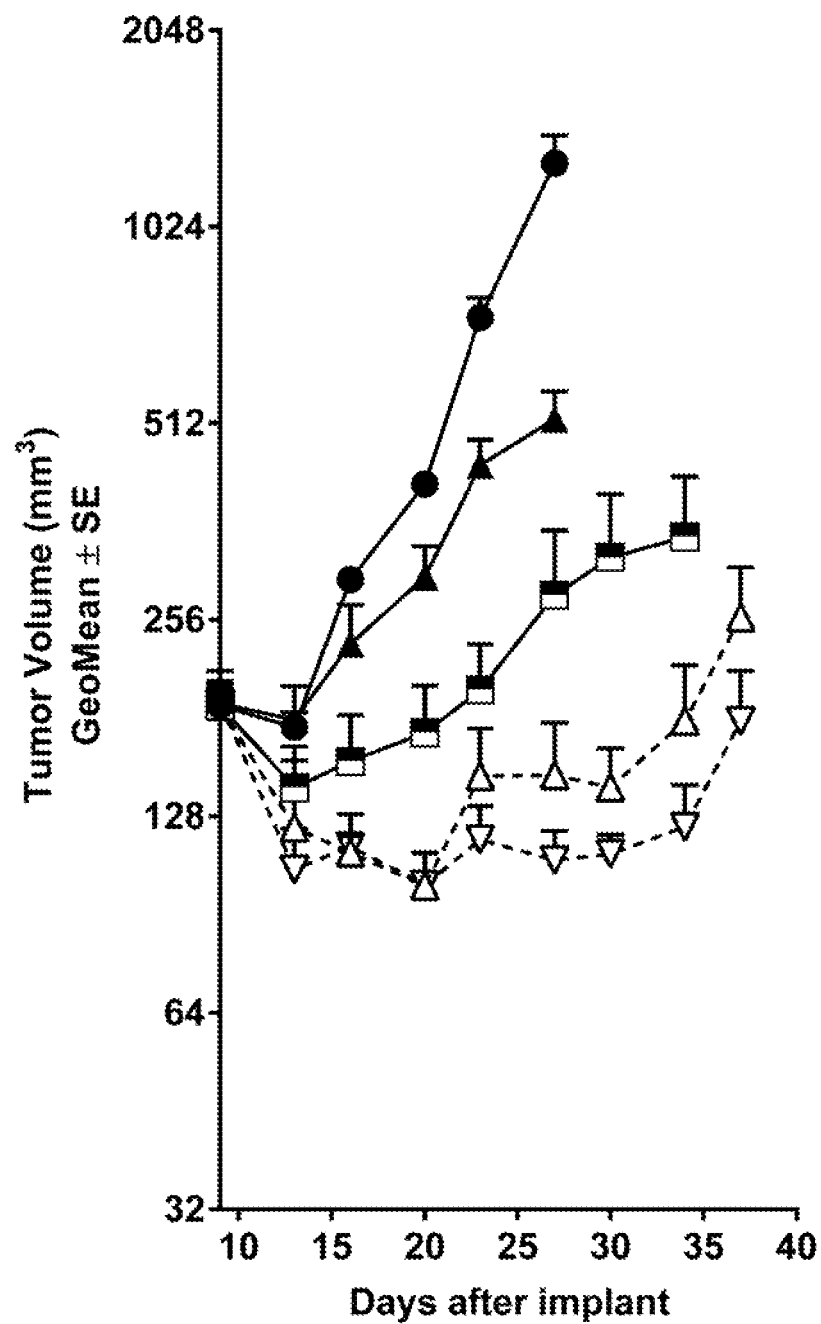

The doses and schedules of Example 32 and osimertinib used in this experiment resulted in robust knockdown of pSTAT3 and pEGFR after 5 days of treatment, measured at 4H after the final dose (FIG. 30).

CONCLUSION: The increased antitumor activity of Example 32 in combination with osimertinib compared to single agent osimertinib, and the correlation with pSTAT3 knockdown by Example 32, is consistent with a role for STAT3 signaling in escape from, or resistance to, EGFR inhibition in this model of EGFR T790M mutant non-small cell lung cancer. The results support the hypothesis that inhibition of STAT3 signaling can enhance the antitumor activity of an EGFR inhibitor in T790M EGFR mutant NSCLC.

Example 73: Example 32 in Combination with Osimertinib—In Vivo Efficacy of Intermittent Example 32 Dosing Schedules in the H1975 Xenograft Model SUMMARY: NCI-H1975 tumor xenografts were grown subcutaneously in female nude mice. The mice were treated by oral dosing with vehicle, Example 32 as a single agent, the EGFR inhibitor osimertinib (an irreversible inhibitor of T790M mutant EGFR) as a single agent, or combinations of osimertinib and Example 32 on different intermittent dosing schedules. Average tumor size at the start of treatment was 185 mm$^3$. Tumor volume was measured twice a week.

Compared to treatment with osimertinib alone, the combination of Example 32 and osimertinib resulted in enhanced antitumor activity on all the schedules of the treatment tested. There was a trend to reduced efficacy with less intensive dosing schedules. The enhanced antitumor activity of the combination and the correlation of greater efficacy with more intensive dosing schedules of Example 32 is consistent with a role for JAK/STAT signaling in escape from pEGFR inhibition.

This study was carried out to evaluate the ability of Example 32 to enhance the antitumor response to osimertinib in mice bearing subcutaneous NCI-H1975 tumor xenografts, and to investigate the frequency of target coverage with Example 32 that is required to retain combination activity. The EGFR gene in the NCI-H1975 tumors is mutated at L858R and also contains the T790M resistance mutation.

MATERIALS AND METHODS: NCI-H1975 cells (a human NSCLC cell line with L858R and T790M mutations in the EGFR gene), were implanted subcutaneously in female NCr nude mice (Taconic Laboratories), 3×10$^6$ cells/mouse. Nine days after cell implantation, mice were randomized into 13 groups (8 mice/group, average tumor volume 185 mm$^3$, range 127-327 mm$^3$), and were dosed orally with either vehicle, Example 32 as a single agent, osimertinib as a single agent, or Example 32 in combination with osimertinib, at the different doses and schedules of Example 32 indicated in FIGS. 31A-31E, for 19 to 29 days (better responding groups were dosed longer). Tumor length and width were measured by caliper, and tumor volume calculated using the formula volume=(length×width$^2$)*π/6. Example 32 was formulated in water, adjusted to pH 2 with methane sulfonic acid. Osimertinib was formulated in 0.5% HPMC in water. All formulations were administered by oral gavage, at a volume of 5 ml/kg. Osimertinib was dosed QD (AM), and Example 32 was dosed BID (AM and PM, 8 hours apart). In the groups that were dosed with Example 32 in combination with osimertinib, the AM dose of osimertinib was administered 3 hours before Example 32 to minimize exposure interactions.

Figure 32:
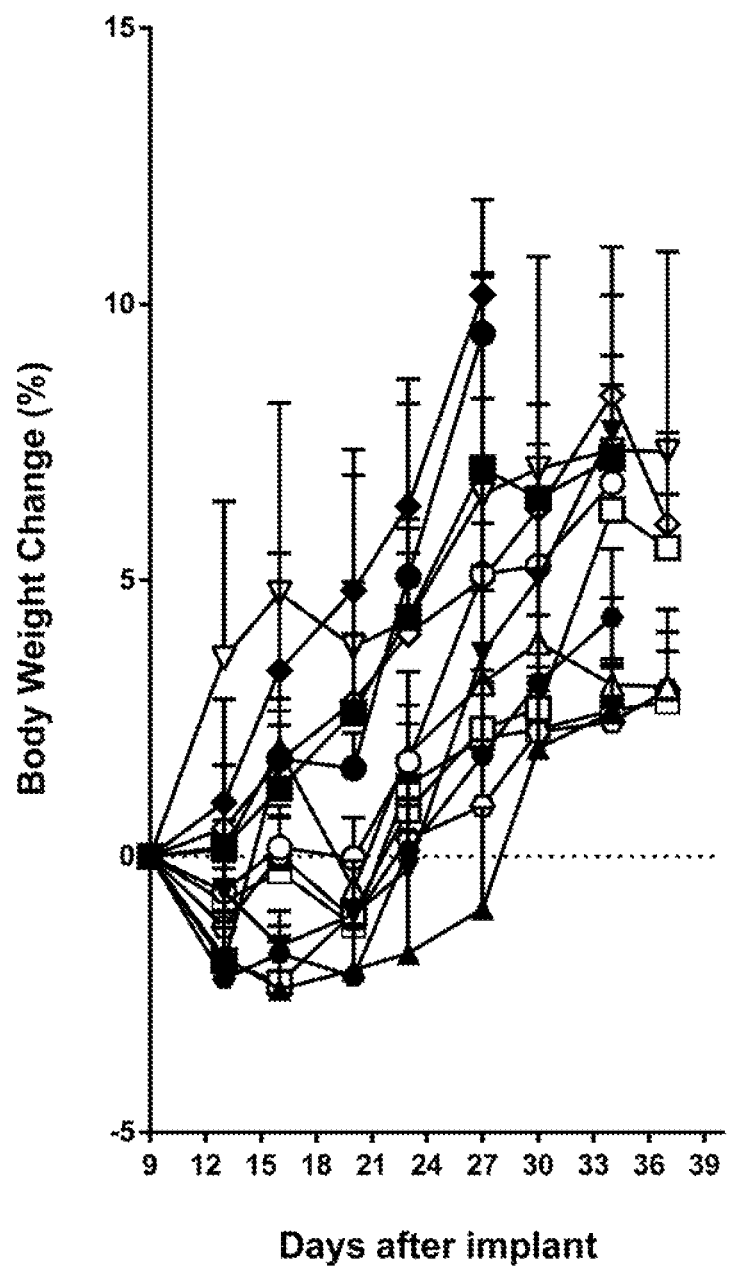
FIG. 32 illustrates body weight over time after treatment with vehicle, Example 32 as a single agent, osimertinib as a single agent, and Example 32 in combination with osimertinib. ◆ represents vehicle dosed for 19 days; ▬ represents 2.5 mg/kg QD osimertinib dosed for 26 days; ◆ represents 50 mg/kg BID Example 32 dosed for 19 days; ▲ represents 2.5 mg/kg QD osimertinib administered in combination with 12.5 mg/kg BID Example 32 dosed for 26 days; ● represents 2.5 mg/kg QD osimertinib administered in combination with 50 mg/kg BID Example 32 dosed for 26 days; ▼ represents 2.5 mg/kg QD osimertinib administered for 26 days in combination with 25 mg/kg BID Example 32 dosed for 7 days; ○ represents 2.5 mg/kg QD osimertinib administered for 26 days in combination with 50 mg/kg BID Example 32 dosed for 7 days; ☐ represents 2.5 mg/kg QD osimertinib administered for 29 days in combination with 50 mg/kg BID Example 32 dosed for 7 days on/7 days off for one week; ◇ represents 2.5 mg/kg QD osimertinib administered for 29 days in combination with 50 mg/kg BID Example 32 dosed for 7 days on/7 days off for 2 weeks; △ represents 2.5 mg/kg QD osimertinib administered for 29 days in combination with 25 mg/kg BID Example 32 dosed for 4 days on/3 days off for one week; ○ represents 2.5 mg/kg QD osimertinib administered for 29 days in combination with 50 mg/kg BID Example 32 dosed for 4 days on/3 days off for one week; ▽ represents 2.5 mg/kg QD osimertinib administered for 29 days in combination with 25 mg/kg BID Example 32 dosed for 2 days on/5 days off for one week; and ▬ represents 2.5 mg/kg QD osimertinib administered for 29 days in combination with 50 mg/kg BID Example 32 dosed for 2 days on/5 days off for one week.

RESULTS: The addition of Example 32 enhanced the antitumor activity of osimertinib, compared to treatment with osimertinib alone. Example 32 administered as a single agent had no significant activity relative to vehicle control treatment (FIG. 31A-31E). For the combination treatment of Example 32 and osimertinib, enhancement of antitumor activity was greater at the higher dose of Example 32 (50 mg/kg BID vs. 25 mg/kg BID). Although the enhancement of osimertinib activity decreased with decreasing schedule intensity of Example 32 (daily >4on/3off >7on/7off >2on/5off > just first 7 days), the difference was statistically significant after 26 days of treatment at all schedules of Example 32, with the exception of the groups in which Example 32 was dosed only for the first 7 days (Table 32). All treatments were well tolerated, with no significant weight loss (FIG. 32) or other outward signs observed over the course of treatment.

TABLE 32 p values For Antitumor Activity of AZD9291 Plus JAK1 Inhibitor combinations, After 26 Days of Treatment

| Treatment | vs. osimertinib single agent[a] |
|---|---|
| osimertinib, 2.5 mg/kg QD | — |
| osimertinib, 2.5 mg/kg QD + Example 32, 12.5 mg/kg BID, daily | 0.0156 |
| osimertinib, 2.5 mg/kg QD + Example 32, 50 mg/kg BID, daily | <0.0001 |
| osimertinib, 2.5 mg/kg QD + Example 32, 25 mg/kg BID, 4 on/3 off | 0.0002 |
| osimertinib, 2.5 mg/kg QD + Example 32, 50 mg/kg BID, 4 on/3 off | <0.0001 |
| osimertinib, 2.5 mg/kg QD + Example 32, 25 mg/kg BID, 7 on/7 off | 0.0079 |
| osimertinib, 2.5 mg/kg QD + Example 32, 50 mg/kg BID, 7 on/7 off | 0.0002 |
| osimertinib, 2.5 mg/kg QD + Example 32, 25 mg/kg BID, 2 on/5 off | 0.0391 |
| osimertinib, 2.5 mg/kg QD + Example 32, 50 mg/kg BID, 2 on/5 off | 0.0010 |
| osimertinib, 2.5 mg/kg QD + Example 32, 25 mg/kg BID, just first 7 days | 0.4744 |
| osimertinib, 2.5 mg/kg QD + Example 32, 50 mg/kg BID, just first 7 days | 0.4101 |

[a]Two-sided test

CONCLUSION: The increased antitumor activity of Example 32 in combination with osimertinib compared to single agent Example 32 is consistent with a role for STAT3 signaling in escape from, or resistance to, EGFR inhibition in this model of non-small cell lung cancer. The results support the hypothesis that inhibition of STAT3 signaling can enhance the antitumor activity of an EGFR inhibitor in T790M EGFR mutant NSCLC. The significant combination activity observed even when Example 32 was administered as infrequently as 2on/5off (i.e., only days 1 and 2 of a weekly cycle), suggests that enhancement of osimertinib activity may be achievable with only intermittent inhibition of pSTAT3 signaling.

The invention claimed is:

1. A solid form A of compound of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propanamide, which has an X-ray powder diffraction (XRPD) pattern comprising at least one, two or three specific peaks expressed as 2θ (±0.2°) selected from the peaks listed in Table 17.

2. The solid form of claim 1, which has
   (a) an XRPD pattern comprising at least one, two or three specific peaks expressed as 2θ (±0.2°) selected from about 6.4°, 7.9°, 8.7°, 16.4°, 18.8°, 20.4°, 21.6° and 22.2°, or
   (b) an XRPD pattern substantially similar to FIG. 1, or
   (c) a DSC thermogram comprising an endotherm with a desolvation onset at about 110° C. and a peak at about 113° C., or
   (d) a TGA thermogram exhibiting a mass loss of about 7.8% upon heating from about 25° C. to about 150° C., or
   (e) a DSC/TGA thermogram substantially similar to FIG. 2.

3. A solid form C of compound of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propanamide, which has an X-ray powder diffraction (XRPD) pattern comprising at least one, two or three specific peaks expressed as 2θ (±0.2°) selected from the peaks listed in Table 19.

4. The solid form of claim 3, which has
   (a) an XRPD pattern comprising at least one, two or three specific peaks expressed as 2θ (±0.2°) selected from about 6.3°, 7.9°, 8.7°, 13.8°, 18.9°, 20.4°, 21.5° and 22.2°, or
   (b) an XRPD pattern substantially similar to FIG. 5, or
   (c) a DSC thermogram comprising an endotherm with a desolvation onset at about 112° C. and a peak at about 114° C., or
   (d) a TGA thermogram exhibiting a mass loss of about 9.2% upon heating from about 25° C. to about 175° C., or
   (e) a DSC/TGA thermogram substantially similar to FIG. 6.

5. A solid form of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide salt, wherein the salt is selected from the group consisting of saccharine salt, hydrochloride saccharine salt, napadisylic salt and trimesic salt.

6. The solid form of claim 5, which is solid form A of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide saccharine salt.

7. The solid form of claim 6, which has
   (a) an X-ray powder diffraction (XRPD) pattern comprising at least one, two or three specific peaks expressed as 2θ (±0.2°) selected from the peaks listed in Table 21, or
   (b) an XRPD pattern comprising at least one, two or three specific peaks expressed as 2θ (±0.2°) selected from about 7.1°, 8.2°, 8.5°, 10.1°, 10.7°, 14.4°, 16.3°, 17.3° and 21.4°, or
   (c) an XRPD pattern substantially similar to FIG. 9, or
   (d) a DSC thermogram comprising an endotherm with a desolvation onset at about 163° C. and a peak at about 169° C., or
   (e) a TGA thermogram exhibiting a mass loss of about 3.1% upon heating from about 25° C. to about 150° C., or
   (f) a DSC/TGA thermogram substantially similar to FIG. 10.

8. The solid form of claim 5, which is solid form B of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide saccharine salt.

9. The solid of claim 8, which has
   (a) an X-ray powder diffraction (XRPD) pattern comprising at least one, two or three specific peaks expressed as 2θ (±0.2°) selected from the peaks listed in Table 22, or
   (b) an XRPD pattern comprising at least one, two or three specific peaks expressed as 2θ (±0.2°) selected from about 6.6°, 8.0°, 9.1°, 13.4°, 17.2°, 18.1°, 21.8° and 25.3°, or
   (c) an XRPD pattern substantially similar to FIG. 11, or
   (d) a DSC thermogram comprising one endotherm with a desolvation onset at about 53° C. and a peak at about 169° C., and another endotherm with a desolvation onset at about 176° C. and a peak at about 182° C., or
   (e) a TGA thermogram exhibiting a mass loss of about 2.7% upon heating from about 25° C. to about 100° C., or (f) a DSC/TGA thermogram substantially similar to FIG. 12.

10. The solid form of claim 5, which is solid form C of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide saccharin salt.

11. The solid of claim 10, which has
(a) an X-ray powder diffraction (XRPD) pattern comprising at least one, two or three specific peaks expressed as 2θ (±0.2°) selected from the peaks listed in Table 23, or
(b) an XRPD pattern comprising at least one, two or three specific peaks expressed as 2θ (±0.2°) selected from about 5.5°, 8.2°, 14.4°, 14.9°, 16.0°, 17.0°, 24.9° and 26.3°, or
(c) an XRPD pattern substantially similar to FIG. 13.

12. The solid form of claim 5, which is solid form D of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide saccharine salt.

13. The solid of claim 12, which has
(a) an X-ray powder diffraction (XRPD) pattern comprising at least one, two or three specific peaks expressed as 2θ (±0.2°) selected from the peaks listed in Table 24, or
(b) an XRPD pattern comprising at least one, two or three specific peaks expressed as 2θ (±0.2°) selected from about 5.4°, 6.8°, 7.7°, 13.8°, 15.4°, 19.2°, 20.1° and 20.8°, or
(c) an XRPD pattern substantially similar to FIG. 14.

14. The solid form of claim 5, which is solid form E of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide saccharine salt.

15. The solid of claim 14, which has
(a) an X-ray powder diffraction (XRPD) pattern comprising at least one, two or three specific peaks expressed as 2θ (±0.2°) selected from the peaks listed in Table 25, or
(b) an XRPD pattern comprising at least one, two or three specific peaks expressed as 2θ (±0.2°) selected from about 5.5°, 6.7°, 7.8°, 14.7°, 15.4°, 19.3°, 20.1° and 23.2°, or
(c) an XRPD pattern substantially similar to FIG. 15.

16. The solid form of claim 5, which is solid form of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide hydrochloride saccharine salt.

17. The solid of claim 16, which has
(a) an X-ray powder diffraction (XRPD) pattern comprising at least one, two or three specific peaks expressed as 2θ (±0.2°) selected from the peaks listed in Table 26, or
(b) an XRPD pattern comprising at least one, two or three specific peaks expressed as 2θ (±0.2°) selected from about 8.4°, 13.7°, 17.3°, 20.2°, 20.6°, 25.4°, 26.0° and 27.6°, or
(c) an XRPD pattern substantially similar to FIG. 16.

18. The solid form of claim 5, which is solid form of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide napadisylic salt.

19. The solid of claim 18, which has
(a) an X-ray powder diffraction (XRPD) pattern comprising at least one, two or three specific peaks expressed as 2θ (±0.2°) selected from the peaks listed in Table 27, or
(b) an XRPD pattern comprising at least one, two or three specific peaks expressed as 2θ (±0.2°) selected from about 5.2°, 7.8°, 10.4°, 15.0°, 17.3°, 18.3°, 20.9°, 22.1° and 25.6°, or
(c) an XRPD pattern substantially similar to FIG. 17.

20. The solid form of claim 5, which is solid form of (2R)—N-(3-{2-[(3-methoxy-1-methyl-1H-pyrazol-4-yl)amino]pyrimidin-4-yl}-1H-indol-7-yl)-2-(4-methylpiperazin-1-yl) propenamide trimesic salt.

21. The solid of claim 20, which has
(a) an X-ray powder diffraction (XRPD) pattern comprising at least one, two or three specific peaks expressed as 2θ (±0.2°) selected from the peaks listed in Table 28, or
(b) an XRPD pattern comprising at least one, two or three specific peaks expressed as 2θ) (±0.2°) selected from about 2.1°, 4.2°, 7.8°, 12.1°, 12.4°, 15.7°, 24.9°, 25.1° and 27.5°, or
(c) an XRPD pattern substantially similar to FIG. 18.

22. A pharmaceutical composition, which comprises the solid form of claim 1 and a pharmaceutically acceptable carrier, diluent or excipient.

23. A pharmaceutical composition, which comprises the solid form of claim 3 and a pharmaceutically acceptable carrier, diluent or excipient.

24. A pharmaceutical composition, which comprises the solid form of claim 5 and a pharmaceutically acceptable carrier, diluent or excipient.

* * * * *